(12) United States Patent
Nakai et al.

(10) Patent No.: US 7,968,572 B2
(45) Date of Patent: Jun. 28, 2011

(54) NITROGEN-CONTAINING HETEROCYCLIC COMPOUND AND PHARMACEUTICAL APPLICATION THEREOF

(75) Inventors: Hisao Nakai, Osaka (JP); Shingo Yamamoto, Osaka (JP); Shingo Nakatani, Osaka (JP); Tomomi Hirosaki, Osaka (JP)

(73) Assignee: Ono Pharmaceuticals Co., Ltd., Osaka (JP)

( * ) Notice: Subject to any disclaimer, the term of this patent is extended or adjusted under 35 U.S.C. 154(b) by 570 days.

(21) Appl. No.: 12/089,108

(22) PCT Filed: Oct. 2, 2006

(86) PCT No.: PCT/JP2006/319732
§ 371 (c)(1),
(2), (4) Date: Apr. 3, 2008

(87) PCT Pub. No.: WO2007/040208
PCT Pub. Date: Apr. 12, 2007

(65) Prior Publication Data
US 2010/0063104 A1    Mar. 11, 2010

(30) Foreign Application Priority Data

Oct. 3, 2005   (JP) .................. 2005-289542
Mar. 30, 2006  (JP) .................. 2006-093266

(51) Int. Cl.
*A61K 31/4412*  (2006.01)
*A61K 31/426*   (2006.01)
*A61K 31/421*   (2006.01)
*C07D 417/02*   (2006.01)

(52) U.S. Cl. ........ 514/340; 514/359; 514/365; 514/366; 514/374; 514/375; 514/439; 514/461; 514/468; 546/271.4; 546/271.1

(58) Field of Classification Search .......... 514/359, 514/365, 366, 374, 375, 439, 461, 468; 546/271.4, 546/271.1
See application file for complete search history.

(56) References Cited

U.S. PATENT DOCUMENTS

| | | | |
|---|---|---|---|
| 2004/0023973 A1 | 2/2004 | Nagato et al. | |
| 2005/0085509 A1 | 4/2005 | Takahashi et al. | |
| 2006/0135566 A1 | 6/2006 | Ohkawa et al. | |

FOREIGN PATENT DOCUMENTS

| EP | 0 149 884 A2 | 7/1985 |
|---|---|---|
| EP | 1205478 A1 | 5/2002 |
| JP | 60-58981 A | 4/1985 |
| JP | 9-505055 A | 5/1997 |
| JP | 2001-114690 A | 4/2001 |
| JP | 2001-506280 A | 5/2001 |
| JP | 2003-515537 A | 5/2003 |
| JP | 2005-504767 A | 2/2005 |
| JP | 2005-510508 A | 4/2005 |
| WO | 95/13067 A1 | 5/1995 |
| WO | 99/01449 A1 | 1/1999 |
| WO | 99/10331 A1 | 3/1999 |
| WO | 00/35906 A2 | 6/2000 |
| WO | 00/35909 A1 | 6/2000 |
| WO | 00/35921 A1 | 6/2000 |
| WO | 00/64872 A1 | 11/2000 |
| WO | 00/64894 A1 | 11/2000 |
| WO | 00/75118 A1 | 12/2000 |
| WO | 01/30778 A1 | 5/2001 |
| WO | 01/40230 A1 | 6/2001 |
| WO | 01/96308 A1 | 12/2001 |
| WO | 03/015776 A1 | 2/2003 |
| WO | 03/039451 A2 | 5/2003 |
| WO | 03/043988 A1 | 5/2003 |
| WO | 03/097062 A1 | 11/2003 |
| WO | 2006/038734 A1 | 4/2006 |
| WO | 2006/051826 A1 | 5/2006 |

OTHER PUBLICATIONS

Lee, J., et al., "A Protein Kinase Involved in the Regulation of Inflammatory Cytokine Biosynthesis", Nature, Dec. 1994, pp. 739-746, vol. 372.

Surya Prakash Rao, H., et al., "Facile Microwave-Mediated Transformations of 2-Butene-1,4-diones and 2-Butyne-1,4-diones to Furan Derivatives", J. Org. Chem., 2003, pp. 5392-5394, vol. 68, No. 13, American Chemical Society.

Dombroski, M., et al., "Benzimidazolone p38 Inhibitors", Bioorganic & Medicinal Chemistry Letters, 2004, pp. 919-923, vol. 14, No. 4, Elsevier Ltd.

Claiborne, C., et al., "An Efficient Synthesis of Tetrasubstituted Imidazoles from N-(2-Oxo)-amides", Tetrahedron Letters, 1998, pp. 8939-8942, vol. 39, No. 49, Elsevier Science Ltd.

(Continued)

Primary Examiner — Sreeni Padmanabhan
Assistant Examiner — Sahar Javanmard
(74) Attorney, Agent, or Firm — Sughrue Mion, PLLC

(57) ABSTRACT

It is intended to provide a compound represented by the formula (I):

(I)

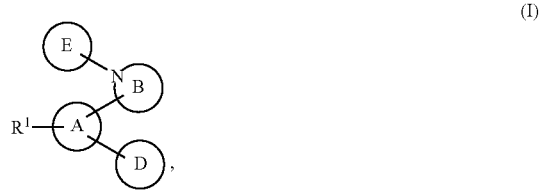

wherein all the symbols are as defined in the description; which has a p38 MAP kinase inhibitory activity, a salt thereof, an N-oxide thereof, a solvate thereof, or a prodrug thereof. The compound of the invention is useful for preventing or treating a disease in which the abnormal production of a cytokine such as an inflammatory cytokine or a chemokine or overreaction to them is considered to be involved in the cause and aggravation of pathological conditions, in other words, an inflammatory disease, a respiratory disease, a cardiovascular disease, a central nervous system disease or the like, which is a cytokine-mediated disease.

7 Claims, No Drawings

OTHER PUBLICATIONS

Strassler, C., et al., "Novel Heterospirocyclic 3-Amino-2H-azirines as Synthons for Heterocyclic α-Amino Acids", Helvetica Chimica Acta, 1997, pp. 1528-1554, vol. 80, No. 5.

Jiao, G.S., et al., "Syntheses of Regioisomerically Pure 5- or 6-Halogenated Fluoresceins", J. Org. Chem., 2003, pp. 8264-8267, vol. 68, No. 13, American Chemical Society.

Smith, N., et al., "Enantioselective Synthesis of α-Methyl-D-cysteine and Lanthionine Building Blocks via α-Methyl-D-serine-β-lactone", Organic Letters, 2003, pp. 1035-1037, vol. 5, No. 7, American Chemical Society.

Shao, H., et al., "An Enantiomeric Synthesis of allo-Threonines and β-Hydroxyvalines", J. Org. Chem, 1996, pp. 2582-2583, vol. 61, No. 8, American Chemical Society.

Abdiche, Y., et al., "Probing the Mechanism of Drug/Lipid Membrane Interactions Using Biacore", Analytical Biochemistry, 2004, pp. 233-243, vol. 328, Elsevier Inc.

Russian Office Action, issued Jul. 12, 2010 in corresponding Russian patent application No. 2008112691.

"Khimicheskii enciklopedicheskii slovar", Moskva, "Sovetskaya enciklopediya", 1983, pp. 130-131.

M.D. Mashkovsky "Lekarstvennie sredstva", Moskva, 1993 vol. 1, p. 8.

European Patent Office, Extended European Search Report issued on Feb. 9, 2011 in the corresponding European Patent Application No. 06811080.8.

NITROGEN-CONTAINING HETEROCYCLIC COMPOUND AND PHARMACEUTICAL APPLICATION THEREOF

TECHNICAL FIELD

The present invention relates to the nitrogenous heterocyclic compound that has p38 MAP kinase inhibitory activity and is useful as drug medicine, the process for preparation thereof and the use thereof.

BACKGROUND ART p38 mitogen-activated protein (MAP) kinase (p38α/Mpk2/RK/SAPK2a/CSBP) (hereinafter referred to as "p38 MAP kinase") was cloned as an enzyme which induces tyrosine phosphorylation in monocyte after stimulation with lipopolysaccharide (LPS) (*Nature,* 372, 739 (1994)), and is activated by various extracellular stimuli (physical stimuli such as osmotic shock, heat shock, UV irradiation, and so forth, and chemical stimuli such as endotoxin, hydrogen peroxide, arsenic trioxide, an inflammatory cytokine, a growth factor, and so forth). Also, since p38 MAP kinase is involved in the production of cytokine (for example, an inflammatory cytokine such as tumor necrosis factor-α (TNF-α), interleukin-1 (IL-1), IL-6, IL-8 and a chemokine), and so on, an association between the activation of this enzyme and diseases is strongly suggested. Therefore, an improvement effect on various disease symptoms typified by inflammatory diseases is expected by suppression of p38 MAP kinase activation.

Accordingly, a p38 MAP kinase inhibitor is expected to be useful in prevention and/or treatment of those diseases that are supposedly caused or deteriorated by abnormal production of cytokines including inflammatory cytokine or chemokine, or by over response thereto, namely cytokine-mediated diseases such as various inflammatory diseases [for example, inflammation, dermatitis, atopic dermatitis, hepatitis, nephritis, glomerulonephritis, pancreatitis, psoriasis, gout, Addison's disease, arthritis(e.g., rheumatoid arthritis, osteoarthritis, rheumatoid spondylitis, gouty arthritis, synovitis, etc.), inflammatory ocular diseases, inflammatory pulmonary diseases (e.g., chronic pneumonia, silicosis, pulmonary sarcoidosis, pulmonary tuberculosis, adult respiratory distress syndrome (ARDS), severe acute respiratory syndrome (SARS), etc.), inflammatory bowel diseases (e.g., Crohn's disease, ulcerative colitis, etc.), allergic diseases (e.g., allergic dermatitis, allergic rhinitis, etc.), autoimmune disease, autoimmune hemolytic anemia, systemic lupus erythematosus, rheumatism, Castleman's disease, immune rejection accompanying transplantation (e.g., graft versus host reaction, etc.), and so forth], central nervous system disorders [for example, central neuropathy (e.g., cerebrovascular disease such as cerebral hemorrhage and cerebral infarction, head trauma, spinal cord injury, cerebral edema, multiple sclerosis, etc.), neurodegenerative disease (e.g., Alzheimer's disease, Parkinson's disease, amyotrophic lateral sclerosis (ALS), AIDS encephalopathy, etc.), meningitis, Creutzfeldt-Jakob syndrome, and so forth], respiratory diseases [for example, asthma, chronic obstructive pulmonary disease (COPD), and so forth], cardiovascular diseases [for example, angina, heart failure, congestive heart failure, acute heart failure, chronic heart failure, myocardial infarction, acute myocardial infarction, myocardial infarction prognosis, atrial myxoma, arteriosclerosis, hypertension, dialysis-induced hypotension, thrombosis, disseminated intravascular coagulation (DIC), reperfusion injury, restenosis after percutaneous transluminal coronary angioplasty (PTCA), and so forth], urinary diseases [for example, renal failure, and so forth], metabolic diseases or endocrine diseases [for example, diabetes, and so forth], bone diseases [for example, osteoporosis, and so forth], cancerous diseases [for example, malignant tumor (e.g., tumor growth and metastasis, etc.), multiple myeloma, plasma cell leukemia, cancerous cachexia, and so forth], and infectious diseases [for example, viral infection (e.g., cytomegalovirus infection, influenza virus infection, herpes virus infection, corona virus infection, etc.), cachexia associated with infections, cachexia caused by acquired immune deficiency syndrome (AIDS), toxemia (e.g., sepsis, septic shock, endotoxin shock, gram negative bacterial sepsis, toxic shock syndrome, severe acute respiratory syndrome (SARS) accompanying virus infection, etc.), and so forth], and so on.

On the other hand, WO 2006/051826 discloses that the compound represented by formula (U), the salt thereof, the N-oxide thereof or the solvate thereof, or the prodrug thereof is useful as a p38 MAP kinase inhibitor, and does not have mention about the compound which is not a substituent that $R^{1U}$ contains nitrogen atom(s) having the basicity at all:

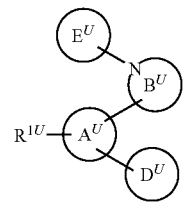

(U)

wherein ring $A^U$ represents a 5-membered monocyclic hetero ring which contains 1 to 3 atom(s) selected from the group consisting of oxygen atom, nitrogen atom and sulfur atom as a hetero atom, and which may have a further substituent(s);

ring $B^U$ represents an optionally substituted hetero ring containing at least one nitrogen atom;

ring $D^U$ represents an optionally substituted cyclic group;

ring $E^U$ represents an optionally substituted cyclic group; and $R^{1U}$ represents a substituent which contains nitrogen atom(s) having basicity.

Also, WO 01/096308 discloses that the compounds represented by formula (W), the salts thereof, or the hydrate thereof have an inhibitory effect on AMPA receptor and/or kainic acid receptor:

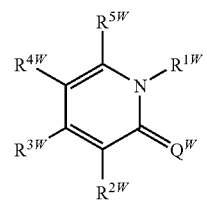

(W)

wherein $Q^W$ represents NH, O or S;

$R^{1W}$, $R^{2W}$, $R^{3W}$, $R^{4W}$ and $R^{5W}$ represent, samely or differently, hydrogen atom, halogen atom, C1-6 alkyl, or —$X^W$-$A^W$ (wherein $X^W$ represents a single bond, an optionally substituted C1-6 alkylene, an optionally substituted C2-6 alkenylene, an optionally substituted C2-6 alkynylene, —O—, —S—, —CO—, —SO—, —SO$_2$—, —N(R$^{6W}$)—, —N(R$^{7W}$)—CO—, —CO—N(R$^{8W}$)—, —N(R$^{9W}$)—CH$_2$—, —CH$_2$—N(R$^{10W}$)—, —CH$_2$—CO—, —CO—CH$_2$, —N(R$^{11W}$)—S(O)$_{mW}$—, —S(O)$_{nW}$—N(R$^{12W}$)—, —CH$_2$—S(O)$_{pW}$—, —S(O)$_{qW}$—CH$_2$—, —CH$_2$—, —CH$_2$—O—, —O—CH$_2$—, —N(R$^{13W}$)—CO—N(R$^{14W}$)—, or —N(R$^{15W}$)—CS—N(R$^{16W}$)— (wherein R$^{6W}$, R$^{7W}$, R$^{8W}$, R$^{9W}$, R$^{10W}$, R$^{11W}$, R$^{12W}$, R$^{13W}$, R$^{14W}$, R$^{15W}$ and R$^{16W}$ represent hydrogen atom, C1-6 alkyl or C1-6 alkoxy; mW, nW, pW and qW each independently represents 0 or an integer of 1 or 2); A$^W$ represents C3-8 cycloalkyl, C3-8 cycloalkenyl, a non-aromatic 5- to 14-membered hetero ring, an aromatic C6-14 hydrocarbon ring or an aromatic 5- to 14-membered hetero ring, and these rings are optionally substituted by substituent respectively);

with the proviso that, three of R$^{1W}$, R$^{2W}$, R$^{3W}$, R$^{4W}$ and R$^{5W}$, samely or differently, represent —X$^W$-A$^W$ and residual two always represent hydrogen atom, halogen atom, or C1-6 alkyl;

provided that in the above-mentioned definition, the cases where (1) Q$^W$ is O; R$^{1W}$ and R$^{5W}$ are hydrogen atom; and R$^{2W}$, R$^{3W}$ and R$^{4W}$ are phenyl groups, (2) Q$^W$ is O; R$^{1W}$ and R$^{4W}$ are hydrogen atom; and R$^{2W}$, R$^{3W}$ and R$^{5W}$ are phenyl groups, and (3) Q$^W$ is O; R$^{1W}$ and R$^{2W}$ are hydrogen atom; and R$^{3W}$, R$^{4W}$ and R$^{5W}$ are phenyl groups, are excluded.

Also, Japanese Publication Toku-Kai-Syo 60-58981 discloses that 1,3-thiazole derivatives represented by formula (Y) or the salts thereof have inhibitory effects on pain, fever, inflammation, ulcer, thromboxane A$_2$ (TXA$_2$) synthesis, and platelet aggregation:

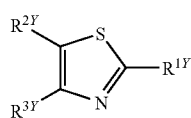

(Y)

wherein R$^{1Y}$ represents cycloalkyl, cyclic amino, amino having 1 or 2 substituent(s) selected from the group consisting of lower alkyl, phenyl, acetyl, and lower alkoxycarbonylacetyl, alkyl which may be substituted by hydroxyl, carboxyl or lower alkoxycarbonyl, or phenyl which may be substituted by carboxyl, 2-carboxyetenyl or 2-carboxy-1-propenyl;

R$^{2Y}$ represents pyridyl which may be substituted by lower alkyl;

R$^{3Y}$ represents lower alkoxy, lower alkyl, hydroxyl, halogen, or phenyl which may be substituted by methylenedioxy.

Moreover, WO 00/064894 discloses that the compounds represented by formula (Z) which may be N-oxidated or the salts thereof are useful as p38 MAP kinase inhibitors:

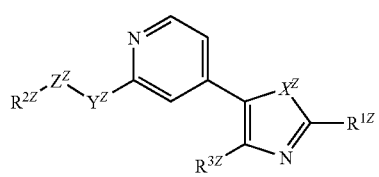

(Z)

wherein R$^{1Z}$ represents hydrogen atom, an optionally substituted hydrocarbon, an optionally substituted hetero ring, an optionally substituted amino or acyl;

R$^{2Z}$ represents an optionally substituted aromatic group;

R$^{3Z}$ represents hydrogen atom, an optionally substituted pyridyl, or an optionally substituted aromatic hydrocarbon;

X$^Z$ represents oxygen atom or an optionally oxidized sulfur atom;

Y$^Z$ represents a bond, oxygen atom, an optionally oxidized sulfur atom, or NR$^{4Z}$ (wherein R$^{4Z}$ represents hydrogen atom, an optionally substituted hydrocarbon, or acyl);

Z$^Z$ represents a bond or a bivalent aliphatic hydrocarbon which may have a substituent(s).

Furthermore, WO 03/043988 discloses that the compounds represented by formula (A) or the non-toxic salts thereof are useful as p38 MAP kinase inhibitors:

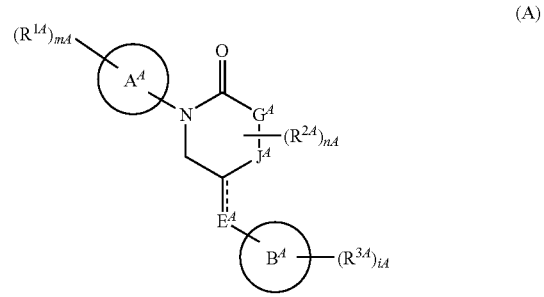

(A)

wherein A$^A$ represents a C5-10 mono- or bi-cyclic carbon ring, or a 5- to 10-membered mono- or bi-cyclic hetero ring containing 1 to 5 nitrogen atom(s), 1 to 2 oxygen atom(s) and/or 1 sulfur atom;

R$^{1A}$ represents (1) C1-8 alkyl, (2) C2-8 alkenyl, (3) C2-8 alkynyl, (4) halogen atom, (5) —OR$^{4A}$, (6) —NR$^{5A}$R$^{6A}$, (7) —NR$^{7A}$COR$^{8A}$, (8) —CONR$^{9A}$R$^{10A}$, (9) —COOR$^{11A}$, (10) —SO$_2$NR$^{12A}$R$^{13A}$, (11) —NR$^{14A}$SO$_2$R$^{15A}$, (12) —SR$^{16A}$, (13) —S(O)R$^{17A}$, (14) —SO$_2$R$^{18A}$, (15) —NR$^{22A}$COOR$^{23A}$, (16) —NR$^{24A}$CONR$^{25A}$R$^{26A}$, (17) —COR$^{27A}$, (18) nitro, (19) cyano, (20) trifluoromethyl, (21) trifluoromethoxy, (22) Cyc1$^A$, or the like;

R$^{4A}$-R$^{18A}$ and R$^{22A}$-R$^{27A}$ each independently represent a hydrogen atom, C1-8 alkyl, Cyc1$^A$, or the like;

Cyc1$^A$ represents a C5-10 mono- or bi-cyclic carbon ring or the like (with the proviso that, the carbon ring or the like may be substituted by one to five R$^{48A}$(s));

R$^{48A}$ represents C1-8 alkyl, halogen atom, nitro, cyano, or the like;

R$^{2A}$ represents C1-8 alkyl, —OR$^{20A}$, NR$^{64A}$R$^{65A}$, —COOR$^{66A}$, —CONR$^{67A}$R$^{68A}$, —NR$^{69A}$COR$^{70A}$, —SO$_2$R$^{71A}$, —SO$_2$NR$^{72A}$R$^{73A}$, —NR$^{74A}$SO$_2$R$^{75A}$, —NR$^{76A}$COOR$^{77A}$, Cyc2$^A$, or the like;

R$^{20A}$ and R$^{64A}$-R$^{77A}$ each independently represent hydrogen atom, C1-8 alkyl, Cyc2$^A$, or the like;

Cyc2$^A$ represents a C5-6 monocyclic carbon ring or the like (with the proviso that, the carbon ring or the like may be substituted by one to five substituent(s) such as C1-8 alkoxy, halogen atom or the like);

G$^A$ and J$^A$ each independently represent a carbon, nitrogen, oxygen, or sulfur atom;

E$^A$ represents C1-4 alkylene, —O—, —S—, or the like (with the proviso that, the C1-4 alkylene may be substituted by one to five substituent(s) such as C1-8 alkoxy, halogen atom, hydroxy, or the like);

B$^A$ represents a C5-10 mono- or bi-cyclic carbon ring, or a 5- to 10-membered mono- or bi-cyclic hetero ring containing 1 to 4 nitrogen atom(s), 1 to 2 oxygen atom(s) and/or 1 sulfur atom;

$R^{3A}$ represents C1-8 alkyl, C2-8 alkenyl, C2-8 alkynyl, halogen atom, —OR$^{81A}$, —NR$^{82A}$R$^{83A}$, —NR$^{84A}$COR$^{85A}$, —CONR$^{86A}$R$^{87A}$, —COOR$^{88A}$, —SO$_2$NR$^{89A}$R$^{90A}$, —NR$^{91A}$SO$_2$R$^{92A}$, —SR$^{93A}$, —S(O)R$^{94A}$, —SO$_2$R$^{95A}$, —NR$^{96A}$COOR$^{97A}$, —NR$^{98A}$CONR$^{99A}$R$^{100A}$, —OCONR$^{101A}$R$^{102A}$, nitro, cyano, trifluoromethyl, trifluoromethoxy, Cyc4$^A$, or the like;

$R^{81A}$-$R^{102A}$ each independently represents hydrogen atom, C1-8 alkyl, Cyc4$^A$, or the like;

Cyc4$^A$ represents a C5-10 mono- or bi-cyclic carbon ring or the like (with the proviso that, the carbon ring or the like may be substituted by one to five substituent(s) such as C1-8 alkoxy, halogen atom or the like);

mA represents 0 or an integer of 1 to 5;

nA represents 0 or an integer of 1 to 7;

iA represents 0 or an integer of 1 to 12, with the proviso that, only necessary part of the meanings of the symbols in the formula were excerpted.

And more, WO 01/030778 discloses that the compounds represented by formula (B), the pharmaceutically-acceptable cleavable esters thereof, or the acid-addition salts thereof are useful as p38 MAP kinase inhibitors:

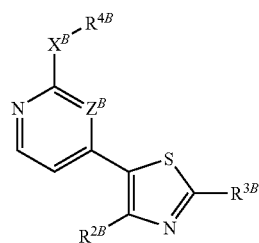

(B)

wherein $Z^B$ represents N or CH;

$X^B$ represents —NR$^{6B}$—Y$^B$—, —O— or —S— (wherein R$^{6B}$ represents hydrogen atom, C1-4 alkyl, C3-8 cycloalkyl, (C3-8 cycloalkyl) C1-3 alkyl, C6-18 aryl, C3-18 heteroaryl, C7-19 aralkyl, or C4-19 heteroaralkyl, and —Y$^B$— represents C1-4 alkylene or a bond);

$R^{2B}$ represents phenyl which may be substituted by one or more substituent(s), the substituent(s) are selected from the group consisting of halo, trifluoromethyl, cyano, amide, thioamide, carboxylate, thiocarboxylate, C1-4 alkoxy, C1-4 alkyl, or amino which may be substituted by mono- or di-C1-4 alkyl optionally;

$R^{3B}$ represents hydrogen atom, C1-10 alkyl, C3-10 cycloalkyl, C3-18 heterocycloalkyl, C6-18 aryl, or C3-18 heteroaryl, and each may have up to four substituent(s) selected from the group consisting of C1-4 alkyl, halogen atom, halogen-substituted C1-4 alkyl, hydroxy, C1-4 alkoxy, C1-4 alkylthio, or amino which may be substituted by mono- or di-C1-4 alkyl optionally, or 5- to 7-membered nitrogenous hetero ring optionally containing further hetero atom selected from oxygen, sulfur or nitrogen atom;

$R^{4B}$ represents C6-18 aryl, C3-18 heteroaryl or C3-12 cycloalkyl, substituted by up to four substituent(s) selected from the group consisting of C1-4 alkyl, halogen atom, halogen-substituted C1-4 alkyl, hydroxy, C1-4 alkoxy, C1-4 alkylthio, or amino which may be substituted by mono- or di-C1-4 alkyl optionally, or by N-heterocyclyl containing from 5 to 7 ring atoms and optionally containing a further hetero atom selected from O, S or N.

DISCLOSURE OF THE INVENTION

Problems to be Solved by the Invention

A p38 MAP kinase inhibitor is useful as an agent for preventing and/or treating various diseases represented by inflammatory diseases. However, the p38 MAP kinase inhibitors which has been known have possibility of causing high hepatopathy risks indicated by such as showing a hepatotoxicity in a clinical test and showing a CYP inhibitory activity or hepatic metabolism enzyme inducing activity in an in vitro tests. Additionally, it has been revealed that the compound represented by the aforementioned formula (U) having a markedly high p38 MAP kinase inhibitory activity has a phospholipidosis inducing activity having a high possibility of leading to serious side effects (e.g., hepatopathy and the like). Thus, great concern has been directed toward the development of a p38 MAP kinase inhibitor which does not show the phospholipidosis inducing activity; is highly safe; and is excellent in oral absorption.

Means for Solving the Problems

With the aim of finding out a compound which could become a safe therapeutic agent for various diseases represented by inflammatory diseases with inhibiting activation of p38 MAP kinase, the inventors of the present invention have conducted intensive studies and found as a result that novel nitrogen-containing heterocyclic compounds represented by formula (I), which are described later, have a strong p38 MAP kinase inhibitory activity and also show a strong TNF-α production inhibitory activity in an in vitro test and in vivo test, and further that these compounds do not show in an in vitro experiment a phospholipidosis inducing activity which is considered as a factor of side effects, thereby accomplishing the present invention.

Thus, the present invention relates to:

[1] a compound represented by formula (I):

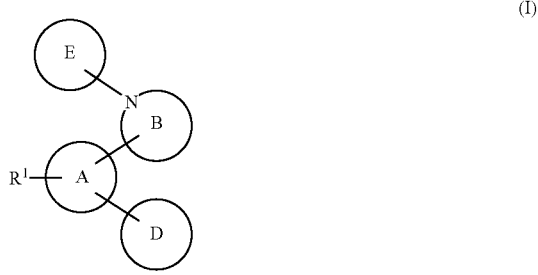

(I)

wherein ring A represents a 5-membered monocyclic hetero ring which contains 1 to 3 atom(s) selected from the group consisting of an oxygen atom, a nitrogen atom and a sulfur atom, and which may have a further substituent(s);

ring B represents a hetero ring which may be substituted and may contain 1 to 3 atom(s) selected from the group consisting of an oxygen atom, a nitrogen atom and a sulfur atom in addition to described nitrogen atom;

ring D represents a cyclic group which may be substituted;

ring E represents a cyclic group which may be substituted; and $R^1$ represents a neutral group or an acidic group which contains an oxygen atom(s) and/or a sulfur atom(s);

or a salt thereof, N-oxide or solvate thereof, or a prodrug thereof;

[2] the compound according to above [1], wherein ring A is

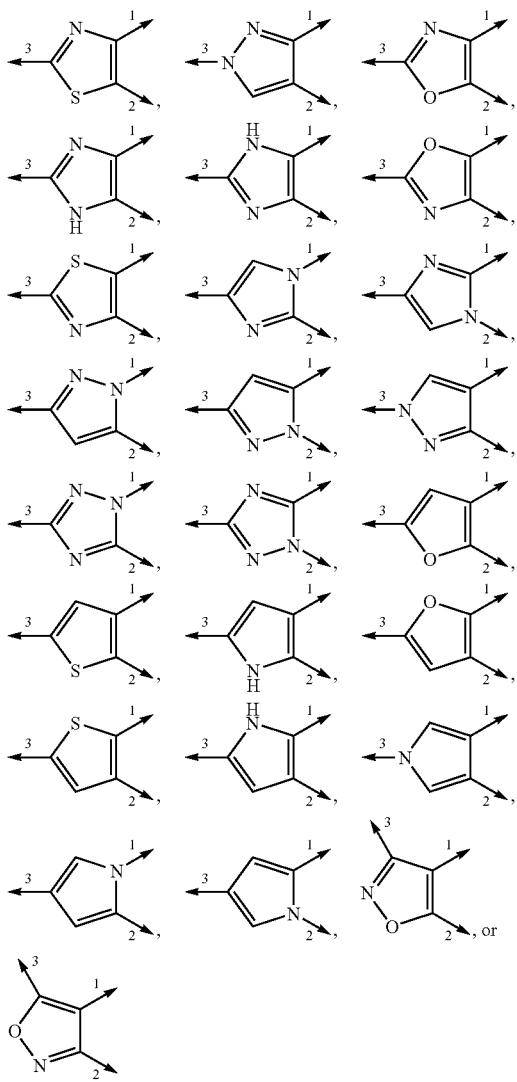

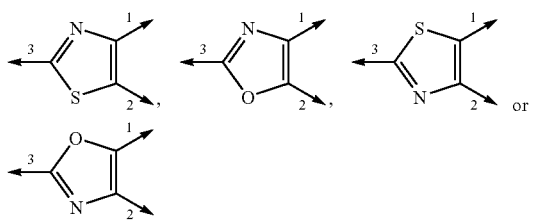

in which arrowhead 1 represents a bond with ring B;
arrowhead 2 represents a bond with ring D; and
arrowhead 3 represents a bond with $R^1$;
wherein the hydrogen atom in NH may be substituted by a substituent; and may have a further substituent(s);

[3] the compound according to above [1], wherein ring A is

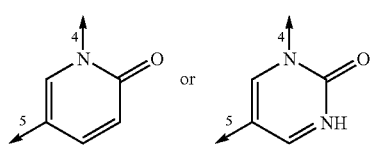

in which all symbols have the same meanings as described in above [2];

[4] the compound according to above [1], wherein ring B is

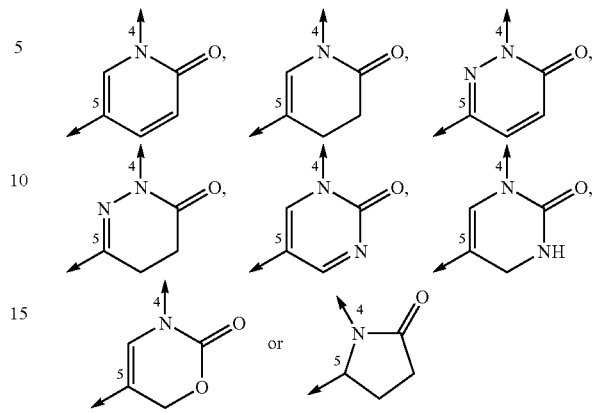

in which arrowhead 4 represents a bond with ring E; and arrowhead 5 represents a bond with ring A;
wherein the hydrogen atom in NH may be substituted by a substituent; and may have a substituent(s);

[5] the compound according to above [1], wherein ring B is

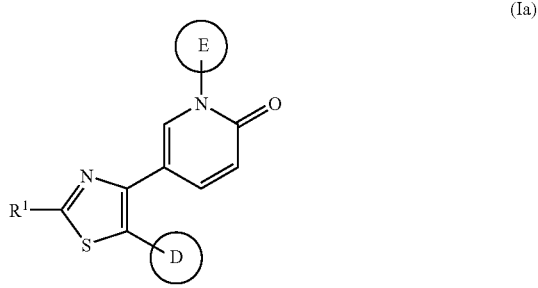

in which all symbols have the same meanings as described in above [4];
wherein the hydrogen atom in NH may be substituted by a substituent; and may have a substituent(s);

[6] the compound according to above [1], wherein ring D and ring E are each independently a C5-10 monocyclic or bicyclic carbon ring which may be substituted, or a 5- to 10-membered monocyclic or bicyclic hetero ring which may be substituted;

[7] the compound according to above [1], wherein ring D and ring E are each independently a C5-10 monocyclic or bicyclic carbon ring which may be substituted;

[8] the compound according to above [1], wherein a neutral group or an acidic group represented by $R^1$ is a hydroxyl group which may be protected, a hydrocarbon group substituted by the hydroxyl group which may be protected, a cyclic group substituted by the hydroxyl group which may be protected, a cyclic ether group which may be substituted, or a cyclic thioether group which may be substituted;

[9] the compound according to above [1], represented by formula (Ia), (Ib), (Ic), or (Id):

-continued (Ib)
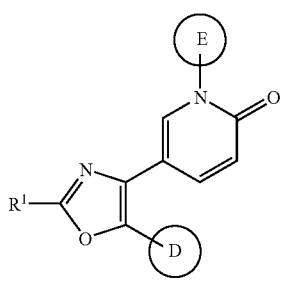

(Ic)
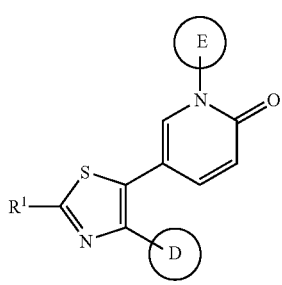

(Id)
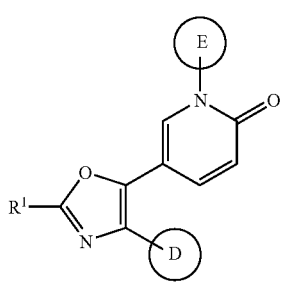

in which all symbols have the same meanings as described in above [1];

[10] the compound according to above [9], wherein ring D and ring E are each independently a C5-10 monocyclic or bicyclic carbon ring which may be substituted;

[11] the compound according to above [1], represented by formula (I-A), (I-B), (I-C), or (I-D):

(I-A)
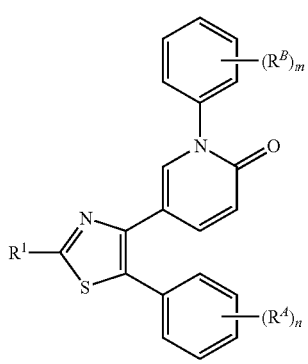

-continued (I-B)
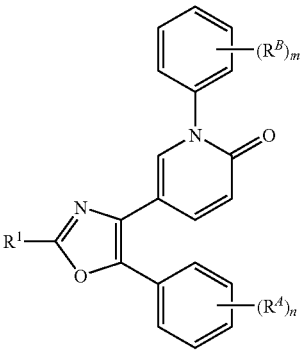

(I-C)
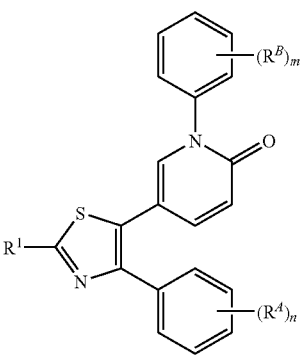

(I-D)
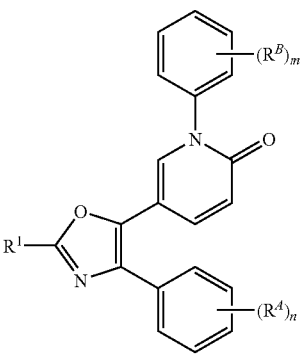

in which $R^A$ represents a substituent;
$R^B$ represents a substituent;
n represents 0 or an integer of 1 to 5;
m represents 0 or an integer of 1 to 5;
wherein when n is 2 or more, $R^A$ may be the same or different, and when m is 2 or more, $R^B$ may be the same or different; and
$R^1$ has the same meanings as described in above [1];

[12] the compound according to above [11], wherein $R^A$ is a C1-4 alkyl group which may be substituted, a C1-4 alkoxy group which may be substituted or halogen atom, and n is an integer of 1 to 3;

[13] the compound according to above [11], wherein $R^B$ is a C1-8 alkyl group which may be substituted, a C2-8 alkynyl group which may be substituted or halogen atom, and m is an integer of 1 to 3;

[14] the compound according to above [11], wherein a neutral group or an acidic group represented by $R^1$ is a hydroxyl group which may be protected, a hydrocarbon group substituted by the hydroxyl group which may be protected, a cyclic group substituted by the hydroxyl group which may be protected, a cyclic ether group which may be substituted, or a cyclic thioether group which may be substituted;

[15] the compound according to above [14], wherein the hydrocarbon group substituted by the hydroxyl group which may be protected is C1-8 alkyl group substituted by 1-3 hydroxyl group(s), and the cyclic group substituted by the hydroxyl group which may be protected is C3-6 mono-cyclic carbon ring substituted by 1-2 hydroxyl group(s);

[16] the compound according to above [1] selected from a group that consists of 1-(2,6-difluorophenyl)-5-[5-(2,4-difluorophenyl)-2-(1-hydroxy-1-methylethyl)-1,3-oxazol-4-yl]-2(1H)-pyridinone, 1-(2,6-difluorophenyl)-5-{5-(2,4-difluorophenyl)-2-[1,2-dihydroxy-1-(hydroxymethyl)ethyl]-1,3-oxazol-4-yl}-2(1H)-pyridinone, 1-(2,6-difluorophenyl)-5-[4-(2,4-difluorophenyl)-2-(1-hydroxy-1-methylethyl)-1,3-oxazol -5-yl]-2(1H)-pyridinone, 1-(2,6-difluorophenyl)-5-{5-(2,4-difluorophenyl)-2-[(1R)-1,2-dihydroxy-1-methylethyl]-1,3-oxazol-4-yl}-2(1H)-pyridinone, 1-(2,6-difluorophenyl)-5-{5-(2,4-difluorophenyl)-2-[(1S)-1,2-dihydroxy-1-methylethyl]-1,3-oxazol-4-yl}-2(1H)-pyridinone, 1-(2,6-difluorophenyl)-5-{4-(2,4-difluorophenyl)-2-[(1S)-1,2-dihydroxy-2-methylpropyl]-1,3-oxazol-5-yl}-2(1H)-pyridinone, 1-(2,6-difluorophenyl)-5-{4-(2,4-difluorophenyl)-2-[(1R)-1,2-dihydroxy-2-methylpropyl]-1,3-oxazol-5-yl}-2(1H)-pyridinone, 1-(2,6-difluorophenyl)-5-{4-(2,4-difluorophenyl)-2-[(1S)-1,2-dihydroxy-1-methylethyl]-1,3-oxazol-5-yl}-2(1H)-pyridinone, 1-(2,6-difluorophenyl)-5-{4-(2,4-difluorophenyl)-2-[(1R)-1,2-dihydroxy-1-methylethyl]-1,3-oxazol-5-yl}-2(1H)-pyridinone, 1-(2,6-difluorophenyl)-5-[4-(2,4-difluorophenyl)-2-(2-hydroxy-2-methylpropyl)-1,3-oxazol-5-yl]-2(1H)-pyridinone, 1-(2,6-difluorophenyl)-5-{4-(2,4-difluorophenyl)-2-[1,2-dihydroxy-1-(hydroxymethyl)ethyl]-1,3-oxazol-5-yl}-2(1H)-pyridinone, 1-(2,6-difluorophenyl)-5-{5-(2,4-difluorophenyl)-2-[(1S)-1,2-dihydroxy-2-methylpropyl]-1,3-oxazol-4-yl}-2(1H)-pyridinone, or 1-(2,6-difluorophenyl)-5-{5-(2,4-difluorophenyl)-2-[(1R)-1,2-dihydroxy-2-methylpropyl]-1,3-oxazol-4-yl}-2(1H)-pyridinone;

[17] a pharmaceutical composition comprising a compound represented by formula (I) described in above [1], a salt thereof, an N-oxide thereof or a solvate thereof, or a prodrug thereof;

[18] the composition according to above [17], which is a p38 MAP kinase inhibitor and/or a TNF-α production inhibitor;

[19] the composition according to above [17], which is an agent for prevention and/or treatment of a cytokine-mediated disease;

[20] the composition according to above [19], wherein the cytokine-mediated disease is an inflammatory disease, a cardiovascular disease, a respiratory disease, and/or a bone disease;

[21] the composition according to above [20], wherein the inflammatory disease is rheumatoid arthritis;

[22] a medicine comprising a compound represented by formula (I) described in above [1], or a salt thereof, an N-oxide thereof or a solvate thereof, or a prodrug thereof, and one or two or more compound(s) selected from the group consisting of a non-steroidal anti-inflammatory agent, a disease modifying anti-rheumatic drug, an anticytokine protein preparation, a cytokine inhibitor, an immunomodulator, a steroidal agent, an adhesion molecule inhibitor, an elastase inhhibitor, a cannabinoid-2 receptor stimulant, a prostaglandin, a prostaglandin synthase inhibitor, a phosphodiesterase inhibitor and a metalloproteinase inhibitor in combination;

[23] a method for prevention and/or treatment of a cytokine-mediated disease in a mammal, which comprises administering an effective amount of a compound represented by formula (I) described in above [1], a salt thereof, an N-oxide thereof or a solvate thereof, or a prodrug thereof to a mammal;

[24] use of a compound represented by formula (I) described in above [1], a salt thereof, an N-oxide thereof or a solvate thereof, or a prodrug thereof for the manufacture of an agent for prevention and/or treatment of a cytokine-mediated disease; and

[25] a process for preparation of a compound represented by formula (I) described in above [1], a salt thereof, an N-oxide thereof or a solvate thereof, or a prodrug thereof, or the like.

In the description of the present invention, the "cyclic group" in the "optionally substituted cyclic group" represented by ring D or ring E includes, for example, a "carbon ring" or a "hetero ring". Said "carbon ring" only has to be a carbon ring, and there is no particular limitation for the number of atoms that constitute said "carbon ring". As preferable carbon ring, for example, a "C5-10 mono- or bi-cyclic carbon ring" and so forth can be cited. It includes, for example, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene ring, and so forth. Also, said "C5-10 mono- or bi-cyclic carbon ring" includes, a spiro-fused poly-cyclic carbon ring and a bridged poly-cyclic carbon ring, too. It includes, for example, spiro[4.4]nonane, spiro[4.5]decane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane ring, and so forth. Among these, as a "C5-10 mono- or bi-cyclic aromatic carbon ring", for example, benzene ring and naphthalene ring can be cited. Said "hetero ring" only has to be a hetero ring, and there is no particular limitation for the number of atoms that constitute said "hetero ring". As preferable hetero ring, for example, a "5- to 10-membered mono- or bi-cyclic hetero ring" and so forth can be cited. As said "5- to 10-membered mono- or bi-cyclic hetero ring", a "5- to 10-membered mono- or bi-cyclic hetero ring containing 1 to 5 nitrogen atom(s), 1 to 2 oxygen atom(s) and/or 1 sulfur atom, a spiro-fused poly-cyclic hetero ring, and a bridged poly-cyclic hetero ring" and so forth can be cited. Among said "5- to 10-membered mono- or bi-cyclic hetero ring containing 1 to 5 nitrogen atom(s), 1 to 2 oxygen atom(s) and/or 1 sulfur atom, a spiro-fused poly-cyclic hetero ring, and a bridged poly-cyclic hetero ring", a "5- to 10-membered mono- or bi-cyclic hetero ring containing 1 to 5 nitrogen atom(s), 1 to 2 oxygen atom(s) and/or 1 sulfur atom" includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydropyran, tetrahydropyran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole(oxazolidine), dihydroisoxazole, tetrahydroisoxazole(isoxazolidine), dihydrothiazole, tetrahydrothiazole(thiazolidine), dihydroisothiazole, tetrahydroisothiazole(isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole(thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dioxaindan, benzodioxane, chroman ring, and so forth. Moreover, among said "5- to 10-membered mono- or bi-cyclic hetero ring containing 1 to 5 nitrogen atom(s), 1 to 2 oxygen atom(s) and/or 1 sulfur atom, a spiro-fused poly-cyclic hetero ring, and a bridged poly-cyclic hetero ring", "a spiro-fused poly-cyclic hetero ring, and a bridged poly-cyclic hetero ring" includes, for example, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane ring, and so forth. Among these, a "5- to 10-membered mono- or bi-cyclic aromatic hetero ring containing 1 to 4 nitrogen atom(s), 1 to 2 oxygen atom(s) and/or 1 sulfur atom" is preferable, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole ring, and so forth can be given concretely.

In the description of the present invention, there is no particular limitation for the "substituent" in the "optionally substituted cyclic group" represented by ring D or ring E so long as it can be a substituent. Said "substituent" includes, for example, (1) an optionally substituted aliphatic hydrocarbon group, (2) a substituent selected from the Group I shown below, (3) an optionally substituted C5-10 mono- or bi-cyclic carbon ring, (4) an optionally substituted 5- to 10-membered mono- or bi-cyclic hetero ring, or the like. One to twelve substituent(s), preferably one to three substituent(s) among these optional substituents may be located at any position where substitution is possible.

The "aliphatic hydrocarbon group" in the "optionally substituted aliphatic hydrocarbon group" includes, for example, a "straight or branched aliphatic hydrocarbon group", and so forth. Said "straight or branched aliphatic hydrocarbon group" includes, for example, a "C1-8 aliphatic hydrocarbon group", and so forth. Said "C1-8 aliphatic hydrocarbon group" includes, for example, C1-8 alkyl such as methyl, ethyl, propyl, isopropyl, butyl, sec-butyl, tert-butyl, pentyl, hexyl, heptyl, octyl, and isomers thereof, etc., C2-8 alkenyl such as vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl, and isomers thereof, etc., C2-8 alkynyl such as ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, octatriynyl, and isomers thereof, etc., and so forth.

There is no particular limitation for the "substituent" in the "optionally substituted aliphatic hydrocarbon group" so long as it can be a substituent. Said "substituent" includes, for example, (1) a substituent selected from the Group I shown below, (2) an optionally substituted C5-10 mono- or bi-cyclic carbon ring, (3) an optionally substituted 5- to 10-membered mono- or bi-cyclic hetero ring, or the like. One to five substituent(s) among these optional substituents may be located at any position where substitution is possible.

<Group I>

(a) halogen atom such as chlorine, bromine, fluorine, iodine atom, (b) —$OR^{a1}$, (c) —$NR^{a1}R^{a2}$, (d) —$NR^{a1}COR^{a2}$, (e) —$CONR^{a1}R^{a2}$, (f) —$COOR^{a1}$, (g) —$SO_2NR^{a1}R^{a2}$, (h) —$NR^{a1}SO_2R^{a2}$, (i) —$SR^{a1}$, (j) —$S(O)R^{a1}$, (k) —$SO_2R^{a1}$, (l) —$COR^{a1}$, (m) nitro, (n) cyano, (o) trifluoromethyl, (r) trifluoromethoxy, and (s) —$C=(NOR^{a1})R^{a2}$;

in these groups, $R^{a1}$ and $R^{a2}$ each independently represent a hydrogen atom, an optionally substituted C1-8 alkyl, an optionally substituted C5-10 mono- or bi-yclic carbon ring, or an optionally substituted 5- to 10-membered mono- or bi-cyclic hetero ring.

Here, the "C1-8 alkyl" in the "optionally substituted C1-8 alkyl" represented by $R^{a1}$ and $R^{a2}$ has the same meaning as defined above. Also, there is no particular limitation for the "substituent" in the "optionally substituted C1-8 alkyl" represented by $R^{a1}$ and $R^{a2}$ so long as it can be a substituent. Said "substituent" includes, for example, (1) a substituent selected from the Group II shown below, (2) an optionally substituted C5-10 mono- or bi-cyclic carbon ring, (3) an optionally substituted 5- to 10-membered mono- or bi-cyclic hetero ring, or the like. One to five substituent(s) among these optional substituents may be located at any position where substitution is possible.

<Group II>
(a) —OR$^{b1}$, (b) —NR$^{b1}$R$^{b2}$, (c) —NR$^{b1}$COR$^{b2}$, (d) —CONR$^{b1}$R$^{b2}$, (e) —COOR$^{b1}$, (f) —SO$_2$NR$^{b1}$R$^{b2}$, (g) —NR$^{b1}$SO$_2$R$^{b2}$, (h) —CONR$^{b1}$NR$^{b2}$R$^{b3}$ and (i) —CONR$^{b1}$OR$^{b2}$;

in these groups, R$^{b1}$, R$^{b2}$ and R$^{b3}$ each independently represent a hydrogen atom, an optionally substituted C1-8 alkyl, an optionally substituted C5-10 mono- or bi-cyclic carbon ring, or an optionally substituted 5- to 10-membered mono- or bi-cyclic hetero ring.

Here, the "C1-8 alkyl" in the "optionally substituted C1-8 alkyl" represented by R$^{b1}$, R$^{b2}$ and R$^{b3}$ has the same meaning as defined above. Also, there is no particular limitation for the "substituent" in the "optionally substituted C1-8 alkyl" represented by R$^{b1}$, R$^{b2}$ and R$^{b3}$ so long as it can be a substituent. Said "substituent" includes, for example, (1) a substituent selected from the Group III shown below, (2) an optionally substituted C5-10 mono- or bi-cyclic carbon ring, (3) an optionally substituted 5- to 10-membered mono- or bi-cyclic hetero ring, or the like. One to five substituent(s) among these optional substituents may be located at any position where substitution is possible.

<Group III>
(a) —OR$^{c1}$ and (b) —NR$^{c1}$R$^{c2}$;

in these groups, R$^{c1}$ and R$^{c2}$ each independently represent a hydrogen atom, an optionally substituted C1-8 alkyl, an optionally substituted C5-10 mono- or bi-cyclic carbon ring, or an optionally substituted 5- to 10-membered mono- or bi-cyclic hetero ring.

Here, the "C1-8 alkyl" in the "optionally substituted C1-8 alkyl" represented by R$^{c1}$ and R$^{c2}$ has the same meaning as defined above. Also, there is no particular limitation for the "substituent" in the "optionally substituted C1-8 alkyl" represented by R$^{c1}$ and R$^{c2}$ so long as it can be a substituent. Said "substituent" includes, for example, (1) an optionally substituted C5-10 mono- or bi-cyclic carbon ring, (2) an optionally substituted 5- to 10-membered mono- or bi-cyclic hetero ring, or the like. One to five substituent(s) among these optional substituents may be located at any position where substitution is possible.

The "C5-10 mono- or bi-cyclic carbon ring" in the "optionally substituted C5-10 mono- or bi-cyclic carbon ring" in the "substituent" of ring D or ring E has the same meaning as the "C5-10 mono- or bi-cyclic carbon ring" which the "cyclic group" in the "optionally substituted cyclic group" represented by ring D or ring E defined above means. Also, the "5- to 10-membered mono- or bi-cyclic hetero ring" in the "optionally substituted 5- to 10-membered mono- or bi-cyclic hetero ring" has the same meaning as the "5- to 10-membered mono- or bi-cyclic hetero ring" which the "cyclic group" in the "optionally substituted cyclic group" represented by ring D or ring E defined above means. Moreover, there is no particular limitation for the "substituent" in the "optionally substituted C5-10 mono- or bi-cyclic carbon ring" or the "optionally substituted 5- to 10-membered mono- or bi-cyclic hetero ring" so long as it can be a substituent. Said "substituent" includes, for example, (1) a substituent selected from the Group IV shown below, (2) an optionally substituted 5- to 6-membered cyclic group, or the like. One to five substituent(s) among these optional substituents may be located at any position where substitution is possible.

<Group IV>
(a) C1-8 alkyl, having the same meaning as defined above, (b) halogen atom, having the same meaning as defined above, (c) nitro, (d) cyano, (e) —OR$^{d1}$, (f) —NR$^{d1}$R$^{d2}$, (g) —COOR$^{d1}$, (h) —COR$^{d1}$, (i) —CONR$^{d1}$R$^{d2}$, (j) —NR$^{d1}$COR$^{d2}$, (k) —SO$_2$NR$^{d1}$R$^{d2}$, (l) —NR$^{d1}$SO$_2$R$^{d2}$, (m) —SR$^{d1}$, (n) —SO$_2$R$^{d1}$, (o) oxo, and (p) thioxo, in these groups, R$^{d1}$ and R$^{d2}$ each independently represent a hydrogen atom or a C1-8 alkyl, having the same meaning as defined above.

The "5- to 6-membered cyclic group" in the "optionally substituted 5- to 6-membered cyclic group" in the "substituent" of ring D or ring E includes, for example, a "C5-6 monocyclic carbon ring", a "5- to 6-membered monocyclic hetero ring", or the like. Said "C5-6 monocyclic carbon ring" includes, for example, cyclopentane, cyclohexane, cyclopentene, cyclohexene, cyclopentadiene, cyclohexadiene, benzene ring or the like. On the other hand, as the "5- to 6-membered monocyclic hetero ring", for example, a "5- to 6-membered monocyclic hetero ring containing 1 to 4 nitrogen atom(s), 1 to 2 oxygen atom(s) and/or 1 sulfur atom", and so forth can be cited. Said "5- to 6-membered monocyclic hetero ring containing 1 to 4 nitrogen atom(s), 1 to 2 oxygen atom(s) and/or 1 sulfur atom" includes, for example, pyrrole, imidazole, triazole, tetrazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole(oxazolidine), dihydroisoxazole, tetrahydroisoxazole(isoxazolidine), dihydrothiazole, tetrahydrothiazole(thiazolidine), dihydroisothiazole, tetrahydroisothiazole(isothiazolidine), dihydrofurazan, tetrahydrofurazan, dihydrooxadiazole, tetrahydrooxadiazole(oxadiazolidine), dihydrooxazine, tetrahydrooxazine, dihydrooxadiazine, tetrahydrooxadiazine, dihydrothiadiazole, tetrahydrothiadiazole(thiadiazolidine), dihydrothiazine, tetrahydrothiazine, dihydrothiadiazine, tetrahydrothiadiazine, morpholine, thiomorpholine, oxathiane, dioxolane, dioxane ring, and so forth.

There is no particular limitation for the "substituent" in the "optionally substituted 5- to 6-membered cyclic group" in the "substituent" of ring D or ring E so long as it can be a substituent. Said "substituent" includes, for example, (1) C1-8 alkyl, having the same meaning as defined above, (2) C1-8 alkoxy such as methoxy, ethoxy, propoxy, isopropoxy, butoxy, sec-butoxy, tent-butoxy, pentyloxy, hexyloxy, heptyloxy, octyloxy, and isomers thereof, etc., (3) halogen atom, having the same meaning as defined above, (4) trifluoromethyl, (5) trifluoromethoxy, or the like. One to five substituent(s) among these optional substituents may be located at any position where substitution is possible.

In the description of the present invention, the "substituent" represented by R$^A$ or R$^B$ has the same meaning as the "substituent" in the "optionally substituted cyclic group" represented by ring D or ring E defined above.

In the description of the present invention, the "5-membered monocyclic hetero ring which contains 1 to 3 atom(s) selected from the group consisting of oxygen atom, nitrogen atom and sulfur atom" in the "5-membered monocyclic hetero ring which contains 1 to 3 atom(s) selected from the group consisting of oxygen atom, nitrogen atom and sulfur atom, and which may have a further substituent(s)" represented by ring A includes, for example, pyrrole, imidazole, triazole, pyrazole, furan, thiophene, oxazole, isoxazole, thiazole, isothiazole, pyrroline, pyrrolidine, imidazoline, imidazolidine, triazoline, triazolidine, pyrazoline, pyrazolidine, dihydrofuran, tetrahydrofuran, dihydrothiophene, tetrahydrothiophene, dihydrooxazole, tetrahydrooxazole, dihydroisoxazole, tetrahydroisoxazole, dihydrothiazole, tetrahydrothiazole, dihydroisothiazole, tetrahydroisothiazole, dioxolane, dithiolane ring, and so forth. Among these, a "5-membered monocyclic aromatic hetero ring which contains 1 to 3 atom(s) selected from the group consisting of oxygen atom, nitrogen atom and sulfur atom" is preferable, for example, pyrrole, imidazole, triazole, pyrazole, furan, thiophene, oxazole, isoxazole, thiazole, isothiazole ring, and so forth can be given concretely.

In the description of the present invention, there is no particular limitation for the "substituent" in the "5-membered monocyclic hetero ring which contains 1 to 3 atom(s) selected from the group consisting of oxygen atom, nitrogen atom and sulfur atom, and which may have a further substituent(s)" represented by ring A so long as it can be a substituent. Said "substituent" includes, for example, (1) the "optionally substituted 5- to 6-membered cyclic group" defined above, (2) a substitient selected from the Group V shown below, (3) an optionally substituted aliphatic hydrocarbon group, or the like. One or two substituent(s) among these optional substituents may be located at any position where substitution is possible.

<Group V>
(a) —$OR^{e1}$, (b) —$NR^{e1}R^{e2}$, (C) —$COOR^{e1}$, (d) —$CONR^{e1}R^{e2}$, (e) —$NR^{e1}COR^{e2}$, (f) —$SO_2R^{e1}$, (g) —$SO_2NR^{e1}R^{e2}$, (h) —$NR^{e1}SO_2R^{e2}$, (i) —$SR^{e1}$, (j) —$S(O)R^{e1}$, (k) —$COR^{e1}$, (l) —$C=(NOR^{e1})R^{e2}$, (m) nitro, (n) cyano, (o) trifluoromethyl and (p) trifluoromethoxy, in these groups, $R^{e1}$ and $R^{e2}$ each independently represent a hydrogen atom or an optionally substituted C1-8 alkyl.

Here, the "C1-8 alkyl" in the "optionally substituted C1-8 alkyl" represented by $R^{e1}$ and $R^{e2}$ has the same meaning as defined above. Also, there is no particular limitation for the "substituent" in the "optionally substituted C1-8 alkyl" represented by $R^{e1}$ and $R^{e2}$ so long as it can be a substituent. Said "substituent" includes, for example, the "optionally substituted 5- to 6-membered cyclic group" defined above or the like. One to five substituent(s) among these optional substituents may be located at any position where substitution is possible.

The "aliphatic hydrocarbon group" in the "optionally substituted aliphatic hydrocarbon group" has the same meaning as the "aliphatic hydrocarbon group" in the "optionally substituted aliphatic hydrocarbon group" as defined in the "substituent" of ring D or ring E described above.

There is no particular limitation for the "substituent" in the "optionally substituted aliphatic hydrocarbon group" so long as it can be a substituent. Said "substituent" includes, for example, (1) the "optionally substituted 5- to 6-membered cyclic group" defined above, (2) a substitient selected from the Group VI shown below, or the like. One to five substituent(s) among these optional substituents may be located at any position where substitution is possible.

<Group VI>
(a) —$OR^{f1}$, (b) —$NR^{f1}R^{f2}$, (c) —$COOR^{f1}$, (d) —$CONR^{f1}R^{f2}$, (e) —$NR^{f1}COR^{f2}$, (f) —$SO_2R^{f1}$, (g) —$SO_2NR^{f1}R^{f2}$, (h) —$NR^{f1}SO_2R^{f2}$ and (i) —$NR^{f1}COOR^{f2}$, in these groups, $R^{f1}$ and $R^{f2}$ each independently represent a hydrogen atom or an optionally substituted C1-8 alkyl.

Here the "C1-8 alkyl" in the "optionally substituted C1-8 alkyl" represented by $R^{f1}$ and $R^{f2}$ has the same meaning as defined above. Also, there is no particular limitation for the "substituent" in the "optionally substituted C1-8 alkyl" represented by $R^{f1}$ and $R^{f2}$ so long as it can be a substituent. Said "substituent" includes, for example, the "optionally substituted 5- to 6-membered cyclic group" defined above or the like. One to five substituent(s) among these optional substituents may be located at any position where substitution is possible.

In the description of the present invention, the "hetero ring which may contain 1 to 3 atom(s) selected from the group consisting of oxygen atom, nitrogen atom and sulfur atom in addition to described nitrogen atom" in the "optionally substituted hetero ring which may contain 1 to 3 atom(s) selected from the group consisting of oxygen atom, nitrogen atom and sulfur atom in addition to described nitrogen atom" by represented ring B, includes the hetero ring in which one atom is nitrogen atom binding to above-mentioned ring E among atom contributing to constitution of ring, and which may contain 1 to 3 atom(s) selected from the group consisting of oxygen atom, nitrogen atom and sulfur atom in addition to its nitrogen atom. As said "hetero ring which may contain 1 to 3 atom(s) selected from the group consisting of oxygen atom, nitrogen atom and sulfur atom in addition to described nitrogen atom", a "5- to 10-membered mono- or bi-cyclic hetero ring which may contain 1 to 3 atom(s) selected from the group consisting of oxygen atom, nitrogen atom and sulfur atom in addition to described nitrogen atom" and so forth can be cited. Said "5- to 10-membered mono- or bi-cyclic hetero ring which may contain 1 to 3 atom(s) selected from the group consisting of oxygen atom, nitrogen atom and sulfur atom in addition to described nitrogen atom" includes, for example, pyrrole, imidazole, triazole, tetrazole, pyrazole, pyridine, pyrazine, pyrimidine, pyridazine, azepine, diazepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole(oxazolidine), dihydroisoxazole, tetrahydroisoxazole(isoxazolidine), dihydrothiazole, tetrahydrothiazole(thiazolidine), dihydroisothiazole, tetrahydroisothiazole(isothiazolidine), dihydrofurazan, tetrahydrofurazan, dihydrooxadiazole, tetrahydrooxadiazole(oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole(thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzofurazan, benzothiadiazole, benzotriazole, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole ring, and so forth.

In the description of the present invention, there is no particular limitation for the "substituent" in the "optionally substituted hetero ring which may contain 1 to 3 atom(s) selected from the group consisting of oxygen atom, nitrogen atom and sulfur atom in addition to described nitrogen atom" represented by ring B so long as it can be a substituent. Said "substituent" includes, for example, (1) an optionally substituted C1-8 alkyl, (2) the "optionally substituted 5- to 6-membered cyclic group" defined above, (3) a substitient selected from the Group V shown above, (4) oxo, (5) thioxo, or the like. One to nine substituent(s), preferably one to three substituent(s) among these optional substituents may be located at any position where substitution is possible. Here, "C1-8 alkyl" in the "optionally substituted C1-8 alkyl" as the "substituent" of ring B has the same meanings as defined above. Also, there is no particular limitation for the "substituent" in the "optionally substituted C1-8 alkyl" so long as it can be a substituent. Said substituent includes, for example, (1) the "optionally substituted 5- to 6-membered cyclic group" defined above or (2) a substituent selected from the Group VI shown above, or the like. One to five substituent(s) among these optional substituents may be located at any position where substitution is possible.

In the description of the present invention, the "neutral group or acidic group which contains an oxygen atom(s) and/or a sulfur atom(s)" represented by $R^1$ represents group in which at least one oxygen atom or sulfur atom is contained and in which the basicity is not shown, and which does not have a nitrogen atom(s). These may be substituted by more one to six halogen atom(s), having the same meaning defined above. Said "neutral group or acidic group which contains an oxygen atom(s) and/or a sulfur atom(s)" includes, for example, (1) a "hydroxyl group which may be protected", (2) a "hydrocarbon group substituted by the hydroxyl group which may be protected", (3) a "cyclic group substituted by the hydroxyl group which may be protected", (4) an "optionally substituted cyclic ether group", or (5) an "optionally substituted cyclic thioether group", or the like.

In the description of the present invention, the "protecting group" in the "hydroxyl group which may be protected" represented by $R^1$ includes C1-8 alkyl group such as methyl, ethyl, propyl, butyl, pentyl, hexyl, heptyl, octyl group and the isomer group thereof, C2-8 alkenyl group such as ethenyl, propenyl, butenyl, pentenyl, hexenyl, heptenyl, octenyl group and the isomer group thereof, C2-8 alkynyl group such as ethynyl, propynyl, butynyl, pentynyl, hexynyl, heptynyl, octynyl group and the isomer group thereof, C7-15 aralkyl group such as benzyl, phenethyl, phenylpropyl, naphthylmethyl, naphthylethyl group, etc., C3-8 cycloalkyl group such as cyclopropyl, cyclobutyl, cyclopentyl, cyclohexyl, cycloheptyl, cyclooctyl group, etc., phenyl group, naphthyl group, C1-8 acyl group such as formyl, acetyl, propanoyl, butanoyl, pentanoyl, hexanoyl, heptanoyl group and the isomer group thereof, C1-8 alkylsulfonyl group such as mesyl, ethylsulfonyl, propylsulfonyl, butylsulfonyl, pentylsulfonyl, hexylsulfonyl, heptylsulfonyl, octylsulfonyl group and the isomer group thereof, C7-15 aralkylsulfonyl group such as benzylsulfonyl, phenethylsulfonyl, phenylpropylsulfonyl, naphthylmethylsulfonyl, naphthylethylsulfonyl group, etc., C3-8 cycloalkylsulfonyl group such as cyclopropylsulfonyl, cyclobutylsulfonyl, cyclopentylsulfonyl, cyclohexylsulfonyl, cycloheptylsulfonyl, cyclooctylsulfonyl group, etc., phenylsulfonyl group and p-tosyl group, or the like. These groups may be substituted by more one to six halogen atom(s), having the same meaning defined above, and/or C1-8 alkoxy group such as methoxy, ethoxy, propoxy, butoxy, pentyloxy, hexyloxy, heptyloxy, octyloxy group and the isomer group thereof or the like.

In the description of the present invention, the "hydroxyl group which may be protected" in the "hydrocarbon group substituted by the hydroxyl group which may be protected" and the "cyclic group substituted by the hydroxyl group which may be protected" represented by $R^1$ has the same meanings as the "hydroxyl group which may be protected" described above, or represents oxo group.

In the description of the present invention, the "hydrocarbon group" in the "hydrocarbon group substituted by the hydroxyl group which may be protected" represented by $R^1$ has the same meaning as the "aliphatic hydrocarbon group" in the "optionally substituted aliphatic hydrocarbon group" as defined in the "substituent" of ring D or ring E described above.

In the description of the present invention, the "cyclic group" in the "cyclic group substituted by the hydroxyl group which may be protected" represented by $R^1$ has the same meaning as the "cyclic group" in the "optionally substituted cyclic group" represented by ring D or ring E described above.

The "hydrocarbon group substituted by the hydroxyl group which may be protected" and the "cyclic group substituted by the hydroxyl group which may be protected" described above, may be substituted by, in addition to the "hydroxyl group which may be protected", more one to six halogen atom(s), having the same meaning defined above, oxo group, thioxo group, C1-8 alkylthio group such as methylthio, ethylthio, propylthio, butylthio, pentylthio, hexylthio, heptylthio, octylthio group and the isomer group thereof, C1-8 alkylsulfinyl group such as methylsulfinyl, ethylsulfinyl, propylsulfinyl, butylsulfinyl, pentylsulfinyl, hexylsulfinyl, heptylsulfinyl, octylsulfinyl group and the isomer group thereof, etc., C1-8 alkylsulfonyl group such as mesyl, ethylsulfonyl, propylsulfonyl, butylsulfonyl, pentylsulfonyl, hexylsulfonyl, heptylsulfonyl, octylsulfonyl group and the isomer group thereof, C7-15 aralkylthio group such as benzylthio, phenethylthio, phenylpropylthio, naphthylmethylthio, naphthylethylthio group, etc., C7-15 aralkylsulfonyl group such as benzylsulfonyl, phenethylsulfonyl, phenylpropylsulfonyl, naphthylmethylsulfonyl, naphthylethylsulfonyl group, etc., C3-8 cycloalkylthio group such as cyclopropylthio, cyclobutylthio, cyclopentylthio, cyclohexylthio, cycloheptylthio, cyclooctylthio group, etc., C3-8 cycloalkylsulfonyl group such as cyclopropylsulfonyl, cyclobutylsulfonyl, cyclopentylsulfonyl, cyclohexylsulfonyl, cycloheptylsulfonyl, cyclooctylsulfonyl group, etc., phenylthio group, phenylsulfonyl group and p-tosyl group or the like.

In the description of the present invention, the "substituent" in the "optionally substituted cyclic ether group" and the "optionally substituted cyclic thioether group" represented by $R^1$ includes the group illustrated as the "protecting group" in the "hydroxyl group which may be protected" described above, halogen atom(s), having the same meaning defined above, oxo group, thioxo group, C1-8 alkylthio group such as methylthio, ethylthio, propylthio, butylthio, pentylthio, hexylthio, heptylthio, octylthio group and the isomer group thereof, C1-8 alkylsulfinyl group such as methylsulfinyl, ethylsulfinyl, propylsulfinyl, butylsulfinyl, pentylsulfinyl, hexylsulfinyl, heptylsulfinyl, octylsulfinyl group and the isomer group thereof, C1-8 alkylsulfonyl group such as mesyl, ethylsulfonyl, propylsulfonyl, butylsulfonyl, pentylsulfonyl, hexylsulfonyl, heptylsulfonyl, octylsulfonyl group and the isomer group thereof, C7-15 aralkylthio group such as benzylthio, phenethylthio, phenylpropylthio, naphthylmethylthio, naphthylethylthio group, etc., C7-15 aralkylsulfonyl group such as benzylsulfonyl, phenethylsulfonyl, phenylpropylsulfonyl, naphthylmethylsulfonyl, naphthylethylsulfonyl group, etc., C3-8 cycloalkylthio group such as cyclopropylthio, cyclobutylthio, cyclopentylthio, cyclohexylthio, cycloheptylthio, cyclooctylthio group, etc., C3-8 cycloalkylsulfonyl group such as cyclopropylsulfonyl, cyclobutylsulfonyl, cyclopentylsulfonyl, cyclohexylsulfonyl, cycloheptylsulfonyl, cyclooctylsulfonyl group, etc., phenylthio group, phenylsulfonyl group and p-tosyl group or the like. One to six substituent(s) among these optional substituents may be located at any position where substitution is possible.

In the description of the present invention, the "cyclic ether group" in the "optionally substituted cyclic ether group" represented by $R^1$ includes, for example, oxiranyl, oxetanyl, furyl, dihydrofuryl, tetrahydrofuryl, pyranyl, dihydropyranyl, tetrahydropyranyl, oxepinyl, dihydrooxepinyl, tetrahydrooxepinyl, perhydrooxepinyl, dioxolanyl, dioxanyl group or the like.

In the description of the present invention, the "cyclic thioether group" in the "optionally substituted cyclic thioether group" represented by $R^1$ includes, for example, thiiranyl, thiethanyl, thienyl, dihydrothienyl, tetrahydrothienyl, thiopyranyl, dihydrothiopyranyl, tetrahydrothiopyranyl, thiepinyl, dihydrothiepinyl, tetrahydrothiepinyl, perhydrothiepinyl, dithiolanyl, dithianyl group or the like.

In the description of the present invention, "C1-8 alkyl group" in "C1-8 alkyl group substituted by 1 to 3 hydroxyl group(s)" represented by $R^1$ includes, for example, methyl, ethyl, propyl, isopropyl, butyl, sec-butyl, tert-butyl, pentyl, hexyl, heptyl, octyl group and the isomer group thereof or the like.

In the description of the present invention, "C3-6 monocyclic carbon ring" in "C3-6 monocyclic carbon ring substituted by 1 or 2 hydroxyl group(s)" represented by $R^1$ includes, for example, cyclopropane, cyclobutane, cyclopentane, cyclohexane, cyclobutene, cyclopentene, cyclohexene, cyclopentadiene, cyclohexadiene ring or the like.

In the description of the present invention, any rings, any groups and any atoms represented by ring A, ring B, ring D, ring E, $R^1$, $R^A$ and $R^B$ are all preferable. Hereinafter, preferable groups, preferable rings and preferable atoms are listed, and all symbols as used herein have the same meanings as those defined above.

In the description of the present invention, preferable example of the "5-membered monocyclic hetero ring which contains 1 to 3 atom(s) selected from the group consisting of oxygen atom, nitrogen atom and sulfur atom" in the "5-membered monocyclic hetero ring which contains 1 to 3 atom(s) selected from the group consisting of oxygen atom, nitrogen atom and sulfur atom, and which may have a further substituent(s)" represented by ring A includes, for example, a "5-membered monocyclic aromatic hetero ring which contains 1 to 3 atom(s) selected from the group consisting of oxygen atom, nitrogen atom and sulfur atom", and so forth. More preferable example includes, for example, pyrrole, furan, thiophene, pyrazole, imidazole, oxazole, isoxazole, thiazole, isothiazole, triazole ring, and so forth. More preferable example includes, for example, ring:

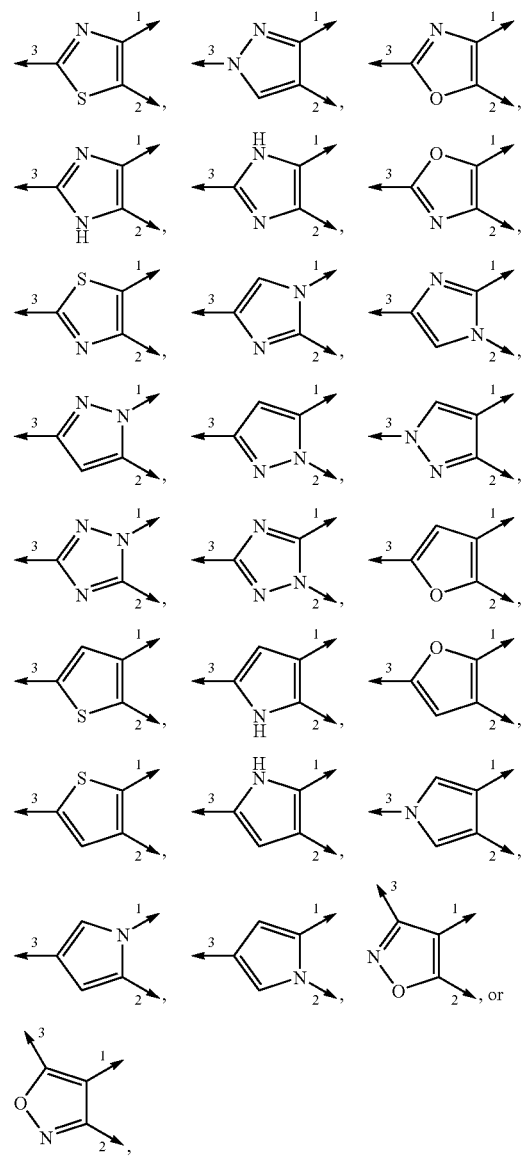

in which all other symbols have the same meanings as described above, with the proviso that, the hydrogen atom represented by NH may be substituted by a substituent, and so forth. Most preferable example includes, for example, imidazole, oxazole, thiazole ring and so forth. Above all, ring:

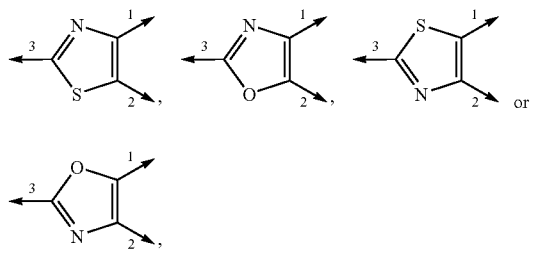

in which all other symbols have the same meanings as described above, is preferable example, ring:

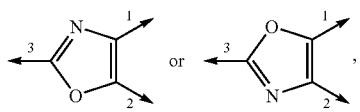

in which all other symbols have the same meanings as described above, is most preferable example.

And preferable example of the "substituent" in the "5-membered monocyclic hetero ring which contains 1 to 3 atom(s) selected from the group consisting of oxygen atom, nitrogen atom and sulfur atom, and which may have a further substituent(s)" includes, for example, C1-8 alkyl, and so forth. More preferable example includes, for example, methyl, and so forth. And also, ring A is preferable at the unsubstituted state.

In the description of the present invention, preferable example of the "hetero ring which may contain 1 to 3 atom(s) selected from the group consisting of oxygen atom, nitrogen atom and sulfur atom in addition to described nitrogen atom" in the "optionally substituted hetero ring which may contain 1 to 3 atom(s) selected from the group consisting of oxygen atom, nitrogen atom and sulfur atom in addition to described nitrogen atom" represented by ring B includes, for example, a "5- to 10-membered mono- or bi-cyclic hetero ring which may contain 1 to 3 atom(s) selected from the group consisting of oxygen atom, nitrogen atom and sulfur atom in addition to described nitrogen atom", and so forth. More preferable example includes, for example, a "5- to 7-membered monocyclic hetero ring which may contain 1 to 3 atom(s) selected from the group consisting of oxygen atom, nitrogen atom and sulfur atom in addition to described nitrogen atom", and so forth. Most preferable example includes, for example, a "6-membered monocyclic hetero ring which may contain 1 to 3 atom(s) selected from the group consisting of oxygen atom, nitrogen atom and sulfur atom in addition to described nitrogen atom", and so forth. In other words, preferable example of the "optionally substituted hetero ring which may contain 1 to 3 atom(s) selected from the group consisting of oxygen atom, nitrogen atom and sulfur atom in addition to described nitrogen atom" represented by ring B includes, for example, ring:

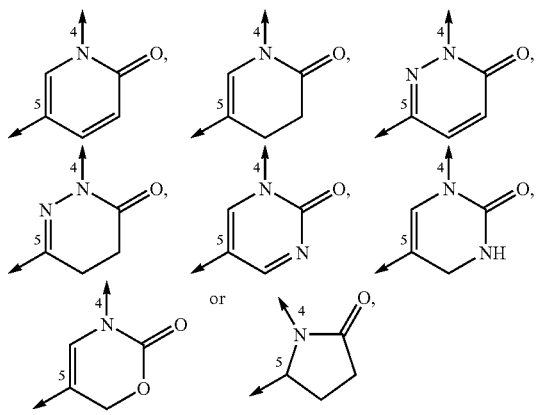

in which all other symbols have the same meanings as described above, with the proviso that, the hydrogen atom represented by NH may be substituted by a substituent, and so forth. More preferable example includes, for example, ring:

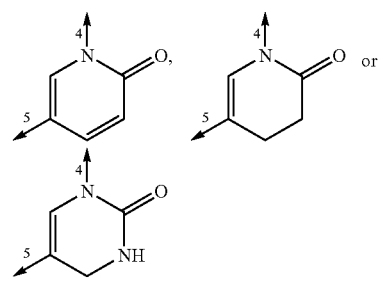

in which all other symbols have the same meanings as described above, with the proviso that, the hydrogen atom represented by NH may be substituted by a substituent, and so forth. Particularly preferable example includes ring:

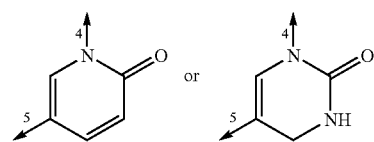

in which all other symbols have the same meanings as described above, with the proviso that, the hydrogen atom represented by NH may be substituted by a substituent. Most preferable example includes ring:

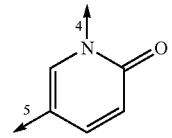

in which all other symbols have the same meanings as described above. And preferable example of the "substituent" in the "optionally substituted hetero ring which may contain 1 to 3 atom(s) selected from the group consisting of oxygen atom, nitrogen atom and sulfur atom in addition to described nitrogen atom" includes, for example, oxo group. More preferable example includes, for example, oxo group which binds to carbon atom adjacent to nitrogen atom. And there is not a substituent(s) aside from oxo group. Also, in addition to oxo group, it is preferable that there is C1-4alkyl, —OR$^{e1}$, —COOR$^{e1}$, and so forth as other substituent(s). More preferably, there is not a substituent(s) aside from oxo group or there is methyl, ethyl, —OH, —OCH$_3$, —COOH, —COOCH$_3$, and so forth as substituent(s), in addition to oxo group. Most preferably, there is not a substituent(s) aside from oxo group.

In the description of the present invention, preferable example of ring D includes, for example, a "C5-10 mono- or bi-cyclic carbon ring", a "5- to 10-membered mono- or bi-cyclic hetero ring", and so forth. More preferable example includes, for example, a "C5-10 mono- or bi-cyclic aromatic carbon ring", a "5- to 10-membered mono- or bi-cyclic aromatic hetero ring", and so forth. More preferable example includes, for example, a "C5-6 monocyclic aromatic carbon ring", a "5- to 6-membered monocyclic aromatic hetero ring having 1 to 2 nitrogen atom(s), 1 oxygen atom and/or 1 sulfur atom", and so forth. Most preferable example includes, for example, benzene, thiophen, pyrrole, pyridine ring, and so forth. Above all, benzene ring is most preferable example. And preferable example of the "substituent" in said "optionally substituted cyclic group" includes, for example, an "optionally substituted 5- to 10-membered hetero ring", C1-8 alkyl, halogen atom, having the same meaning defined above, —NR$^{a1}$R$^{a2}$, —NR$^{a1}$COR$^{a2}$, —COOR$^{a2}$, —CONR$^{a1}$R$^{a1}$R$^{a2}$, —COR$^{a1}$, —SO$_2$NR$^{a1}$R$^{a2}$, —NR$^{a1}$SO$_2$R$^{a2}$, —OR$^{a1}$, C1-4 alkyl substituted by —OR$^{a1}$, and so forth. More preferable example includes, for example, C1-4 alkyl, C1-4 alkoxy, halogen atom, having the same meaning defined above, —CONR$^{a1}$R$^{a2}$, —NR$^{a1}$R$^{a2}$, —NR$^{a1}$COR$^{a2}$, and so forth. Most preferable example includes, for example, C1-4 alkyl such as methyl, ethyl, propyl, isopropyl, butyl, sec-butyl, tent-butyl and isomers thereof, etc., C1-4 alkoxy such as methoxy, ethoxy, propoxy, isopropoxy, butoxy, sec-butoxy, tent-butoxy and isomers thereof, etc., halogen atom, having the same meaning defined above, and so forth. Above all, methyl, ethyl, methoxy, fluorine atom or chlorine atom is preferable, and methyl, fluorine atom is more preferable. The number of substituent(s) is preferably 1 to 3, and more preferably 1 to 2. In addition, in case where ring D is benzene ring, the position of the substituent(s) of said benzene ring is preferably 2-position and/or 4-position as the position of atom that binds to ring A is 1-position.

In the description of the present invention, preferable example of R$^A$ includes, for example, the "optionally substituted 5- to 10-membered hetero ring", C1-8 alkyl, halogen atom, having the same meaning defined above, —NR$^{a1}$R$^{a2}$, —NR$^{a1}$COR$^{a2}$, —COOR$^{a2}$, —CONR$^{a1}$R$^{a2}$, —COR$^{a1}$, —SO$_2$NR$^{a1}$R$^{a2}$, —NR$^{a1}$SO$_2$R$^{a2}$, —OR$^{a1}$, C1-4 alkyl substituted by —OR$^{a1}$, and so forth. More preferable example includes, for example, C1-4 alkyl, C1-4 alkoxy, halogen atom, having the same meaning defined above, —CONR$^{a1}$R$^{a2}$, —NR$^{a1}$R$^{a2}$, —NR$^{a1}$COR$^{a2}$, and so forth. Most preferable example includes, for example, C1-4 alkyl such as methyl, ethyl, propyl, isopropyl, butyl, sec-butyl, tent-butyl and isomers thereof, etc., C1-4 alkoxy such as methoxy, ethoxy, propoxy, isopropoxy, butoxy, sec-butoxy, tent-butoxy and isomers thereof, etc., halogen atom, having the same meaning defined above, and so forth. Above all, methyl, ethyl, methoxy, fluorine atom or chlorine atom is preferable, and methyl, fluorine atom is more preferable. In addition, in case where ring D is benzene ring, the position of the substituent(s) of said benzene ring is preferably 2-position and/or 4-position as the position of atom that binds to ring A is 1-position.

In the description of the present invention, preferable example of n includes an integer of 1 to 3. More preferable example includes an integer of 1 to 2. Most preferable example includes an integer of 2.

In the description of the present invention, preferable example of ring E includes, for example, a "C5-10 mono- or by-cyclic carbon ring", a "5- to 10-membered mono- or by-cyclic hetero ring", and so forth. More preferable example includes, for example, a "C5-10 mono- or by-cyclic aromatic carbon ring", a "5- to 10-membered mono- or by-cyclic aromatic hetero ring", and so forth. More preferable example includes, for example, a "C5-6 monocyclic aromatic carbon ring", a "5- to 6-membered monocyclic aromatic hetero ring having 1 to 2 nitrogen atom(s), 1 oxygen atom and/or 1 sulfur atom", and so forth. Most preferable example includes, for example, benzene, thiophen, pyrrole, pyridine ring, and so forth. Above all, benzene ring is most preferable. And preferable example of the "substituent" in said "optionally substituted cyclic group" includes, for example, an "optionally substituted 5- to 10-membered hetero ring", C1-8 alkyl, halogen atom, having the same meaning defined above, —NR$^{a1}$R$^{a2}$, —NR$^{a1}$COR$^{a2}$, —COOR$^{a2}$, —CONR$^{a1}$R$^{a2}$, —COR$^{a1}$, —SO$_2$NR$^{a1}$R$^{a2}$, —NR$^{a1}$SO$_2$R$^{a2}$, —OR$^{a1}$, C1-4alkyl substituted by —OR$^{a1}$, and so forth. More preferable example includes, for example, C1-4 alkyl, C1-4 alkoxy, halogen atom, having the same meaning defined above, —CONR$^{a1}$R$^{a2}$, —NR$^{a1}$R$^{a2}$, —NR$^{a1}$COR$^{a2}$, and so forth. Most preferable example includes, for example, C1-4 alkyl such as methyl, ethyl, propyl, isopropyl, butyl, sec-butyl, tert-butyl and isomers thereof, etc., C1-4 alkoxy such as methoxy, ethoxy, propoxy, isopropoxy, butoxy, sec-butoxy, tert-butoxy and isomers thereof, etc., halogen atom, having the same meaning defined above, and so forth. Above all, methyl, ethyl, methoxy, fluorine atom or chlorine atom is preferable, and methyl, fluorine atom is more preferable. The number of substituent(s) is preferably 1 to 3, and more preferably 1 to 2. In addition, in case where ring E is benzene ring, the position of the substituent(s) of said benzene ring is preferably 2-position, 4-position and/or 6-position as the position of atom that binds to ring B is 1-position.

In the description of the present invention, preferable example of R$^B$ includes, for example, the "optionally substituted 5- to 10-membered hetero ring", C1-8 alkyl, halogen atom, having the same meaning defined above, —NR$^{a1}$R$^{a2}$, —NR$^{a1}$COR$^{a2}$, —COOR$^{a2}$, —CONR$^{a1}$R$^{a2}$, —COR$^{a1}$, —SO$_2$NR$^{a1}$R$^{a2}$, —NR$^{a1}$SO$_2$R$^{a2}$, —OR$^{a1}$, C1-4alkyl substituted by —OR$^{a1}$, and so forth. More preferable example includes, for example, C1-4 alkyl, C1-4 alkoxy, halogen atom, having the same meaning defined above, —CONR$^{a1}$R$^{a2}$, —NR$^{a1}$R$^{a2}$, —NR$^{a1}$COR$^{a2}$, and so forth. Most preferable example includes, for example, C1-4 alkyl such as methyl, ethyl, propyl, isopropyl, butyl, sec-butyl, tert-butyl and isomers thereof, etc., C1-4 alkoxy such as methoxy, ethoxy, propoxy, isopropoxy, butoxy, sec-butoxy, tert-butoxy and isomers thereof, etc., halogen atom, having the same meaning defined above, and so forth. Above all, methyl, ethyl, methoxy, fluorine atom or chlorine atom is preferable, and methyl, fluorine atom is more preferable. In addition, in case where ring E is benzene ring, the position of the substituent(s) of said benzene ring is preferably 2-position, 4-position and/or 6-position as the position of atom that binds to ring B is 1-position.

In the description of the present invention, preferable example of m includes an integer of 1 to 3. More preferable example includes an integer of 1 to 2. Most preferable example includes an integer of 2.

In the description of the present invention, preferable example of the "neutral group or acidic group which contains an oxygen atom(s) and/or a sulfur atom(s)" represented by R$^1$ includes, for example, a "hydroxyl group which may be protected", a "hydrocarbon group substituted by the hydroxyl group which may be protected", a "cyclic group substituted by the hydroxyl group which may be protected", an "optionally substituted cyclic ether group", or an "optionally substituted cyclic thioether group", and so forth. More preferable example includes, for example, a "hydrocarbon group substituted by the hydroxyl group which may be protected", a "cyclic group substituted by the hydroxyl group which may be protected", or an "optionally substituted cyclic ether group", and so forth. Most preferable example includes, for example, a "hydrocarbon group substituted by the hydroxyl group which may be protected", and so forth.

In the description of the present invention, preferable example of the "hydroxyl group which may be protected" represented by R$^1$ includes, for example, hydroxyl group, C1-8 alkoxy group such as methoxy, ethoxy, propoxy, butoxy, pentyloxy, hexyloxy, heptyloxy, octyloxy group and the isomer group thereof, and so forth. More preferable example includes, for example, hydroxyl group, methoxy group and ethoxy group.

In the description of the present invention, preferable example of the "hydroxyl group which may be protected" in the "hydrocarbon group substituted by the hydroxyl group which may be protected" represented by $R^1$ includes, for example, hydroxyl group, C1-8 alkoxy group such as methoxy, ethoxy, propoxy, butoxy, pentyloxy, hexyloxy, heptyloxy, octyloxy group and the isomer group thereof, C7-15 aralkyloxy group such as benzyloxy, phenethyloxy, phenylpropyloxy group, etc., C3-8 cycloalkyloxy group such as cyclopropyloxy, cyclobutyloxy, cyclopentyloxy, cyclohexyloxy, cycloheptyloxy, cyclooctyloxy group, etc., phenyloxy group, C1-8 acyloxy group such as formyloxy, acetyloxy, propanoyloxy, butanoyloxy, pentanoyloxy, hexanoyloxy, heptanoyloxy, octanoyloxy group and the isomer group thereof, C1-8 alkylsulfonyloxy group such as mesyloxy, ethylsulfonyloxy, propylsulfonyloxy, butylsulfonyloxy, pentylsulfonyloxy, hexylsulfonyloxy, heptylsulfonyloxy, octylsulfonyloxy group and the isomer group thereof, C7-15 aralkylsulfonyloxy group such as benzylsulfonyloxy, phenethylsulfonyloxy, phenylpropylsulfonyloxy group, etc., C3-8 cycloalkylsulfonyloxy group such as cyclopropylsulfonyloxy, cyclobutylsulfonyloxy, cyclopentylsulfonyloxy, cyclohexylsulfonyloxy, cycloheptylsulfonyloxy, cyclooctylsulfonyloxy group, etc., phenylsulfonyloxy, p-toluenesulfonyloxy group, oxo group, and so forth. More preferable example includes, for example, hydroxyl group, C1-4 alkoxy group such as methoxy, ethoxy, propoxy, butoxy group and the isomer group thereof, benzyloxy group, phenyloxy group, C1-4 acyloxy group such as formyloxy, acetyloxy, propanoyloxy group and the isomer group thereof, C1-4 alkylsulfonyloxy group such as mesyloxy, ethylsulfonyloxy, propylsulfonyloxy, butylsulfonyloxy group, and the isomer group thereof, phenylsulfonyloxy group, p-toluenesulfonyloxy group, oxo group, and so forth. Most preferable example includes, for example, hydroxyl group, methoxy group, ethoxy group, propoxy group, benzyloxy group, formyloxy group, acetyloxy group, propanoyloxy group, mesyloxy, p-toluenesulfonyloxy group, oxo group, and so forth.

In the description of the present invention, preferable example of the "hydrocarbon group" in the "hydrocarbon group substituted by the hydroxyl group which may be protected" represented by $R^1$ includes, for example, C1-8 aliphatic hydrocarbon group and so forth. More preferable example includes C1-8 alkyl group. Most preferable example includes C1-4 alkyl group. Above all, methyl, ethyl, propyl, isopropyl, butyl, sec-butyl, tert-butyl or the isomer group thereof is preferable.

In the description of the present invention, most preferable example of the "hydrocarbon group substituted by the hydroxyl group which may be protected" represented by $R^1$ includes, for example, "C1-8 alkyl group substituted by 1 to 3 hydroxyl group(s)". Above all, for example, 1-hydroxy-1-methylethyl, 1,2-dihydroxy-1-methylethyl, 1,2-dihydroxy-1-(hydroxymethyl)ethyl, 2-hydroxy-2-methylpropyl or 1,2-dihydroxy-2-methylpropyl group is preferable.

In the description of the present invention, preferable example of the "the hydroxyl group which may be protected" in the "cyclic group substituted by the hydroxyl group which may be protected" represented by $R^1$ includes, for example, hydroxyl group, C1-8 alkoxy group such as methoxy, ethoxy, propoxy, butoxy, pentyloxy, hexyloxy, heptyloxy, octyloxy group and the isomer group thereof, C7-15 aralkyloxy group such as benzyloxy, phenethyloxy, phenylpropyloxy group, etc., C3-8 cycloalkyloxy group such as cyclopropyloxy, cyclobutyloxy, cyclopentyloxy, cyclohexyloxy, cycloheptyloxy, cyclooctyloxy group, etc., phenyloxy group, C1-8 acyloxy group such as formyloxy, acetyloxy, propanoyloxy, butanoyloxy, pentanoyloxy, hexanoyloxy, heptanoyloxy, octanoyloxy group and the isomer group thereof, C1-8 alkylsulfonyloxy group such as mesyloxy, ethylsulfonyloxy, propylsulfonyloxy, butylsulfonyloxy, pentylsulfonyloxy, hexylsulfonyloxy, heptylsulfonyloxy, octylsulfonyloxy group and the isomer group thereof, C7-15 aralkylsulfonyloxy group such as benzylsulfonyloxy, phenethylsulfonyloxy, phenylpropylsulfonyloxy group, etc., C3-8 cycloalkylsulfonyloxy group such as cyclopropylsulfonyloxy, cyclobutylsulfonyloxy, cyclopentylsulfonyloxy, cyclohexylsulfonyloxy, cycloheptylsulfonyloxy, cyclooctylsulfonyloxy group, etc., phenylsulfonyloxy, p-toluenesulfonyloxy group, oxo group, and so forth. More preferable example includes, for example, hydroxyl group, C1-4 alkoxy group such as methoxy, ethoxy, propoxy, butoxy group and the isomer group thereof, benzyloxy group, phenyloxy group, C1-4 acyloxy group such as formyloxy, acetyloxy, propanoyloxy group and the isomer group thereof, C1-4 alkylsulfonyloxy group such as mesyloxy, ethylsulfonyloxy, propylsulfonyloxy, butylsulfonyloxy group, and the isomer group thereof, phenylsulfonyloxy group, p-toluenesulfonyloxy group, oxo group, and so forth. Most preferable example includes, for example, hydroxyl group, methoxy group, ethoxy group, propoxy group, benzyloxy group, formyloxy group, acetyloxy group, propanoyloxy group, mesyloxy, p-toluenesulfonyloxy group, oxo group, and so forth.

In the description of the present invention, preferable example of the "cyclic group" in the "cyclic group substituted by the hydroxyl group which may be protected" represented by $R^1$ includes, for example, C5-10 mono- or bi-cyclic carbon ring such as cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene ring and so forth. More preferable example includes, for example, C3-6 monocyclic carbon ring such as cyclopropane, cyclobutane, cyclopentane, cyclohexane, cyclopropene, cyclobutene, cyclopentene, cyclohexene, cyclopentadiene, cyclohexadiene, benzene ring and so forth. Most preferable example includes cyclopropane, cyclobutane, cyclopentane ring.

In the description of the present invention, most preferable example of the "cyclic group substituted by the hydroxyl group which may be protected" represented by $R^1$ includes "C3-6 monocyclic carbon ring substituted by 1 or 2 hydroxyl group(s)".

In the description of the present invention, preferable example of the "optionally substituted cyclic ether group" represented by $R^1$ includes, for example, optionally substituted oxiranyl, optionally substituted oxetanyl, optionally substituted furyl, optionally substituted dihydrofuryl, optionally substituted tetrahydrofuryl, optionally substituted pyranyl, optionally substituted dihydropyranyl, optionally substituted tetrahydropyranyl, optionally substituted oxepinyl, optionally substituted dihydrooxepinyl, optionally substituted tetrahydrooxepinyl, optionally substituted perhydrooxepinyl, optionally substituted dioxolanyl, optionally substituted dioxanyl group and so forth. More preferable example includes optionally substituted furyl, optionally substituted dihydrofuryl, optionally substituted tetrahydrofuryl, optionally substituted pyranyl, optionally substituted dihydropyranyl, optionally substituted tetrahydropyranyl group and so forth. Most preferable example includes optionally substituted tetrahydropyrany group.

In the description of the present invention, preferable example of the "optionally substituted cyclic thioether group" represented by R$^1$ includes, for example, optionally substituted thiiranyl, optionally substituted thiethanyl, optionally substituted thienyl, optionally substituted dihydrothienyl, optionally substituted tetrahydrothienyl, optionally substituted thiopyranyl, optionally substituted dihydrothiopyranyl, optionally substituted tetrahydrothiopyranyl, optionally substituted thiepinyl, optionally substituted dihydrothiepinyl, optionally substituted tetrahydrothiepinyl, optionally substituted perhydrothiepinyl, optionally substituted dithiolanyl, optionally substituted dithianyl group and so forth. More preferable example includes optionally substituted thienyl, optionally substituted dihydrothienyl, optionally substituted tetrahydrothienyl, optionally substituted thiopyranyl, optionally substituted dihydrothiopyranyl, optionally substituted tetrahydrothiopyranyl group and so forth. Most preferable example includes optionally substituted tetrahydrothiopyranyl group.

In the description of the present invention, a compound represented by formula (I) comprising a combination of preferable groups, preferable rings, and preferable atoms as defined above is preferable. The preferable example includes, for example, a compound represented by formula (Ia):

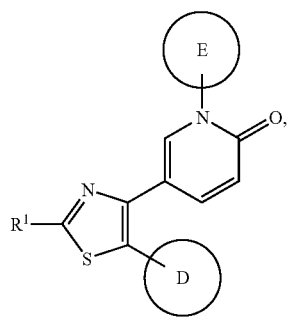

(Ia)

in which all symbols have the same meanings as described above, a compound represented by formula (Ib):

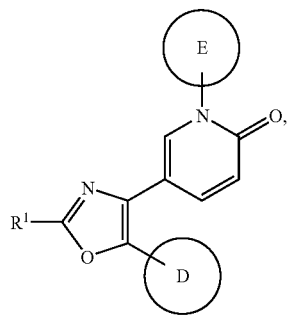

(Ib)

in which all symbols have the same meanings as described above, a compound represented by formula (Ic):

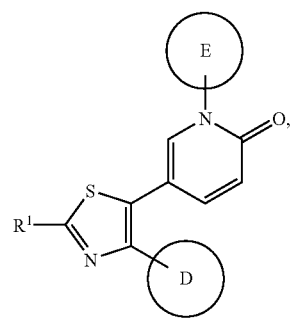

(Ic)

in which all symbols have the same meanings as described above, or a compound represented by formula (Id):

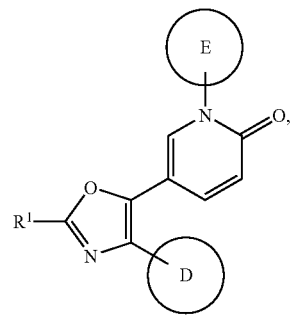

(Id)

in which all symbols have the same meanings as described above, or a salt thereof, an N-oxide thereof or a solvate thereof, or a prodrug thereof.

The most preferable example includes, for example,
a compound represented by formula (I-A):

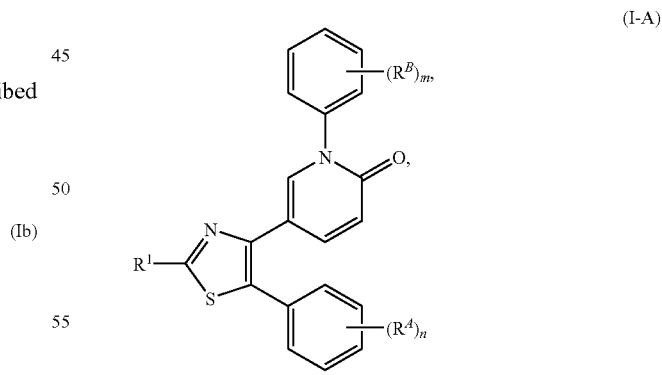

(I-A)

wherein R$^A$ and R$^B$ represent the "substituent" in the "optionally substituted cyclic group" described above;
n represents 0 or an integer of 1 to 5;
m represents 0 or an integer of 1 to 5;
with the proviso that, when n is 2 or more, R$^A$ may be same or different;
when m is 2 or more, R$^B$ may be same or different; and
all other symbols have the same meanings as described above, a compound represented by formula (I-B):

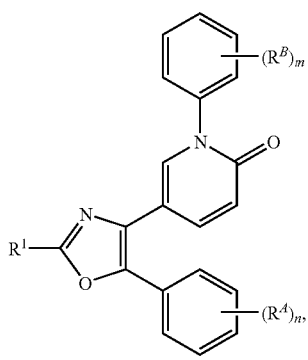

a compound represented by formula (I-C):

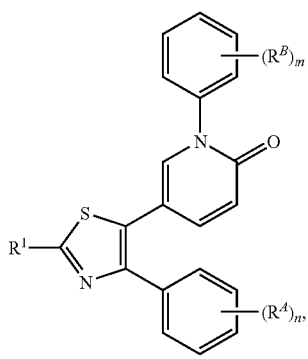

in which all symbols have the same meanings as described above, or a compound represented by formula (I-D):

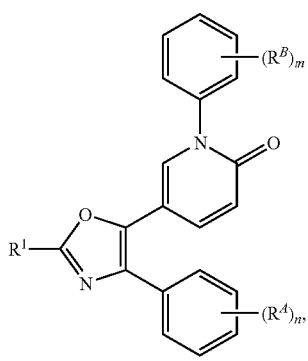

in which all symbols have the same meanings as described above, or a salt thereof, an N-oxide thereof or a solvate thereof, or a prodrug thereof.

Above all, formula (I-B):

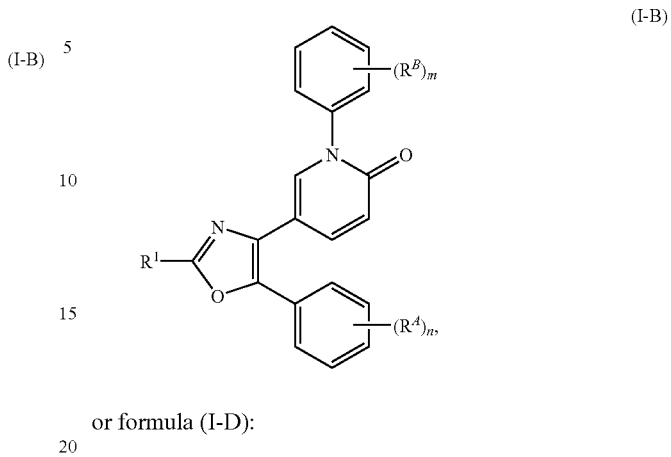

or formula (I-D):

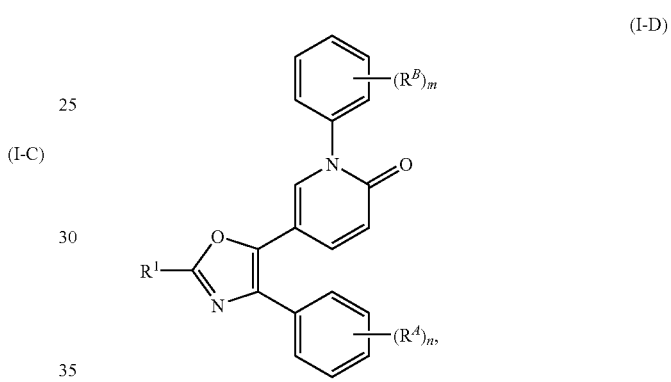

in which all other symbols have the same meanings as described above, or a salt thereof, an N-oxide thereof or a solvate thereof, or a prodrug thereof, is preferable example.

Also, in the description of the present invention, the compounds disclosed in Examples including in claims of the present invention, or a salt thereof, an N-oxide thereof, or a solvate thereof, or a prodrug thereof are all preferable. Most preferable example includes 1-(2,6-difluorophenyl)-5-[5-(2,4-difluorophenyl)-2-(1-hydroxy-1-methylethyl)-1,3-oxazol-4-yl]-2(1H)-pyridinone, 1-(2,6-difluorophenyl)-5-{5-(2,4-difluorophenyl)-2-[1,2-dihydroxy-1-(hydroxymethyl)ethyl]-1,3-oxazol-4-yl}-2(1H)-pyridinone, 1-(2,6-difluorophenyl)-5-[4-(2,4-difluorophenyl)-2-(1-hydroxy-1-methylethyl)-1,3-oxazol-5-yl]-2(1H)-pyridinone, 1-(2,6-difluorophenyl)-5-{5-(2,4-difluorophenyl)-2-[(1R)-1,2-dihydroxy-1-methylethyl]-1,3-oxazol-4-yl}-2(1H)-pyridinone, 1-(2,6-difluorophenyl)-5-{5-(2,4-difluorophenyl)-2-[(1S)-1,2-dihydroxy-1-methylethyl]-1,3-oxazol-4-yl}-2(1H)-pyridinone, 1-(2,6-difluorophenyl)-5-{4-(2,4-difluorophenyl)-2-[(1S)-1,2-dihydroxy-2-methylpropyl]-1,3-oxazol-5-yl}-2(1H)-pyridinone, 1-(2,6-difluorophenyl)-5-{4-(2,4-difluorophenyl)-2-[(1R)-1,2-dihydroxy-2-methylpropyl]-1,3-oxazol-5-yl}-2(1H)-pyridinone, 1-(2,6-difluorophenyl)-5-{4-(2,4-difluorophenyl)-2-[(1S)-1,2-dihydroxy-1-methylethyl]-1,3-oxazol-5-yl}-2(1H)-pyridinone, 1-(2,6-difluorophenyl)-5-{4-(2,4-difluorophenyl)-2-[(1R)-1,2-dihydroxy-1-methylethyl]-1,3-oxazol-5-yl}-2(1H)-pyridinone, 1-(2,6-difluorophenyl)-5-[4-(2,4-difluorophenyl)-2-(2-hydroxy-2-methylpropyl)-1,3-oxazol-5-yl]-2(1H)-pyridinone, 1-(2,6-difluorophenyl)-5-{4-(2,4-difluorophenyl)-2-[1,2-dihydroxy-1-(hydroxymethyl)ethyl]-1,3-oxazol-5-yl}-2(1H)-pyridinone, 1-(2,6-difluorophenyl)-5-{5-(2,4-difluorophenyl)-2-[(1S)-1,2-dihydroxy-2-methylpropyl]-1,3-oxazol-4-yl}-2(1H)-pyridinone, or 1-(2,6-difluorophenyl)-5-{5-(2,4-difluorophenyl)-2-[(1R)-1,2-dihydroxy-2-methylpropyl]-1,3-oxazol-4-yl}-2(1H)-pyridinone, a salt thereof, an N-oxide thereof or a solvate thereof, or a prodrug thereof.

Unless otherwise specified, any isomers are all included in the present invention. For example, linear or branched ones are included in the alkyl, alkoxy, and alkylene groups. Further, the present invention includes isomers due to double bond, ring, and fused ring (E-form, Z-form, cis-form, trans-form), isomers due to the presence of asymmetric carbon atom (R-form, S-form, α-form, β-form, enantiomer, diastereomer), optically active compounds with optical rotation (D-form, L-form, d-form, l-form), polar compounds obtained by chromatographic separation (high polar compound, low polar compound), equilibrium compounds, and mixtures of these compounds in an arbitrary ratio, and racemates. Moreover, the present invention includes all tautomers.

[Salt, N-oxide, Solvate and Prodrug]

Pharmacologically acceptable salts are all included in the salts of compounds represented by formula (I). The pharmacologically acceptable salts are preferably those which are low toxic and soluble in water. Examples of suitable salts are salts of alkali metals (e.g., potassium, sodium, lithium, etc.), salts of alkaline earth metals (e.g., calcium, magnesium, etc.), ammonium salts (e.g., tetramethylammonium salt, tetrabutylammonium salt, etc.), salts of organic amines (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts [inorganic acid salts (e.g., hydrochloride, hydrobromide, hydroiodide, sulfate, phosphate, nitrate, etc.), organic acid salts (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucronate, gluconate, etc.), etc.].

Further, such salts include quaternary ammonium salts. The quaternary ammonium salts can be those wherein the nitrogen atom in the compound represented by formula (I) is quaternized by $R^0$ group. Examples of $R^0$ are a phenyl-substituted C1-8 alkyl group.

The N-oxides of the compounds represented by formula (I) are ones wherein the nitrogen atom of the compound represented by formula (I) is oxidized. Also, the N-oxides of the compound of the present invention may be present in the form of alkaline metal salts, alkaline earth metal salts, ammonium salts, organic amine salts or acid addition salts.

Suitable solvates of the compounds represented by formula (I) includes, for example, a solvate with water or an alcoholic solvent (e.g., ethanol, etc.). The solvates are preferably low toxic and soluble in water. The solvates of the compounds represented by formula (I) includes solvates of alkali metal salts, alkaline earth metal salts, ammonium salts, organic amine salts, acid addition salts or N-oxides of the compounds represented by formula (I) described above.

The compounds represented by formula (I) may be converted into the above salts, the above N-oxides, or the above solvates by the known method.

The prodrugs of the compounds represented by formula (I) are those which can be converted into the compounds of the formula (I) of the present invention by the in vivo action of enzymes or gastric acid. Examples of the prodrugs of compounds represented by formula (I) are (1) those wherein the amino group is acylated, alkylated, or phosphorylated (for example, compounds wherein the amino group is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.), when compounds represented by formula (I) contain an amino group; (2) those wherein the hydroxy group is acylated, alkylated, phosphorylated, or borated (for example, compounds wherein the hydroxy group is acetylated, palmitoylated, propanoylated, pivaloylated, succinylated, fumarylated, alanylated, dimethylaminocarbonylated, etc.), when compounds represented by formula (I) contain a hydroxy group; and (3) those wherein the carboxyl group is esterified, or amidated (for example, compounds wherein the carboxyl group is converted into an ester such as ethyl ester, phenyl ester, carboxymethyl ester, dimethylaminomethyl ester, pivaloyloxymethyl ester, 1-{(ethoxycarbonyl)oxy}ethyl ester, phthalidyl ester, (5-methyl-2-oxo-1,3-dioxolen-4-yl)methyl ester, and 1-{[(cyclohexyloxy)carbonyl]oxy}ethyl ester, or compounds wherein the carboxyl group is methylamidated), when compounds represented by formula (I) contain a carboxyl group. These compounds can be prepared by the conventional method. The prodrug of the compound represented by formula (I) is any one of hydrates and non-hydrates. Also, the prodrugs of the compound represented by the formula (I) may be converted into the compounds represented by the formula (I) under such physiological conditions as described in "Bunshisekkei" pages 163-198, in the "Iyakuhin no Kaihatsu" Vol. 7, 1990, Hirokawa Shoten. Further, the compound represented by formula (I) may be labelled with an isotope (e.g., $^3H$, $^{14}C$, $^{35}S$, $^{125}I$, etc.).

Mechanical IUPAC nomenclature of the compounds of the present invention was performed using a computer program ACD/NAME (registered trademark) available from Advanced Chemistry Development Inc. For example, the following compound was named 1-(4-chloro-2,6-dimethylphenyl)-5-{5-(2,4-difluorophenyl)-2-[2-hydroxy-1-(hydroxymethyl)-1-methylethyl]-1,3-oxazol-4-yl}-2(1H)-pyridinone.

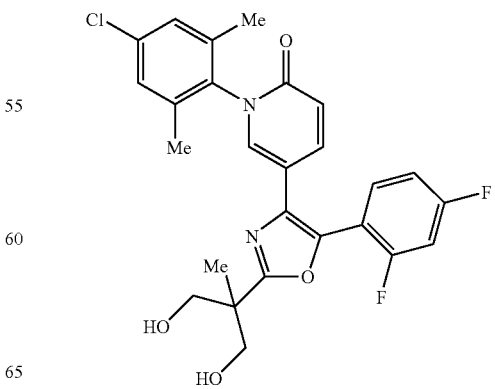

[Process for Preparation of the Compounds of the Present Invention]

The compounds represented by formula (I), or a salt thereof, an N-oxide thereof or a solvate thereof, or a prodrug thereof (hereinafter, abbreviated to "the compound(s) of the present invention") can be prepared by the known method, for example, an appropriately improved or combined method of Methods (A) to (G) shown below, similar methods thereof, the method as described in Examples, and the method described in Comprehensive Organic Transformations: A Guide to Functional Group Preparations, 2nd Edition (Richard C. Larock, John Wiley & Sons Inc., 1999). The starting material in each preparation method shown below may be used in the form of a salt. Such salt used is the salt of the compounds represented by formula (I) as defined above.

(A) Among the compounds represented by formula (I) of the present invention, a compound wherein ring A represents a thiazole ring, that is, a compound represented by formula (I-1):

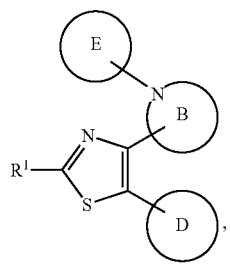

wherein all symbols have the same meanings as described above,
or a compound represented by formula (I-2):

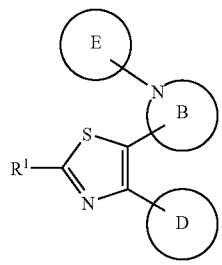

wherein all symbols have the same meanings as described above, can be prepared by subjecting a compound represented by formula (1):

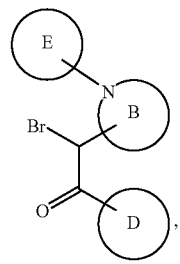

wherein all symbols have the same meanings as described above, or a compound represented by formula (2):

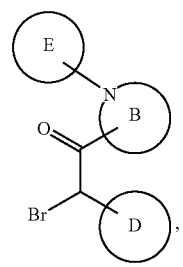

wherein all symbols have the same meanings as described above,
and a compound represented by formula (3):

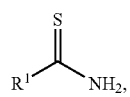

wherein all symbols have the same meanings as described above, to a ring formation reaction. If required, protection and/or deprotection of functional moiety may be carried out.

The above-described thiazole ring formation reaction is known, and is carried out, for example, in water or an organic solvent (e.g., alcohols such as methanol, ethanol, propanol, isopropanol, etc., dimethylformamide, dimethylsulfoxide, acetonitrile, dichloroethane, dimethoxyethane, toluene, tetrahydrofuran, 1,4-dioxane, etc.: These solvents are used separately or are used by mixture of two or more in just proportion (for example, by a ratio of 1:1~1:10, etc.), if required) or in the absence of solvent, in the presence or absence of a base (e.g., a hydroxide of alkali metal (e.g., potassium hydroxide, sodium hydroxide, cesium hydroxide, etc.), a carbonate (e.g., potassium carbonate, cesium carbonate, sodium carbonate, sodium hydrogen carbonate, etc.), or its aqueous solution, or a mixture thereof), with or without ultrasonic irradiation at a temperature of about −78° C. to about 100° C.

Though it is easily understood by those skilled in the art, in the case that the compounds represented by formula (I-1) or formula (I-2) of the present invention and the compounds represented by formula (1), (2) or (3) used as starting materials contain a hydroxy group(s), a carboxy group(s), an amino group(s), or a mercapto group(s), such compounds can be prepared by subjecting to a reaction of above-described ring formation reaction after appropriate protection of said group in advance, and then removing the protecting group.

As the amino-protecting group, there are exemplified benzyloxycarbonyl group, tert-butoxycarbonyl group, allyloxycarbonyl (Alloc) group, 1-methyl-1-(4-biphenyl)ethoxycarbonyl (Bpoc) group, trifluoroacetyl group, 9-fluorenylmethoxycarbonyl group, benzyl (Bn) group, p-methoxybenzyl group, benzyloxymethyl (BOM) group, 2-(trimethylsilyl)ethoxymethyl (SEM) group, and so forth.

As the hydroxy-protecting group, there are exemplified methyl group, trityl group, methoxymethyl (MOM) group, 1-ethoxyethyl (EE) group, methoxyethoxymethyl (MEM) group, 2-tetrahydropyranyl (THP) group, trimethylsilyl (TMS) group, triethylsilyl (TES) group, tert-butyldimethylsilyl (TBDMS) group, tert-butyldiphenylsilyl (TBDPS) group, acetyl (Ac) group, pivaloyl group, benzoyl group, benzyl (Bn) group, p-methoxybenzyl group, allyloxycarbonyl (Alloc) group, and 2,2,2-trichloroethoxycarbonyl (Troc) group, and so forth.

As the mercapto-protecting group, there are exemplified benzyl group, methoxybenzyl group, methoxymethyl (MOM) group, 2-tetrahydropyranyl (THP) group, diphenylmethyl group, acetyl (Ac) group, and so forth.

As the carboxyl-protecting group, there are exemplified methyl group, ethyl group, tent-butyl group, allyl group, phenacyl group, benzyl group, and so forth.

In addition to the above protecting groups for carboxyl, hydroxy, amino, or mercapto groups, there is no particular limitation so long as it can be easily and selectively removed. For example, protecting groups described in Protective Groups in Organic Synthesis (T. W. Greene, John Wiley & Sons Inc., 1999) also can be used.

The protection method for carboxy, hydroxy, amino, or mercapto group is well known. For example, it is described in Protective Groups in Organic Synthesis (T. W. Greene, John Wiley & Sons Inc., 1999).

The deprotection method for the protecting group of carboxy, hydroxy, amino, and mercapto group is well known. For example, it is described in Protective Groups in Organic Synthesis (T. W. Greene, John Wiley & Sons Inc., 1999).

Examples of such deprotection are
(1) alkali hydrolysis
(2) deprotection under acidic conditions
(3) deprotection by hydrogenolysis
(4) deprotection using a metal complex
(5) deprotection using a metal, and
(6) deprotection of silyl groups.

Details of these deprotection methods are hereinafter illustrated.

(1) The deprotection by alkali hydrolysis such as deprotection of trifluoroacetyl group is carried out at about 0° C. to about 40° C., using an alkali hydroxide (e.g., sodium hydroxide, potassium hydroxide, lithium hydroxide, etc.), an alkaline earth metal hydroxide (e.g., barium hydroxide, calcium hydroxide, etc.) or a carbonate (e.g., sodium carbonate, potassium carbonate, etc.) or an aqueous solution thereof or a mixture thereof, in an organic solvent (e.g., methanol, tetrahydrofuran, 1,4-dioxane, etc.).

(2) The deprotection under acidic conditions such as deprotection of tert-butoxycarbonyl, trityl and so forth, is carried out at about 0° C. to about 100° C. with an organic acid (e.g., acetic acid, trifluoroacetic acid, methanesulfonic acid, etc.) or an inorganic acid (e.g., hydrochloric acid, sulfuric acid, etc.) or a mixture thereof (e.g., hydrogen bromide/acetic acid) in water or an organic solvent (e.g., dichloromethane, chloroform, 1,4-dioxane, ethyl acetate, anisole, etc.).

(3) The deprotection by hydrogenolysis such as deprotection of benzyl, benzhydryl, benzyloxycarbonyl, allyloxycarbonyl and so forth, is carried out at about 0° C. to about 200° C. in a solvent [ethers (e.g., tetrahydrofuran, 1,4-dioxane, dimethoxyethane, diethyl ether, etc.), alcohols (e.g., methanol, ethanol, etc.), benzenes (e.g., benzene, toluene, etc.), ketones (e.g., acetone, methyl ethyl ketone, etc.), nitriles (e.g., acetonitrile, etc.), amides (e.g., N,N-dimethylformamide, etc.), water, ethyl acetate, acetic acid or a mixture of two or more solvents thereof] in the presence of a catalyst (e.g., palladium-carbon, palladium black, palladium hydroxide, platinum oxide, Raney-Ni, etc.) under a normal pressure or an increased pressure in a hydrogen stream or in the presence of ammonium formate.

(4) The deprotection using a metal, such as deprotection of allyloxycarbonyl group or the like, is carried out at about 0° C. to about 40° C. in an organic solvent (e.g., dichloromethane, N,N-dimethylformamide, tetrahydrofuran, ethyl acetate, acetonitrile, 1,4-dioxane, ethanol, etc.), water or a mixture thereof in the presence of a trapping reagent (e.g., tributyltin hydride, triethylsilane, dimedone, morpholine, diethylamine, pyrrolidine, etc.), an organic acid (e.g., acetic acid, formic acid, 2-ethylhexanoic acid, etc.) and/or an organic acid salt (e.g., sodium 2-ethylhexanoate, potassium 2-ethylhexanoate, etc.) and in the presence or absence of a phosphine reagent (e.g., triphenylphosphine, etc.), using a metal complex [e.g., tetrakistriphenylphosphine palladium(0), bis(triphenylphosphine)palladium(II) dichloride, palladium(II) acetate, tris(triphenylphosphine)rhodium(I) chloride].

(5) The deprotection using a metal is carried out in an acidic solvent (e.g., acetic acid, a buffer of pH 4.2 to 7.2, or a mixture of a solvent thereof and an organic solvent such as tetrahydrofuran) in the presence of a zinc dust at about 0° C. to about 40° C. while applying ultrasonic waves, if required.

(6) The deprotection of the silyl group is carried out in a water-miscible organic solvent (e.g., tetrahydrofuran, acetonitrile, etc.) using tetrabutylammonium fluoride at about 0° C. to about 40° C.

Those skilled in the art can easily understand that the desired compounds of the present invention can be easily produced by selectively employing these deprotection methods.

If necessary, conversion into desired salts may be followed according to the known method.

(B) Among the compounds represented by formula (I) of the present invention, a compound wherein ring A represents an oxazole ring, that is, a compound represented by formula (I-3):

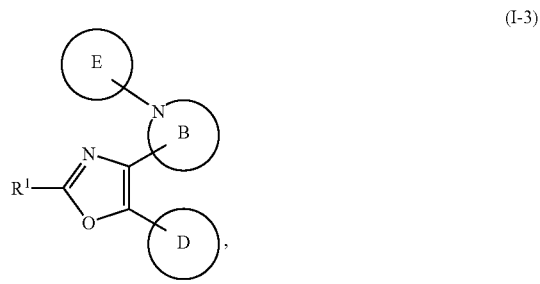

(I-3)

wherein all symbols have the same meanings as described above, or a compound represented by formula (I-4):

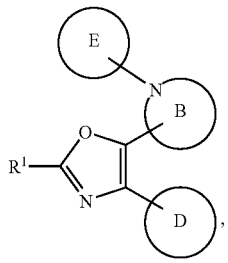
(I-4)

wherein all symbols have the same meanings as described above, can be prepared by subjecting an above-described compound represented by formula (1) or (2) and a compound represented by formula (4):

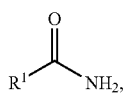
(4)

wherein all symbols have the same meanings as described above, to a ring formation reaction. If required, protection and/or deprotection of functional moiety may be carried out.

This oxazole ring formation reaction can be carried out in the same manner as above-described thiazole ring formation reaction. Also, protection and/or deprotection of functional moiety may be carried out in the same manner as described above.

(C) Among the compounds represented by formula (I) of the present invention, a compound wherein ring A represents a thiophene ring, that is, a compound represented by formula (I-5):

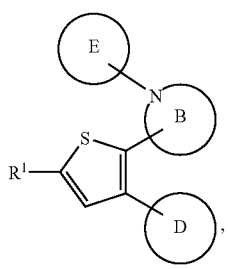
(I-5)

wherein all symbols have the same meanings as described above, or a compound represented by formula (I-6):

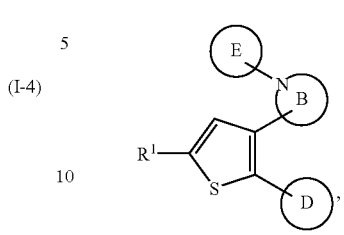
(I-6)

wherein all symbols have the same meanings as described above, can be prepared by subjecting a compound represented by formula (5):

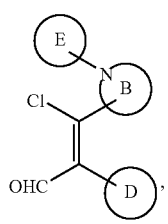
(5)

wherein all symbols have the same meanings as described above,
or a compound represented by formula (6):

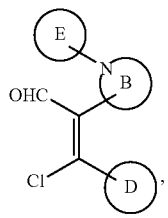
(6)

wherein all symbols have the same meanings as described above, and a compound represented by formula (7):

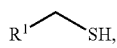
(7)

wherein all symbols have the same meanings as described above, to a ring formation reaction. If required, protection and/or deprotection of functional moiety may be carried out.

The above-described thiophene ring formation reaction is known and is carried out, for example, in an organic solvent (e.g., alcohols such as methanol, ethanol, propanol, tent-butanol, etc., pyridine, etc.) in the presence of a base (e.g., sodium methoxide, sodium ethoxide, potassium tert-butoxide, triethylamine, diisopropylamine, etc.) at a temperature of about 0° C. to about 100° C.

Also, protection and/or deprotection of functional moiety may be carried out in the same manner as described above.

(D) Among the compounds represented by formula (I) of the present invention, a compound wherein ring A represents a furan ring, that is, a compound represented by formula (I-7):

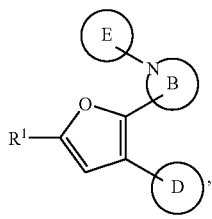

(I-7)

wherein all symbols have the same meanings as described above, or a compound represented by general formula (I-8):

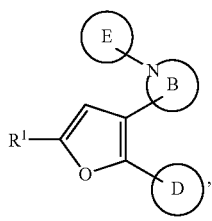

(I-8)

wherein all symbols have the same meanings as described above, can be prepared by subjecting a compound represented by formula (8):

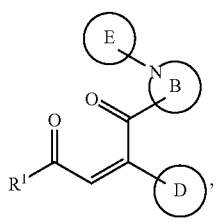

(8)

wherein all symbols have the same meanings as described above, or a compound represented by formula (9):

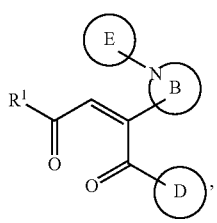

(9)

wherein all symbols have the same meanings as described above, to a ring formation reaction. If required, protection and/or deprotection of functional moiety may be carried out.

The above-described furan ring formation reaction is known and is carried out, for example, in an organic solvent (e.g., polyethylene glycol 200, polyethylene glycol 400, ethanol, diethyleneglycol, triethyleneglycol, tetraethyleneglycol, etc.) in the presence of an organic acid (e.g., formic acid, etc.) and a catalyst (e.g., palladium-carbon/concentrated sulfuric acid, concentrated hydrochloric acid, etc.) at a temperature of about −78° C. to about 100° C.

Also, this furan ring formation reaction can be carried out in the same manner as described in *J. Org. Chem.*, 68(13), 5392, (2003).

Also, protection and/or deprotection of functional moiety may be carried out in the same manner as described above.

(E) Among the compounds represented by formula (I) of the present invention, a compound wherein ring A represents a imidazole ring, that is, a compound represented by formula (I-9):

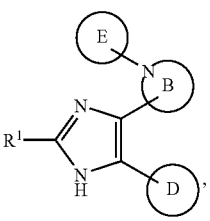

(I-9)

wherein all symbols have the same meanings as described above, can be prepared by subjecting a compound represented by formula (10):

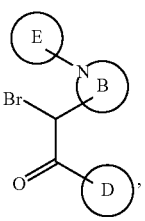

(10)

wherein all symbols have the same meanings as described above, or a compound represented by formula (11):

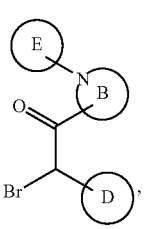

(11)

wherein all symbols have the same meanings as described above, and a compound represented by formula (12):

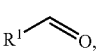

(12)

wherein all symbols have the same meanings as described above, to a ring formation reaction. If required, protection and/or deprotection of functional moiety may be carried out.

The above-described imidazole ring formation reaction is known and is carried out, for example, in an organic solvent (e.g., formic acid, acetic acid, etc.) in the presence of ammonium base (e.g., ammonium formate, ammonium acetate, etc.) and copper reagent (e.g., copper acetate (Cu(OAc)₂), etc.) at a temperature of about 0° C. to about 100° C., after an reaction, for example, in water or an organic solvent (e.g., alcohols such as methanol, ethanol, propanol, etc., or a mixture thereof, etc.) in the presence of a base (e.g., sodium methoxide, sodium ethoxide, etc.) at a temperature of about 0° C. to about 100° C.

Also, this imidazole ring formation reaction can be carried out in the same manner as described in Bioorg. Med. Chem. Lett., 14(4), 919, (2004).

Also, protection and/or deprotection of functional moiety may be carried out in the same manner as described above.

(F) Among the compounds represented by formula (I) of the present invention, a compound wherein ring A represents a imidazole ring, that is, an above-described compound represented by formula (I-9) can be prepared by subjecting a compound represented by general formula (13):

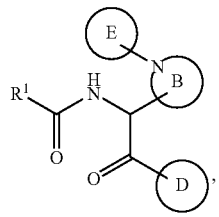

(13)

wherein all symbols have the same meanings as described above, or a compound represented by formula (14):

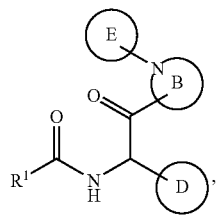

(14)

wherein all symbols have the same meanings as described above, to a ring formation reaction. If required, protection and/or deprotection of functional moiety may be carried out.

The above-described imidazole ring formation reaction is known and is carried out, for example, in an organic solvent (e.g., halogenated hydrocarbons such as methylene chloride, etc., dimethylsulfoxide, dimethylformamide, acetic acid, formic acid, xylene, etc.) in the presence of an ammonium salt (e.g., ammonium acetate, ammonium formate, ammonium trifluoroacetate, etc.) and p-toluenesulfonic acid at a temperature of about −78° C. to about 150° C.

Also, this imidazole ring formation reaction can be carried out in the same manner as described in Tetrahedron Lett., 39(49), 8939, (1998).

Also, protection and/or deprotection of functional moiety may be carried out in the same manner as described above.

(G) The compounds represented by formula (I) of the present invention can be prepared by subjecting a compound represented by formula (15):

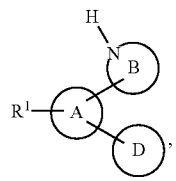

(15)

wherein all symbols have the same meanings as described above, and a compound represented by formula (16):

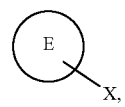

(16)

wherein X represents a halogen atom or —B(OH)₂, and the other symbols have the same meanings as described above, to a reaction. If required, protection and/or deprotection of functional moiety may be carried out.

The above-described reaction for the case when X represents a halogen atom is known and is carried out, for example, in an organic solvent (e.g., dimethylsulfoxide, dimethylformamide, 1,4-dioxane, 1-methyl-2-pyrrolidinone, 1,3-dimethyl-2-imidazolidinone, etc.) in the presence of a base (e.g., a hydroxide of alkali metal such as potassium hydroxide, sodium hydroxide, cesium hydroxide, etc., or a carbonate such as potassium carbonate, cesium carbonate, sodium carbonate, sodium hydrogen carbonate, etc. or a mixture thereof, etc.) and copper reagent (e.g., copper iodide, copper chloride, copper cyanide, copper acetate, copper bromide, copper oxide, copper, etc.) at a temperature of about 0° C. to about 100° C.

The above-described reaction for the case when X represents —B(OH)₂ is known and is carried out, for example, in an organic solvent (e.g., dichloromethane, chloroform, dichloroethane, dimethylsulfoxide, dimethylformamide, etc.) in the presence of a base (e.g., pyridine, triethylamine, diisopropylamine, or a mixture thereof, etc.) and an organic metal reagent (e.g., tetrakis(triphenylphosphine)palladium Pd(PPh₃)₄), bis(triphenylphosphine)palladium dichloride (PdCl₂(PPh₃)₂), palladium acetate (Pd(OAc)₂), copper acetate (Cu(OAc)₂), etc.), in the presence or absence of a molecular sieves, at a temperature of about −20° C. to about 150° C.

Also, protection and/or deprotection of functional moiety may be carried out in the same manner as described above.

Among the compounds of the present invention, the compounds having optical activity can be produced by using a starting material having optical activity or a reagent, or an optical resolution of manufacturing intermediate of racemate, and subsequently by leading to the compounds of the present invention, or by an optical resolution of the compound of the present invention of racemate.

The above-described method of optical resolution is known, and for example, a method isolating a desired compound after making the compound which have formed the salt/the chelate with the other optical active compound and having recrystalized, or a method dividing by means of the direct chiral column and so forth is given.

The compounds represented by formula (1) to (16) as the starting material or the reagent to be used are known per se, or can be easily produced by the known method, for example, the method described in Comprehensive Organic Transformations: A Guide to Functional Group Preparations, 2nd Edition (Richard C. Larock, John Wiley & Sons Inc, 1999), or a combination method thereof.

In each reaction of the present invention, a reagent appropriately carried on a solid carrier of polymers (e.g., polystyrene, polyacrylamide, polypropylene, polyethylene glycol, etc.) may be used.

The end products of the present invention can be purified by the conventional purification means such as distillation under normal pressure or reduced pressure, high performance liquid chromatography with silica gel or magnesium silicate, thin layer chromatography, or column chromatography, or wasing or recrystallization. Such purification may be carried out in each reaction or may be performed after several reactions.

The heating reaction in each reaction of the present invention may be performed using a water bath, an oil bath, a sand bath or a microwave, though it is apparent to those skilled in the art.

[Pharmacological Activity of the Compounds of the Present Invention]

Except for the pharmacological test described in Examples, there are exemplified the following methods to prove the pharmacological activity of the compounds of the present invention. p38 MAP kinase inhibitory activity of the compounds of the present invention can be proven by these methods.

(a) Study on p38α MAP Kinase Inhibitory Activity

Using activation transcription factor 2 (activating transcription factor 2; ATF-2, Cell Signaling Inc., #9224L) which is a substrate of p38α MAP kinase, the inhibitory effect of the compound of the present invention on the ATF-2 phosphorylation by recombinant human p38α MAP kinase (Upstate Biotechnology Inc., #14-251) is studied by the Western-blotting method using the anti-phosphorylated ATF-2 antibody (Cell Signaling Inc., #9221L). In other words, 10 μL of a solution of the compound of the present invention at a known concentration is added to 10 μL of the kinase buffer (Cell Signaling Inc., #9802) containing recombinant human p38α MAP kinase (100 ng/tube) and pre-incubated for 10 minutes at 30° C. Then, 20 μL of adenosine triphosphate (ATP)/ATF-2 mixture is added, and after the incubation of 30 minutes at 30° C., 20 μL of SDS buffer (187.5 mM Tris/6% SDS/30% glycerol/150 mM DTT/0.03% bromophenol blue) is added to stop the enzyme reaction. After heating at 100° C. for 5 minutes, mixing and centrifugation are performed. After remixing, 20 μL of the sample is subjected to an electrophoresis on SDS-PAGE gel (10 to 20%, Daiichi Pure Chemicals Co., Ltd.). After the electrophoresis, blotting is performed on PVDF membrane (Sequi-Blot (proprietary name), 0.2 (m, BIO-RAD) by a conventional method. After that, the PVDF membrane is treated with Block Ace (Snow Brand Milk Products Co., Ltd.) (at room temperature, for 1 hour). After reacted with the anti-phosphorylated ATF-2 antibody for 1.5 hours, the membrane is washed with TBS-T solution (0.02 M Tris/0.137 M NaCl/0.05% Tween 20, pH 7.6). Furthermore, the reaction with a secondary antibody (anti-rabbit IgG, horseradish peroxide linked whole antibody, Amersham LIFE SCIENCE) is carried out for 1 hour. After washing with TBS-T solution, phosphorylated ATF-2 is detected using Western blotting detection reagent (Amersham Pharmacia Biotech).

(b) Mouse Cytokine-Producing Model

By the method shown below, the in vivo effect of the compounds of the present invention can be proven. The vehicle used for administering the compound of the present invention can be any vehicle so long as it is safe and is able to suspend or dissolve into an orally administerable form. For example, such medium includes methylcellulose, carboxymethylcellulose, hydroxypropylcellulose, hydroxypropylmethycellulose, propylene glycol, polyethylene glycol, sugar, sugar alcohol, edible oil, distilled water, physiological saline, and a mixture thereof, all of which have been used for administering a compound to an animal by those skilled in the art.

[Experimental Method]

The compound of the present invention suspended or dissolved in 0.5% methylcellulose (MC) is orally administered to a male Balb/c mouse (Charles River Japan, Inc.), and after 0.5 hour, lipopolysaccharide (LPS, 055:B5, Difco) is intraperitoneally administered at the dose of 1 mg/kg (5 animals/group). MC (0.5%) is orally administered to a control group (5 animals). Ninety minutes after the LPS treatment, heparinized blood collection is performed via the abdominal main vein under anesthesia with ether, and blood plasma is obtained by centrifugation (12,000 rpm, 3 minutes, 4° C.). The obtained blood plasma sample is stored at −80° C. until it is used. TNF-α and IL-6 in the blood plasma are measured using ELISA kits from R&D Inc. (#MTA00) and Endogen Inc. (#EM2IL6), respectively.

[Toxicity]

Since the toxicity of a compound of the present invention is low enough, and, besides, the phospholipidosis inducing activity is not provided in in vitro experiment system, it was confirmed to be safe enough for use as pharmaceuticals.

[Application for Pharmaceuticals]

Since the compounds of the present invention suppress p38 MAP kinase activation in animals including human, particularly in human, they are expected to be useful in the prevention and/or the treatment of cytokine-mediated diseases such as various inflammatory diseases [for example, inflammation, dermatitis, atopic dermatitis, hepatitis, nephritis, glomerulonephritis, pancreatitis, psoriasis, gout, Addison's disease, arthritis (e.g., rheumatoid arthritis, osteoarthritis, rheumatoid spondylitis, gouty arthritis, synovitis, etc.), inflammatory ocular diseases, inflammatory pulmonary diseases (e.g., chronic pneumonia, silicosis, pulmonary sarcoidosis, pulmonary tuberculosis, adult respiratory distress syndrome (ARDS), severe acute respiratory syndrome (SARS), etc.), inflammatory bowel diseases (e.g., Crohn's disease, ulcerative colitis, etc.), allergic diseases (e.g., allergic dermatitis, allergic rhinitis, etc.), autoimmune disease, autoimmune hemolytic anemia, systemic lupus erythematosus, rheumatism, Castleman's disease, immune rejection accompanying transplantation (e.g., graft versus host reaction, etc.), and so forth], central nervous system disorders [for example, central neuropathy (e.g., cerebrovascular disease such as cerebral hemorrhage and cerebral infarction, head trauma, spinal cord injury, cerebral edema, multiple sclerosis, etc.), neurodegenerative disease (e.g., Alzheimer's disease, Parkinson's disease, amyotrophic lateral sclerosis (ALS), AIDS encephalopathy, etc.), meningitis, Creutzfeldt-Jakob syndrome, and so forth], respiratory diseases [for example, asthma, chronic obstructive pulmonary disease (COPD), and so forth], cardiovascular diseases [for example, angina, heart failure, congestive heart failure, acute heart failure, chronic heart failure, myocardial infarction, acute myocardial infarction, myocardial infarction prognosis, atrial myxoma, arteriosclerosis, hypertension, dialysis-induced hypotension, thrombosis, disseminated intravascular coagulation (DIC), reperfusion injury, restenosis after percutaneous transluminal coronary angioplasty (PTCA), and so forth], urinary diseases [for example, renal failure, and so forth], metabolic diseases or endocrine diseases [for example, diabetes, and so forth], bone diseases [for example, osteoporosis, and so forth], cancerous diseases [for example, malignant tumor (e.g., tumor growth and metastasis, etc.), multiple myeloma, plasma cell leukemia, cancerous cachexia, and so forth], and infectious diseases [for example, viral infection (e.g., cytomegalovirus infection, influenza virus infection, herpes virus infection, corona virus infection, etc.), cachexia associated with infections, cachexia caused by acquired immune deficiency syndrome (AIDS), toxemia (e.g., sepsis, septic shock, endotoxin shock, gram negative bacterial sepsis, toxic shock syndrome, severe acute respiratory syndrome (SARS) accompanying virus infection, etc.), and so forth], and so on.

Among subtypes ($\alpha$, $\beta$, $\beta_2$, $\gamma$, $\delta$) of p38 MAP kinase, the compounds of the present invention include compounds selectively inhibiting subtype $\alpha$, and compounds inhibiting other subtypes other than subtype $\alpha$.

The compounds of the present invention can be usually administered systemically or topically in the form of oral or parenteral administration.

Since the compounds of the present invention are safe and have low toxicity, they can be administered to a human or a mammal other than humans (e.g., rat, mouse, rabbit, sheep, pig, cow, cat, dog, monkey, etc.).

Although the dose varies depending on age, body weight, symptom, therapeutic effect, administration route and treatment time, the dose for a human adult is generally within a range of about 1 mg to about 1000 mg per administration that is orally administered up to several times a day, or within a range of about 0.1 mg to about 100 mg per administration that is parenterally or preferebaly intravenously administered up to several times a day or intravenously administered over a period of continuous 1 to 24 hours a day.

As mentioned above, the dose to be prescribed depends upon various conditions, and thus there are cases in which doses lower than the range as specified above may be enough or doses greater than the range as specified above may be required.

In the administration of the compounds of the present invention, they are used as solid preparations or liquid preparations for oral administration, or as injections, external preparations or suppositories for parenteral administration.

In the production of these compositions, the compounds of the present invention are not limited to a substantially chemically pure single substance, they may contain impurities (for example, by-products derived from the production process, solvents, starting materials, or decomposition products) so long as such impurities are within an acceptable range as a pharmaceutical bulk.

The solid preparations for oral administration include tablets, pills, capsules, dispersible powders, granules, and so forth. The capsules include hard capsules and soft capsules.

In such solid preparations for oral use, one or more of the active compound(s) may be admixed solely or with diluents (e.g., lactose, mannitol, glucose, microcrystalline cellulose, starch, etc.), binders (e.g., hydroxypropylcellulose, polyvinylpyrrolidone, magnesium aluminometasilicate, etc.), disintegrators (e.g., cellulose calcium glycolate, etc.), lubricants (e.g., magnesium stearate, etc.), stabilizers, solubilizers (e.g., glutamic acid, aspartic acid, etc.), and then formulated into a preparation in the conventional manner. When necessary, such preparations may be coated with a coating agent (e.g., sucrose, gelatin, hydroxypropylcellulose, hydroxypropylmethyl cellulose phthalate, etc.) or they may be coated with two or more coating layers. Furthermore, the solid preparations for oral use include capsules of absorbable materials like gelatin.

The liquid preparations for oral administration include pharmaceutically acceptable aqueous solutions, suspensions, emulsions, syrups, elixirs, and so forth. In such preparations, one or more of the active compound(s) may be dissolved, suspended or emulsified in a commonly used diluent (e.g., purified water, ethanol or a mixed solution thereof). Besides such diluents, said compositions may also contain wetting agents, suspending agents, emulsifiers, sweetening agents, flavouring agents, perfumes, preservatives, and buffers, and so forth.

Injections for parenteral administration include any injection and also include instillation solutions. For example, such injections for parenteral administration include intramuscular injection, subcutaneous injection, intracutaneous injection, intraarterial injection, intravenous injection, intraperitoneal injection, intraspinally injection, and intravenous instillation.

Injections for parenteral administration include solutions, suspensions, emulsions, and solid injection which are dissolved or suspended in a solvent immediately before use. The injections are used by dissolving, suspending or emulsifying one or more of the active compound(s) in a diluent. Said diluents may contain distilled water for injection, physiological saline, vegetable oil, alcohol (e.g., propylene glycol, polyethylene glycol, ethanol, etc.), and a combination thereof. Further, the injections may contain stabilizers, solubilizers (e.g., glutamic acid, aspartic acid, polysorbate 80 (registered trademark), etc.), suspending agents, emulsifiers, soothing agents, buffers, preservatives, etc. The injections are sterilized in the final formulation step or prepared by sterile procedure. The injections may also be formulated into sterile solid preparation, for example, by freeze-drying, and may be used after sterilized or dissolved in sterile injectable water or other sterile diluent(s) immediately before use.

Other preparations for parenteral administration may contain one or more active compounds, and as such compositions, there are exemplified conventionally formulated external solutions, ointments, pastes, inhalations, sprays, suppositories, or vaginal pessaries.

Sprays may contain stabilizers such as sodium hydrogen sulfite, and buffers capable of imparting isotonicity, including isotonic agents such as sodium chloride, sodium citrate and citric acid, in addition to a commonly used diluent.

The compounds of the present invention may be administered in combination with other drugs for the purpose of:
1) complement and/or enhancement of preventing and/or treating effect of the compound,
2) improvement of dynamics and absorption of the compound, and lowering of dose, and/or
3) alleviation of side effect of the compound.

Also, a combination of the compounds of the present invention may be administered as a combination drug for the purpose of:
1) complement and/or enhancement of preventing and/or treating effect of the other drugs,
2) improvement of dynamics and absorption of the other drugs, and lowering of dose, and/or
3) alleviation of side effect of the other drugs.

The compounds of the present invention may be administered in combination with other drugs as a preparation in one drug product comprising these components, or may be administered separately. When they are administered independently, they may be administered simultaneously or with time lag. Administration with time lag includes the method of administering first the compounds of the present invention and subsequently administering other drugs, and the method of administering first the other drug and subsequently administering the compound of the present invention, and they may be administered in the same route or not.

There is no limitation on the diseases on which the above combination drugs have a preventing and/or treatment effect, so long as the preventing and/or treatment effect of the compound represented by formula (I) is complemented and/or enhanced in the disease.

The weight proportion of the compounds of the present invention and the other drugs is not specifically limited.

Arbitrary two or more of the other drugs may be administered in combination.

Examples of the other drugs for complementing for and/or enhancing the preventive and/or treatment effect of the compounds of the present invention include not only those which have so far been found but also those which will be found on the basis of the aforementioned mechanism.

Other agents to complement and/or enhance a prevention and/or a treatment effect of the compound of the present invention on rheumatoid arthritis, osteoarthritis, arthritis or the like include a steroidal agent, an elastase inhibitor, a cannabinoid-2 receptor stimulating agent, a prostaglandin, a prostaglandin synthase inhibitor, a phosphodiesterase inhibitor, a metalloproteinase inhibitor, an adhesion molecule inhibitor, an anti-cytokine protein preparation (e.g., anti-TNF-α pharmaceutical, anti-IL-1 pharmaceutical, anti-IL-6 pharmaceutical etc.), a cytokine inhibitor, an immunomodulator, a disease modifying anti-rheumatic drug, a non-steroidal anti-inflammatory agent, c-Jun N-terminal kinase inhibitor, and so forth.

Other agents to complement and/or enhance prevention and/or treatment effect of the compound of the present invention on inflammatory bowel disease, Crohn's disease or ulcerative colitis include a steroidal agent, an elastase inhibitor, a cannabinoid-2 receptor stimulating agent, a prostaglandin, a prostaglandin synthase inhibitor, a phosphodiesterase inhibitor, a metalloproteinase inhibitor, an adhesion molecule inhibitor, an anti-cytokine protein preparation, a cytokine inhibitor, an immunomodulator, a leukotoriene receptor antagonist, an anticholinergic agent, a 5-lipoxygenase inhibitor, a nitric monooxide synthase inhibitor, an interleukin-8 antagonist, a poly(ADP)-ribose polymerase inhibitor, a mitochondrial benzodiazepine receptor agonist, an anti-oxidation agent, a local anesthetic, an agent for digestive tract ulcer, a defense factor enhancing agent, mesalazine, salazosulfapyridine and so forth.

Other agents to complement and/or enhance prevention and/or treatment effect of the compound of the present invention on asthma, chronic pulmonary inflammatory diseases or adult respiratory distress syndrome (ARDS) include a steroidal agent, an elastase inhibitor, a cannabinoid-2 receptor stimulating agent, a prostaglandin, a prostaglandin synthase inhibitor, a phosphodiesterase inhibitor, a metalloproteinase inhibitor, an adhesion molecule inhibitor, a leukotoriene receptor antagonist, an anticholinergic agent, a thromboxane A2 receptor antagonist, a thromboxane synthase inhibitor, a $\beta_2$ adrenergic receptor stimulating agent, a xanthine derivative, an expectorant agent, an antibiotic, an anti-histamine agent, an anti-cytokine protein preparation, a cytokine inhibitor, a forskolin preparation, a mediator release inhibitor, and so forth.

Examples of the steroidal agent include, for example, clobetasol propionate, diflorasone diacetate, fluocinonide, mometasone furoate, betamethasone dipropionate, betamethasone butyrate propionate, betamethasone valerate, difluprednate, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone acetate valerate, fluocinolone acetonide, beclometasone dipropionate, triamcinolone acetonide, flumetasone pivalate, alclometasone dipropionate, clobetasone butyrate, prednisolone, fludroxycortide, cortisone acetate, hydrocortisone, hydrocortisone sodium phosphate, hydrocortisone sodium succinate, fludrocortisone acetate, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, dexamethasone sodium phosphate, dexamethasone palmitate, paramethason acetate, betamethasone, fluticasone propionate, budesonide, flunisolide, ST-126P, ciclesonide, dexamethasone palmitate, mometasone furoate, prasterone sulfonate, deflazacort, methylprednisolone suleptanate, methylprednisolone sodium succinate, and so forth.

Examples of an elastase inhibitor include, for example, ONO-5046, ONO-6818, MR-889, PBI-1101, EPI-HNE-4, R-665, ZD-0892, ZD-8321, GW-311616, DMP-777, L-659286, L-658758, L-680833, L-683845, AE-3763, and so forth.

Examples of a prostaglandin (hereinafter abbreviated to PG) include, for example, PG receptor agonist, PG receptor antagonist, and so forth.

Examples of PG receptor include, for example, PGE receptor ($EP_1$, $EP_2$, $EP_3$, $EP_4$), PGD receptor (DP, CRTH2), PGF receptor (FP), PGI receptor (IP), TX receptor (TP), and so forth.

Examples of a prostaglandin synthase inhibitor include, for example, salazosulfapyridine, mesalazine, olsalazine, 4-aminosalicylic acid, JTE-522, auranofin, carprofen, diphenpyramide, flunoxaprofen, flurbiprofen, indomethacin, ketoprofen, lornoxicam, loxoprofen, meloxicam, oxaprozin, parsalmide, piproxen, piroxicam, piroxicam betadex, piroxicam cinnamate, tropine indomethacinate, zaltoprofen, pranoprofen, and so forth.

Examples of a phosphodiesterase inhibitor include, for example, PDE4 inhibitor such as rolipram, cilomilast (proprietary name: Ariflo), Bay19-8004, NIK-616, roflumilast (BY-217), cipamfylline (BRL-61063), atizoram (CP-80633), SCH-351591, YM-976, V-11294A, PD-168787, D-4396, and IC-485, and a PDE5 inhibitor such as sildenafil, and so forth.

Examples of an adhesion molecule inhibitor include, for example, an antagonist for α4-integrin, and so forth.

Examples of an anti-TNF-α preparations include a preparation containing an anti-TNF-α antibody, a soluble TNF-α receptor, an anti-TNF-α receptor antibody or a protein bound to a soluble TNF-α, such as a preparation containing infliximab or etanercept, or the like.

Examples of the anti-IL-1 preparations include a preparation containing an anti-IL-1 antibody, a soluble IL-1 receptor, IL-1Ra or an anti-IL-1 receptor antibody, such as a preparation containing anakinra or the like.

Examples of the anti-IL-6 preparations include a preparation containing an anti-IL-6 antibody, a soluble IL-6 receptor or an anti-IL-6 receptor antibody, such as a preparation containing MRA or the like.

Examples of an immunomodulator include, for example, methotrexate, cyclosporine, ascomycin, leflunomide, bucillamine, salazosulfapyridine, azathioprine, tacrolimus, cyclophosphamide, and so forth.

Examples of a disease modifying anti-rheumatic drug include, for example, gold thioglucose, sodium aurothiomalate, auranofin, chloroquine, actarit, D-penicillamine preparation, lobenzarit disodium, bucillamine, hydroxychloroquine, salazosulfapyridine, and so forth.

Examples of a non-steroidal anti-inflammatory agents include, for example, sasapyrine, sodium salicylate, aspirin, aspirin/dialuminate composition, diflunisal, indomethacin, suprofen, ufenamate, dimethyl isopropylazulene, bufexamac, felbinac, diclofenac, tolmetin sodium, Clinoril, fenbufen, nabumetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofenaxetil, ketoprofen, fenoprofen calcium, thiaprofen, oxaprozin, pranoprofen, loxoprofen sodium, alminoprofen, zaltoprofen, mefenamic acid, aluminum mefenamate, tolfenamic acid, floctafenine, ketophenylbutazon, oxyphenbutasone, piroxicam, tenoxicam, ampiroxicam, Napageln ointment, epirizole, tiaramide hydrochloride, tinoridine hydrochloride, emorfazone, sulpyrine, migrenin, Saridon, Sedes G, Amipylo-N, Sorbon, pyrine preparation for cold syndrome, acetaminophen, phenacetin, dimetotiazine mesilate, simetride combinations, a non-pyrine cough and cold preparation, and so forth.

Examples of a leukotoriene receptor antagonist include, for example, pranlukast hydrate, montelukast, zafirlukast, seratrodast, MCC-847, KCA-757, CS-615, YM-158, L-740515, CP-195494, LM-1484, RS-635, A-93178, S-36496, BIIL-284, ONO-4057, and so forth.

Examples of an anti-cholinergic agents include, for example, ipratropium bromide, oxitropium bromide, flutropium bromide, cimetropium bromide, temiverine, tiotropium bromide, revatropate (UK-112166), and so forth.

Examples of a topical anesthetics include, for example, cocaine hydrochloride, procaine hydrochloride, lidocaine, dibucaine hydrochloride, tetracaine hydrochloride, and so forth.

Examples of a defence factor enhancing agents include sucralfate, aldioxa, teprenone, cetraxate hydrochloride, ornoprostil, and so forth.

Examples of a thromboxane A2 receptor antagonist include, for example, seratrodast, ramatroban, domitroban calcium hydrate, KT-2-962, and so forth.

Examples of a thromboxane synthase inhibitor include, for example, ozagrel hydrochloride, imitrodast sodium, and so forth.

Examples of a $\beta_2$ adrenergic receptor stimulating agent include, for example, fenoterol hydrobromide, salbutamol sulfate, terbutaline sulfate, formoterol fumarate, salmeterol xinafoate, isoproterenol sulfate, orciprenaline sulfate, chlorprenaline sulfate, epinephrine, trimetoquinol hydrochloride, hexoprenalinemesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, R,R-formoterol, KUR-1246, KUL-7211, AR-C89855, S-1319, and so forth.

Examples of a xanthine derivative include, for example, aminophylline, theophylline, doxophylline, cipamfylline, diprophylline, and so forth.

Examples of a expectorant agent include, for example, foeniculated ammonia spirit, sodium hydrogen carbonate, bromhexine hydrochloride, carbocysteine, ambroxol hydrochloride, ambroxol hydrochloride sustained preparation, methylcysteine hydrochloride, acetylcysteine, L-ethylcysteine hydrochloride, tyloxapol, and so forth.

Examples of the antibiotic include, for example, cefuroxime sodium, meropenem trihydrate, netilmicin sulfate, sisomicin sulfate, ceftibuten, PA-1806, IB-367, tobramycin, PA-1420, doxorubicin, astromicin sulfate, cefetamet pivoxil hydrochloride, and so forth. Examples of the antibiotic as an inhalation include, for example, PA-1806, IB-367, tobramycin, PA-1420, doxorubicin, astromicin sulfate, cefetamet pivoxil hydrochloride, and so forth.

Examples of an anti-histamine agent include, for example, ketotifen fumarate, mequitazine, azelastine hydrochloride, oxatomide, terfenadine, emedastine difumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, acrivastine, and so forth.

Examples of the cytokine inhibitors include any one of non-protein preparations which can block the action of cytokines, containing a MAP kinase inhibitor, a gene regulating agent, a cytokine production inhibitor, a TNF-α converting enzyme inhibitor, an IL-1β converting enzyme inhibitor, an IL-6 antagonist, an IL-8 antagonist, a chemokine antagonist, a gene therapy agent, and an anti-sense compound, and so forth. The MAP kinase inhibitor includes, for example, PD-98059 and so forth. The gene regulating agent includes an inhibitor to molecules involved in signal transmission, such as NF-κB, IKK-1, IKK-2, and AP-1, and so forth. The cytokine production inhibitor includes, for example, suplatast tosilate (proprietary name: IPD), T-614, SR-31747, sonatimod, and so forth. The chemokine antgonist includes, for example, ONO-4128 and so forth. The gene therapy agent includes, for example, a gene therapy agent for accelerating expression of genes having antiinflammatory action, such as interleukin-4, interleukin-10, a soluble IL-1 receptor and a soluble TNF-α receptor, and so forth.

Examples of a mediator release inhibitor include, for example, tranilast, sodium cromoglicate, amlexanox, repirinast, ibudilast, tazanolast, pemirolast potassium, and so forth.

Examples of the c-Jun N-terminal kinase inhibitor include compounds described in WO 00/35906, WO 00/35909, WO 00/35921, WO 00/64872, WO 00/75118, and so forth.

EFFECT OF THE INVENTION

The compounds of the present invention are compounds which have a strong p38 MAP kinase inhibitory activity and/or TNF-α production inhibitory activity and also in which the hepatopathy risk as a problem of the p38 MAP kinase inhibitors which has been known is alleviated. Particularly, it has been revealed from a result of an in vitro experiment which is described that they also do not show the phospholipidosis inducing activity which is found in the compound represented by the aforementioned formula (U). Based on the above results, the compounds of the present invention are markedly safe and useful as an agent for preventing and/or treating cytokine-mediated diseases (e.g., an inflammatory disease, a central nervous system disease, a respiratory organ system disease, a circulatory organ system disease, a urinary organ system disease, a metabolic system disease, an internal secretion system disease, a bone disease, a cancer, an infection and the like) and the like, as low toxicity compounds having alleviated hepatopathy risk.

BEST MODE FOR CARRYING OUT THE INVENTION

The present invention is explained below in detail based on Examples, but the present invention is not limited thereto.

In chromatographic separations and TLC, the solvents in parenthesis show the eluting and developing solvents and the

EXAMPLE A1

Sodium 3-hydroxy-2-(hydroxymethyl)-2-methylpropanoate

To a solution of 2,2-bis(hydroxymethyl)propionic acid (2.21 g) in ethanol (30 mL) was added 5N aqueous solution of sodium hydroxide (3.30 mL) and the mixture was stirred at room temperature for 5 minutes. The reaction mixture was concentrated to give the title compound.

EXAMPLE A2

Methyl 3-methoxy-2-(methoxymethyl)propanoate

To a 28% sodium methoxide/methanol solution (4.24 g) in methanol (35 mL) was added methyl 2-(bromomethyl)acrylate (1.79 g) in methanol (10 mL). The mixture was stirred at room temperature for 2 hours and was heated to reflux for 3 hours. The reaction mixture was poured into 2N hydrochloric acid-ice, then extracted with ethyl acetate. The obtained organic layer was washed with brine, dried and concentrated to give the title compound (1.33 g) having the following physical data.
TLC: Rf 0.56 (hexane:ethyl acetate=2:1);
NMR: δ 3.73 (s, 3H), 3.64 (dd, J=9.3, 6.6 Hz, 2H), 3.57 (dd, J=9.3, 5.7 Hz, 2H), 3.34 (s, 6H), 3.00-2.88 (m, 1H).

EXAMPLE A3

3-methoxy-2-(methoxymethyl)propanoic acid

To a solution of the compound prepared in Example A2 (243 mg) in methanol (1.5 mL) was added 5N aqueous solution of sodium hydroxide (612 μL) and the mixture was stirred at 50° C. for 4 hours. The reaction mixture was poured into 1N hydrochloric acid-ice, then extracted with ethyl acetate. The obtained organic layer was washed with brine, dried and concentrated to give the title compound having the following physical data quantitatively.
TLC: Rf 0.47 (dichloromethane:methanol=9:1);
NMR: δ 3.68 (dd, J=9.3, 6.6 Hz, 2H), 3.63 (dd, J=9.3, 5.7 Hz, 2H), 3.38 (s, 6H), 3.00-2.88 (m, 1H).

EXAMPLE A4

1-cyano-1-[(trimethylsilyl)oxy]-1,2-ethanediyl diacetate

To a solution of 1,3-diacetoxyacetone (7.42 g) in dichloromethane (140 mL) were added trimethylsilylnitrile (12.68 g) and zinc iodide (II) (1.36 g) and the mixture was stirred at room temperature for 8 hours. To the reaction mixture was added an aqueous sodium hydrogen carbonate solution. The mixture was extracted with dichloromethane. The obtained organic layer was dried and concentrated to give the title compound (11.65 g) having the following physical data.
TLC: Rf 0.71 (hexane:ethyl acetate=2:1);
NMR: δ 0.28 (s, 9H), 2.14 (s, 6H), 4.22 (q, J=11.3 Hz, 4H).

EXAMPLE A5

2,3-dihydroxy-2-(hydroxymethyl)propanoic acid

A solution of the compound prepared in Example A4 (7.47 g) in 5N hydrochloric acid (100 mL) was stirred at 100° C. for 16 hours. The reaction mixture was concentrated and dried. To the obtained residue was added ethanol. The deposited insoluble matter (ammonium chloride) was filtered. The obtained ethanol solution was concentrated and dried to give the title compound (4.42 g) having the following physical data.
TLC: Rf 0.20 (chloroform:methanol=2:1);
NMR (CD$_3$OD): δ 3.55-3.80 (m, 4H).

EXAMPLE A6

Methyl 3-methoxy-2-(methoxymethyl)-2-methylpropanoate

Under an atmosphere of argon, to a solution of 3-hydroxy-2-(hydroxymethyl)-2-methylpropanoic acid (1 g) in N,N-dimethylformamide (30 mL) were added silver oxide (8.6 g) and iodomethane (4.6 mL) and the mixture was stirred at room temperature for 28 hours. The reaction mixture was filtered through Celite (Trade name). To the obtained filtrate was added water and the mixture was extracted with ethyl acetate. The obtained organic layer was washed with brine, dried and concentrated. The obtained residue was purified by column chromatography on silica gel (hexane:ethyl acetate=20:1→15:1) to give the title compound (450 mg) having the following physical data.
TLC: Rf 0.65 (hexane:ethyl acetate=2:1);
NMR: δ 3.70 (s, 3H), 3.49 (s, 4H), 3.34 (s, 6H), 1.19 (s, 3H).

EXAMPLE A7

3-methoxy-2-(methoxymethyl)-2-methylpropanoic acid

By the same procedure as a reaction of Example A3, using the compound prepared in Example A6 instead of the compound prepared in Example A2, the title compound having the following physical data was obtained.
TLC: Rf 0.37 (dichloromethane:methanol=10:1);
NMR: δ 3.52 (s, 4H), 3.38 (s, 6H), 1.23 (s, 3H).

EXAMPLE A8

3-hydroxy-2,2-bis(hydroxymethyl)propanoic acid

To a solution of pentaerythritol (10.0 g) in water (600 mL) was 5% platinum/carbon (hydrous article, 13.3 g). While maintaining pH of the reaction mixture to 6~7 by means of 8% sodium hydrogen carbonate solution, it was stirred at 35° C. for 8 hours under an atmosphere of oxygen. After catalyst was filtered, and having removed, the reaction mixture was concentrated. After having put the obtained residue through ion exchange resin Amberlyst (Amberlyst: trade name) A-21 by means of 2N hydrochloric acid, it was purified by preparative medium pressure liquid chromatography W-prep 2XY (column: main column L, inject column M; automatic condition setting: dichloromethane:methanol=4:1, Rf=0.25, preparative isolation mode GR). Furthermore, the obtained residue was purified by preparative TLC (dichloromethane: methanol=4:1) to give the title compound (123 mg) having the following physical data.
TLC: Rf 0.10 (dichloromethane:methanol=2:1);
MS (APCI, Neg. 20 V): m/z 149 (M−H)−.

EXAMPLE A9

Ethyl 2,3-dihydroxy-2,3-dimethylbutanoate

Under an atmosphere of argon, to a solution of ethyl pyruvate (1.03 g) in acetone (53 mL) was added 15% titanium trichloride (18.14 g) and the mixture was stirred at room temperature for 10 hours. The reaction mixture was concentrated and the obtained residue was poured into water. The mixture was extracted with ethyl acetate. The obtained organic layer was washed with brine, dried and concentrated. The obtained residue was purified by column chromatography on silica gel (hexane:ethyl acetate=5:1→3:1→2:1) to give the title compound (520 mg) having the following physical data.
TLC: Rf 0.19 (hexane:ethyl acetate=3:1);
NMR: δ 4.34-4.24 (m, 2H), 3.58 (br s, 1H), 2.62 (br s, 1H), 1.43 (s, 3H), 1.33 (t, J=7.2 Hz, 3H), 1.29 (s, 3H), 1.21 (s, 3H).

EXAMPLE A 10

2,3-dihydroxy-2,3-dimethylbutanoic acid

By the same procedure as a reaction of Example A3, using the compound prepared in Example A9 instead of the compound prepared in Example A2, the title compound having the following physical data was obtained.
TLC: Rf 0.24 (dichloromethane:methanol:acetic acid=10:2:1);
NMR: δ 3.35 (br s, 3H), 1.49 (s, 3H), 1.36 (s, 3H), 1.35 (s, 3H).

EXAMPLE A11

2,2,5-trimethyl-1,3-dioxolane-4-carboxylic acid

To a solution of methyl 2,2,5-trimethyl-1,3-dioxolane-4-carboxylate (1 mL) in tetrahydrofuran (10 mL) was added 1N aqueous lithium hydroxide (10 mL) and the mixture was stirred at room temperature for an hour. The reaction mixture was poured into iced 10% citric acid, then extracted with ethyl acetate. The obtained organic layer was washed with brine, dried and concentrated to give the title compound (425 mg) having the following physical data.
TLC: Rf 0.05 (hexane:ethyl acetate=2:1);
NMR: δ 6.70 (br s, 1H), 4.24 (m, 1H), 4.09 (d, J=8.1 Hz, 1H), 1.49-1.46 (m, 9H)

EXAMPLE A12

Methyl 4-(hydroxymethyl)tetrahydro-2H-pyran-4-carboxylate

Under an atmosphere of argon, to a solution of lithium aluminum tri(tert-butoxy)hydride (1.93 g) in tetrahydrofuran (15 mL) was added a solution of dimethyl tetrahydro-2H-pyran-4,4-dicarboxylate (606 mg) in tetrahydrofuran (5 mL) and the mixture was stirred at room temperature for an hour. To the reaction mixture was added an an aqueous saturated sodium sulfate solution till being cloudy. An insoluble matter was filtered and the filtrate was concentrated. The obtained residue was purified by column chromatography on silica gel (hexane:ethyl acetate=2:1→1:2→1:4→ethyl acetate:methanol=10:1→dichloromethane:methanol=10:1) to give the title compound (245 mg) having the following physical data.
TLC: Rf 0.16 (hexane:ethyl acetate=1:1);
NMR: δ 3.86-3.77 (m, 5H), 3.67 (d, J=5.7 Hz, 2H), 3.59-3.50 (m, 2H), 2.11-2.04 (m, 2H), 1.97 (t, J=5.7 Hz, 1H), 1.64-1.49 (m, 2H).

EXAMPLE A13

4-(hydroxymethyl)tetrahydro-2H-pyran-4-carboxylic acid

By the same procedure as a reaction of Example A3, using the compound prepared in Example A12 instead of the compound prepared in Example A2, the title compound having the following physical data was obtained.
TLC: Rf 0.50 (dichloromethane:methanol:acetic acid=10:2:1);
NMR: δ 3.87-3.50 (m, 6H), 2.20-2.00 (m, 2H), 1.66-1.52 (m, 2H).

EXAMPLE A14

2,3-dimethoxy-2-[(trimethylsilyl)oxy]propanenitrile

By the same procedure as a reaction of Example A4, using 1,3-dimethoxyacetone instead of 1,3-diacetoxyacetone, the title compound having the following physical data was obtained.
TLC: Rf 0.63 (hexane:ethyl acetate=4:1);
NMR: δ 0.24 (s, 9H), 3.44 (s, 6H), 3.54 (q, J=9.9 Hz, 4H).

EXAMPLE A15

2-hydroxy-3-methoxy-2-(methoxymethyl)propanoic acid (compound 15a); 2,3-dihydroxy-2-(methoxymethyl)propanoic acid (compound 15b)

By the same procedure as a reaction of Example A5, using the compound prepared in Example A14 instead of the compound prepared in Example A4, the title compound having the following physical data was obtained.
Compound 15a:
MS (APCI, Neg, 20 V): 163 (M−H)+.
Compound 15b:
MS (APCI, Neg, 20 V): 149 (M−H)+.

EXAMPLE A16

2,3-dihydroxy-2-methylpropanoic acid

According to a method of Z. W. An (Synthesis, 1992, (3), 273-275), the title compound (8.53 g) having the following physical data was obtained.
TLC: Rf 0.23 (chloroform:methanol:acetic acid=12:7:1);
NMR (DMSO-$d_6$): δ 1.17 (s, 3H), 3.34 (d, J=10.7 Hz, 1H), 3.46 (d, J=10.7 Hz, 1H), 4.74 (s, 2H), 12.27 (s, 1H).

EXAMPLE A17

Tetrahydro-2H-pyran-4-carboxamide

By the same procedure as a reaction of Example A5, using tetrahydro-2H-pyran-4-carbonitrile instead of the compound prepared in Example A4, the title compound having the following physical data was obtained.

TLC: Rf 0.26 (dichloromethane:methanol=10:1);
NMR: δ 5.45 (br s, 2H), 4.05-3.99 (m, 2H), 3.46-3.38 (m, 2H), 2.40 (m, 1H), 1.83-1.76 (m, 4H).

EXAMPLE A18

Tetrahydro-2H-pyran-4-carbothioamide

Under an atmosphere of argon, to a solution of the compound prepared in Example A17 (229 mg) in tetrahydrofuran (5 mL) was added Belleau's Reagent (2,4-bis(4-phenoxyphenyl)-1,3-dithia-2,4-diphosphetane-2,4-disulfide, 470 mg) and the mixture was stirred at room temperature for 10 minutes. The reaction mixture was poured into an aqueous saturated sodium hydrogen carbonate solution, then extracted with ethyl acetate. The obtained organic layer was washed with brine, dried and concentrated. The obtained residue was purified by column chromatography on silica gel (hexane:ethyl acetate=3:1→1:1) to give the title compound (190 mg) having the following physical data.

TLC: Rf 0.49 (dichloromethane:methanol=10:1);
NMR: δ 7.45 (br s, 1H), 6.80 (br s, 1H), 4.09-4.03 (m, 2H), 3.49-3.40 (m, 2H), 2.80 (m, 1H), 2.00-1.85 (m, 4H).

EXAMPLE A19

Tetrahydro-2H-thiopyran-4-carbonitrile

According to a method of C. Strässler (Helv. Chim. Acta, 80 (5), 1528-1554, (1997)), the title compound (7.37 g) having the following physical data was obtained.

TLC: Rf 0.55 (ethyl acetate:hexane=1:2);
NMR: δ 2.06-2.22 (m, 4H), 2.52-2.65 (m, 2H), 2.77-2.94 (m, 3H).

EXAMPLE A20

Tetrahydro-2H-thiopyran-4-carboxylic acid

By the same procedure as a reaction of Example A5, using the compound prepared in Example A19 instead of the compound prepared in Example A4, the title compound having the following physical data was obtained.

TLC: Rf 0.33 (ethyl acetate:hexane=2:1);
NMR (DMSO-$d_6$): δ 1.53-1.70 (m, 2H), 2.04-2.17 (m, 2H), 2.25-2.39 (m, 1H), 2.56-2.64 (m, 4H), 12.20 (s, 1H).

EXAMPLE A21

Tetrahydro-2H-thiopyran-4-carboxamide

Under an atmosphere of argon, to a solution of the compound prepared in Example A20 (1.50 g) in dichloromethane (50 mL) were added oxalyl chloride (1.1 mL) and catalyst quantity of N,N-dimethylformamide and the mixture was stirred at room temperature for 2 hours. To the reaction mixture was added 30% ammonia water (5 mL) and the mixture was stirred at room temperature for 5 minutes. The reaction mixture was poured into iced aqueous sodium hydrogen carbonate solution, then extracted with a mixed solvent of dichloromethane:methanol=3:1. The obtained organic layer was washed with water and brine, dried and concentrated to give the title compound (1.26 g) having the following physical data.

TLC: Rf 0.37 (ethyl acetate:methanol=19:1);
NMR: δ 1.77-1.95 (m, 2H), 2.16-2.28 (m, 3H), 2.64-2.77 (m, 4H), 5.30-5.56 (m, 2H).

EXAMPLE A22

Tetrahydro-2H-thiopyran-4-carbothioamide

By the same procedure as a reaction of Example A18, using the compound prepared in Example A21 instead of the compound prepared in Example A17, the title compound having the following physical data was obtained.

TLC: Rf 0.49 (ethyl acetate:hexane=2:1);
NMR: δ 1.83-2.02 (m, 2H), 2.20-2.31 (m, 2H), 2.55-2.84 (m, 5H), 6.61-6.92 (m, 1H), 7.24-7.51 (m, 1H).

EXAMPLE 1

Coumaric Acid Chloride

To a solution of coumaric acid (36.3 g) in dichloromethane (1.03 L) were added oxalyl chloride (45.2 mL) and N,N-dimethylformamide (0.6 mL). After foaming calmed down, the mixture was heated to reflux for 3 hours. The reaction mixture was concentrated to give the title compound. The obtained compound was used for the next reaction without being purified.

EXAMPLE 2

5-[(2,4-difluorophenyl)acetyl]-2H-pyran-2-one

Zinc powder (50.8 g) and ethylene glycol dimethyl ether (210 mL) were mixed. To this solution were added 1,2-dibromoethane (0.3 mL) and 2,4-difluorobenzylbromide (42.7 mL) and the mixture was stirred at 75° C. for an hour. To the reaction mixture were added the compound prepared in Example 1 and tetrakis(triphenylphosphine)palladium (15 g) and the mixture was stirred at room temperature for an hour. The reaction mixture was filtered through Celite (trade name) and Florisil (trade name) and a filtered matter was washed with ethyl acetate. To the filtrate was added 1N hydrochloric acid and the mixture was extracted with ethyl acetate. The obtained organic layer was washed with brine, dried over anhydrous sodium sulfate and concentrated. The obtained residue was purified by column chromatography on silica gel (hexane:ethyl acetate=2:1) to give the title compound (26.5 g) having the following physical data.

TLC: Rf 0.36 (hexane:ethyl acetate=2:1);
NMR: δ 8.41 (dd, J=2.7, 1.2 Hz, 1H), 7.87 (dd, J=9.9, 2.7 Hz, 1H), 7.20 (m, 1H), 6.94-6.82 (m, 2H), 6.39 (dd, J=9.9, 1.2 Hz, 1H), 4.03 (s, 2H).

EXAMPLE 3

1-(4-chloro-2,6-dimethylphenyl)-5-[(2,4-difluorophenyl)acetyl]-2(1H)-pyridinone

To a solution of the compound prepared in Example 2 (10.0 g) in pyridine (40 mL) was added 4-chloro-2,6-dimethylaniline (7.46 g) and the mixture was stirred at 80° C. for an hour. The reaction mixture was poured into 1N hydrochloric acid-ice, then extracted with ethyl acetate. The obtained organic layer was washed with 1N hydrochloric acid and brine, dried and concentrated to give the title compound (12.5 g) having the following physical data.

TLC: Rf 0.29 (hexane:ethyl acetate=2:1);

NMR: δ 8.02 (dd, J=9.6, 2.4 Hz, 1H), 7.97 (dd, J=2.4, 0.6 Hz, 1H), 7.25-7.15 (m, 3H), 6.92-6.75 (m, 2H), 6.71 (dd, J=9.6, 0.6 Hz, 1H), 4.03 (s, 2H), 2.07 (s, 6H).

EXAMPLE 4

5-[bromo(2,4-difluorophenyl)acetyl]-1-(4-chloro-2,6-dimethylphenyl)-2(1H)-pyridinone To a solution of the compound prepared in Example 3 (12.5 g) in tetrahydrofuran (323 mL) was added phenyltrimethylammonium tribromide (13.9 g) and the mixture was stirred at 60° C. for 20 minutes. After the insoluble matter was filtered, and having removed, the reaction mixture was concentrated. The obtained residue was purified by preparative medium pressure liquid chromatography W-prep 2XY (column: main column 3L, inject column 2L; automatic condition setting: hexane:ethyl acetate=2:1, Rf=0.50, preparative isolation mode GR) to give the title compound (12.0 g) having the following physical data.
TLC: Rf 0.50 (hexane:ethyl acetate=2:1);
NMR: δ 8.05-7.98 (m, 2H), 7.70 (td, J=8.4, 6.3 Hz, 1H), 7.24-7.21 (m, 2H), 7.05-6.93 (m, 1H), 6.88-6.78 (m, 1H), 6.75-6.69 (m, 1H), 6.26 (s, 1H), 2.09 (s, 3H), 2.04 (s, 3H).

EXAMPLE 5

2-[1-(4-chloro-(2,6-dimethylphenyl)-6-oxo-1,6-dihydro-3-pyridinyl]-1-(2,4-difluorophenyl)-2-oxoethyl 3-hydroxy-2-(hydroxymethyl)-2-methylpropanoate To a solution of the compound prepared in Example 4 (303 mg) in ethanol (6 mL) was added the compound prepared in Example A1 (122 mg) and the mixture was stirred at 70° C. for 12 hours. The reaction mixture was concentrated. To the obtained residue was added water, then the mixture was extracted with ethyl acetate. The obtained organic layer was dried and concentrated. The obtained residue was purified by column chromatography on silica gel (hexane:ethyl acetate=1:2) to give the title compound (269 mg) having the following physical data.
TLC: Rf 0.30 (hexane:ethyl acetate=1:2);
NMR: δ 1.19 (s, 3H), 1.93 (s, 3H), 2.06 (s, 3H), 2.74-2.88 (m, 1H), 2.92-3.08 (m, 1H), 3.68-3.81 (m, 2H), 3.83-4.04 (m, 2H), 6.67 (dd, J=9.9, 0.6 Hz, 1H), 6.84-7.02 (m, 3H), 7.21 (s, 2H), 7.34-7.51 (m, 1H), 7.89 (dd, J=9.9, 2.7 Hz, 1H), 8.02 (dd, J=2.7, 0.6 Hz, 1H).

EXAMPLE 6

1-(4-chloro-2,6-dimethylphenyl)-5-{5-(2,4-difluorophenyl)-2-[2-hydroxy-1-(hydroxymethyl)-1-methylethyl]-1,3-oxazol-4-yl}-2(1H)-pyridinone (compound 6a);

2-[4-[1-(4-chloro-2,6-dimethylphenyl)-6-oxo-1,6-dihydro-3-pyridinyl]-5-(2,4-difluorophenyl)-1,3-oxazol-2-yl]-3-hydroxy-2-methylpropyl acetate (compound 6b)

To a solution of the compound prepared in Example 5 (266 mg) in acetic acid (5 mL) was added ammonium acetate (788 mg) and the mixture was stirred at 100° C. for 3 hours. The reaction mixture was concentrated. To the obtained residue was added water, then the mixture was extracted with ethyl acetate. The obtained organic layer was dried and concentrated. The obtained residue was purified by preparative TLC (ethyl acetate) to give the compound of the present invention 6a (84 mg) and 6b (64 mg) having the following physical data.

Compound 6a:
TLC: Rf 0.28 (ethyl acetate);
NMR: δ 1.27 (s, 3H), 2.09 (s, 6H), 3.22 (t, J=6.3 Hz, 2H), 3.85-3.97 (m, 2H), 4.00-4.10 (m, 2H), 6.68 (dd, J=9.7, 0.7 Hz, 1H), 6.89-7.07 (m, 2H), 7.18 (s, 2H), 7.38 (d, J=2.7 Hz, 1H), 7.48-7.58 (m, 2H).

Compound 6b:
TLC: Rf 0.53 (ethyl acetate);
NMR: δ 1.40 (s, 3H), 2.07 (s, 3H), 2.09 (s, 6H), 3.06-3.21 (m, 1H), 3.78-3.93 (m, 2H), 4.36-4.49 (m, 2H), 6.67 (d, J=9.5 Hz, 1H), 6.89-7.07 (m, 2H), 7.18 (s, 2H), 7.40 (d, J=2.6 Hz, 1H), 7.45-7.56 (m, 2H).

EXAMPLE 7(1)~Example 7(39)

By the same procedure as a series of reactions of Example 3→Example 4→Example 5→Example 6, using the corresponding aniline compounds instead of 4-chloro-2,6-dimethylaniline and the corresponding sodium salts (said sodium salts were produced by the same procedure as a reaction of Example A1, using the commercial available carboxylic acids or the carboxylic acids prepared in Example A2~A13) instead of the compound prepared in Example A1, the compound of the present invention having the following physical data was obtained.

EXAMPLE 7(1)

1-(4-chloro-2,6-dimethylphenyl)-5-[5-(2,4-difluorophenyl)-2-(1-hydroxycyclopropyl)-1,3-oxazol-4-yl]-2(1H)-pyridinone TLC: Rf 0.32 (ethyl acetate:hexane=7:3);
NMR: δ 1.32-1.41 (m, 4H), 2.08 (s, 6H), 3.06-3.21 (m, 1H), 6.65 (dd, J=8.97, 1.28 Hz, 1H), 6.87-7.04 (m, 2H), 7.16 (s, 2H), 7.42-7.52 (m, 3H).

EXAMPLE 7(2)

1-(4-chloro-2,6-dimethylphenyl)-5-[5-(2,4-difluorophenyl)-2-(2-hydroxy-1,1-dimethylethyl)-1,3-oxazol-4-yl]-2(1H)-pyridinone TLC: Rf 0.22 (ethyl acetate:hexane=3:2);
NMR: δ 1.40 (s, 6H), 2.09 (s, 6H), 3.16 (br s, 1H), 3.75 (s, 2H), 6.67 (d, J=9.51 Hz, 1H), 6.89-7.07 (m, 2H), 7.18 (s, 2H), 7.38 (d, J=2.20 Hz, 1H), 7.46-7.56 (m, 2H).

EXAMPLE 7(3)

1-(4-chloro-2,6-dimethylphenyl)-5-{5-(2,4-difluorophenyl)-2-[(2-methoxyethoxy)methyl]-1,3-oxazol-4-yl}-2(1H)-pyridinone TLC: Rf 0.17 (ethyl acetate:hexane=3:2);
NMR: δ 2.08 (s, 6H), 3.38 (s, 3H), 3.57-3.63 (m, 2H), 3.74-3.81 (m, 2H), 4.68 (s, 2H), 6.66 (dd, J=9.33, 0.91 Hz, 1H), 6.88-7.07 (m, 2H), 7.16 (s, 2H), 7.44-7.62 (m, 3H).

EXAMPLE 7(4)

1-(4-chloro-2,6-dimethylphenyl)-5-[5-(2,4-difluorophenyl)-2-(2-hydroxy-2-methylpropyl)-1,3-oxazol-4-yl]-2(1H)-pyridinone TLC: Rf 0.30 (hexane:ethyl acetate=1:2);
NMR: δ 7.55-7.47 (m, 2H), 7.42 (m, 1H), 7.17 (s, 2H), 7.05-6.91 (m, 2H), 6.67 (dd, J=9.6, 0.6 Hz, 1H), 3.20 (br s, 1H), 2.98 (s, 2H), 2.08 (s, 6H), 1.37 (s, 6H).

EXAMPLE 7(5)

1-(2,6-difluorophenyl)-5-{5-(2,4-difluorophenyl)-2-[2-hydroxy-1-(hydroxymethyl)-1-methylethyl]-1,3-oxazol-4-yl}-2(1H)-pyridinone TLC: Rf 0.23 (ethyl acetate:hexane=4:1);
NMR: δ 1.27 (s, 3H), 3.21 (t, J=6.40 Hz, 2H), 3.91 (dd, J=11.16, 6.40 Hz, 2H), 4.05 (dd, J=11.16, 6.40 Hz, 2H), 6.64 (dd, J=9.70, 0.73 Hz, 1H), 6.90-7.14 (m, 4H), 7.38-7.61 (m, 4H).

EXAMPLE 7(6)

1-(4-chloro-2,6-dimethylphenyl)-5-[5-(2,4-difluorophenyl)-2-(1-hydroxy-1-methylethyl)-1,3-oxazol-4-yl]-2(1H)-pyridinone TLC: Rf 0.21 (ethyl acetate:hexane=3:2);
NMR: δ 1.69 (s, 6H), 2.09 (s, 6H), 2.65 (s, 1H), 6.67 (dd, J=9.51, 0.73 Hz, 1H), 6.90-7.06 (m, 2H), 7.16-7.19 (m, 2H), 7.44-7.58 (m, 3H).

EXAMPLE 7(7)

5-{5-(2,4-difluorophenyl)-2-[2-hydroxy-1-(hydroxymethyl)-1-methylethyl]-1,3-oxazol-4-yl}-1-(4-fluoro-2,6-dimethylphenyl)-2(1H)-pyridinone TLC: Rf 0.36 (ethyl acetate);
NMR: δ 1.27 (s, 3H), 2.10 (s, 6H), 3.24 (t, J=6.22 Hz, 2H), 3.90 (dd, J=10.79, 6.22 Hz, 2H), 4.04 (dd, J=10.79, 6.22 Hz, 2H), 6.66 (dd, J=9.61, 0.64 Hz, 1H), 6.85-7.05 (m, 4H), 7.38 (d, J=2.20 Hz, 1H), 7.46-7.56 (m, 2H).

EXAMPLE 7(8)

1-(4-chloro-2,6-dimethylphenyl)-5-{5-(2,4-difluorophenyl)-2-[2-methoxy-1-(methoxymethyl)ethyl]-1,3-oxazol-4-yl}-2(1H)-pyridinone TLC: Rf 0.48 (hexane:ethyl acetate=1:2);
NMR: δ 2.08 (s, 6H), 3.37 (s, 6H), 3.40-3.54 (m, 1H), 3.68-3.86 (m, 4H), 6.64 (d, J=9.51 Hz, 1H), 6.83-7.06 (m, 2H), 7.15 (s, 2H), 7.42 (d, J=2.38 Hz, 1H), 7.45-7.58 (m, 2H).

EXAMPLE 7(9a)

1-(4-chloro-2,6-dimethylphenyl)-5-{5-(2,4-difluorophenyl)-2-[1,2-dihydroxy-1-(hydroxymethyl)ethyl]-1,3-oxazol-4-yl}-2(1H)-pyridinone TLC: Rf 0.42 (ethyl acetate:methanol=19:1);
NMR: δ 2.08 (s, 6H), 2.46-2.71 (m, 2H), 3.62-3.80 (m, 1H), 3.90-4.10 (m, 4H), 6.68 (d, J=9.7 Hz, 1H), 6.89-7.07 (m, 2H), 7.18 (s, 2H), 7.41 (d, J=2.0 Hz, 1H), 7.47-7.60 (m, 2H).

EXAMPLE 7(9b)

2-[4-[1-(4-chloro-2,6-dimethylphenyl)-6-oxo-1,6-dihydro-3-pyridinyl]-5-(2,4-difluorophenyl)-1,3-oxazol-2-yl]-2,3-dihydroxypropyl acetate TLC: Rf 0.61 (ethyl acetate:methanol=19:1);
NMR: δ 2.04-2.11 (m, 9H), 2.69 (t, J=7.7 Hz, 1H), 3.60 (s, 1H), 3.86-4.10 (m, 2H), 4.44-4.57 (m, 2H), 6.67 (d, J=9.0 Hz, 1H), 6.89-7.08 (m, 2H), 7.18 (s, 2H), 7.44 (d, J=1.8 Hz, 1H), 7.46-7.59 (m, 2H).

EXAMPLE 7(9c)

1-(4-chloro-2,6-dimethylphenyl)-5-{5-(2,4-difluorophenyl)-2-[1,2-dihydroxy-1-(hydroxymethyl)ethyl]-1H-imidazol-4-yl}-2(1H)-pyridinone TLC: Rf 0.19 (ethyl acetate:methanol=19:1);
NMR (CD$_3$OD): δ 2.01 (s, 6H), 3.87 (s, 4H), 6.66 (d, J=9.5 Hz, 1H), 6.97-7.12 (m, 2H), 7.23 (s, 2H), 7.35 (d, J=2.0 Hz, 1H), 7.45-7.58 (m, 1H), 7.67 (dd, J=9.5, 2.4 Hz, 1H).

EXAMPLE 7(10)

1-(4-chloro-2,6-dimethylphenyl)-5-{5-(2,4-difluorophenyl)-2-[2-methoxy-1-(methoxymethyl)-1-methylethyl]-1,3-oxazol-4-yl}-2(1H)-pyridinone TLC: Rf 0.35 (hexane:ethyl acetate=1:1);
NMR: δ 7.57-7.46 (m, 2H), 7.40 (d, J=2.7 Hz, 1H), 7.17 (s, 2H), 7.04-6.88 (m, 2H), 6.67 (d, J=9.6 Hz, 1H), 3.68 (s, 4H), 3.36 (s, 6H), 2.08 (s, 6H), 1.41 (s, 3H).

EXAMPLE 7(11)

1-(4-chloro-2,6-dimethylphenyl)-5-[5-(2,4-difluorophenyl)-2-(hydroxymethyl)-1,3-oxazol-4-yl]-2(1H)-pyridinone TLC: Rf 0.20 (ethyl acetate:hexane=7:3);
NMR: δ 2.08 (s, 6H), 2.21-2.36 (m, 1H), 4.79 (s, 2H), 6.67 (d, J=10.43 Hz, 1H), 6.90-7.07 (m, 2H), 7.16-7.18 (m, 2H), 7.46-7.59 (m, 3H).

EXAMPLE 7(12)

5-[5-(2,4-difluorophenyl)-2-(1-hydroxy-1-methylethyl)-1,3-oxazol-4-yl]-1-(4-fluoro-2,6-dimethylphenyl)-2-(1H)-pyridinone TLC: Rf 0.32 (hexane:ethyl acetate=1:2);
NMR: δ 7.57-7.48 (m, 3H), 7.06-6.87 (m, 4H), 6.67 (dd, J=9.0, 1.2 Hz, 1H), 2.68 (s, 1H), 2.10 (s, 6H), 1.69 (s, 6H).

EXAMPLE 7(13)

5-[5-(2,4-difluorophenyl)-2-(1-hydroxy-2-methylpropyl)-1,3-oxazol-4-yl]-1-(4-fluoro-2,6-dimethylphenyl)-2(1H)-pyridinone TLC: Rf 0.27 (ethyl acetate:hexane=3:2);
NMR: δ 1.00-1.05 (m, 6H), 2.10 (s, 6H), 2.13-2.29 (m, 1H), 2.46-2.55 (m, 1H), 4.56-4.63 (m, 1H), 6.66 (d, J=10.43 Hz, 1H), 6.84-7.07 (m, 4H), 7.45-7.57 (m, 3H).

EXAMPLE 7(14)

5-[5-(2,4-difluorophenyl)-2-(2-hydroxy-2-methylpropyl)-1,3-oxazol-4-yl]-1-(4-fluoro-2,6-dimethylphenyl)-2(1H)-pyridinone TLC: Rf 0.21 (hexane:ethyl acetate=1:2);
NMR: δ 7.55-7.44 (m, 3H), 7.05-6.86 (m, 4H), 6.67 (dd, J=9.6, 0.9 Hz, 1H), 3.22 (br s, 1H), 2.98 (s, 2H), 2.09 (s, 6H), 1.36 (s, 6H).

EXAMPLE 7(15)

5-[5-(2,4-difluorophenyl)-2-(1-hydroxyethyl)-1,3-oxazol-4-yl]-1-(4-fluoro-2,6-dimethylphenyl)-2(1H)-pyridinone TLC: Rf 0.39 (ethyl acetate:hexane=4:1);
NMR: δ 1.66 (d, J=6.59 Hz, 3H), 2.09 (s, 6H), 2.50-2.60 (m, 1H), 4.93-5.06 (m, 1H), 6.67 (d, J=10.25 Hz, 1H), 6.83-7.08 (m, 4H), 7.45-7.62 (m, 3H).

EXAMPLE 7(16)

5-[5-(2,4-difluorophenyl)-2-(1-ethyl-1-hydroxypropyl)-1,3-oxazol-4-yl]-1-(4-fluoro-2,6-dimethylphenyl)-2(1H)-pyridinone TLC: Rf 0.25 (ethyl acetate:hexane=1:1);
NMR: δ 0.90 (t, J=7.41 Hz, 6H), 1.83-2.02 (m, 4H), 2.11 (s, 6H), 2.93 (s, 1H), 6.66 (d, J=10.43 Hz, 1H), 6.86-7.06 (m, 4H), 7.45-7.56 (m, 3H).

EXAMPLE 7(17)

5-{5-(2,4-difluorophenyl)-2-[2-hydroxy-1,1-bis(hydroxymethyl)ethyl]-1,3-oxazol-4-yl}-1-(4-fluoro-2,6-dimethylphenyl)-2(1H)-pyridinone TLC: Rf 0.18 (dichloromethane:methanol=19:1);
NMR: δ 2.09 (s, 6H), 2.57-3.13 (m, 3H), 4.08 (s, 6H), 6.67 (d, J=9.7 Hz, 1H), 6.80-7.08 (m, 4H), 7.37-7.43 (m, 1H), 7.44-7.57 (m, 2H).

EXAMPLE 7(18)

5-[5-(2,4-difluorophenyl)-2-(2,2,2-trifluoro-1-hydroxy-1-methylethyl)-1,3-oxazol-4-yl]-1-(4-fluoro-2,6-dimethylphenyl)-2(1H)-pyridinone TLC: Rf 0.30 (hexane:ethyl acetate=1:1);
NMR: δ 7.58-7.46 (m, 3H), 7.08-6.88 (m, 4H), 6.68 (d, J=10.5 Hz, 1H), 3.92 (br s, 1H), 2.10 (s, 3H), 1.83 (s, 3H).

EXAMPLE 7(19)

5-[5-(2,4-difluorophenyl)-2-(1-hydroxy-1-methylpropyl)-1,3-oxazol-4-yl]-1-(4-fluoro-2,6-dimethylphenyl)-2(1H)-pyridinone TLC: Rf 0.45 (hexane:ethyl acetate=1:2);
NMR: δ 0.93 (t, J=7.4 Hz, 3H), 1.63 (s, 3H), 1.85-2.03 (m, 2H), 2.10 (s, 6H), 2.80 (s, 1H), 6.58-6.76 (m, 1H), 6.81-7.10 (m, 4H), 7.41-7.61 (m, 3H).

EXAMPLE 7(20)

5-[5-(2,4-difluorophenyl)-2-(2-hydroxy-2-methylbutyl)-1,3-oxazol-4-yl]-1-(4-fluoro-2,6-dimethylphenyl)-2(1H)-pyridinone TLC: Rf 0.25 (hexane:ethyl acetate=1:2);
NMR: δ 7.55-7.45 (m, 3H), 7.05-6.87 (m, 4H), 6.67 (dd, J=9.3, 0.9 Hz, 1H), 3.16 (br s, 1H), 3.00 (dd, J=22.8, 7.5 Hz, 1H), 2.92 (dd, J=22.8, 7.5 Hz, 1H), 2.10 (s, 6H), 1.66-1.50 (m, 2H), 1.28 (s, 3H), 0.98 (t, J=7.8 Hz, 3H).

EXAMPLE 7(21)

1-(2,6-difluorophenyl)-5-[5-(2,4-difluorophenyl)-2-(1-hydroxy-1-methylethyl)-1,3-oxazol-4-yl]-2(1H)-pyridinone TLC: Rf 0.21 (ethyl acetate:hexane=1:1);
NMR: δ 1.68 (s, 6H), 2.68 (s, 1H), 6.62 (dd, J=9.70, 0.73 Hz, 1H), 6.88-7.12 (m, 4H), 7.35-7.57 (m, 3H), 7.63-7.67 (m, 1H).

EXAMPLE 7(22)

1-(4-chloro-2,6-dimethylphenyl)-5-[5-(2,4-difluorophenyl)-2-(1,2-dihydroxy-1,2-dimethylpropyl)-1,3-oxazol-4-yl]-2(1H)-pyridinone TLC: Rf 0.22 (hexane:ethyl acetate=1:2);
NMR: δ 7.56-7.48 (m, 2H), 7.42 (m, 1H), 7.18 (s, 2H), 7.06-6.91 (m, 2H), 6.67 (dd, J=9.6, 0.9 Hz, 1H), 3.59 (s, 1H), 3.11 (s, 1H), 2.09 (s, 6H), 1.65 (s, 3H), 1.36 (s, 3H), 1.24 (s, 3H).

EXAMPLE 7(23)

Methyl 5-[4-[1-(4-chloro-2,6-dimethylphenyl)-6-oxo-1,6-dihydro-3-pyridinyl]-5-(2,4-difluorophenyl)-1,3-oxazol-2-yl]pentanoate TLC: Rf 0.33 (hexane:ethyl acetate=1:1);
NMR: δ 7.58-7.45 (m, 2H), 7.45-7.40 (m, 1H), 7.18 (s, 2H), 7.05-6.88 (m, 2H), 6.66 (dd, J=9.3, 0.6 Hz, 1H), 3.66 (s, 3H), 2.83 (t, J=7.5 Hz, 2H), 2.38 (t, J=7.2 Hz, 2H), 2.09 (s, 6H), 1.90-1.70 (m, 4H).

EXAMPLE 7(24)

1-(4-chloro-2,6-dimethylphenyl)-5-{5-(2,4-difluorophenyl)-2-[(4S)-2,2-dimethyl-1,3-dioxolan-4-yl]-1,3-oxazol-4-yl}-2(1H)-pyridinone TLC: Rf 0.31 (ethyl acetate:hexane=1:1);
NMR: δ 1.47 (s, 3H), 1.54 (s, 3H), 2.08 (s, 6H), 4.37 (d, J=6.31 Hz, 2H), 5.19 (t, J=6.31 Hz, 1H), 6.66 (dd, J=9.51, 0.73 Hz, 1H), 6.89-7.07 (m, 2H), 7.17 (s, 2H), 7.45 (d, J=1.83 Hz, 1H), 7.47-7.59 (m, 2H).

EXAMPLE 7(25a)

5-{5-(2,4-difluorophenyl)-2-[(4R,5S)-2,2,5-trimethyl-1,3-dioxolan-4-yl]-1,3-oxazol-4-yl}-1-(4-fluoro-2,6-dimethylphenyl)-2(1H)-pyridinone

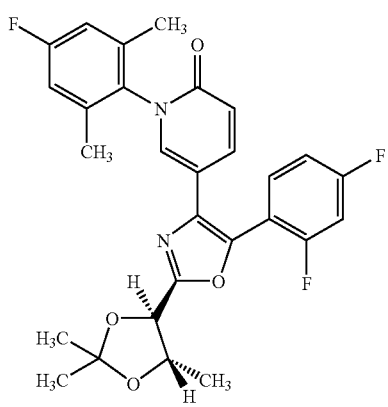

TLC: Rf 0.44 (hexane:ethyl acetate=1:1);
NMR: δ 7.58-7.47 (m, 3H), 7.06-6.86 (m, 4H), 6.67 (dd, J=9.3, 0.9 Hz, 1H), 4.63-4.50 (m, 2H), 2.09 (s, 6H), 1.52 (s, 6H), 1.44 (d, J=6.0 Hz, 3H).

EXAMPLE 7(25b)

5-{5-(2,4-difluorophenyl)-2-[(4S,5S)-2,2,5-trimethyl-1,3-dioxolan-4-yl]-1H-imidazol-4-yl}-1-(4-fluoro-2,6-dimethylphenyl)-2(1H)-pyridinone

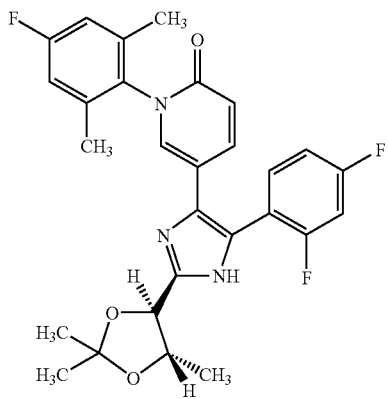

TLC: Rf 0.09 (hexane:ethyl acetate=1:1);
NMR: δ 9.78 (br s, 1H), 7.57 (m, 1H), 7.40-7.30 (m, 2H), 7.00-6.80 (m, 4H), 6.64 (dd, J=9.6, 0.6 Hz, 1H), 4.63 (d, J=8.4 Hz, 1H), 4.19 (m, 1H), 2.06 (s, 3H), 2.05 (s, 3H), 1.60-1.40 (m, 9H).

EXAMPLE 7(26)

1-(4-chloro-2,6-dimethylphenyl)-5-[5-(2,4-difluorophenyl)-2-(2-methyl-1-propen-1-yl)-1,3-oxazol-4-yl]-2(1H)-pyridinone TLC: Rf 0.37 (hexane:ethyl acetate=3:2);
NMR: δ 1.99 (s, 3H), 2.08 (s, 6H), 2.24 (s, 3H), 6.11 (s, 1H), 6.66 (d, J=9.5 Hz, 1H), 6.84-7.05 (m, 2H), 7.15 (s, 2H), 7.40 (d, J=2.6 Hz, 1H), 7.45-7.58 (m, 2H).

EXAMPLE 7(27)

5-[5-(2,4-difluorophenyl)-2-(cis-4-hydroxycyclohexyl)-1,3-oxazol-4-yl]-1-(4-fluoro-2,6-dimethylphenyl)-2(1H)-pyridinone

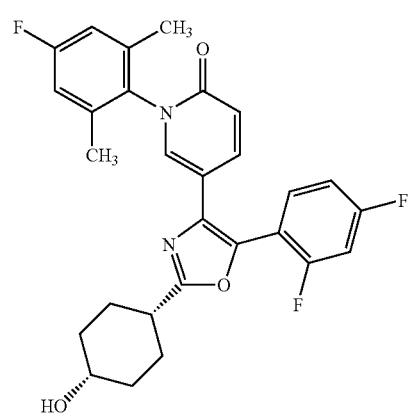

TLC: Rf 0.22 (ethyl acetate);
NMR: δ 1.30-1.39 (m, 1H), 1.66-1.96 (m, 6H), 2.05-2.25 (m, 8H), 2.86-3.00 (m, 1H), 3.95-4.05 (m, 1H), 6.66 (d, J=9.70 Hz, 1H), 6.83-7.06 (m, 4H), 7.41-7.57 (m, 3H).

EXAMPLE 7(28)

5-[5-(2,4-difluorophenyl)-2-(cis-4-hydroxycyclohexyl)-1,3-oxazol-4-yl]-1-(2,6-dimethylphenyl)-2(1H)-pyridinone TLC: Rf 0.25 (ethyl acetate);
NMR: δ 1.65-1.95 (m, 6H), 2.06-2.25 (m, 8H), 2.85-3.02 (m, 1H), 3.90-4.07 (m, 1H), 6.67 (dd, J=9.5, 0.7 Hz, 1H), 6.88-7.05 (m, 2H), 7.13-7.20 (m, 2H), 7.20-7.31 (m, 1H), 7.44-7.57 (m, 3H).

EXAMPLE 7(29)

1-(4-chloro-2,6-dimethylphenyl)-5-[5-(2,4-difluorophenyl)-2-(cis-4-hydroxycyclohexyl)-1,3-oxazol-4-yl]-2(1H)-pyridinone TLC: Rf 0.26 (ethyl acetate);

NMR: δ 1.30-1.38 (m, 1H), 1.65-1.95 (m, 6H), 2.06-2.25 (m, 8H), 2.86-3.01 (m, 1H), 3.94-4.07 (m, 1H), 6.66 (dd, J=9.61, 0.64 Hz, 1H), 6.81-7.08 (m, 2H), 7.17 (s, 2H), 7.42 (d, J=2.01 Hz, 1H), 7.46-7.57 (m, 2H).

EXAMPLE 7(30)

rel-1-(4-chloro-2,6-dimethylphenyl)-5-{5-(2,4-difluorophenyl)-2-[(3R,4S,5R)-3,4,5-trihydroxy-1-cyclohexen-1-yl]-1,3-oxazol-4-yl}-2(1H)-pyridinone TLC: Rf 0.29 (ethyl acetate: methanol=19:1);

NMR: δ 2.07 (s, 6H), 2.36-2.70 (m, 3H), 2.83-3.00 (m, 1H), 3.20 (dd, J=17.4, 5.5 Hz, 1H), 3.67 (dd, J=9.8, 4.8 Hz, 1H), 4.00-4.11 (m, 1H), 4.47-4.55 (m, 1H), 6.67 (d, J=9.5 Hz, 1H), 6.77 (dd, J=4.9, 1.6 Hz, 1H), 6.88-7.06 (m, 2H), 7.16 (s, 2H), 7.43 (d, J=2.6 Hz, 1H), 7.46-7.57 (m, 2H).

EXAMPLE 7(31)

5-{5-(2,4-difluorophenyl)-2-[(3R,4S,5R)-3,4,5-trihydroxy-1-cyclohexen-1-yl]-1,3-oxazol-4-yl}-1-(4-fluoro-2,6-dimethylphenyl)-2(1H)-pyridinone

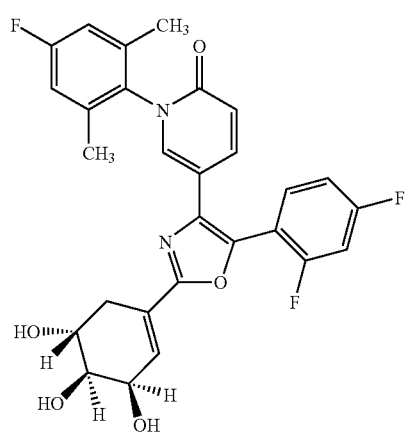

TLC: Rf 0.44 (ethyl acetate: methanol=19:1);

NMR: δ 2.08 (s, 6H), 2.34-2.72 (m, 3H), 2.82-2.99 (m, 1H), 3.21 (dd, J=17.5, 5.6 Hz, 1H), 3.67 (dd, J=9.5, 4.2 Hz, 1H), 3.99-4.10 (m, 1H), 4.52 (t, J=4.2 Hz, 1H), 6.67 (d, J=9.5 Hz, 1H), 6.77 (dd, J=4.9, 1.6 Hz, 1H), 6.81-7.06 (m, 4H), 7.45 (d, J=2.6 Hz, 1H), 7.47-7.57 (m, 2H).

EXAMPLE 7(32)

1-(4-chloro-2,6-dimethylphenyl)-5-{5-(2,4-difluorophenyl)-2-[(1S,3R,4S,5R)-1,3,4,5-tetrahydroxycyclohexyl]-1,3-oxazol-4-yl}-2(1H)-pyridinone

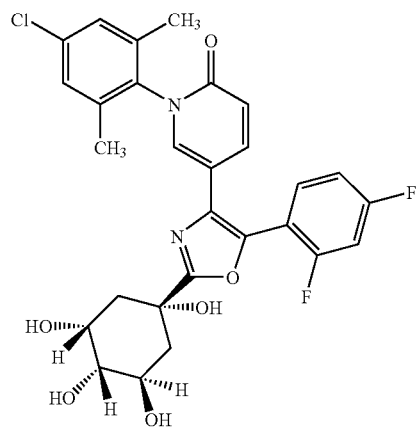

TLC: Rf 0.16 (ethyl acetate: methanol=19:1);

NMR (CD₃OD): δ 2.04 (s, 6H), 2.12 (dd, J=13.6, 8.7 Hz, 1H), 2.30 (d, J=4.7 Hz, 1H), 2.39 (dd, J=13.6, 4.7 Hz, 1H), 3.51 (dd, J=7.8, 3.2 Hz, 1H), 4.03-4.20 (m, 3H), 6.69 (dd, J=9.5, 0.7 Hz, 1H), 7.08-7.19 (m, 2H), 7.26 (s, 2H), 7.60 (d, J=1.8 Hz, 1H), 7.64-7.74 (m, 2H).

EXAMPLE 7(33)

5-[2-(3-cyclopenten-1-yl)-5-(2,4-difluorophenyl)-1,3-oxazol-4-yl]-1-(4-fluoro-2,6-dimethylphenyl)-2(1H)-pyridinone TLC: Rf 0.26 (hexane:ethyl acetate=3:2);

NMR: δ 2.09 (s, 6H), 2.80-2.88 (m, 4H), 3.56-3.74 (m, 1H), 5.70-5.80 (m, 2H), 6.66 (dd, J=9.5, 0.7 Hz, 1H), 6.83-7.06 (m, 4H), 7.44 (d, J=2.0 Hz, 1H), 7.46-7.58 (m, 2H).

EXAMPLE 7(34)

5-{5-(2,4-difluorophenyl)-2-[(1S)-1-hydroxy-1-phenylethyl]-1,3-oxazol-4-yl}-1-(4-fluoro-2,6-dimethylphenyl)-2(1H)-pyridinone TLC: Rf 0.32 (hexane:ethyl acetate=1:1);

NMR: δ 2.00 (s, 3H), 2.09 (s, 3H), 2.10 (s, 3H), 3.38 (s, 1H), 6.60-6.74 (m, 1H), 6.81-7.07 (m, 4H), 7.26-7.43 (m, 3H), 7.43-7.61 (m, 5H).

EXAMPLE 7(35)

5-{5-(2,4-difluorophenyl)-2-[(1R)-1-hydroxy-1-phenylethyl]-1,3-oxazol-4-yl}-1-(4-fluoro-2,6-dimethylphenyl)-2(1H)-pyridinone TLC: Rf 0.32 (hexane:ethyl acetate=1:1);
NMR: δ 7.55-7.31 (m, 8H), 7.04-6.85 (m, 4H), 6.66 (m, 1H), 3.37 (s, 1H), 2.10 (s, 3H), 2.09 (s, 3H), 2.00 (s, 3H).

EXAMPLE 7(36)

5-[5-(2,4-difluorophenyl)-2-(tetrahydro-2H-pyran-4-yl)-1,3-oxazol-4-yl]-1-(4-fluoro-2,6-dimethylphenyl)-2(1H)-pyridinone

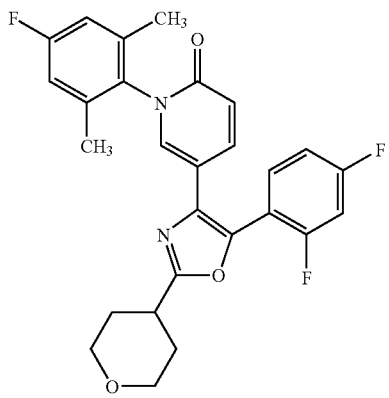

TLC: Rf 0.26 (hexane:ethyl acetate=1:2);
NMR: δ 7.55-7.43 (m, 3H), 7.04-6.86 (m, 4H), 6.67 (dd, J=9.3, 0.6 Hz, 1H), 4.05 (dt, J=11.7, 3.3 Hz, 2H), 3.58-3.49 (m, 2H), 3.09 (m, 1H), 2.10 (s, 6H), 2.05-1.90 (m, 4H).

EXAMPLE 7(37)

1-(4-bromo-2,6-dimethylphenyl)-5-[5-(2,4-difluorophenyl)-2-(tetrahydro-2H-pyran-4-yl)-1,3-oxazol-4-yl]-2(1H)-pyridinone TLC: Rf 0.48 (ethyl acetate);
NMR: δ 1.93-2.05 (m, 4H), 2.08 (s, 6H), 3.03-3.15 (m, 1H), 3.49-3.59 (m, 2H), 4.01-4.09 (m, 2H), 6.67 (d, J=9.5 Hz, 1H), 6.89-7.05 (m, 2H), 7.33 (s, 2H), 7.40-7.43 (m, 1H), 7.46-7.55 (m, 2H).

EXAMPLE 7(38)

1-(4-chloro-2,6-dimethylphenyl)-5-{5-(2,4-difluorophenyl)-2-[4-(hydroxymethyl)tetrahydro-2H-pyran-4-yl]-1,3-oxazol-4-yl}-2(1H)-pyridinone TLC: Rf 0.14 (hexane:ethyl acetate=1:4);
NMR: δ 7.55-7.47 (m, 2H), 7.41 (m, 1H), 7.18 (s, 2H), 7.05-6.92 (m, 2H), 6.68 (dd, J=9.6, 0.6 Hz, 1H), 3.94-3.80 (m, 2H), 3.83 (s, 2H), 3.74-3.60 (m, 2H), 2.32-2.20 (m, 2H), 2.09 (s, 6H), 1.90-1.75 (m, 2H), 1.59 (br s, 1H).

EXAMPLE 7(39)

1-(2,6-difluorophenyl)-5-{5-(2,4-difluorophenyl)-2-[1,2-dihydroxy-1-(hydroxymethyl)ethyl]-1,3-oxazol-4-yl}-2(1H)-pyridinone TLC: Rf 0.34 (ethyl acetate);
NMR: δ 3.94 (d, J=11.73 Hz, 2H), 4.06 (d, J=11.73 Hz, 2H), 6.62 (d, J=9.53 Hz, 1H), 6.90-7.13 (m, 4H), 7.37-7.56 (m, 3H), 7.59 (d, J=2.57 Hz, 1H).

EXAMPLE 8

2-[1-(4-chloro-2,6-dimethylphenyl)-6-oxo-1,6-dihydro-3-pyridinyl]-1-(2,4-difluorophenyl)-2-oxoethyl 2,2-bis(hydroxymethyl)butanoate To a solution of 20% sodium ethoxide/ethanol solution (146 mg) in ethanol (4.3 mL) was added 2,2-bis(hydroxymethyl)butyric acid (63 mg) and the mixture was stirred at 70° C. for 50 minutes. To the reaction mixture was added the compound prepared in Example 4 (200 mg) and the mixture was stirred for 50 minutes. The reaction mixture was poured into cold water and extracted with ethyl acetate. The obtained organic layer was washed with water and brine, dried and concentrated to give the title compound (232 mg) having the following physical data.

TLC: Rf 0.29 (ethyl acetate:hexane=2:1);
NMR: δ 0.88 (t, J=7.6 Hz, 3H), 1.60-1.69 (m, 2H), 1.93 (s, 3H), 2.06 (s, 3H), 2.58-2.82 (m, 1H), 3.01-3.23 (m, 1H), 3.75 (d, J=11.2 Hz, 1H), 3.85 (d, J=11.3 Hz, 1H), 3.93 (d, J=11.3 Hz, 1H), 4.10 (d, J=11.2 Hz, 1H), 6.67 (dd, J=9.8, 0.5 Hz, 1H), 6.86-7.02 (m, 3H), 7.18-7.24 (m, 2H), 7.38-7.48 (m, 1H), 7.86-7.93 (m, 1H), 8.00-8.04 (m, 1H).

EXAMPLE 9

5-[2-[1,1-bis(hydroxymethyl)propyl]-5-(2,4-difluorophenyl)-1,3-oxazol-4-yl]-1-(4-chloro-2,6-dimethylphenyl)-2(1H)-pyridinone By the same procedure as a reaction of Example 6, using the compound prepared in Example 8 instead of the compound prepared in Example 5, the compound of the present invention having the following physical data was obtained.

TLC: Rf 0.33 (ethyl acetate);
NMR: δ 0.87 (t, J=7.7 Hz, 3H), 1.73 (q, J=7.7 Hz, 2H), 2.09 (s, 6H), 3.16 (t, J=6.6 Hz, 2H), 3.94 (dd, J=11.2, 6.6 Hz, 2H), 4.17 (dd, J=11.2, 6.6 Hz, 2H), 6.68 (dd, J=9.5, 0.5 Hz, 1H), 6.90-7.06 (m, 2H), 7.18 (d, J=0.5 Hz, 2H), 7.38 (d, J=2.6 Hz, 1H), 7.48-7.57 (m, 2H).

EXAMPLE 10(1)~Example 10(11)

By the same procedure as a series of reactions of Example 3→Example 4→Example 8→Example 6, using the corresponding aniline compounds instead of 4-chloro-2,6-dimethylaniline and the corresponding carboxylic acids (said carboxylic acids were commercial available, or the compounds prepared in Example A14~A16) instead of the compound prepared in Example A1, the compound of the present invention having the following physical data was obtained.

EXAMPLE 10(1)

5-{5-(2,4-difluorophenyl)-2-[2-hydroxy-1-(hydroxymethyl)-1-methylethyl]-1,3-oxazol-4-yl}-1-[2,6-dimethyl-4-(methylthio)phenyl]-2(1H)-pyridinone TLC: Rf 0.49 (ethyl acetate:methanol=19:1);
NMR: δ 1.27 (s, 3H), 2.08 (s, 6H), 2.49 (s, 3H), 3.19-3.29 (m, 2H), 3.91 (d, J=11.7 Hz, 2H), 4.05 (d, J=11.7 Hz, 2H), 6.68 (dd, J=9.6, 0.6 Hz, 1H), 6.90-7.03 (m, 2H), 7.04 (s, 2H), 7.38-7.42 (m, 1H), 7.48-7.57 (m, 2H).

EXAMPLE 10(2)

1-(4-bromo-2,6-dimethylphenyl)-5-{5-(2,4-difluorophenyl)-2-[2-hydroxy-1-(hydroxymethyl)-1-methylethyl]-1,3-oxazol-4-yl}-2(1H)-pyridinone TLC: Rf 0.46 (ethyl acetate:methanol=19:1);

NMR: δ 1.27 (s, 3H), 2.09 (s, 6H), 3.17-3.27 (m, 2H), 3.91 (d, J=11.4 Hz, 2H), 4.05 (d, J=11.4 Hz, 2H), 6.68 (dd, J=9.5, 0.5 Hz, 1H), 6.90-7.07 (m, 2H), 7.34 (s, 2H), 7.36-7.39 (m, 1H), 7.48-7.57 (m, 2H).

EXAMPLE 10(3)

1-(4-bromo-2,6-dimethylphenyl)-5-[5-(2,4-difluorophenyl)-2-(1-hydroxy-1-methylethyl)-1,3-oxazol-4-yl]-2(1H)-pyridinone TLC: Rf 0.68 (ethyl acetate:methanol=19:1);

NMR: δ 1.69 (s, 6H), 2.09 (s, 6H), 2.65 (s, 1H), 6.66 (d, J=9.5 Hz, 1H), 6.90-7.07 (m, 2H), 7.34 (s, 2H), 7.43-7.59 (m, 3H).

EXAMPLE 10(4)

5-{5-(2,4-difluorophenyl)-2-[1-hydroxy-2-methoxy-1-(methoxymethyl)ethyl]-1,3-oxazol-4-yl}-1-(4-fluoro-2,6-dimethylphenyl)-2(1H)-pyridinone TLC: Rf 0.21 (hexane:ethyl acetate=1:2);

NMR: δ 2.09 (s, 6H), 3.42 (s, 6H), 3.45-3.52 (m, 1H), 3.73-3.87 (m, 4H), 6.65 (d, J=10.4 Hz, 1H), 6.83-7.08 (m, 4H), 7.44-7.60 (m, 3H).

EXAMPLE 10(5)

5-{5-(2,4-difluorophenyl)-2-[1,2-dihydroxy-1-(methoxymethyl)ethyl]-1,3-oxazol-4-yl}-1-(4-fluoro-2,6-dimethylphenyl)-2(1H)-pyridinone TLC: Rf 0.23 (ethyl acetate);

NMR: δ 2.09 (s, 6H), 2.62-2.79 (m, 1H), 3.42 (s, 3H), 3.56-3.61 (m, 1H), 3.82 (s, 2H), 3.86-4.08 (m, 2H), 6.65 (d, J=9.3 Hz, 1H), 6.82-7.07 (m, 4H), 7.42-7.59 (m, 3H).

EXAMPLE 10(6)

1-(4-chloro-2,6-dimethylphenyl)-5-[5-(2,4-difluorophenyl)-2-(1,2-dihydroxy-1-methylethyl)-1,3-oxazol-4-yl]-2(1H)-pyridinone TLC: Rf 0.40 (ethyl acetate);

NMR: δ 1.60 (s, 3H), 2.09 (s, 6H), 2.76 (dd, J=8.1, 5.9 Hz, 1H), 3.37 (s, 1H), 3.72 (dd, J=11.5, 8.1 Hz, 1H), 4.06 (dd, J=11.5, 5.9 Hz, 1H), 6.67 (d, J=9.5 Hz, 1H), 6.90-7.07 (m, 2H), 7.18 (s, 2H), 7.40-7.43 (m, 1H), 7.47-7.60 (m, 2H).

EXAMPLE 10(7)

1-(4-chloro-2,6-dimethylphenyl)-5-{5-(2,4-difluorophenyl)-2-[(2S)-tetrahydro-2-furanyl]-1,3-oxazol-4-yl}-2(1H)-pyridinone

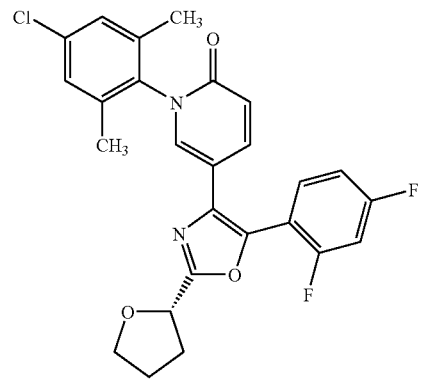

TLC: Rf 0.37 (ethyl acetate:hexane=2:1);

NMR: δ 1.98-2.21 (m, 8H), 2.34 (q, J=6.9 Hz, 2H), 3.91-4.11 (m, 2H), 5.04 (t, J=6.9 Hz, 1H), 6.65 (dd, J=9.5, 0.5 Hz, 1H), 6.88-7.05 (m, 2H), 7.15 (s, 2H), 7.42-7.57 (m, 3H).

EXAMPLE 10(8)

1-(4-chloro-2,6-dimethylphenyl)-5-{5-(2,4-difluorophenyl)-2-[(2R)-tetrahydro-2-furanyl]-1,3-oxazol-4-yl}-2(1H)-pyridinone TLC: Rf 0.37 (ethyl acetate:hexane=2:1);

NMR: δ 1.98-2.20 (m, 8H), 2.34 (q, J=6.9 Hz, 2H), 3.91-4.10 (m, 2H), 5.04 (t, J=6.9 Hz, 1H), 6.65 (dd, J=9.4, 0.6 Hz, 1H), 6.88-7.04 (m, 2H), 7.15 (s, 2H), 7.43-7.57 (m, 3H).

EXAMPLE 10(9)

1-(4-chloro-2,6-dimethylphenyl)-5-[5-(2,4-difluorophenyl)-2-(tetrahydro-2H-thiopyran-4-yl)-1,3-oxazol-4-yl]-2(1H)-pyridinone TLC: Rf 0.44 (ethyl acetate:hexane=2:1);

NMR: δ 2.00-2.17 (m, 8H), 2.34-2.46 (m, 2H), 2.73-2.80 (m, 4H), 2.88-2.99 (m, 1H), 6.67 (d, J=9.7 Hz, 1H), 6.89-7.06 (m, 2H), 7.17 (s, 2H), 7.40-7.43 (m, 1H), 7.45-7.56 (m, 2H).

EXAMPLE 10(10)

5-[5-(2,4-difluorophenyl)-2-(tetrahydro-2H-thiopyran-4-yl)-1,3-oxazol-4-yl]-1-(4-fluoro-2,6-dimethylphenyl)-2(1H)-pyridinone TLC: Rf 0.39 (ethyl acetate:hexane=2:1);

NMR: δ 1.99-2.14 (m, 8H), 2.34-2.45 (m, 2H), 2.72-2.79 (m, 4H), 2.87-2.99 (m, 1H), 6.65 (dd, J=9.6, 0.6 Hz, 1H), 6.86 (d, J=9.0 Hz, 2H), 6.89-7.04 (m, 2H), 7.40-7.44 (m, 1H), 7.44-7.54 (m, 2H).

EXAMPLE 10(11)

1-(4-bromo-2,6-dimethylphenyl)-5-[5-(2,4-difluorophenyl)-2-(tetrahydro-2H-thiopyran-4-yl)-1,3-oxazol-4-yl]-2(1H)-pyridinone TLC: Rf 0.52 (ethyl acetate:hexane=2:1);
NMR: δ 2.00-2.15 (m, 8H), 2.35-2.45 (m, 2H), 2.72-2.79 (m, 4H), 2.88-2.98 (m, 1H), 6.67 (dd, J=9.6, 0.5 Hz, 1H), 6.89-7.04 (m, 2H), 7.33 (s, 2H), 7.39-7.42 (m, 1H), 7.45-7.54 (m, 2H).

EXAMPLE 11

1-(4-chloro-2,6-dimethylphenyl)-5-{5-(2,4-difluorophenyl)-2-[1,2-dimethoxy-1-(methoxymethyl)ethyl]-1,3-oxazol-4-yl}-2(1H)-pyridinone To a solution of the compound prepared in Example 7(9a) (79 mg) and iodomethane (111 mg) in tetrahydrofuran (6 mL) was added sodium hydride (60% in oil, 13 mg) and the mixture was stirred at room temperature for 12 hours. To the reaction mixture was added an aqueous solution of ammonium chloride and the mixture was extracted with ethyl acetate. The obtained organic layer was dried and concentrated. The obtained residue was purified by preparative TLC (ethyl acetate) to give the compound of the present invention (30 mg) having the following physical data.
TLC: Rf 0.71 (ethyl acetate);
NMR: δ 2.09 (s, 6H), 3.30 (s, 3H), 3.40-3.45 (m, 6H), 3.83-4.02 (m, 4H), 6.67 (d, J=9.7 Hz, 1H), 6.88-7.07 (m, 2H), 7.18 (s, 2H), 7.45 (d, J=2.6 Hz, 1H), 7.48-7.59 (m, 2H).

EXAMPLE 12

1-(4-chloro-2,6-dimethylphenyl)-5-{5-(2,4-difluorophenyl)-2-[4-(hydroxymethyl)-2,2-dimethyl-1,3-dioxolan-4-yl]-1,3-oxazol-4-yl}-2(1H)-pyridinone To a solution of the compound prepared in Example 7(9a) (200 mg) and acetonedimethylacetal (207 mg) in dichloromethane (8 mL) was added p-toluenesulfonic acid pyridinium salt (10 mg) and the mixture was stirred at room temperature for 3 days. To the reaction mixture was added an aqueous solution of sodium hydrogen carbonate and the mixture was extracted with dichloromethane. The obtained organic layer was dried and concentrated. The obtained residue was purified by preparative TLC (ethyl acetate) to give the compound of the present invention (55 mg) having the following physical data.
TLC: Rf 0.73 (ethyl acetate:methanol=9:1);

EXAMPLE 13

1-(4-chloro-2,6-dimethylphenyl)-5-{5-(2,4-difluorophenyl)-2-[1,2-dihydroxy-1-(methoxymethyl)ethyl]-1,3-oxazol-4-yl}-2(1H)-pyridinone To a solution of the compound prepared in Example 12 (55 mg) and iodomethane (43 mg) in tetrahydrofuran (5 mL) was added sodium hydride (60% in oil, 8 mg) and the mixture was stirred at room temperature for 2 hours. To the reaction mixture was added an aqueous solution of ammonium chloride and the mixture was extracted with ethyl acetate. The obtained organic layer was dried and concentrated. The obtained residue was dissolved in tetrahydrofuran (5 mL). To the mixture was added 1N hydrochloric acid (1 mL). The mixture was stirred at 70° C. for 3 hours. The reaction mixture was concentrated. The obtained residue was purified by preparative TLC (ethyl acetate) to give the compound of the present invention (15 mg) having the following physical data.
TLC: Rf 0.36 (ethyl acetate);
NMR: δ 2.08 (s, 6H), 2.60-2.84 (m, 1H), 3.42 (s, 3H), 3.55-3.64 (m, 1H), 3.82 (s, 2H), 3.87-4.08 (m, 2H), 6.67 (d, J=9.5 Hz, 1H), 6.87-7.09 (m, 2H), 7.17 (s, 2H), 7.44 (d, J=2.0 Hz, 1H), 7.46-7.60 (m, 2H).

EXAMPLE 14

1-(4-chloro-2,6-dimethylphenyl)-5-{5-(2,4-difluorophenyl)-2-[2-hydroxy-1-(hydroxymethyl)-1-methoxyethyl]-1,3-oxazol-4-yl}-2(1H)-pyridinone To a solution of the compound prepared in Example 7(9b) (64 mg) and iodomethane (83 mg) in N,N-dimethylformamide (5 mL) was added silver oxide (I) (81 mg) and the mixture was stirred at room temperature for 2 days. To the reaction mixture were added water and ethyl acetate. After the mixture was filtered through Celite (trade name), the obtained organic layer was dried and concentrated. The obtained residue was purified by preparative TLC (hexane:ethyl acetate=1:3). The obtained compound was dissolved in methanol (5 mL). To the mixture was added 2N aqueous solution of sodium hydroxide (1 mL), and the mixture was stirred at room temperature for 10 minutes. The reaction mixture was concentrated. The obtained residue was added 2N hydrochloric acid and the mixture was extracted with ethyl acetate. The obtained organic layer was dried and concentrated. The obtained residue was purified by preparative TLC (ethyl acetate:methanol=20:1) to give the compound of the present invention (9 mg) having the following physical data.
TLC: Rf 0.61 (ethyl acetate:methanol=19:1);
NMR: δ 2.09 (s, 6H), 2.49-2.75 (m, 2H), 3.38 (s, 3H), 4.05-4.23 (m, 4H), 6.68 (d, J=9.7 Hz, 1H), 6.89-7.10 (m, 2H), 7.18 (s, 2H), 7.42 (d, J=2.6 Hz, 1H), 7.47-7.60 (m, 2H).

EXAMPLE 14(1)

1-(2,6-difluorophenyl)-5-{5-(2,4-difluorophenyl)-2-[2-hydroxy-1-(hydroxymethyl)-1-methoxyethyl]-1,3-oxazol-4-yl}-2(1H)-pyridinone By the same procedure as a reaction of Example 14, using the compound prepared in Example 7(39) instead of the compound prepared in Example 7(9b), the compound of the present invention having the following physical data was obtained.
TLC: Rf 0.52 (ethyl acetate);
NMR: δ 2.57-2.68 (m, 2H), 3.38 (s, 3H), 4.07-4.23 (m, 4H), 6.65 (d, J=9.70 Hz, 1H), 6.93-7.15 (m, 4H), 7.39-7.59 (m, 3H), 7.62 (d, J=2.01 Hz, 1H).

EXAMPLE 15

5-[4-[1-(4-chloro-2,6-dimethylphenyl)-6-oxo-1,6-dihydro-3-pyridinyl]-5-(2,4-difluorophenyl)-1,3-oxazol-2-yl]pentanoic acid By the same procedure as a reaction of Example A3, using the compound prepared in Example 7(23) instead of the compound prepared in Example A2, the compound of the present invention having the following physical data was obtained.
TLC: Rf 0.63 (dichloromethane:methanol=9:1);

NMR: δ 7.55-7.45 (m, 2H), 7.41 (d, J=2.4 Hz, 1H), 7.15 (s, 2H), 7.05-6.85 (m, 2H), 6.67 (d, J=9.6 Hz, 1H), 2.83 (t, J=7.5 Hz, 2H), 2.41 (t, J=7.2 Hz, 2H), 2.07 (s, 6H), 1.98-1.70 (m, 4H).

EXAMPLE 16

1-(4-chloro-2,6-dimethylphenyl)-5-[5-(2,4-difluorophenyl)-2-(6,6,6-trifluoro-5-oxohexyl)-1,3-oxazol-4-yl]-2(1H)-pyridinone To a solution of the compound prepared in Example 15 (306 mg) in dichloromethane (6 mL) was added oxalyl chloride (105 μL) and the mixture was stirred at room temperature for an hour. The reaction mixture was concentrated. The obtained acid chloride was dissolved in dichloromethane (4 mL). To the mixture was added trifluoroacetic anhydride (500 μL). The reaction mixture was cooled to 0° C. To the mixture was added pyridine (388 μL). The mixture was stirred for 20 minutes. To the reaction mixture was added water (3 mL), and the obtained organic layer was washed with an aqueous saturated sodium hydrogen carbonate solution and brine, dried and concentrated. The obtained residue was purified by preparative medium pressure liquid chromatography W-prep 2XY (column: main column L, inject column M; automatic condition setting: hexane:ethyl acetate=1:4, Rf=0.50, preparative isolation mode GR). Furthermore the coarsely purified compound was purified by preparative TLC (hexane: ethyl acetate=1:4) to give the compound of the present invention (205 mg) having the following physical data.

TLC: Rf 0.50 (hexane:ethyl acetate=1:4);
NMR: δ 1.68-2.02 (m, 5H), 2.05-2.14 (m, 6H), 2.71-2.96 (m, 3H), 6.57-6.75 (m, 1H), 6.85-7.08 (m, 2H), 7.12-7.21 (m, 2H), 7.36-7.59 (m, 3H).

EXAMPLE 17

1-(4-chloro-2,6-dimethylphenyl)-5-{5-(2,4-difluorophenyl)-2-[(1S)-1,2-dihydroxyethyl]-1,3-oxazol-4-yl}-2(1H)-pyridinone To a solution of the compound prepared in Example 7(24) (20 mg) in methanol (2 mL) was added one drop of concentrated hydrochloric acid and the mixture was stirred at 60° C. for an hour. To the reaction mixture was added ethyl acetate. The mixture was washed with an aqueous saturated sodium hydrogen carbonate solution and brine, dried and concentrated. The obtained residue was purified by preparative TLC (ethyl acetate) to give the compound of the present invention (15 mg) having the following physical data.

TLC: Rf 0.43 (ethyl acetate);
NMR: δ 2.06 (s, 6H), 2.52-3.12 (m, 1H), 3.22-3.78 (m, 1H), 3.95-4.06 (m, 2H), 4.87 (t, J=4.39 Hz, 1H), 6.66 (dd, J=9.51, 0.73 Hz, 1H), 6.88-6.97 (m, 1H), 6.97-7.07 (m, 1H), 7.14-7.16 (m, 2H), 7.40-7.45 (m, 1H), 7.45-7.58 (m, 1H).

EXAMPLE 17(1)

5-{5-(2,4-difluorophenyl)-2-[(1R,2S)-1,2-dihydroxypropyl]-1,3-oxazol-4-yl}-1-(4-fluoro-2,6-dimethylphenyl)-2(1H)-pyridinone By the same procedure as a reaction of Example 17, using the compound prepared in Example 7(25a) instead of the compound prepared in Example 7(24), the compound of the present invention having the following physical data was obtained.

TLC: Rf 0.42 (dichloromethane:methanol=10:1);
NMR: δ 7.61-7.47 (m, 3H), 7.06-6.87 (m, 4H), 6.67 (dd, J=8.7, 1.8 Hz, 1H), 4.59 (dd, J=7.5, 3.9 Hz, 1H), 4.26 (m, 1H), 3.01 (d, J=7.5 Hz, 1H), 2.73 (d, J=4.5 Hz, 1H), 2.09 (s, 6H), 1.35 (d, J=6.6 Hz, 3H).

EXAMPLE 18

1-(4-chloro-2,6-dimethylphenyl)-5-[5-(2,4-difluorophenyl)-2-(1,2-dihydroxy-2-methylpropyl)-1,3-oxazol-4-yl]-2(1H)-pyridinone To a mixed solution of the compound prepared in Example 7(26) (262 mg) in tert-butanol (10 mL)-water (5 mL) were added 4% aqueous solution of osmium tetraoxide (356 mg), potassium hexacyanoferrate (III) (369 mg), potassium carbonate (232 mg) and 1,4-diazabicyclo[2.2.2]octane (126 mg) and the mixture was stirred at room temperature for 2 days. To the reaction mixture was added water and the mixture was extracted with ethyl acetate. The obtained organic layer was dried and concentrated. The obtained residue was purified by column chromatography on silica gel (hexane:ethyl acetate=1:4→ethyl acetate→ethyl acetate:methanol=20:1) to give the compound of the present invention (240 mg) having the following physical data.

TLC: Rf 0.29 (hexane:ethyl acetate=1:3);
NMR: δ 1.27 (s, 3H), 1.39 (s, 3H), 2.09 (s, 6H), 2.69 (s, 1H), 3.11 (d, J=7.7 Hz, 1H), 4.57 (d, J=7.7 Hz, 1H), 6.67 (d, J=9.7 Hz, 1H), 6.88-7.09 (m, 2H), 7.18 (s, 2H), 7.42-7.58 (m, 3H).

EXAMPLE 19

5-[5-(2,4-difluorophenyl)-2-(4-oxocyclohexyl)-1,3-oxazol-4-yl]-1-(4-fluoro-2,6-dimethylphenyl)-2(1H)-pyridinone Under an atmosphere of argon, oxalyl chloride (110 μL) was dissolved in dichloromethane (6 mL) and the mixture was cooled to −78° C. To the mixture was added a solution of dimethyl sulfoxide (116 μL) in dichloromethane (0.5 mL) and the mixture was stirred for 10 minutes. To the reaction mixture was added a solution of the compound prepared in Example 7(27) (312 mg) in dichloromethane (2.0 mL) and the mixture was stirred at −78° C. for 15 minutes and at −45° C. for an hour. To the reaction mixture was added triethylamine (638 μL) and the mixture was stirred at 0° C. for 20 minutes. To the reaction mixture was added ethyl acetate. The mixture was washed with 1N hydrochloric acid, an aqueous saturated sodium hydrogen carbonate solution and brine, dried and concentrated. The obtained residue was purified by column chromatography on silica gel (hexane:ethyl acetate=1:4→0: 1) to give the compound of the present invention (281 mg) having the following physical data.

TLC: Rf 0.37 (ethyl acetate);
NMR: δ 2.10 (s, 6H), 2.14-2.32 (m, 2H), 2.35-2.64 (m, 6H), 3.26-3.38 (m, 1H), 6.67 (dd, J=9.51, 0.73 Hz, 1H), 6.85-7.06 (m, 4H), 7.43-7.56 (m, 3H).

EXAMPLE 19(1)

5-[5-(2,4-difluorophenyl)-2-(4-oxocyclohexyl)-1,3-oxazol-4-yl]-1-(2,6-dimethylphenyl)-2(1H)-pyridinone By the same procedure as a reaction of Example 19, using the compound prepared in Example 7(28) instead of the compound prepared in Example 7(27), the compound of the present invention having the following physical data was obtained.

TLC: Rf 0.41 (ethyl acetate);
NMR: δ 2.11 (s, 6H), 2.14-2.31 (m, 2H), 2.35-2.65 (m, 6H), 3.25-3.38 (m, 1H), 6.68 (dd, J=9.3, 0.9 Hz, 1H), 6.89-7.06 (m, 2H), 7.14-7.21 (m, 2H), 7.22-7.29 (m, 1H), 7.45-7.56 (m, 3H).

EXAMPLE 19(2)

1-(4-chloro-2,6-dimethylphenyl)-5-[5-(2,4-difluorophenyl)-2-(4-oxocyclohexyl)-1,3-oxazol-4-yl]-2(1H)-pyridinone By the same procedure as a reaction of Example 19, using the compound prepared in Example 7(29) instead of the compound prepared in Example 7(27), the compound of the present invention having the following physical data was obtained.

TLC: Rf 0.38 (ethyl acetate:hexane=4:1);
NMR: δ 2.09 (s, 6H), 2.14-2.32 (m, 2H), 2.33-2.67 (m, 6H), 3.25-3.39 (m, 1H), 6.67 (dd, J=9.70, 0.73 Hz, 1H), 6.89-7.06 (m, 2H), 7.17 (s, 2H), 7.43 (d, J=2.01 Hz, 1H), 7.46-7.56 (m, 2H).

EXAMPLE 20

5-[5-(2,4-difluorophenyl)-2-(trans-4-hydroxycyclohexyl)-1,3-oxazol-4-yl]-1-(4-fluoro-2,6-dimethylphenyl)-2(1H)-pyridinone

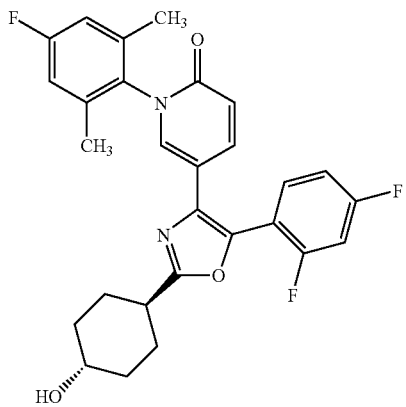

To a solution of the compound prepared in Example 19 (62 mg) in acetic acid (5 mL) were added 1-aminoethanol (15 mg) and sodium triacetoxyborohydride (80 mg) and the mixture was stirred at room temperature for 12 hours. The reaction mixture was concentrated. To the obtained residue were added ethyl acetate and an aqueous solution of sodium hydrogen carbonate. The obtained organic layer was dried and concentrated. The obtained residue was purified by preparative TLC (dichloromethane:methanol:triethylamine=120:10:

3) to give the compound of the present invention (60 mg) having the following physical data.

TLC: Rf 0.59 (dichloromethane:methanol:triethylamine=60:10:1);
NMR: δ 1.32-1.50 (m, 2H), 1.62-1.79 (m, 2H), 2.03-2.28 (m, 10H), 2.71-2.86 (m, 1H), 3.60-3.77 (m, 1H), 6.65 (d, J=9.5 Hz, 1H), 6.80-7.05 (m, 4H), 7.41 (d, J=2.6 Hz, 1H), 7.43-7.54 (m, 2H).

EXAMPLE 21

5-{5-(2,4-difluorophenyl)-2-[(1S,3R,4S,5R)-3,4,5-trihydroxycyclohexyl]-1,3-oxazol-4-yl}-1-(4-fluoro-2,6-dimethylphenyl)-2(1H)-pyridinone To a solution of the compound prepared in Example 7(31) (170 mg) in ethanol (13 mL) was added 10% palladium/carbon (85 mg, 50% wt) and the mixture was stirred at room temperature for 2 hours under an atmosphere of hydrogen. The reaction mixture was filtered through Celite (trade name), and the filtrate was concentrated. The obtained residue was purified by preparative TLC (ethyl acetate:methanol=20:1) to give the compound of the present invention (71 mg) having the following physical data.

TLC: Rf 0.35 (ethyl acetate:methanol=9:1);
NMR (CD$_3$OD): δ 1.82-2.20 (m, 10H), 3.24-3.39 (m, 1H), 3.75-3.83 (m, 1H), 3.92-4.10 (m, 2H), 6.69 (d, J=9.5 Hz, 1H), 6.97 (d, J=9.1 Hz, 2H), 7.06-7.20 (m, 2H), 7.49-7.77 (m, 3H).

EXAMPLE 22

5-{5-(2,4-difluorophenyl)-2-[3-hydroxy-1-(2-hydroxyethyl)propyl]-1,3-oxazol-4-yl}-1-(4-fluoro-2,6-dimethylphenyl)-2(1H)-pyridinone (Step A) To a mixed solution of the compound prepared in Example 7(33) (245 mg) in tetrahydrofuran (10 mL)-water (3 mL) were added 4% aqueous solution of osmium tetraoxide (337 mg) and sodium periodate (227 mg) and the mixture was stirred at room temperature for 2 hours. To the reaction mixture was added acetone (5 mL), and furthermore the mixture was stirred for an hour. The reaction mixture was concentrated.

(Step B) To a solution of the obtained rough product in tetrahydrofuran (10 mL) was added sodium borohydride (200 mg) and the mixture was stirred for 10 minutes. To the reaction mixture was added an aqueous solution of ammonium chloride and the mixture was extracted with ethyl acetate. The obtained organic layer was dried and concentrated. The obtained residue was purified by preparative TLC (ethyl acetate:methanol=20:1) to give the compound of the present invention (119 mg) having the following physical data.

TLC: Rf 0.29 (ethyl acetate:methanol=19:1);
NMR: δ 1.89-2.24 (m, 12H), 3.26-3.45 (m, 1H), 3.63-3.86 (m, 4H), 6.66 (d, J=9.7 Hz, 1H), 6.83-7.07 (m, 4H), 7.42 (d, J=2.0 Hz, 1H), 7.45-7.56 (m, 2H).

EXAMPLE 23 rel-5-{5-(2,4-difluorophenyl)-2-[(1R,3R,4S)-3,4-dihydroxycyclopentyl]-1,3-oxazol-4-yl}-1-(4-fluoro-2,6-dimethylphenyl)-2(1H)-pyridinone

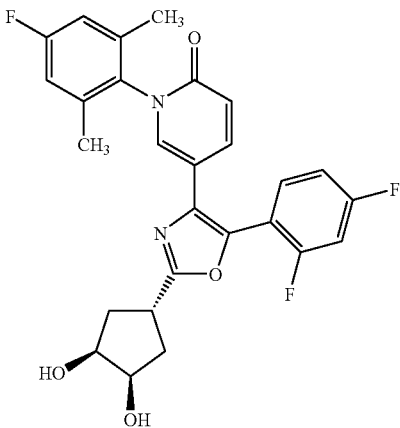

To a mixed solution of the compound prepared in Example 7(33) (118 mg) in tetrahydrofuran (6 mL)-water (1 mL) were added 4% aqueous solution of osmium tetraoxide (162 mg) and N-methylmorpholine N-oxide (90 mg) and the mixture was stirred at room temperature for 30 minutes. The reaction mixture was concentrated. The obtained residue was purified by preparative TLC (ethyl acetate:methanol=30:1) to give the compound of the present invention (89 mg) having the following physical data.

TLC: Rf 0.57 (ethyl acetate:methanol=19:1);

NMR (CD$_3$OD): δ 2.04 (s, 6H), 2.13-2.23 (m, 4H), 3.62-3.78 (m, 1H), 4.12-4.25 (m, 2H), 6.69 (dd, J=9.4, 0.6 Hz, 1H), 6.97 (d, J=9.1 Hz, 2H), 7.05-7.20 (m, 2H), 7.54 (d, J=2.0 Hz, 1H), 7.58-7.74 (m, 2H).

EXAMPLE 24 rel-5-{5-(2,4-difluorophenyl)-2-[(1R,3R,4R)-3,4-dihydroxycyclopentyl]-1,3-oxazol-4-yl}-1-(4-fluoro-2,6-dimethylphenyl)-2(1H)-pyridinone To a solution of the compound prepared in Example 7(33) (164 mg) in dichloromethane (7 mL) were added m-chloroperbenzoic acid (122 mg) and sodium hydrogen carbonate (60 mg) and the mixture was stirred at room temperature for 3 hours. To the reaction mixture was added water and the mixture was extracted with dichloromethane. The obtained organic layer was dried and concentrated. The obtained residue was purified by preparative TLC (ethyl acetate:methanol=30:1) to give epoxide compounds (trans form: 86 mg, and cis form: 27 mg). Among the obtained epoxide compounds, a trans form (79 mg) and a cis form (25 mg) were dissolved in a mixed solution of tetrahydrofuran (5 mL and 3 mL)-water (1 mL and 0.5 mL) respectively. To the each reaction mixture was several drops of concentrated sulfuric acid and the each mixture was stirred at room temperature for 3 hours and 6 hours. Both the reaction mixtures were put together, and they were concentrated. To the obtained residue was added water and the mixture was extracted with ethyl acetate. The obtained organic layer was dried and concentrated. The obtained residue was purified by preparative TLC (ethyl acetate:methanol=20:1) to give the compound of the present invention (74 mg) having the following physical data.

TLC: Rf 0.26 (ethyl acetate);

NMR: δ 1.83 (s, 1H), 2.02-2.23 (m, 8H), 2.34-2.48 (m, 1H), 2.51-2.65 (m, 1H), 3.16 (d, J=6.2 Hz, 1H), 3.51-3.70 (m, 1H), 4.06-4.19 (m, 1H), 4.24-4.35 (m, 1H), 6.61-6.71 (m, 1H), 6.83-7.07 (m, 4H), 7.39 (d, J=2.0 Hz, 1H), 7.43-7.57 (m, 2H).

EXAMPLE 25

Methyl 4-[5-[5-(2,4-difluorophenyl)-2-(tetrahydro-2H-pyran-4-yl)-1,3-oxazol-4-yl]-2-oxo-1(2H)-pyridinyl]-3,5-dimethylbenzoate Under an atmosphere of argon, to a mixed solution of the compound prepared in Example 7(37) (500 mg) in N,N-dimethylformamide (3.6 mL)-methanol (3.6 mL) were added triethylamine (0.64 mL) and 1,1'-bis(diphenylphosphino)ferrocene (dppf, 102 mg). To the reaction mixture was added palladium acetate (20 mg), and argon was replaced with carbon monoxide and the mixture was stirred at 80° C. vigorously for 10 hours. To the reaction mixture was added water and the mixture was extracted with a mixed solution of ethyl acetate:hexane=4:1. The obtained organic layer was washed with water and brine, dried and concentrated. The obtained residue was purified by column chromatography on silica gel (ethyl acetate:hexane=1:1→1:0) to give the compound of the present invention (350 mg) having the following physical data.

TLC: Rf 0.42 (ethyl acetate);

NMR: δ 1.90-2.04 (m, 4H), 2.15 (s, 6H), 3.02-3.14 (m, 1H), 3.47-3.58 (m, 2H), 3.92 (s, 3H), 4.04 (dt, J=11.7, 3.4 Hz, 2H), 6.67 (d, J=9.7 Hz, 1H), 6.88-7.03 (m, 2H), 7.39-7.42 (m, 1H), 7.45-7.55 (m, 2H), 7.84 (s, 2H).

EXAMPLE 26

4-[5-[5-(2,4-difluorophenyl)-2-(tetrahydro-2H-pyran-4-yl)-1,3-oxazol-4-yl]-2-oxo-1(2H)-pyridinyl]-3,5-dimethylbenzoic acid By the same procedure as a reaction of Example A3, using the compound prepared in Example 25 instead of the compound prepared in Example A2, the compound of the present invention having the following physical data was obtained.

TLC: Rf 0.27 (ethyl acetate:methanol=9:1);

NMR: δ 1.94-2.06 (m, 4H), 2.16 (s, 6H), 3.06-3.20 (m, 1H), 3.48-3.60 (m, 2H), 4.01-4.10 (m, 2H), 6.74 (d, J=9.5 Hz, 1H), 6.90-7.07 (m, 2H), 7.47-7.61 (m, 3H), 7.76 (s, 2H).

EXAMPLE 27

4-[5-[5-(2,4-difluorophenyl)-2-(tetrahydro-2H-pyran-4-yl]-1,3-oxazol-4-yl]-2-oxo-1(2H)-pyridinyl]-N,N,3,5-tetramethylbenzamide

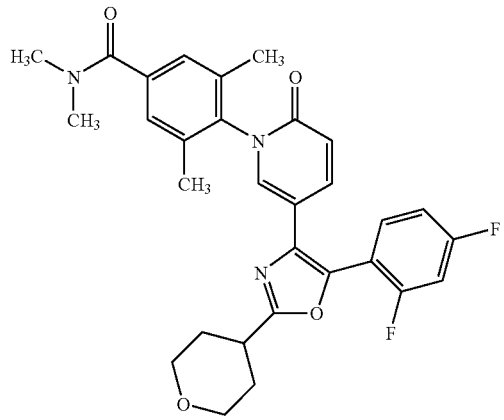

By the same procedure as a reaction of Example A21, using the compound prepared in Example 26 instead of the compound prepared in Example A20 and dimethylamine instead of 30% aqueous ammonia, the compound of the present invention having the following physical data was obtained.

TLC: Rf 0.31 (ethyl acetate:methanol=9:1);

NMR: δ 1.93-2.05 (m, 4H), 2.11 (s, 6H), 3.01-3.15 (m, 7H), 3.49-3.60 (m, 2H), 4.06 (dt, J=7.8, 3.9 Hz, 2H), 6.69 (dd, J=9.6, 0.6 Hz, 1H), 6.88-7.04 (m, 2H), 7.20 (s, 2H), 7.32-7.35 (m, 1H), 7.45-7.61 (m, 2H).

EXAMPLE 27(1)

4-[5-[5-(2,4-difluorophenyl)-2-(tetrahydro-2H-pyran-4-yl]-1,3-oxazol-4-yl]-2-oxo-1(2H)-pyridinyl]-3,5-dimethylbenzamide By the same procedure as a reaction of Example A21, using the compound prepared in Example 26 instead of the compound prepared in Example A20, the compound of the present invention having the following physical data was obtained.

TLC: Rf 0.40 (ethyl acetate:methanol=9:1);

NMR: δ 1.91-2.07 (m, 4H), 2.15 (s, 6H), 3.03-3.16 (m, 1H), 3.47-3.60 (m, 2H), 4.00-4.09 (m, 2H), 5.48-5.72 (m, 1H), 6.04-6.26 (m, 1H), 6.69 (d, J=9.7 Hz, 1H), 6.89-7.06 (m, 2H), 7.38-7.43 (m, 1H), 7.45-7.59 (m, 2H), 7.60 (s, 2H).

EXAMPLE 28

4-[5-[5-(2,4-difluorophenyl)-2-(tetrahydro-2H-pyran-4-yl]-1,3-oxazol-4-yl]-2-oxo-1(2H)-pyridinyl]-3,5-dimethylbenzonitrile To a solution of the compound prepared in Example 27(1) (61 mg) in dichloromethane (1.2 mL) was added pyridine (0.058 mL) and the mixture was stirred on ice bath. To the reaction solution was added dropwise trifluoromethanesulfonic anhydride (0.062 mL) and the mixture was stirred at room temperature for 3.5 hours. The reaction mixture was poured into iced diluted hydrochloric acid and extracted with ethyl acetate. The obtained organic layer was washed with water and brine, dried and concentrated. The obtained residue was purified by column chromatography on silica gel (ethyl acetate) to give the compound of the present invention (53 mg) having the following physical data.

TLC: Rf 0.58 (ethyl acetate:methanol=19:1);

NMR: δ 1.93-2.05 (m, 4H), 2.16 (s, 6H), 3.03-3.14 (m, 1H), 3.49-3.58 (m, 2H), 4.05 (dt, J=11.7, 3.6 Hz, 2H), 6.67 (dd, J=9.5, 0.7 Hz, 1H), 6.91-7.06 (m, 2H), 7.40-7.42 (m, 1H), 7.47-7.56 (m, 4H).

EXAMPLE 29

(1Z)-N'-({4-[5-[5-(2,4-difluorophenyl)-2-(tetrahydro-2H-pyran-4-yl]-1,3-oxazol-4-yl]-2-oxo-1(2H)-pyridinyl]-3,5-dimethylbenzoyl}oxy)ethanimidamide A solution of the compound prepared in Example 26 (147 mg) and N-hydroxyacetamidine (52 mg) in N,N-dimethylformamide (1.5 mL) was stirred on ice bath. To the reaction mixture were added hydroxybenzotriazole (HOBt, 49 mg) and 1-ethyl-3-[3-(dimethylamino)propyl]carbodiimide (EDC) hydrochloride (61 mg). After the mixture was stirred for an hour, it was left at rest for 2 days. A postprocessing of the reaction mixture was done by a conventional method. The obtained residue was purified by column chromatography on silica gel (ethyl acetate:methanol=1:0→9:1) to give the compound of the present invention (30 mg) having the following physical data.

TLC: Rf 0.48 (ethyl acetate:methanol=9:1);

NMR: δ 1.92-2.08 (m, 7H), 2.15 (s, 3H), 2.16 (s, 3H), 3.02-3.15 (m, 1H), 3.46-3.60 (m, 2H), 3.98-4.08 (m, 2H), 4.77-4.98 (m, 1H), 5.48-5.78 (m, 1H), 6.08-6.35 (m, 1H), 6.87-7.05 (m, 2H), 7.36-7.43 (m, 1H), 7.44-7.57 (m, 2H), 7.58 (s, 1H), 7.83 (s, 1H).

EXAMPLE 30

5-[5-(2,4-difluorophenyl)-2-(tetrahydro-2H-pyran-4-yl)-1,3-oxazol-4-yl]-1-[2,6-dimethyl-4-(3-methyl-1,2,4-oxadiazol-5-yl)phenyl]-2(1H)-pyridinone A solution of the compound prepared in Example 29 (30 mg) in toluene (3 mL) was heated to reflux for 6 hours. The reaction mixture was concentrated. The obtained residue was purified by column chromatography on silica gel (ethyl acetate) to give the compound of the present invention (8 mg) having the following physical data.

TLC: Rf 0.60 (ethyl acetate:methanol=19:1);

NMR: δ 1.93-2.07 (m, 4H), 2.20 (s, 6H), 2.48 (s, 3H), 3.03-3.15 (m, 1H), 3.47-3.59 (m, 2H), 4.04 (dt, J=11.5, 3.5 Hz, 2H), 6.68 (dd, J=9.6, 0.6 Hz, 1H), 6.89-7.05 (m, 2H), 7.42-7.45 (m, 1H), 7.46-7.56 (m, 2H), 7.93 (s, 2H).

EXAMPLE 31

5-{5-(2,4-difluorophenyl)-2-[2-hydroxy-1-(hydroxymethyl)-1-methylethyl]-1,3-oxazol-4-yl}-1-[2,6-dimethyl-4-(methylsulfonyl)phenyl]-2(1H)-pyridinone To a solution of the compound prepared in Example 10(1) (86 mg) in acetone (2.0 mL) were added water (0.060 mL) and Oxone (trade name, 309 mg) on ice bath and the mixture was stirred overnight. An insoluble matter was filtered, and the filtrate was concentrated. The obtained residue was purified by column chromatography on silica gel (ethyl acetate:methanol=1:0→20:3) to give the compound of the present invention (75 mg) having the following physical data.

TLC: Rf 0.45 (ethyl acetate);
NMR: δ 1.30 (s, 3H), 2.21 (s, 6H), 2.68-2.82 (m, 2H), 3.10 (s, 3H), 3.95 (d, J=11.4 Hz, 2H), 4.05 (d, J=11.4 Hz, 2H), 6.77 (dd, J=9.6, 0.5 Hz, 1H), 6.92-7.10 (m, 2H), 7.44-7.47 (m, 1H), 7.52-7.61 (m, 2H), 7.78 (s, 2H).

EXAMPLE 32

5-{5-(2,4-difluorophenyl)-2-[2-hydroxy-1-(hydroxymethyl)-1-methylethyl]-1,3-oxazol-4-yl}-1-[4-(3-hydroxy-1-propyn-1-yl)-2,6-dimethylphenyl]-2(1H)-pyridino Under an atmosphere of argon, to a solution of the compound prepared in Example 10(2) (124 mg) in N,N-dimethylformamide (2.3 mL) were added propargyl alcohol (0.033 mL), copper(I) bromide (10 mg) and triethylamine (0.063 mL). To the reaction mixture was added tetrakis(triphenylphosphine)palladium (26 mg) and the mixture was stirred at 90° C. for 4 hours. To the reaction mixture was added water and the mixture was extracted with ethyl acetate. The obtained organic layer was washed with water and brine, dried and concentrated. The obtained residue was purified by column chromatography on silica gel (ethyl acetate:methanol=1:0→15:1) to give the compound of the present invention (62 mg) having the following physical data.

TLC: Rf 0.34 (ethyl acetate:methanol=19:1);
NMR: δ 1.27 (s, 3H), 1.46-1.88 (m, 3H), 2.08 (s, 6H), 3.90 (d, J=11.1 Hz, 2H), 4.04 (d, J=11.1 Hz, 2H), 4.48 (s, 2H), 6.67 (dd, J=9.6, 0.6 Hz, 1H), 6.88-7.05 (m, 2H), 7.25 (s, 2H), 7.34-7.38 (m, 1H), 7.47-7.56 (m, 2H).

EXAMPLE 32(1)

5-{5-(2,4-difluorophenyl)-2-[2-hydroxy-1-(hydroxymethyl)-1-methylethyl]-1,3-oxazol-4-yl}-1-[4-(3-hydroxy-3-methyl-1-butyn-1-yl)-2,6-dimethylphenyl]-2(1H)-pyridinone By the same procedure as a reaction of Example 32, using 2-methyl-3-pentyn-2-ol instead of propargyl alcohol, the compound of the present invention having the following physical data was obtained.

TLC: Rf 0.41 (ethyl acetate:methanol=19:1);
NMR: δ 1.27 (s, 3H), 1.61 (s, 6H), 2.02 (s, 1H), 2.06-2.10 (m, 6H), 3.22 (t, J=6.6 Hz, 2H), 3.91 (dd, J=11.4, 6.6 Hz, 2H), 4.05 (dd, J=11.4, 6.6 Hz, 2H), 6.68 (d, J=9.7 Hz, 1H), 6.89-7.05 (m, 2H), 7.24 (s, 2H), 7.35 (d, J=2.7 Hz, 1H), 7.48-7.57 (m, 2H)

EXAMPLE 33

5-{5-(2,4-difluorophenyl)-2-[2-hydroxy-1-(hydroxymethyl)-1-methylethyl]-1,3-oxazol-4-yl}-1-[4-(1-ethoxyvinyl)-2,6-dimethylphenyl]-2(1H)-pyridinone Under an atmosphere of argon, to a solution of the compound prepared in Example 10(2) (200 mg) in toluene (4.0 mL) was added tributyl(1-ethoxyvinyl)tin (0.146 mL). To the reaction mixture was added tetrakis(triphenylphosphine)palladium (42 mg). The mixture was heated to reflux and stirred for 3 hours. To the reaction mixture was added ethyl acetate. The mixture was washed with 15% aqueous solution of potassium fluoride and water, dried and concentrated. The obtained residue was purified by column chromatography on silica gel (ethyl acetate:methanol=1:0→15:1) to give the compound of the present invention (100 mg) having the following physical data.

TLC: Rf 0.60 (ethyl acetate:methanol=19:1);
NMR: δ 1.26 (s, 3H), 1.42 (t, J=7.1 Hz, 3H), 2.11 (s, 6H), 3.30-3.42 (m, 2H), 3.83-3.96 (m, 2H), 3.98-4.08 (m, 2H), 4.12 (q, J=7.1 Hz, 2H), 4.21 (d, J=2.6 Hz, 1H), 4.62 (d, J=2.6 Hz, 1H), 6.69 (d, J=9.5 Hz, 1H), 6.87-7.05 (m, 2H), 7.35-7.39 (m, 1H), 7.40-7.44 (m, 2H), 7.45-7.57 (m, 2H).

EXAMPLE 34

1-(4-acetyl-2,6-dimethylphenyl)-5-{5-(2,4-difluorophenyl)-2-[2-hydroxy-1-(hydroxymethyl)-1-methylethyl]-1,3-oxazol-4-yl}-2(1H)-pyridinone To a solution of the compound prepared in Example 33 (100 mg) in tetrahydrofuran (1.0 mL) was added 2N hydrochloric acid (1.0 mL) and the mixture was stirred at room temperature for 40 minutes. To the reaction mixture was added water and the mixture was extracted with ethyl acetate. The obtained organic layer was washed with water and brine, dried and concentrated. The obtained residue was purified by column chromatography on silica gel (ethyl acetate:methanol=1:0→30:1) to give the compound of the present invention (66 mg) having the following physical data.

TLC: Rf 0.27 (ethyl acetate:methanol=19:1);
NMR: δ 1.27 (s, 3H), 2.18 (s, 6H), 2.61 (s, 3H), 3.21 (t, J=6.3 Hz, 2H), 3.91 (dd, J=11.1, 6.3 Hz, 2H), 4.05 (dd, J=11.1, 6.3 Hz, 2H), 6.69 (d, J=9.7 Hz, 1H), 6.89-7.07 (m, 2H), 7.38 (d, J=2.6 Hz, 1H), 7.48-7.60 (m, 2H), 7.77 (s, 2H).

EXAMPLE 35

2-[4-[1-(4-acetyl-2,6-dimethylphenyl)-6-oxo-1,6-dihydro-3-pyridinyl]-5-(2,4-difluorophenyl)-1,3-oxazol-2-yl]-2-methyl-1,3-propanediyl diacetate

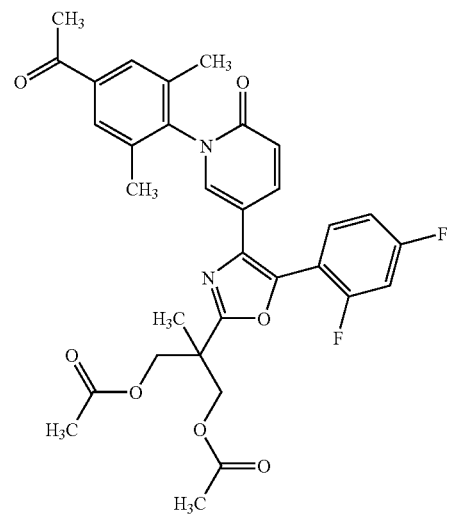

To a solution of the compound prepared in Example 34 (85 mg) in pyridine (1.0 mL) was added acetic anhydride (0.5 mL) on ice bath and the mixture was stirred at room temperature for 4 hours. The reaction mixture was poured into iced water and extracted with tert-butyl methyl ether. The obtained organic layer was washed with water and brine, dried and concentrated. The obtained residue was purified by column chromatography on silica gel (ethyl acetate:hexane=1:1→4:1) to give the compound of the present invention (98 mg) having the following physical data.

TLC: Rf 0.29 (ethyl acetate:hexane=2:1);
NMR: δ 1.47 (s, 3H), 2.05 (s, 6H), 2.19 (s, 6H), 2.61 (s, 3H), 4.37 (d, J=11.4 Hz, 2H), 4.45 (d, J=11.4 Hz, 2H), 6.68 (dd, J=9.8, 0.6 Hz, 1H), 6.91-7.06 (m, 2H), 7.43-7.58 (m, 1H), 7.63-7.73 (m, 2H), 7.78 (s, 2H).

Example 36

2-(5-(2,4-difluorophenyl)-4-{1-[4-(1-hydroxy-1-methylethyl)-2,6-dimethylphenyl]-6-oxo-1,6-dihydro-3-pyridinyl}-1,3-oxazol-2-yl)-2-methyl-1,3-propanediyl diacetate To a solution of the compound prepared in Example 35 (77 mg) in anhydrous tetrahydrofuran (3.9 mL) was added 3.0 mol/L methylmagnesium bromide/diethyl ether solution (0.13 mL) on ice bath with salt and the mixture was stirred at room temperature for 30 minutes. The reaction mixture was poured into an aqueous solution of ammonium chloride and the mixture was extracted with ethyl acetate. The obtained organic layer was washed with water and brine, dried and concentrated to give the compound of the present invention (79 mg) having the following physical data.

TLC: Rf 0.51 (ethyl acetate);
NMR: δ 1.47 (s, 3H), 1.60 (s, 6H), 1.75 (s, 1H), 2.05 (s, 6H), 2.12 (s, 6H), 4.37 (d, J=11.1 Hz, 2H), 4.45 (d, J=11.1 Hz, 2H), 6.63-6.70 (m, 1H), 6.90-7.07 (m, 2H), 7.30 (s, 2H), 7.42-7.57 (m, 2H), 7.63-7.72 (m, 1H).

Example 37

5-{5-(2,4-difluorophenyl)-2-[2-hydroxy-1-(hydroxymethyl)-1-methylethyl]-1,3-oxazol-4-yl}-1-[4-(1-hydroxy-1-methylethyl)-2,6-dimethylphenyl]-2(1H)-pyridinone By the same procedure as a reaction of Example A3, using the compound prepared in Example 36 instead of the compound prepared in Example A2, the compound of the present invention having the following physical data was obtained.

TLC: Rf 0.34 (ethyl acetate:methanol=19:1);
NMR: δ 1.26 (s, 3H), 1.59 (s, 6H), 1.77 (s, 1H), 2.11 (s, 6H), 3.25 (t, J=6.6 Hz, 2H), 3.89 (dd, J=12.0, 6.6 Hz, 2H), 4.03 (dd, J=12.0, 6.6 Hz, 2H), 6.65 (d, J=9.5 Hz, 1H), 6.89-7.04 (m, 2H), 7.28 (s, 2H), 7.41-7.56 (m, 3H).

Example 38

5-[5-(2,4-difluorophenyl)-2-(1-hydroxy-1-methylethyl)-1,3-oxazol-4-yl]-1-[4-(3-hydroxy-3-methyl-1-butyn-1-yl)-2,6-dimethylphenyl]-2(1H)-pyridinone By the same procedure as a reaction of Example 32, using the compound prepared in Example 10(3) instead of the compound prepared in Example 10(2) and 2-methyl-3-pentyn-2-ol instead of propargyl alcohol, the compound of the present invention having the following physical data was obtained.

TLC: Rf 0.45 (ethyl acetate);
NMR: δ 1.61 (s, 6H), 1.68 (s, 6H), 2.02 (s, 1H), 2.07 (s, 6H), 2.68 (s, 1H), 6.66 (d, J=9.5 Hz, 1H), 6.89-7.07 (m, 2H), 7.24 (s, 2H), 7.42-7.46 (m, 1H), 7.48-7.57 (m, 2H).

Example 39

1-(4-acetyl-2,6-dimethylphenyl)-5-[5-(2,4-difluorophenyl)-2-(1-hydroxy-1-methylethyl)-1,3-oxazol-4-yl]-2(1H)-pyridinone By the same procedure as a series of reactions of Example 33→Example 34, using the compound prepared in Example 10(3) instead of the compound prepared in Example 10(2), the title compound having the following physical data was obtained.

TLC: Rf 0.40 (ethyl acetate);
NMR: δ 1.68 (s, 6H), 2.18 (s, 6H), 2.61 (s, 3H), 2.67 (s, 1H), 6.68 (dd, J=9.5, 0.7 Hz, 1H), 6.90-7.07 (m, 2H), 7.45-7.48 (m, 1H), 7.49-7.58 (m, 2H), 7.76 (s, 2H).

Example 40

5-[5-(2,4-difluorophenyl)-2-(1-hydroxy-1-methylethyl)-1,3-oxazol-4-yl]-1-[4-(1-hydroxy-1-methylethyl)-2,6-dimethylphenyl]-2(1H)-pyridinone By the same procedure as a reaction of Example 36, using the compound prepared in Example 39 instead of the compound prepared in Example 35, the compound of the present invention having the following physical data was obtained.

TLC: Rf 0.47 (ethyl acetate:methanol=19:1);
NMR: δ 1.59 (s, 6H), 1.68 (s, 6H), 1.74 (s, 1H), 2.11 (s, 6H), 2.68 (s, 1H), 6.65 (dd, J=9.5, 0.5 Hz, 1H), 6.88-7.04 (m, 2H), 7.27 (s, 2H), 7.45-7.55 (m, 3H).

Example 41

1-(4-chloro-2,6-dimethylphenyl)-5-[5-(2,4-difluorophenyl)-2-(1,1-dioxidetetrahydro-2H-thiopyran-4-yl)-1,3-oxazol-4-yl]-2(1H)-pyridinone To a solution of the compound prepared in Example 10(9) (150 mg) in dichloromethane (2.9 mL) was added m-chloroperbenzoic acid (101 mg) and the mixture was stirred at room temperature for 10 minutes. The reaction mixture was poured into an iced aqueous solution of sodium hydrogen carbonate and extracted with ethyl acetate. The obtained organic layer was washed with water and brine, dried and concentrated. The obtained residue was purified by column chromatography on silica gel (ethyl acetate) to give the compound of the present invention (74 mg) having the following physical data.

TLC: Rf 0.35 (ethyl acetate);
NMR: δ 2.09 (s, 6H), 2.54-2.66 (m, 4H), 3.01-3.13 (m, 2H), 3.19-3.34 (m, 3H), 6.67 (dd, J=9.5, 0.7 Hz, 1H), 6.91-7.07 (m, 2H), 7.18 (s, 2H), 7.41-7.44 (m, 1H), 7.45-7.54 (m, 2H).

Example 41(1)

5-[5-(2,4-difluorophenyl)-2-(1,1-dioxidotetrahydro-2H-thiopyran-4-yl)-1,3-oxazol-4-yl]-1-(4-fluoro-2,6-dimethylphenyl)-2(1H)-pyridinone By the same procedure as a reaction of Example 41, using the compound prepared in Example 10(10) instead of the compound prepared in Example 10(9), the compound of the present invention having the following physical data was obtained.

TLC: Rf 0.32 (ethyl acetate);
NMR: δ 2.11 (s, 6H), 2.53-2.65 (m, 4H), 3.00-3.15 (m, 2H), 3.18-3.37 (m, 3H), 6.68 (d, J=9.5 Hz, 1H), 6.89 (d, J=9.0 Hz, 2H), 6.92-7.08 (m, 2H), 7.42-7.54 (m, 3H).

Example 41(2)

1-(4-bromo-2,6-dimethylphenyl)-5-[5-(2,4-difluorophenyl)-2-(1,1-dioxidotetrahydro-2H-thiopyran-4-yl)-1,3-oxazol-4-yl]-2(1H)-pyridinone By the same procedure as a reaction of Example 41, using the compound prepared in Example 10(11) instead of the compound prepared in Example 10(9), the compound of the present invention having the following physical data was obtained.

TLC: Rf 0.40 (ethyl acetate);
NMR: δ 2.09 (s, 6H), 2.54-2.64 (m, 4H), 3.01-3.12 (m, 2H), 3.18-3.34 (m, 3H), 6.67 (dd, J=9.4, 0.6 Hz, 1H), 6.91-7.07 (m, 2H), 7.34 (s, 2H), 7.41-7.44 (m, 1H), 7.45-7.53 (m, 2H).

Example 42

Methyl 4-[5-[5-(2,4-difluorophenyl)-2-(1,1-dioxidotetrahydro-2H-thiopyran-4-yl)-1,3-oxazol-4-yl]-2-oxo-1(2H)-pyridinyl]-3,5-dimethylbenzoate By the same procedure as a reaction of Example 25, using the compound prepared in Example 41(2) instead of the compound prepared in Example 7(37), the compound of the present invention having the following physical data was obtained.

TLC: Rf 0.59 (ethyl acetate:methanol=19:1);
NMR: δ 2.17 (s, 6H), 2.53-2.64 (m, 4H), 3.01-3.12 (m, 2H), 3.19-3.34 (m, 3H), 3.93 (s, 3H), 6.69 (dd, J=9.6, 0.5 Hz, 1H), 6.92-7.06 (m, 2H), 7.41-7.44 (m, 1H), 7.45-7.54 (m, 2H), 7.87 (s, 2H).

Example 43

5-[5-(2,4-difluorophenyl)-2-(1,1-dioxidotetrahydro-2H-thiopyran-4-yl)-1,3-oxazol-4-yl]-1-[2,6-dimethyl-4-(3-methyl-1,2,4-oxadiazol-5-yl)phenyl]-2(1H)-pyridinone By the same procedure as a series of reactions of Example 26→Example 29→Example 30, using the compound prepared in Example 42 instead of the compound prepared in Example 25, the title compound having the following physical data was obtained.

TLC: Rf 0.56 (ethyl acetate:methanol=19:1);
NMR: δ 2.21 (s, 6H), 2.49 (s, 3H), 2.54-2.64 (m, 4H), 3.00-3.13 (m, 2H), 3.18-3.35 (m, 3H), 6.70 (dd, J=9.5, 0.7 Hz, 1H), 6.92-7.07 (m, 2H), 7.44-7.46 (m, 1H), 7.48-7.55 (m, 2H), 7.96 (s, 2H).

Example 44

5-[5-(2,4-difluorophenyl)-2-(1,1-dioxidotetrahydro-2H-thiopyran-4-yl)-1,3-oxazol-4-yl]-1-[4-(3-hydroxy-1-propyn-1-yl)-2,6-dimethylphenyl]-2(1H)-pyridinone By the same procedure as a reaction of Example 32, using the compound prepared in Example 41(2) instead of the compound prepared in Example 10(2), the compound of the present invention having the following physical data was obtained.

TLC: Rf 0.52 (ethyl acetate:methanol=19:1);
NMR: δ 1.51-1.65 (m, 1H), 2.09 (s, 6H), 2.52-2.66 (m, 4H), 2.99-3.15 (m, 2H), 3.18-3.36 (m, 3H), 4.49 (s, 2H), 6.67 (dd, J=9.5, 0.5 Hz, 1H), 6.89-7.09 (m, 2H), 7.26 (s, 2H), 7.40-7.54 (m, 3H).

Example 45

2-[1-(4-chloro-2,6-dimethylphenyl)-6-oxo-1,6-dihydro-3-pyridinyl]-1-(2,4-difluorophenyl)-2-oxoethyl 2,3-dihydroxybenzoate By the same procedure as a reaction of Example 5, using sodium 2,3-dihydroxybenzoate instead of the compound prepared in Example A1, the compound of the present invention having the following physical data was obtained.

TLC: Rf 0.30 (hexane:ethyl acetate=2:1);
NMR: δ 10.30 (d, J=0.6 Hz, 1H), 8.05 (d, J=2.7 Hz, 1H), 7.95 (dd, J=9.6, 2.7 Hz, 1H), 7.58 (td, J=8.4, 6.3 Hz, 1H), 7.43 (dd, J=7.8, 1.5 Hz, 1H), 7.23-7.18 (m, 2H), 7.13 (ddd, J=7.8, 1.5, 0.6 Hz, 1H), 7.04-6.85 (m, 3H), 6.81 (t, J=7.8 Hz, 1H), 6.69 (d, J=9.6 Hz, 1H), 5.62 (s, 1H), 2.08 (s, 3H), 1.95 (s, 3H).

Example 46

N-{1-[1-(4-chloro-2,6-dimethylphenyl)-6-oxo-1,6-dihydro-3-pyridinyl]-2-(2,4-difluorophenyl)-2-oxoethyl}-2,3-dihydroxybenzamide To a mixed solution of the compound prepared in Example 45 (413 mg) in acetic acid (7.6 mL)-N,N-dimethylformamide (7.0 mL) was added ammonium acetate (1.18 g) and the mixture was stirred at 100° C. for an hour. The reaction mixture was poured into 5N aqueous solution of sodium hydroxide and the mixture was extracted with ethyl acetate. After having made the water layer acidity with 2N hydrochloric acid, the mixture was extracted with ethyl acetate. The organic layer was put together, washed with brine, dried and concentrated. The obtained residue was purified by preparative medium pressure liquid chromatography W-prep 2XY (column: main column L, inject column M; automatic condition setting: hexane:ethyl acetate=1:1, Rf=0.30, preparative isolation mode GR) to give the title compound having the following physical data.

TLC: Rf 0.59 (hexane:ethyl acetate=1:2);
MS: APCI Pos. 20V 539 (M+H)⁺.

Example 47

1-(4-chloro-2,6-dimethylphenyl)-5-[5-(2,4-difluorophenyl)-2-(2,3-dihydroxyphenyl)-1,3-oxazol-4-yl]-2(1H)-pyridinone To a solution of the compound prepared in Example 46 in acetic anhydride (3 mL) was added concentrated sulfuric acid (0.1 mL) at room temperature and the mixture was stirred at 90° C. for an hour. The reaction mixture was poured into 5N aqueous solution of sodium hydroxide-ice. Till precipitated solids were dissolved, to the mixture was added methanol. After having confirmed that the reaction mixture was basicity enough, it was stirred for 30 minutes. Next, to the reaction mixture was added 2N hydrochloric acid and the mixture was made the acidity. The reaction mixture was extracted with ethyl acetate. The obtained organic layer was washed with brine, dried and concentrated. The obtained residue was purified by preparative TLC (hexane:ethyl acetate=1:1) to give the compound of the present invention (10 mg) having the following physical data.

TLC: Rf 0.50 (hexane:ethyl acetate=1:1);
NMR: δ 2.11 (s, 6H), 5.71 (s, 1H), 6.74 (d, J=9.5 Hz, 1H), 6.84-7.12 (m, 4H), 7.16-7.24 (m, 2H), 7.34-7.46 (m, 2H), 7.52-7.72 (m, 2H).

Example 48

1-(4-chloro-2,6-dimethylphenyl)-5-[(1Z)-2-(2,4-difluorophenyl)-N-hydroxyethanimidoyl]-2(1H)-pyridinone To a solution of the compound prepared in Example 3 (618 mg) in acetic acid (15 mL) were added hydroxyamine hydrochloride (166 mg) and sodium acetate (196 mg) and the mixture was stirred at 80° C. for 3 hours. The reaction mixture was concentrated. To the obtained residue was added an aqueous solution of sodium hydrogen carbonate and the mixture was extracted with ethyl acetate. The obtained organic layer was dried and concentrated. The obtained residue was washed with isopropyl ether to give the compound of the present invention (570 mg) having the following physical data.

TLC: Rf 0.30 (hexane:ethyl acetate=1:1);
NMR: δ 1.97 (s, 6H), 3.96 (s, 2H), 6.63-6.85 (m, 3H), 7.11-7.28 (m, 4H), 7.89 (dd, J=9.7, 2.7 Hz, 1H), 7.93-8.04 (m, 1H).

Example 49

1-(4-chloro-2,6-dimethylphenyl)-5-{(1Z)-2-(2,4-difluorophenyl)-N-[(tetrahydro-2H-pyran-4-ylcarbonyl)oxy]ethanimidoyl}-2(1H)-pyridinone To a solution of the compound prepared in Example 48 (109 mg) in toluene (6 mL) was added tetrahydro-2H-pyran-4-carboxylic acid chloride (40 mg) and the mixture was stirred at 110° C. for 18 hours. The reaction mixture was concentrated. The obtained residue was purified by preparative TLC (hexane:ethyl acetate=1:3) to give the compound of the present invention (57 mg) having the following physical data.

TLC: Rf 0.48 (hexane:ethyl acetate=1:2);
NMR: δ 1.76-1.91 (m, 4H), 1.97 (s, 6H), 2.58-2.82 (m, 1H), 3.36-3.53 (m, 2H), 3.92-4.06 (m, 4H), 6.70 (d, J=9.7 Hz, 1H), 6.78-6.89 (m, 2H), 6.98-7.11 (m, 1H), 7.17 (s, 2H), 7.44 (d, J=2.7 Hz, 1H), 7.95 (dd, J=9.8, 2.7 Hz, 1H).

Example 50

1-(4-chloro-2,6-dimethylphenyl)-5-[5-(2,4-difluorophenyl)-2-(tetrahydro-2H-pyran-4-yl)-1,3-oxazol-4-yl]-2(1H)-pyridinone To a solution of the compound prepared in Example 49 (53.3 mg) in toluene (1.5 mL) was added 4N hydrogen chloride/dioxane solution (0.2 mL) and the mixture was irradiated with a microwave (150 W, 200° C.) for 2 hours. The reaction mixture was concentrated. The obtained residue was purified by preparative TLC (hexane:ethyl acetate=1:2) to give the compound of the present invention (17 mg) having the following physical data.

TLC: Rf 0.39 (hexane:ethyl acetate=1:2);
NMR: δ 1.94-2.06 (m, 4H), 2.08 (s, 6H), 3.02-3.17 (m, 1H), 3.48-3.60 (m, 2H), 4.00-4.10 (m, 2H), 6.67 (d, J=9.5 Hz, 1H), 6.87-7.07 (m, 2H), 7.17 (s, 2H), 7.42 (d, J=2.4 Hz, 1H), 7.45-7.56 (m, 2H).

Example 51

(2Z)-1-[1-(4-chloro-2,6-dimethylphenyl)-6-oxo-1,6-dihydro-3-pyridinyl]-2-(2,4-difluorophenyl)-1,2-ethanedione 2-oxime To a solution of the compound prepared in Example 3 (623 mg) in tetrahydrofuran (16 mL) was added 10% hydrochloric acid-methanol solution (8 mL) on ice bath and added dropwise tert-butyl nitrite (182 mg) further. The mixture was stirred at room temperature for 6 hours. The reaction mixture was concentrated. To the obtained residue was added an aqueous solution of sodium hydrogen carbonate and the mixture was extracted with ethyl acetate. The obtained organic layer was dried and concentrated. The obtained residue was purified by column chromatography on silica gel (hexane:ethyl acetate=3:2) to give the title compound (541 mg, less polar:more polar=2:9) having the following physical data.

Less Polar:
TLC: Rf 0.39 (hexane:ethyl acetate=3:2);
NMR: δ 2.05 (s, 6H), 6.72-7.01 (m, 3H), 7.17 (s, 2H), 7.62-7.75 (m, 1H), 7.81 (d, J=2.7 Hz, 1H), 8.02 (dd, J=9.7, 2.7 Hz, 1H), 8.16 (s, 1H).

More Polar:
TLC: Rf 0.36 (hexane:ethyl acetate=3:2);
NMR: δ 2.09 (s, 6H), 6.70-7.04 (m, 3H), 7.19 (s, 2H), 7.37-7.57 (m, 1H), 8.11-8.27 (m, 2H), 9.65 (s, 1H).

Example 52

5-[2-amino-2-(2,4-difluorophenyl)-1-hydroxyethyl]-1-(2,6-dimethylphenyl)-2(1H)-pyridinone hydrochloride To a solution of the compound prepared in Example 51 (250 mg) in methanol (12 mL) was added 10% hydrochloric acid-methanol solution (3 mL) and added 10% palladium/carbon (50 mg, 25% wt) subsequently. The mixture was stirred at room temperature for 5 hours under an atmosphere of hydrogen. The reaction mixture was filtered through Celite (trade name). The filtrate was concentrated and dried to give the title compound (281 mg) having the following physical data. MS (APCI, Pos, 20V): 371 $(M+H)^{30}$.

Example 53

N-{1-(2,4-difluorophenyl)-2-[1-(2,6-dimethylphenyl)-6-oxo-1,6-dihydro-3-pyridinyl]-2-hydroxyethyl}tetrahydro-2H-pyran-4-carboxamide To a solution of the compound prepared in Example 52 (281 mg) in N,N-dimethylformamide (8 mL) were added tetrahydropyran-4-carboxylic acid (78 mg), triethylamine (121 mg), 1-ethyl-3-[3-(dimethylamino)propyl]carbodiimide (EDC) hydrochloride (115 mg) and hydroxybenzotriazole (HOBt, 81 mg). The mixture was stirred at room temperature for 20 hours. The reaction mixture was concentrated. To the obtained residue was added an aqueous solution of sodium hydrogen carbonate and the mixture was extracted with ethyl acetate. The obtained organic layer was dried and concentrated. The obtained residue was purified by preparative TLC (ethyl acetate:methanol=20:1) to give the title compound (88 mg) having the following physical data.

TLC: Rf 0.59 (ethyl acetate:methanol=9:1);

NMR: δ 1.67-1.81 (m, 4H), 1.84 (s, 3H), 2.01 (s, 3H), 2.27-2.48 (m, 1H), 3.23 (d, J=3.8 Hz, 1H), 3.32-3.48 (m, 2H), 3.93-4.06 (m, 2H), 4.87 (t, J=3.8 Hz, 1H), 5.42 (dd, J=8.4, 3.8 Hz, 1H), 6.54-6.76 (m, 3H), 6.77-6.90 (m, 2H), 7.07-7.16 (m, 2H), 7.17-7.31 (m, 3H).

Example 54

N-{1-(2,4-difluorophenyl)-2-[1-(2,6-dimethylphenyl)-6-oxo-1,6-dihydro-3-pyridinyl]-2-oxoethyl}tetrahydro-2H-pyran-4-carboxamide To a solution of the compound prepared in Example 53 (88 mg) in dichloromethane (7 mL) was added Dess-Martin Periodinane (77 mg) and the mixture was stirred at room temperature for an hour. To the reaction mixture was added water and the mixture was extracted with dichloromethane. The obtained organic layer was dried and concentrated. The obtained residue was purified by preparative TLC (ethyl acetate) to give the title compound (69 mg) having the following physical data.

TLC: Rf 0.46 (ethyl acetate);

NMR: δ 1.67-1.84 (m, 4H), 1.87 (s, 3H), 2.06 (s, 3H), 2.34-2.49 (m, 1H), 3.32-3.48 (m, 2H), 3.92-4.05 (m, 2H), 6.32 (d, J=6.6 Hz, 1H), 6.65 (d, J=9.7 Hz, 1H), 6.74-6.94 (m, 2H), 7.01 (d, J=6.6 Hz, 1H), 7.14-7.22 (m, 2H), 7.23-7.34 (m, 2H), 7.92 (dd, J=9.7, 2.7 Hz, 1H), 8.00-8.04 (m, 1H).

Example 55

5-[4-(2,4-difluorophenyl)-2-(tetrahydro-2H-pyran-4-yl)-1,3-oxazol-5-yl]-1-(2,6-dimethylphenyl)-2(1H)-pyridinone To a solution of the compound prepared in Example 54 (67 mg) in toluene (5 mL) was added phosphorus oxychloride (0.5 mL) and the mixture was stirred at 80° C. for 2 hours. The reaction mixture was concentrated. To the obtained residue was added an aqueous solution of sodium hydrogen carbonate and the mixture was extracted with ethyl acetate. The obtained organic layer was dried and concentrated. The obtained residue was purified by preparative TLC (ethyl acetate) to give the compound of the present invention (35 mg) having the following physical data.

TLC: Rf 0.50 (ethyl acetate);

NMR: δ 1.98-2.07 (m, 4H), 2.10 (s, 6H), 3.01-3.16 (m, 1H), 3.46-3.60 (m, 2H), 3.99-4.09 (m, 2H), 6.69 (d, J=9.5 Hz, 1H), 6.81-6.91 (m, 1H), 6.93-7.02 (m, 1H), 7.13-7.20 (m, 2H), 7.21-7.28 (m, 2H), 7.41-7.48 (m, 1H), 7.55-7.66 (m, 1H).

Example 56

1-(4-chloro-2,6-dimethylphenyl)-5-[5-(2,4-difluorophenyl)-2-(tetrahydro-2H-pyran-4-yl)-1,3-thiazol-4-yl]-2(1H)-pyridinone Under an atmosphere of argon, to a solution of the compound prepared in Example 4 (161 mg) in 2-propanol (5 mL) were added the compound prepared in Example A18 (50 mg) and potassium carbonate (95 mg) and the mixture was stirred at 60° C. for 30 minutes. The reaction mixture was poured into water and extracted with ethyl acetate. The obtained organic layer was washed with brine, dried and concentrated.

The obtained residue was purified by column chromatography on silica gel (hexane:ethyl acetate=1:1→1:2→1:5→ethyl acetate:methanol=10:1) to give the compound of the present invention (167 mg) having the following physical data.

TLC: Rf 0.28 (hexane:ethyl acetate=1:5);

NMR: δ 7.52 (dd, J=9.3, 2.4 Hz, 1H), 7.40-7.30 (m, 2H), 7.15 (s, 2H), 6.98-6.86 (m, 2H), 6.62 (dd, J=9.3, 0.6 Hz, 1H), 4.14-4.02 (m, 2H), 3.55 (dt, J=2.4, 11.7 Hz, 2H), 3.24 (m, 1H), 2.13-1.85 (m, 4H), 2.01 (s, 6H).

Example 57

5-[5-(2,4-difluorophenyl)-2-(tetrahydro-2H-pyran-4-yl)-1,3-thiazol-4-yl]-1-(4-fluoro-2,6-dimethylphenyl)-2(1H)-pyridinone By the same procedure as a series of reactions of Example 3→Example 4→Example 56, using the corresponding aniline compounds instead of 4-chloro-2,6-dimethylaniline, the title compound having the following physical data was obtained.

TLC: Rf 0.26 (hexane:ethyl acetate=2:3);

NMR: δ 7.51 (dd, J=9.6, 2.7 Hz, 1H), 7.39-7.30 (m, 2H), 6.98-6.82 (m, 4H), 6.62 (dd, J=9.6, 0.6 Hz, 1H), 4.16-4.02 (m, 2H), 3.55 (dt, J=2.1, 11.7 Hz, 2H), 3.25 (m, 1H), 2.15-1.85 (m, 4H), 2.03 (s, 6H).

Example 57(1)

1-(4-chloro-2,6-dimethylphenyl)-5-[5-(2,4-difluorophenyl)-2-(tetrahydro-2H-thiopyran-4-yl)-1,3-thiazol-4-yl]-2(1H)-pyridinone By the same procedure as a reaction of Example 57, using the compound prepared in Example A22 instead of the compound prepared in Example A18, the title compound having the following physical data was obtained.

TLC: Rf 0.48 (ethyl acetate:hexane=2:1);

NMR: δ 1.91-2.06 (m, 8H), 2.42-2.52 (m, 2H), 2.70-2.89 (m, 4H), 3.00-3.12 (m, 1H), 6.62 (dd, J=9.7, 0.6 Hz, 1H), 6.86-6.99 (m, 2H), 7.15 (s, 2H), 7.29-7.39 (m, 2H), 7.50 (dd, J=9.7, 2.6 Hz, 1H).

Example 57(2)

5-[5-(2,4-difluorophenyl)-2-(tetrahydro-2H-thiopyran-4-yl)-1,3-thiazol-4-yl]-1-(4-fluoro-2,6-dimethylphenyl)-2(1H)-pyridinone By the same procedure as a reaction of Example 57, using 4-fluoro-2,6-dimethylaniline instead of 4-chloro-2,6-dimethylaniline and the compound prepared in Example A22 instead of the compound prepared in Example A18, the title compound having the following physical data was obtained.

TLC: Rf 0.42 (ethyl acetate:hexane=2:1);

NMR: δ 1.90-2.09 (m, 8H), 2.41-2.51 (m, 2H), 2.69-2.89 (m, 4H), 3.00-3.11 (m, 1H), 6.60 (dd, J=9.6, 0.6 Hz, 1H), 6.84 (d, J=8.8 Hz, 2H), 6.88-6.97 (m, 2H), 7.28-7.37 (m, 2H), 7.48 (dd, J=9.6, 2.6 Hz, 1H).

Example 58

1-(4-chloro-2,6-dimethylphenyl)-5-[5-(2,4-difluorophenyl)-2-(1,1-dioxidotetrahydro-2H-thiopyran-4-yl)-1,3-thiazol-4-yl]-2(1H)-pyridinone By the same procedure as a reaction of Example 41, using the compound prepared in Example 57 instead of the compound prepared in Example 10(9), the compound of the present invention having the following physical data was obtained.

TLC: Rf 0.35 (ethyl acetate);
NMR: δ 2.02 (s, 6H), 2.53-2.64 (m, 4H), 3.06-3.18 (m, 2H), 3.24-3.38 (m, 3H), 6.63 (dd, J=9.6, 0.7 Hz, 1H), 6.88-7.00 (m, 2H), 7.16 (s, 2H), 7.31 (dd, J=2.7, 0.7 Hz, 1H), 7.33-7.39 (m, 1H), 7.48 (dd, J=9.6, 2.7 Hz, 1H).

Example 58(1)

5-[5-(2,4-difluorophenyl)-2-(1,1-dioxidotetrahydro-2H-thiopyran-4-yl)-1,3-thiazol-4-yl]-1-(4-fluoro-2,6-dimethylphenyl)-2(1H)-pyridinone By the same procedure as a reaction of Example 58, using the compound prepared in Example 57(1) instead of the compound prepared in Example 57, the compound of the present invention having the following physical data was obtained.

TLC: Rf 0.33 (ethyl acetate);
NMR: δ 2.03 (s, 6H), 2.52-2.66 (m, 4H), 3.05-3.18 (m, 2H), 3.23-3.39 (m, 3H), 6.63 (dd, J=9.6, 0.5 Hz, 1H), 6.87 (d, J=8.8 Hz, 2H), 6.89-7.00 (m, 2H), 7.30-7.39 (m, 2H), 7.48 (dd, J=9.6, 2.7 Hz, 1H).

Example 59

5-{5-(2,4-difluorophenyl)-2-[(1S,2S)-1,2-dihydroxypropyl]-1H-imidazol-4-yl}-1-(4-fluoro-2,6-dimethylphenyl)-2(1H)-pyridinone By the same procedure as a reaction of Example 17, using the compound prepared in Example 7(25b) instead of the compound prepared in Example 7(24), the compound of the present invention having the following physical data was obtained.

TLC: Rf 0.27 (dichloromethane:methanol=10:1);
NMR: δ 9.75 (br s, 1H), 7.58-7.35 (m, 3H), 7.00-6.82 (m, 4H), 6.67 (d, J=9.3 Hz, 1H), 4.63 (m, 1H), 4.29 (m, 1H), 3.13 (br s, 1H), 2.86 (br s, 1H), 2.07 (s, 6H), 1.34 (d, J=6.3 Hz, 3H).

Example 60

1-(4-chloro-2,6-dimethylphenyl)-5-[5-(2,4-difluorophenyl)-2-(2-hydroxy-1-methoxy-2-methylpropyl)-1,3-oxazol-4-yl]-2(1H)-pyridinone By the same procedure as a reaction of Example A6, using the compound prepared in Example 18 instead of 3-hydroxy-2-(hydroxymethyl)-2-methylpropionic acid, the compound of the present invention having the following physical data was obtained.

TLC: Rf 0.43 (hexane:ethyl acetate=1:3);
NMR: δ 1.29 (s, 3H), 1.31 (s, 3H), 2.09 (s, 6H), 2.72 (s, 1H), 3.47 (s, 3H), 4.21 (s, 1H), 6.67 (dd, J=9.3, 1.1 Hz, 1H), 6.89-7.09 (m, 2H), 7.17 (s, 2H), 7.46-7.59 (m, 3H).

Example 61

1-(4-chloro-2,6-dimethylphenyl)-5-[5-(2,4-difluorophenyl)-2-(2-hydroxy-2-methylpropanoyl)-1,3-oxazol-4-yl]-2(1H)-pyridinone By the same procedure as a reaction of Example 54, using the compound prepared in Example 18 instead of the compound prepared in Example 53, the compound of the present invention having the following physical data was obtained.

TLC: Rf 0.50 (hexane:ethyl acetate=1:3);
NMR: δ 1.68 (s, 6H), 2.09 (s, 6H), 4.27 (s, 1H), 6.73 (d, J=9.7 Hz, 1H), 6.92-7.02 (m, 1H), 7.03-7.13 (m, 1H), 7.19 (s, 2H), 7.38 (d, J=2.6 Hz, 1H), 7.50-7.60 (m, 1H), 7.61-7.72 (m, 1H).

Example 62

1-(4-chloro-2,6-dimethylphenyl)-5-[5-(2,4-difluorophenyl)-2-(2-hydroxy-1-methoxy-1-methylethyl)-1,3-oxazol-4-yl]-2(1H)-pyridinone By the same procedure as a series of reactions of Example 3→Example 4→Example 8→Example 6→Example 60→Example A3, using the compound prepared in Example A16 instead of 2,2-bis(hydroxymethyl)butyric acid, the compound of the present invention having the following physical data was obtained.

TLC: Rf 0.31 (hexane:ethyl acetate=1:3);
NMR: δ 1.7 (s, 3H), 2.1 (s, 6H), 2.5 (t, J=6.4 Hz, 1H), 3.3 (s, 3H), 3.9 (d, J=6.4 Hz, 2H), 6.7 (dd, J=9.5, 0.7 Hz, 1H), 7.0 (m, 2H), 7.2 (s, 2H), 7.4 (m, 1H), 7.5 (m, 2H).

Example 85

1-(2,6-difluorophenyl)-5-[(2,4-difluorophenyl)acetyl]-2(1H)-pyridinone

By the same procedure as a reaction of Example 3, using 2,6-difluoroaniline instead of 4-chloro-2,6-dimethylaniline, the title compound having the following physical data was obtained.

TLC: Rf 0.51 (hexane:ethyl acetate=1:1);
NMR: δ 8.12 (m, 1H), 8.02 (dd, J=9.9, 2.4 Hz, 1H), 7.50 (m, 1H), 7.27-7.08 (m, 3H), 6.92-6.80 (m, 2H), 6.71 (dd, J=9.9, 0.6 Hz, 1H), 4.07 (s, 2H).

Example 86

1-(2,4-difluorophenyl)-2-[1-(2,6-difluorophenyl)-6-oxo-1,6-dihydro-3-pyridinyl]-1,2-ethanedione 1-oxime By the same procedure as a reaction of Example 51, using the compound prepared in Example 85, the title compound (E/Z mixture) having the following physical data was obtained.

TLC: Rf 0.20 (hexane:ethyl acetate=3:2);
E Form or Z Form:
NMR: δ 6.77 (d, J=9.7 Hz, 1H), 6.83-7.04 (m, 2H), 7.06-7.19 (m, 2H), 7.39-7.57 (m, 2H), 8.17 (dd, J=9.7, 2.0 Hz, 1H), 8.32 (d, J=2.0 Hz, 1H), 9.54 (s, 1H).
Z Form or E Form:
NMR: δ 6.75 (d, J=10.4 Hz, 1H), 6.83-7.04 (m, 2H), 7.06-7.19 (m, 2H), 7.46-7.57 (m, 1H), 7.65-7.79 (m, 1H), 7.97 (s, 2H).

Example 87

To a solution of the compound prepared in Example 86 (795 mg) in anhydrous tetrahydrofuran (15 mL) were added sodium hydride (60% in oil, 122 mg) and ethyl bromoacetate (409 mg) and the mixture was stirred at room temperature for 15 minutes. To the reaction mixture was added 1N hydrochloric acid and the mixture was extracted with ethyl acetate. The obtained organic layer was dried and concentrated. The obtained residue was purified by column chromatography on silica gel (hexane:ethyl acetate=2:1) to give the compound 87(a) and the compound 87(b) (780 mg in total) having the following physical data.

Compound 87(a)

Ethyl [{(1Z)-1-(2,4-difluorophenyl)-2-[1-(2,6-difluorophenyl)-6-oxo-1,6-dihydro-3-pyridinyl]-2-oxoethylidene}amino)oxy]acetate TLC: Rf 0.60 (hexane:ethyl acetate=1:1);
NMR: δ 1.21 (t, J=7.2 Hz, 3H), 4.00 (q, J=7.2 Hz, 2H), 4.73 (s, 2H), 6.69-6.73 (m, 1H), 6.80-7.02 (m, 2H), 7.05-7.17 (m, 2H), 7.40-7.62 (m, 2H), 8.11 (dd, J=9.8, 2.7 Hz, 1H), 8.53-8.60 (m, 1H).

Compound 87(b)

Ethyl [{(1E)-1-(2,4-difluorophenyl)-2-[1-(2,6-difluorophenyl)-6-oxo-1,6-dihydro-3-pyridinyl]-2-oxoethylidene}amino)oxy]acetate TLC: Rf 0.64 (hexane:ethyl acetate=1:1);
NMR: δ 1.22 (t, J=7.2 Hz, 3H), 4.05 (q, J=7.2 Hz, 2H), 4.68 (s, 2H), 6.71-6.76 (m, 1H), 6.80-7.02 (m, 2H), 7.05-7.17 (m, 2H), 7.40-7.53 (m, 1H), 7.64-7.75 (m, 1H), 8.07 (dd, J=9.8, 2.7 Hz, 1H), 8.48 (d, J=2.7 Hz, 1H).

Example 88

Ethyl 4-(2,4-difluorophenyl)-5-[1-(2,6-difluorophenyl)-6-oxo-1,6-dihydro-3-pyridinyl]-1,3-oxazol-2-carboxylate Under an atmosphere of argon, to a solution of the compound 87(a) and the compound 87(b) prepared in Example 87 (780 mg in total) in anhydrous tetrahydrofuran (30 mL) was added slowly 1.0 mol/L lithium bis(trimethylsilyl)amide/tetrahydrofuran solution (2.13 mL) at −78° C. and the mixture was stirred for 10 minutes. The reaction mixture was risen to 0° C. To the mixture were added methanesulfonyl chloride (562 mg) and triethylamine (331 mg). The reaction mixture was stirred at room temperature for 30 minutes. To the reaction mixture was added 1N hydrochloric acid and the mixture was extracted with ethyl acetate. The obtained organic layer was dried and concentrated. The obtained residue was purified by column chromatography on silica gel (hexane:ethyl acetate=12:7) to give the title compound (423 mg) having the following physical data.

TLC: Rf 0.47 (hexane:ethyl acetate=1:1);
NMR: δ 1.45 (t, J=7.1 Hz, 3H), 4.51 (q, J=7.1 Hz, 2H), 6.69 (dd, J=9.8, 0.6 Hz, 1H), 6.89-7.18 (m, 4H), 7.39-7.54 (m, 2H), 7.59-7.71 (m, 2H).

Example 89

By the same procedure as a reaction of Example 36, using the compound prepared in Example 88 instead of the compound prepared in Example 35, the compounds of the present invention 89(a) and 89(b) having the following physical data were obtained.

Compound 89(a)

5-[2-acetyl-4-(2,4-difluorophenyl)-1,3-oxazol-5-yl]-1-(2,6-difluorophenyl)-2(1H)-pyridinone TLC: Rf 0.65 (hexane:ethyl acetate=2:3);
NMR: δ 2.71 (s, 3H), 6.67 (dd, J=9.8, 0.6 Hz, 1H), 6.90-7.15 (m, 4H), 7.40-7.53 (m, 2H), 7.58-7.68 (m, 1H), 7.69 (d, J=2.7 Hz, 1H).

Compound 89(b)

1-(2,6-difluorophenyl)-5-[4-(2,4-difluorophenyl)-2-(1-hydroxy-1-methylethyl)-1,3-oxazol-5-yl]-2(1H)-pyridinone TLC: Rf 0.37 (hexane:ethyl acetate=2:3);
NMR: δ 1.71 (s, 6H), 2.50-2.72 (m, 1H), 6.67 (d, J=10.6 Hz, 1H), 6.87-7.16 (m, 4H), 7.37-7.52 (m, 3H), 7.58-7.69 (m, 1H).

Example 90

1-(2,6-difluorophenyl)-5-[4-(2,4-difluorophenyl)-2-(1-hydroxyethyl)-1,3-oxazol-5-yl]-2(1H)-pyridinone By the same procedure as Step B of Example 22, using the compound 89(a) prepared in Example 89 instead of the compound prepared in Example 7(33), the compound of the present invention having the following physical data was obtained.

TLC: Rf 0.27 (hexane:ethyl acetate=2:3);
NMR: δ 1.68 (d, J=6.6 Hz, 3H), 5.01 (q, J=6.6 Hz, 1H), 6.67 (dd, J=9.6, 0.8 Hz, 1H), 6.87-7.15 (m, 4H), 7.37-7.51 (m, 3H), 7.55-7.67 (m, 1H).

Example 91

1-(4-chloro-2,6-dimethylphenyl)-5-[(2,4-(difluorophenyl)acetyl]-2(1H)-pyridinone By the same procedure as a reaction of Example 85, using 4-chloro-2,6-dimethylaniline instead of 2,6-difluoroaniline, the title compound having the following physical data was obtained.

TLC: Rf 0.29 (hexane:ethyl acetate=2:1);
NMR: δ 8.02 (dd, J=9.6, 2.4 Hz, 1H), 7.97 (dd, J=2.4, 0.6 Hz, 1H), 7.25-7.15 (m, 3H), 6.92-6.75 (m, 2H), 6.71 (dd, J=9.6, 0.6 Hz, 1H), 4.03 (s, 2H), 2.07 (s, 6H).

Example 92

Ethyl 5-[1-(4-chloro-2,6-dimethylphenyl)-6-oxo-1,6-dihydro-3-pyridinyl]-4-(2,4-difluorophenyl)-1,3-oxazole-2-carboxylate By the same procedure as a series of reactions of Example 86→Example 87→Example 88, using the compound prepared in Example 91 instead of the compound prepared in Example 85, the title compound having the following physical data was obtained.

TLC: Rf 0.44 (hexane:ethyl acetate=1:1);
NMR: δ 1.45 (t, J=7.1 Hz, 3H), 2.08 (s, 6H), 4.51 (q, J=7.1 Hz, 2H), 6.72 (dd, J=9.6, 0.6 Hz, 1H), 6.84-6.96 (m, 1H), 6.98-7.08 (m, 1H), 7.19 (s, 2H), 7.45 (d, J=2.4 Hz, 1H), 7.48-7.56 (m, 1H), 7.63-7.75 (m, 1H).

Example 93

By the same procedure as a reaction of Example 89, using the compound prepared in Example 92 instead of the compound prepared in Example 88, the compounds of the present invention 93(a) and 93(b) having the following physical data were obtained.

Compound 93(a)

1-(4-chloro-2,6-dimethylphenyl)-5-[4-(2,4-difluorophenyl)-2-(1-hydroxy-1-methylethyl)-1,3-oxazol-5-yl]-2(1H)-pyridinone TLC: Rf 0.28 (hexane:ethyl acetate=2:3);
NMR: δ 1.71 (s, 6H), 2.08 (s, 6H), 2.62 (s, 1H), 6.71 (dd, J=9.7, 0.7 Hz, 1H), 6.81-6.94 (m, 1H), 6.96-7.05 (m, 1H), 7.18 (s, 2H), 7.23 (d, J=2.6 Hz, 1H), 7.44-7.53 (m, 1H), 7.59-7.71 (m, 1H).

Compound 93(b)

5-[2-acetyl-4-(2,4-difluorophenyl)-1,3-oxazol-5-yl]-1-(4-chloro-2,6-dimethylphenyl)-2(1H)-pyridinone TLC: Rf 0.67 (hexane:ethyl acetate=2:3);
NMR: δ 2.08 (s, 6H), 2.70 (s, 3H), 6.65-6.74 (m, 1H), 6.87-7.00 (m, 1H), 7.01-7.12 (m, 1H), 7.19 (s, 2H), 7.43-7.54 (m, 2H), 7.60-7.71 (m, 1H).

Example 94

1-(4-chloro-2,6-dimethylphenyl)-5-[4-(2,4-difluorophenyl)-2-(1-hydroxyethyl)-1,3-oxazol-5-yl]-2(1H)-pyridinone By the same procedure as Step B of Example 22, using the compound 93(b) prepared in Example 93 instead of the compound prepared in Example 7(33), the compound of the present invention having the following physical data was obtained.
TLC: Rf 0.26 (hexane:ethyl acetate=1:2);
NMR: δ 1.68 (d, J=6.6 Hz, 3H), 2.08 (s, 6H), 2.50 (d, J=5.5 Hz, 1H), 4.94-5.07 (m, 1H), 6.71 (dd, J=9.6, 0.6 Hz, 1H), 6.83-6.94 (m, 1H), 6.96-7.06 (m, 1H), 7.18 (s, 2H), 7.27-7.28 (m, 1H), 7.42-7.53 (m, 1H), 7.58-7.68 (m, 1H).

Example 95

1-(4-chloro-2,6-dimethylphenyl)-5-[4-(2,4-difluorophenyl)-2-(hydroxymethyl)-1,3-oxazol-5-yl]-2(1H)-pyridinone By the same procedure as Step B of Example 22, using the compound prepared in Example 92 instead of the compound prepared in Example 7(33), the compound of the present invention having the following physical data was obtained.
TLC: Rf 0.45 (ethyl acetate);
NMR: δ 2.08 (s, 6H), 2.47 (t, J=6.6 Hz, 1H), 4.79 (d, J=6.6 Hz, 2H), 6.71 (d, J=9.7 Hz, 1H), 6.83-6.95 (m, 1H), 6.97-7.06 (m, 1H), 7.18 (s, 2H), 7.30 (d, J=2.6 Hz, 1H), 7.43-7.52 (m, 1H), 7.57-7.68 (m, 1H).

Example 96

Methyl 1-(2,6-dimethylphenyl)-6-oxo-1,6-dihydro-3-pyridinecarboxylate

To a suspended solution of sodium hydride (60% in oil, 14.5 g) in tetrahydrofuran (240 mL) were added 2,6-dimethylaniline (29.3 g) and methyl coumalate (18.6 g) and the mixture was stirred at 60° C. for 4 hours. To the reaction mixture was added an aqueous solution of ammonium chloride and the mixture was extracted with ethyl acetate. The obtained organic layer was dried and concentrated. The obtained residue was purified by column chromatography on silica gel (hexane:ethyl acetate=3:2) to give the title compound (10.4 g) having the following physical data.
TLC: Rf 0.39 (hexane:ethyl acetate=1:1);
NMR: δ 2.10 (s, 6H), 3.86 (s, 3H), 6.69 (dd, J=9.3, 0.9 Hz, 1H), 7.14-7.22 (m, 2H), 7.25-7.31 (m, 1H), 7.93-8.03 (m, 2H).

Example 97

1-(2,6-dimethylphenyl)-6-oxo-1,6-dihydro-3-pyridinecarboxylic acid

By the same procedure as a reaction of Example A3, using the compound prepared in Example 96 instead of the compound prepared in Example A2, the title compound having the following physical data was obtained.
TLC: Rf 0.13 (ethyl acetate);
NMR: δ 2.10 (s, 6H), 6.73 (dd, J=9.5, 0.5 Hz, 1H), 7.15-7.23 (m, 2H), 7.23-7.32 (m, 1H), 7.98 (dd, J=9.6, 2.0 Hz, 1H), 8.07 (d, J=2.0 Hz, 1H).

Example 98

Ethyl [1-(2,6-dimethylphenyl)-6-oxo-1,6-dihydro-3-pyridinyl]acetate

To a solution of the compound prepared in Example 97 (4.11 g) in dichloromethane (80 mL) were added oxalyl chloride (3.22 g) and N,N-dimethylformamide (0.3 mL) and the mixture was stirred at room temperature for 30 minutes. The reaction mixture was concentrated and the obtained residue was added to tetrahydrofuran (80 mL). To the mixture were added 2.0 mol/L trimethylsilyldiazomethane/hexane solution (84.5 mL) and triethylamine (17.1 g) and the mixture was stirred at 60° C. for 5 hours. To the reaction mixture was added water and the mixture was extracted with ethyl acetate. The obtained organic layer was dried and concentrated. The obtained residue was dissolved in a mixed solution of ethanol (20 mL) and tetrahydrofuran (60 mL). To the mixture were added silver benzoate (0.77 g) and triethylamine (5.13 g) and the mixture was stirred at 70° C. for 2 hours. The reaction mixture was concentrated. To the obtained residue was added water and the mixture was extracted with ethyl acetate. The obtained organic layer was dried and concentrated. The obtained residue was purified by column chromatography on silica gel (hexane:ethyl acetate=1:2) to give the title compound (1.00 g) having the following physical data.
TLC: Rf 0.44 (ethyl acetate);
NMR: δ 1.26 (t, J=7.1 Hz, 3H), 2.10 (s, 6H), 3.37 (s, 2H), 4.17 (q, J=7.1 Hz, 2H), 6.70 (d, J=9.5 Hz, 1H), 7.03 (dd, J=2.6, 0.8 Hz, 1H), 7.13-7.19 (m, 2H), 7.20-7.28 (m, 1H), 7.41 (dd, J=9.5, 2.6 Hz, 1H).

Example 99

[1-(2,6-dimethylphenyl)-6-oxo-1,6-dihydro-3-pyridinyl]acetic acid

By the same procedure as a reaction of Example A3, using the compound prepared in Example 98 instead of the compound prepared in Example A2, the title compound having the following physical data was obtained.

TLC: Rf 0.06 (ethyl acetate);
NMR: δ 2.08 (s, 6H), 3.41 (s, 2H), 6.77 (d, J=9.3 Hz, 1H), 7.05 (d, J=2.0 Hz, 1H), 7.12-7.19 (m, 2H), 7.20-7.28 (m, 1H), 7.45 (dd, J=9.3, 2.0 Hz, 1H).

Example 100

5-[2-(2,4-difluorophenyl)-2-oxoethyl]-1-(2,6-dimethylphenyl)-2(1H)-pyridinone

To a solution of the compound prepared in Example 99 (429 mg) in dichloromethane (15 mL) were added oxalyl chloride (294 mg) and N,N-dimethylformamide (0.1 mL) and the mixture was stirred at room temperature for 30 minutes. The reaction mixture was concentrated and the obtained residue was added to dichloromethane (15 mL). To the mixture were added 1,5-difluorobenzene (3 mL) and aluminium chloride (618 mg) and the mixture was stirred at room temperature for 4 hours. To the reaction mixture was added an aqueous solution of sodium hydrogen carbonate, and the mixture was filtered through Celite (trade name). The obtained water layer was extracted with dichloromethane. The obtained organic layer was dried and concentrated. The obtained residue was purified by column chromatography on silica gel (hexane:ethyl acetate=1:3) to give the title compound (148 mg) having the following physical data.
TLC: Rf 0.53 (ethyl acetate);
NMR: δ 2.08 (s, 6H), 4.02 (d, J=2.7 Hz, 2H), 6.70 (d, J=9.5 Hz, 1H), 6.83-6.94 (m, 1H), 6.94-7.04 (m, 2H), 7.11-7.18 (m, 2H), 7.19-7.26 (m, 1H), 7.34 (dd, J=9.5, 2.7 Hz, 1H), 7.87-8.01 (m, 1H).

Example 101

Ethyl (2E)-4-(2,4-difluorophenyl)-3-[1-(2,6-dimethylphenyl)-6-oxo-1,6-dihydro-3-pyridinyl]-2-(hydroxyimino)-4-oxobutanoate Under an atmosphere of argon, to a solution of the compound prepared in Example 100 (145 mg) in anhydrous tetrahydrofuran (10 mL) was added 1.0 mol/L lithium bis(trimethylsilyl)amide/tetrahydrofuran solution (1.03 mL) at −78° C. and further added 2-chloro-2-hydroxyiminoacetic acid ethyl ester (75 mg) and the mixture was stirred for 30 minutes. The reaction mixture was risen to room temperature. To the mixture was added 1N hydrochloric acid and the mixture was extracted with ethyl acetate. The obtained organic layer was dried and concentrated. The obtained residue was purified by preparative TLC (hexane:ethyl acetate=1:2) to give the title compound (75 mg) having the following physical data.
TLC: Rf 0.46 (hexane:ethyl acetate=1:2);
NMR: δ 1.33 (t, J=7.1 Hz, 3H), 1.86 (s, 3H), 1.91 (s, 3H), 3.83 (s, 1H), 4.24-4.42 (m, 2H), 4.59 (d, J=2.6 Hz, 1H), 6.41 (d, J=9.9 Hz, 1H), 6.64-6.77 (m, 1H), 6.80-6.96 (m, 3H), 7.09-7.19 (m, 2H), 7.19-7.28 (m, 1H), 7.57-7.71 (m, 1H).

Example 102

Ethyl 5-(2,4-difluorophenyl)-4-[1-(2,6-dimethylphenyl)-6-oxo-1,6-dihydro-3-pyridinyl]-3-isoxazolecarboxylate The compound prepared in Example 101 (74 mg) was dissolved in ethanol (4 mL). To the mixture was added 4N hydrogen chloride/dioxane solution (0.5 mL) and the mixture was stirred at 70° C. for an hour. The reaction mixture was concentrated and dried to give the title compound (72 mg) having the following physical data.
TLC: Rf 0.53 (hexane:ethyl acetate=1:3);
NMR: δ 1.40 (t, J=7.1 Hz, 3H), 2.06 (s, 6H), 4.43 (q, J=7.1 Hz, 2H), 6.86-6.98 (m, 1H), 7.03-7.13 (m, 1H), 7.15-7.22 (m, 2H), 7.28-7.39 (m, 3H), 7.49-7.59 (m, 1H), 7.62-7.73 (m, 1H).

Example 103

By the same procedure as a reaction of Example 36, using the compound prepared in Example 102 instead of the compound prepared in Example 35, the compounds of the present invention 103(a) and 103(b) having the following physical data were obtained.

Compound 103(a)

5-[5-(2,4-difluorophenyl)-3-(1-hydroxy-1-methylethyl)-4-isoxazolyl]-1-(2,6-dimethylphenyl)-2(1H)-pyridinone TLC: Rf 0.25 (hexane:ethyl acetate=1:3);
NMR: δ 1.64 (s, 6H), 2.02 (s, 6H), 2.13 (s, 1H), 6.71 (d, J=9.5 Hz, 1H), 6.83-6.92 (m, 1H), 6.95-7.05 (m, 1H), 7.08-7.17 (m, 3H), 7.18-7.25 (m, 1H), 7.42 (dd, J=9.5, 2.6 Hz, 1H), 7.50-7.59 (m, 1H).

Compound 103(b)

5-[3-acetyl-5-(2,4-difluorophenyl)-4-isoxazolyl]-1-(2,6-dimethylphenyl)-2(1H)-pyridinone TLC: Rf 0.53 (hexane:ethyl acetate=1:3);
NMR: δ 2.08 (s, 6H), 2.71 (s, 3H), 6.67 (d, J=9.5 Hz, 1H), 6.85-6.96 (m, 1H), 6.98-7.08 (m, 1H), 7.09-7.17 (m, 3H), 7.17-7.29 (m, 2H), 7.51-7.65 (m, 1H).

Example 104(a)

1-(4-chloro-2,6-dimethylphenyl)-6-oxo-1,6-dihydro-3-pyridinecarboxylic acid

By the same procedure as a series of reactions of Example 3→Example A3, using methyl coumalate instead of the compound prepared in Example 2, the title compound having the following physical data was obtained.
TLC: Rf 0.28 (ethyl acetate:methanol=2:1);
NMR: δ 2.08 (s, 6H), 6.73 (d, J=9.0 Hz, 1H), 7.20 (s, 2H), 7.96-8.05 (m, 2H).

Example 104(b)

tert-butyl [1-(4-chloro-2,6-dimethylphenyl)-6-oxo-1,6-dihydro-3-pyridinyl]carbamate According to a method of Shioiri et al. (Journal of the American Chemical Society, 1972, 94(17), 6203~6205), using the compound prepared in Example 104(a), the title compound having the following physical data was obtained.
TLC: Rf 0.39 (ethyl acetate);

NMR: δ 1.48 (s, 9H), 2.09 (s, 6H), 6.13-6.25 (m, 1H), 6.68 (d, J=9.9 Hz, 1H), 7.15 (s, 2H), 7.22-7.29 (m, 1H), 7.47-7.58 (m, 1H).

Example 105

5-amino-1-(4-chloro -2,6-dimethylphenyl)-2(1H)-pyridinone

By the same procedure as a reaction of Example 102, using the compound prepared in Example 104(b) instead of the compound prepared in Example 101, the title compound having the following physical data was obtained.

TLC: Rf 0.29 (ethyl acetate:methanol=9:1);

NMR: δ 2.09 (s, 6H), 3.11 (s, 2H), 6.52 (dd, J=3.0, 0.7 Hz, 1H), 6.67 (dd, J=9.7, 0.7 Hz, 1H), 7.14-7.21 (m, 3H).

Example 106

1-(4-chloro-2,6-dimethylphenyl)-5-iodo-2(1H)-pyridinone

According to a method of G-S. Jiao et al. (The Journal of Organic Chemistry, 2003, 68(21), 8264~8267), using the compound prepared in Example 105, the title compound having the following physical data was obtained.

TLC: Rf 0.52 (ethyl acetate:hexane=3:2);

NMR: δ 2.09 (s, 6H), 6.54 (dd, J=9.7, 0.6 Hz, 1H), 7.16-7.19 (m, 2H), 7.30 (dd, J=2.6, 0.5 Hz, 1H), 7.55 (dd, J=9.7, 2.6 Hz, 1H).

Example 107

1-(4-chloro-2,6-dimethylphenyl)-5-(trimethylstannyl)-2(1H)-pyridinone

To a solution of the compound prepared in Example 106 (241 mg) in anhydrous tetrahydrofuran (12 mL) were added lithium chloride (86 mg) and hexamethylditin (286 mg) and tetrakis(triphenylphosphine)palladium(0) (39 mg) and the mixture was stirred at 65° C. for 10 minutes. To the reaction mixture was added an aqueous saturated sodium hydrogen carbonate solution and the mixture was extracted with ethyl acetate. The obtained organic layer was dried and concentrated. The obtained residue was purified by column chromatography on silica gel (hexane:ethyl acetate=3:2) to give the title compound (266 mg) having the following physical data.

TLC: Rf 0.63 (hexane:ethyl acetate=1:2);

NMR: δ 0.15-0.42 (m, 9H), 2.06 (s, 6H), 6.71 (dd, J=9.1, 0.7 Hz, 1H), 6.88 (dd, J=1.9, 0.7 Hz, 1H), 7.16 (s, 2H), 7.44 (dd, J=9.1, 1.9 Hz, 1H).

Example 108

Ethyl (2E)-4-(2,4-difluorophenyl)-2-(hydroxyimino)-4-oxobutanoate

By the same procedure as a reaction of Example 101, using 2,4-difluoroacetophenone instead of the compound prepared in Example 100, the title compound having the following physical data was obtained.

TLC: Rf 0.23 (hexane:ethyl acetate=3:1);

NMR: δ 1.38 (t, J=7.1 Hz, 3H), 3.39-3.99 (m, 2H), 4.37 (q, J=7.1 Hz, 2H), 6.83-7.00 (m, 2H), 7.66-7.86 (m, 1H).

Example 109

Ethyl 5-(2,4-difluorophenyl)-3-isoxazolecarboxylate

By the same procedure as a reaction of Example 102, using the compound prepared in Example 108 instead of the compound prepared in Example 101, the title compound having the following physical data was obtained.

TLC: Rf 0.57 (hexane:ethyl acetate=3:1);

NMR: δ 1.45 (t, J=7.1 Hz, 3H), 4.49 (q, J=7.1 Hz, 2H), 6.90-7.12 (m, 3H), 7.93-8.06 (m, 1H).

Example 110

[5-(2,4-difluorophenyl)-3-isoxazolyl]methanol

Under an atmosphere of argon, to a suspended solution of lithium aluminium hydride (0.52 g) in tetrahydrofuran (30 mL) was added dropwise solution of the compound prepared in Example 109 (1.75 g) in tetrahydrofuran (10 mL) at −78° C. The reaction mixture was stirred for 10 minutes. To the reaction mixture was added 1N hydrochloric acid. The reaction mixture was filtered through Celite (trade name), and extracted with ethyl acetate. The obtained organic layer was dried and concentrated to give the title compound (1.38 g) having the following physical data.

TLC: Rf 0.43 (hexane:ethyl acetate=1:1);

NMR: δ 4.83 (s, 2H), 6.72 (d, J=3.8 Hz, 1H), 6.88-7.08 (m, 2H), 7.86-8.00 (m, 1H).

Example 111

[5-(2,4-difluorophenyl)-3-isoxazolyl]methyl acetate

To a solution of the compound prepared in Example 110 (1.38 g) in pyridine (30 mL) was added acetic anhydride (0.67 g) and the mixture was stirred at room temperature for 4 hours. The reaction mixture was concentrated. To the obtained residue was added 1N hydrochloric acid and the mixture was extracted with ethyl acetate. The obtained organic layer was dried and concentrated to give the title compound (1.74 g) having the following physical data.

TLC: Rf 0.41 (hexane:ethyl acetate=3:1);

NMR: δ 2.15 (s, 3H), 5.22 (s, 2H), 6.69 (d, J=3.8 Hz, 1H), 6.88-7.08 (m, 2H), 7.87-8.01 (m, 1H).

Example 112

[4-bromo-5-(2,4-difluorophenyl)-3-isoxazolyl]methyl acetate

To a solution of the compound prepared in Example 111 (1.59 g) in acetic acid (30 mL) was added N-bromosuccinimide (3.35 g) and the mixture was stirred at 115° C. for 2 hours. The reaction mixture was concentrated. To the obtained residue was added diisopropyl ether and the precipitated white solid was removed in filtration. The obtained organic layer was concentrated. The obtained residue was purified by column chromatography on silica gel (hexane: ethyl acetate=7:1) to give the title compound (1.83 g) having the following physical data.

TLC: Rf 0.58 (toluene: ethyl acetate=10:1);

NMR: δ 2.17 (s, 3H), 5.24 (s, 2H), 6.95-7.11 (m, 2H), 7.64-7.75 (m, 1H).

Example 113

[4-[1-(4-chloro-2,6-dimethylphenyl)-6-oxo-1,6-dihydro-3-pyridinyl]-5-(2,4-difluorophenyl)-3-isoxazolyl]methyl acetate To a solution of the compound prepared in Example 112 (259 mg) and the compound prepared in Example 107 (103 mg) in N,N-dimethylformamide (8 mL) were added tetrakis(triphenylphosphine)palladium (30 mg) and copper iodide (10 mg), and the mixture was stirred at 100° C. for 3 hours. To the reaction mixture was added water and the mixture was extracted with ethyl acetate. The obtained organic layer was dried and concentrated. The obtained residue was purified by preparative TLC (hexane:ethyl acetate=1:1) to give the title compound (23 mg) having the following physical data.
TLC: Rf 0.15 (hexane:ethyl acetate=4:3);
NMR: δ 2.01 (s, 3H), 2.04 (s, 6H), 5.18 (s, 2H), 6.73 (d, J=9.5 Hz, 1H), 6.83-6.95 (m, 1H), 6.96-7.11 (m, 2H), 7.16 (s, 2H), 7.32 (dd, J=9.5, 2.6 Hz, 1H), 7.57-7.72 (m, 1H).

Example 114

1-(4-chloro-2,6-dimethylphenyl)-5-[5-(2,4-difluorophenyl)-3-(hydroxymethyl)-4-isoxazolyl]-2(1H)-pyridinone To a solution of the compound prepared in Example 113 (50 mg) in ethanol (4 mL) was added potassium carbonate (43 mg) and the mixture was stirred at 60° C. for 20 minutes. To the reaction mixture was added 1N hydrochloric acid and the mixture was extracted with ethyl acetate. The obtained organic layer was dried and concentrated. The obtained residue was purified by preparative TLC (hexane:ethyl acetate=1:2) to give the compound of the present invention (30 mg) having the following physical data.
TLC: Rf 0.34 (hexane:ethyl acetate=1:2);
NMR: δ 2.02 (t, J=6.2 Hz, 1H), 2.07 (s, 6H), 4.75 (d, J=6.2 Hz, 2H), 6.70 (dd, J=9.5, 0.7 Hz, 1H), 6.85-6.96 (m, 1H), 6.99-7.10 (m, 1H), 7.17 (s, 2H), 7.24 (dd, J=2.6, 0.7 Hz, 1H), 7.35 (dd, J=9.5, 2.6 Hz, 1H), 7.58-7.70 (m, 1H).

Example 115

Ethyl 5-[1-(4-chloro-2,6-dimethylphenyl)-6-oxo-1,6-dihydro-3-pyridinyl]-4-(2,4-difluorophenyl)-3-isoxazolecarboxylate By the same procedure as a series of reactions of Example 101→Example 102, using the compound prepared in Example 91 instead of the compound prepared in Example 100, the title compound having the following physical data was obtained.
TLC: Rf 0.39 (hexane:ethyl acetate=1:1);
NMR: δ 1.30 (t, J=7.1 Hz, 3H), 2.04 (s, 6H), 4.35 (q, J=7.1 Hz, 2H), 6.67 (dd, J=9.7, 0.7 Hz, 1H), 6.90-7.05 (m, 2H), 7.18 (s, 2H), 7.28-7.37 (m, 1H), 7.41 (dd, J=9.7, 2.7 Hz, 1H), 7.46-7.51 (m, 1H).

Example 116

1-(4-chloro-2,6-dimethylphenyl)-5-[4-(2,4-difluorophenyl)-3-(1-hydroxy-1-methylethyl)-5-isoxazolyl]-2(1H)-pyridinone By the same procedure as a reaction of Example 36, using the compound prepared in Example 115 instead of the compound prepared in Example 35, the compound of the present invention having the following physical data was obtained.
TLC: Rf 0.37 (hexane:ethyl acetate=1:1);
NMR: δ 1.50 (s, 6H), 2.00 (s, 6H), 2.11 (s, 1H), 6.61 (dd, J=9.7, 0.7 Hz, 1H), 6.89-7.06 (m, 2H), 7.17 (s, 2H), 7.23-7.40 (m, 3H).

Example 117(a)

1-[1-(4-chloro-2,6-dimethylphenyl)-6-oxo-1,6-dihydro-3-pyridinyl]-2-(2,4-difluorophenyl)-1,2-ethanedione dioxime By the same procedure as a series of reactions of Example 51→Example 48, using the compound prepared in Example 91 instead of the compound prepared in Example 3, the title compound having the following physical data was obtained.
More Polar:
TLC: Rf 0.19 (hexane:ethyl acetate=2:3).
Less Polar:
TLC: Rf 0.23 (hexane:ethyl acetate=2:3);
MS (APCI, Pos. 20V): m/z 432 (M+H)$^+$.

Example 117(b)

1-(4-chloro-2,6-dimethylphenyl)-5-[4-(2,4-difluorophenyl)-1,2,5-oxadiazol-3-yl]-2(1H)-pyridinone The compound prepared in Example 117(a) (153 mg) was added to thionyl chloride (4 mL) and the mixture was stirred at room temperature for 12 hours. The reaction mixture was concentrated. To the obtained residue was added an aqueous saturated sodium hydrogen carbonate solution and the mixture was extracted with ethyl acetate. The obtained organic layer was dried and concentrated. The obtained residue was purified by preparative TLC (hexane:ethyl acetate=4:3) to give the compound of the present invention (15 mg) having the following physical data.
TLC: Rf 0.53 (hexane:ethyl acetate=4:3);
NMR: δ 2.13 (s, 6H), 6.85 (d, J=10.4 Hz, 1H), 6.95-7.07 (m, 2H), 7.22 (s, 2H), 8.02-8.19 (m, 3H).

Example 118

3-chloro-2-(2,4-difluorophenyl)-3-[1-(2,6-difluorophenyl)-6-oxo-1,6-dihydro-3-pyridinyl]acrylaldehyde To a mixed solution of N,N-dimethylformamide (856 μL) and dichloroethane (5 mL) was added phosphorus oxychloride (1.28 g) and the mixture was stirred at room temperature for 30 minutes. To the mixture was added a suspended solution of the compound prepared in Example 85 (2.0 g) in dichloroethane (10 mL). The mixture was stirred at 90° C. for 31 hours. To the reaction mixture was added water at room temperature and the mixture was extracted with ethyl acetate. The obtained organic layer was dried and concentrated. The obtained residue was purified by column chromatography on silica gel (hexane:ethyl acetate=4:1→7:3) to give the title compound (404 mg) having the following physical data.
TLC: Rf 0.42 (hexane:ethyl acetate=3:2);

NMR: δ 6.52 and 6.82 (dd and dd, J=9.7, 0.7 Hz and J=9.7, 0.7 Hz, 1H), 6.86-7.74 (m, 8H), 9.85 and 10.42 (s, 1H).

Example 119

Ethyl 4-(2,4-difluorophenyl)-5-[1-(2,6-difluorophenyl)-6-oxo-1,6-dihydro-3-pyridinyl]-2-thiophenecarboxylate To a solution of the compound prepared in Example 118 (400 mg) in pyridine (2 mL) were added triethylamine (288 μL) and ethylthioglycolate (109 μL) and the mixture was stirred at 115° C. for an hour. To the reaction mixture was added 1N hydrochloric acid and the mixture was extracted with ethyl acetate. The obtained organic layer was dried and concentrated. The obtained residue was purified by column chromatography on silica gel (hexane:ethyl acetate=7:3) to give the title compound (190 mg) having the following physical data.

TLC: Rf 0.41 (hexane:ethyl acetate=3:2);

NMR: δ 1.39 (t, J=7.2 Hz, 3H), 4.37 (q, J=7.2 Hz, 2H), 6.62 (dd, J=9.5, 0.7 Hz, 1H), 6.85-6.96 (m, 2H), 7.02-7.12 (m, 2H), 7.18-7.30 (m, 3H), 7.37-7.49 (m, 1H), 7.77 (d, J=1.3 Hz, 1H).

Example 120

1-(2,6-difluorophenyl)-5-[3-(2,4-difluorophenyl)-5-(1-hydroxy-1-methylethyl)-2-thienyl]-2(1H)-pyridinone By the same procedure as a reaction of Example 36, using the compound prepared in Example 119 instead of the compound prepared in Example 35, the compound of the present invention having the following physical data was obtained.

TLC: Rf 0.34 (ethyl acetate:hexane=1:1);

NMR: δ 1.70 (s, 6H), 2.02 (s, 1H), 6.58 (dd, J=9.5, 0.7 Hz, 1H), 6.81-6.91 (m, 2H), 6.93 (d, J=1.5 Hz, 1H), 7.00-7.09 (m, 2H), 7.10-7.13 (m, 1H), 7.17-7.28 (m, 2H), 7.34-7.45 (m, 1H).

Example 121

Ethyl 3-[{[(2,6-difluorophenyl)amino]carbonyl}(4-methoxybenzyl)amino]propanoate

A solution of 4-methoxybenzylamine (11.4 g) and ethyl acrylate (8.8 mL) in ethanol (50 mL) was stirred at 80° C. for an hour. The reaction mixture was concentrated. To the obtained residue was added ethyl acetate (100 mL) and the mixture was concentrated again. The obtained residue was dissolved in tetrahydrofuran (50 mL). To the mixture was added a solution of 2,6-difluorophenyl isocyanate (12.6 g) in tetrahydrofuran (25 mL) at 0° C. The reaction mixture was stirred at room temperature for 15 minutes was concentrated. The obtained residue was purified by column chromatography on silica gel (hexane:ethyl acetate=7:3→3:2) to give the title compound (31.2 g) having the following physical data.

TLC: Rf 0.41 (hexane:ethyl acetate=1:1);

NMR: δ 1.28 (t, J=7.1 Hz, 3H), 2.63 (t, J=6.0 Hz, 2H), 3.68 (t, J=6.0 Hz, 2H), 3.81 (s, 3H), 4.20 (q, J=7.1 Hz, 2H), 4.54 (s, 2H), 6.85-6.96 (m, 4H), 7.01-7.15 (m, 1H), 7.22-7.30 (m, 2H), 7.33-7.47 (m, 1H).

Example 122(a)

Ethyl 3-(2,6-difluorophenyl)-4-hydroxy-1-(4-methoxybenzyl)-2-oxohexahydro-5-pyrimidinecarboxylate To a solution of the compound prepared in Example 121 (31.2 g) in anhydrous tetrahydrofuran (100 mL) was added dropwise 1.0 mol/L lithium bis(trimethylsilyl)amide/tetrahydrofuran solution (175 mL) at −78° C. and the mixture was stirred for 10 minutes. To the reaction mixture was added methyl formate (5.9 mL) at −78° C. for an hour. The reaction mixture was risen to −30° C. To the mixture were added a saturated solution of ammonium chloride and water, and the mixture was extracted with ethyl acetate. The obtained organic layer was dried and concentrated. The obtained residue was purified by column chromatography on silica gel (hexane:ethyl acetate=1:1→3:7) to give the title compound (30.3 g) having the following physical data.

TLC: Rf 0.29 and 0.24 (hexane:ethyl acetate=1:1);

NMR: δ 1.14-1.30 (m, 3H), 2.97-3.88 (m, 7H), 4.07-4.24 (m, 2H), 4.44-4.74 (m, 2H), 5.34-5.51 (m, 1H), 6.88 (d, J=8.6 Hz, 2H), 6.93-7.06 (m, 2H), 7.21-7.34 (m, 3H).

Example 122(b)

Ethyl 1-(2,6-difluorophenyl)-3-(4-methoxybenzyl)-2-oxo-1,2,3,4-tetrahydro-5-pyrimidinecarboxylate To a solution of the compound prepared in Example 122(a) (30.2 g) in dichloromethane (100 mL) were added mesyl chloride (6.68 mL) and triethylamine (35.9 mL) and the mixture was stirred at 0° C. for 30 minutes. To the reaction mixture was added 2N hydrochloric acid and the mixture was extracted with ethyl acetate. The obtained organic layer was dried and concentrated to give the title compound having the following physical data.

TLC: Rf 0.31 (hexane:ethyl acetate=7:3);

NMR: δ 1.25 (t, J=7.1 Hz, 3H), 3.81 (s, 3H), 4.10-4.22 (m, 4H), 4.56 (s, 2H), 6.89 (d, J=8.8 Hz, 2H), 6.98-7.06 (m, 2H), 7.16-7.18 (m, 1H), 7.27-7.37 (m, 3H).

Example 123

1-(2,6-difluorophenyl)-3-(4-methoxybenzyl)-2-oxo-1,2,3,4-tetrahydro-5-pyrimidinecarboxylic acid By the same procedure as a reaction of Example A3, using the compound prepared in Example 122(b) instead of the compound prepared in Example A2, the title compound having the following physical data was obtained.

TLC: Rf 0.13 (hexane:ethyl acetate=1:1);

NMR: δ 3.81 (s, 3H), 4.10-4.13 (m, 2H), 4.56 (s, 2H), 6.89 (d, J=8.6 Hz, 2H), 6.97-7.06 (m, 2H), 7.23-7.38 (m, 4H).

Example 124

1-(2,6-difluorophenyl)-5-[(2,4-difluoropheny)acetyl]-3-(4-methoxybenzyl)-3,4-dihydro-2(1H)-pyrimidinone By the same procedure as a series of reactions of Example 1→Example 2, using the compound prepared in Example 123 instead of coumaric acid, the title compound having the following physical data was obtained.

TLC: Rf 0.48 (hexane:ethyl acetate=3:2);

NMR: δ 3.80 (s, 3H), 3.81 (s, 2H), 4.12-4.15 (m, 2H), 4.55 (s, 2H), 6.75-6.91 (m, 4H), 7.01-7.10 (m, 2H), 7.11-7.21 (m, 1H), 7.25-7.32 (m, 3H), 7.32-7.43 (m, 1H).

Example 125

1-(2,6-difluorophenyl)-5-[(2,4-difluoropheny) acetyl]-3,4-dihydro-2(1H)-pyrimidinone The compound prepared in Example 124 (20.6 g) was added to trifluoroacetic acid (60 mL). The mixture was stirred at 70° C. for 3 hours. The reaction mixture was concentrated. To the obtained residue was added an aqueous saturated sodium hydrogen carbonate solution and the mixture was extracted with ethyl acetate. The obtained organic layer was dried and concentrated. The obtained residue was washed with tert-butyl methyl ether to give the title compound (14 g) having the following physical data.

TLC: Rf 0.31 (hexane:ethyl acetate=1:1);
NMR: δ 3.86 (s, 2H), 4.30-4.35 (m, 2H), 5.10-5.16 (m, 1H), 6.77-6.92 (m, 2H), 7.02-7.10 (m, 2H), 7.14-7.25 (m, 1H), 7.31-7.34 (m, 1H), 7.34-7.45 (m, 1H).

Example 126

1-(2,6-difluorophenyl)-5-[5-(2,4-difluorophenyl)-2-(1-hydroxy-1-methylethyl)]-1,3-oxazol-4-yl]-3,4-dihydro-2(1H)-pyrimidinone By the same procedure as a series of reactions of Example 4→Example 5→Example 6, using the compound prepared in Example 125 instead of the compound prepared in Example 3, the compound of the present invention having the following physical data was obtained.

TLC: Rf 0.19 (ethyl acetate:hexane=1:1);
NMR: δ 1.65 (s, 6H), 2.69 (s, 1H), 4.16-4.19 (m, 2H), 4.92-4.97 (m, 1H), 6.66-6.70 (m, 1H), 6.90-7.03 (m, 4H), 7.24-7.36 (m, 1H), 7.41-7.52 (m, 1H).

Example 127(1)~Example 127(2)

By the same procedure as a series of reactions of Example 121→Example 122→Example A3→Example 1→Example 2→Example 4→Example 8→Example 6, using methylamine instead of 4-methoxybenzylamine and using the commercial available carboxylic acids or the carboxylic acid prepared in Example A16 instead of 2,2-bis(hydroxymethyl) butyric acid, the compound of the present invention having the following physical data was obtained.

Example 127(1)

1-(2,6-difluorophenyl)-5-[5-(2,4-difluorophenyl)-2-(1-hydroxy-1-methylethyl)-1,3-oxazol-4-yl]-3-methyl-3,4-dihydro-2(1H)-pyrimidinone TLC: Rf 0.39 (ethyl acetate:hexane=3:2);
NMR: δ 1.65 (s, 6H), 2.68 (s, 1H), 2.96 (s, 3H), 4.12-4.14 (m, 2H), 6.58-6.62 (m, 1H), 6.90-7.04 (m, 4H), 7.22-7.33 (m, 1H), 7.44-7.54 (m, 1H).

Example 127(2)

1-(2,6-difluorophenyl)-5-[5-(2,4-difluorophenyl)-2-(1,2-dihydroxy-1-methylethyl)-1,3-oxazol-4-yl]-3-methyl-3,4-dihydro-2(1H)-pyrimidinone TLC: Rf 0.45 (ethyl acetate);
NMR: δ 1.56 (s, 3H), 2.84-2.93 (m, 1H), 2.96 (s, 3H), 3.33-3.43 (m, 1H), 3.63-3.73 (m, 1H), 3.99-4.08 (m, 1H), 4.12 (d, J=1.3 Hz, 2H), 6.57 (s, 1H), 6.90-7.04 (m, 4H), 7.21-7.33 (m, 1H), 7.45-7.56 (m, 1H).

Example 128(1)~Example 128(6)

By the same procedure as a series of reactions of Example 4→Example 5→Example 6, using the compound prepared in Example 125, using the compound prepared in Example A1 or the corresponding sodium salts (said sodium salts were produced by the same procedure as a reaction of Example A1, using the commercial available carboxylic acids or the carboxylic acids prepared in Example A5~A16), or using the lithium salts prepared in Example 131(a)~(b), the compound of the present invention having the following physical data was obtained.

Example 128(1)

1-(2,6-difluorophenyl)-5-[5-(2,4-difluorophenyl)-2-(1,2-dihydroxy-1-methylethyl)-1,3-oxazol-4-yl]-3,4-dihydro-2(1H)-pyrimidinone TLC: Rf 0.27 (ethyl acetate:hexane=4:1);
NMR: δ 1.56 (s, 3H), 2.85 (dd, J=8.1, 5.8 Hz, 1H), 3.38 (s, 1H), 3.68 (dd, J=11.4, 8.1 Hz, 1H), 4.03 (dd, J=11.4, 5.8 Hz, 1H), 4.14-4.20 (m, 2H), 4.96-5.03 (m, 1H), 6.61-6.66 (m, 1H), 6.89-7.05 (m, 4H), 7.23-7.37 (m, 1H), 7.42-7.53 (m, 1H).

Example 128(2)

1-(2,6-difluorophenyl)-5-[5-(2,4-difluorophenyl)-2-(2-hydroxy-2-methylpropyl)-1,3-oxazol-4-yl]-3,4-dihydro-2(1H)-pyrimidinone TLC: Rf 0.29 (ethyl acetate:hexane=7:3);
NMR: δ 1.33 (s, 6H), 2.93 (s, 2H), 3.40 (s, 1H), 4.16-4.19 (m, 2H), 4.92-4.98 (m, 1H), 6.64-6.66 (m, 1H), 6.90-7.04 (m, 4H), 7.24-7.35 (m, 1H), 7.39-7.51 (m, 1H).

Example 128(3)

1-(2,6-difluorophenyl)-5-{5-(2,4-difluorophenyl)-2-[2-hydroxy-1-(hydroxymethyl)-1-methylethyl]-1,3-oxazol-4-yl}-3,4-dihydro-2(1H)-pyrimidinone TLC: Rf 0.19 (ethyl acetate:hexane=4:1);
NMR: δ 1.23 (s, 3H), 3.25 (t, J=6.2 Hz, 2H), 3.88 (dd, J=11.0, 6.2 Hz, 2H), 4.01 (dd, J=11.0, 6.2 Hz, 2H), 4.16-4.20 (m, 2H), 4.93-4.99 (m, 1H), 6.59-6.64 (m, 1H), 6.89-7.06 (m, 4H), 7.26-7.37 (m, 1H), 7.42-7.53 (m, 1H).

Example 128(4)

1-(2,6-difluorophenyl)-5-{5-(2,4-difluorophenyl)-2-[1,2-dihydroxy-1-(hydroxymethyl)ethyl]-1,3-oxazol-4-yl}-3,4-dihydro-2(1H)-pyrimidinone TLC: Rf 0.44 (ethyl acetate:methanol=19:1);
NMR: δ 2.47-2.60 (m, 2H), 3.68 (br. s, 1H), 3.87-3.97 (m, 2H), 3.99-4.08 (m, 2H), 4.17-4.20 (m, 2H), 5.02-5.09 (m, 1H), 6.61-6.65 (m, 1H), 6.90-7.05 (m, 4H), 7.25-7.37 (m, 1H), 7.43-7.54 (m, 1H).

Example 128(5)

1-(2,6-difluorophenyl)-5-{5-(2,4-difluorophenyl)-2-[(1S)-1,2-dihydroxy-1-methylethyl]-1,3-oxazol-4-yl}-3,4-dihydro-2(1H)-pyrimidinone TLC: Rf 0.31 (hexane:ethyl acetate=1:4);
NMR: δ 1.55 (s, 3H), 2.80-2.92 (m, 1H), 3.37-3.46 (m, 1H), 3.67 (dd, J=11.5, 7.7 Hz, 1H), 4.02 (dd, J=11.5, 5.2 Hz, 1H), 4.17 (s, 2H), 5.05 (s, 1H), 6.62 (s, 1H), 6.87-7.04 (m, 4H), 7.23-7.35 (m, 1H), 7.40-7.52 (m, 1H).

Example 128(6)

1-(2,6-difluorophenyl)-5-{5-(2,4-difluorophenyl)-2-[(1R)-1,2-dihydroxy-1-methylethyl]-1,3-oxazol-4-yl}-3,4-dihydro-2(1H)-pyrimidinone TLC: Rf 0.31 (hexane:ethyl acetate=1:4);
NMR: δ 1.51-1.60 (m, 3H), 2.80-2.90 (m, 1H), 3.40 (s, 1H), 3.67 (dd, J=11.5, 8.1 Hz, 1H), 4.02 (dd, J=11.5, 5.5 Hz, 1H), 4.17 (t, J=1.4 Hz, 2H), 5.04 (s, 1H), 6.62 (s, 1H), 6.87-7.06 (m, 4H), 7.22-7.35 (m, 1H), 7.41-7.52 (m, 1H).

Example 129→Example 130(a)

According to a method of N. D. Smith et al. (Organic Letters, 2003, 5(7), 1035~1037), the title compound having the following physical data was obtained.

Example 129

N-methoxy-N,2-dimethylacrylamide

TLC: Rf 0.37 (ethyl acetate:hexane=2:1);
NMR: δ 1.97-2.03 (m, 3H), 3.24 (s, 3H), 3.66 (s, 3H), 5.22-5.28 (m, 1H), 5.29-5.35 (m, 1H).

Example 130(a)

(2S)-2,3-dihydroxy-N-methoxy-N,2-dimethylpropanamide

TLC: Rf 0.23 (ethyl acetate);
NMR: δ 1.39 (s, 3H), 2.30 (dd, J=9.6, 4.8 Hz, 1H), 3.30 (s, 3H), 3.62 (dd, J=11.3, 4.8 Hz, 1H), 3.76 (s, 3H), 3.87-3.96 (m, 1H), 4.52 (s, 1H).

Example 130(b)

(2R)-2,3-dihydroxy-N-methoxy-N,2-dimethylpropanamide

According to a method of N. D. Smith et al. (Organic Letters, 2003, 5(7), 1035~1037), using AD-mix-α instead of AD-mix-β, the title compound having the following physical data was obtained.
TLC: Rf 0.23 (ethyl acetate);
NMR: δ 1.39 (s, 3H), 2.30 (dd, J=9.6, 4.8 Hz, 1H), 3.30 (s, 3H), 3.62 (dd, J=11.3, 4.8 Hz, 1H), 3.76 (s, 3H), 3.87-3.96 (m, 1H), 4.52 (s, 1H).

Example 131(a)

Lithium (2S)-2,3-dihydroxy-2-methylpropanoate

To a solution of the compound prepared in Example 130(a) (565 mg) in methanol (7.0 mL) was added lithium hydroxide monohydrate (146 mg) and the mixture was stirred at room temperature for 4 hours. The reaction mixture was concentrated to give the title compound (446 mg) having the following physical data.
TLC: Rf 0.23 (chloroform:methanol:acetic acid=12:7:1);
NMR (DMSO-$d_6$): δ 1.09 (s, 3H), 3.14 (d, J=9.9 Hz, 1H), 3.18 (d, J=9.9 Hz, 1H), 4.55-5.35 (m, 2H).

Example 131(b)

Lithium (2R)-2,3-dihydroxy-2-methylpropanoate

By the same procedure as a reaction of Example 131(a), using the compound prepared in Example 130(b), the title compound having the following physical data was obtained.
TLC: Rf 0.23 (chloroform:methanol:acetic acid=12:7:1);
NMR: δ 1.09 (s, 3H), 3.12-3.22 (m, 2H), 4.71 (s, 1H), 5.02-5.23 (m, 1H).

Example 132

1-(2,6-difluorophenyl)-5-[5-(2,4-difluorophenyl)-2-(1,2-dihydroxy-2-methylpropyl)-1,3-oxazol-4-yl]-3,4-dihydro-2(1H)-pyrimidinone By the same procedure as a series of reactions of Example 4→Example 5→Example 6→Example 13, using the compound prepared in Example 125 instead of the compound prepared in Example 3 and using the sodium salt prepared in Example 135 instead of the compound prepared in Example A1, the compound of the present invention having the following physical data was obtained.
TLC: Rf 0.44 (hexane:ethyl acetate=1:4);
NMR (CD$_3$OD): δ 1.25 (s, 3H), 1.28 (s, 3H), 4.01-4.23 (m, 2H), 4.54 (s, 1H), 6.55-6.69 (m, 1H), 6.95-7.22 (m, 4H), 7.32-7.48 (m, 1H), 7.52-7.74 (m, 1H).

Example 133(a)

Benzyl 3-methyl-2-butenoate

According to a method of H. Shao et al. (The Journal of Organic Chemistry, 1996, 61(8), 2582~2583), the title compound having the following physical data was obtained.
TLC: Rf 0.44 (ethyl acetate:hexane=1:7);
NMR: δ 1.90 (d, J=1.3 Hz, 3H), 2.19 (d, J=1.3 Hz, 3H), 5.14 (s, 2H), 5.72-5.76 (m, 1H), 7.29-7.40 (m, 5H).

Example 133(b)

Benzyl 2,3-dihydroxy-3-methylbutanoate

By the same procedure as a reaction of Example 18, using the compound prepared in Example 133(a) instead of the compound prepared in Example 7(26), the title compound having the following physical data was obtained.
TLC: Rf 0.40 (ethyl acetate:hexane=3:2);
NMR: δ 1.17 (s, 3H), 1.26 (s, 3H), 2.52 (s, 1H), 3.13 (d, J=6.8 Hz, 1H), 4.01 (d, J=6.8 Hz, 1H), 5.23 (d, J=12.0 Hz, 1H), 5.29 (d, J=12.0 Hz, 1H), 7.34-7.42 (m, 5H).

Example 134

Benzyl 2,2,5,5-tetramethyl-1,3-dioxolane-4-carboxylate

To a solution of the compound prepared in Example 133(b) (1.79 g) in acetone (12 mL) were added acetone dimethylacetal (1.96 mL) and p-toluenesulfonic acid monohydrate (152 mg) and the mixture was stirred at room temperature for 2 hours. The reaction mixture was concentrated. The obtained residue was purified by preparative medium pressure liquid chromatography W-prep 2XY (column: main column M, inject column M; automatic condition setting: hexane:ethyl acetate=9:1, preparative isolation mode GR) to give the title compound (1.79 g) having the following physical data.

TLC: Rf 0.47 (ethyl acetate:hexane=1:3);
NMR: δ 1.09 (s, 3H), 1.37 (d, J=0.5 Hz, 3H), 1.45 (s, 3H), 1.53 (d, J=0.5 Hz, 3H), 4.38 (s, 1H), 5.23 (s, 2H), 7.33-7.41 (m, 5H).

Example 135

Sodium 2,2,5,5-tetramethyl-1,3-dioxolane-4-carboxylate

By the same procedure as a reaction of Example A1, using the compound prepared in Example 134 instead of 2,2-bis(hydroxymethyl)propionic acid, the title compound having the following physical data was obtained.

NMR (CD$_3$OD): δ 4.17 (s, 1H), 1.47-1.43 (m, 3H), 1.43 (s, 3H), 1.33-1.29 (m, 3H), 1.16 (s, 3H).

Example 136

To a solution of the compound prepared in Example 126 (111 mg) in toluene (5 mL) was added activated manganese dioxide (216 mg) and the mixture was stirred at 110° C. for an hour. The reaction mixture was filtered through Celite (trade name) and concentrated. The obtained residue was purified by preparative TLC (hexane:ethyl acetate=1:3) to give the compound of the present invention 136(a) (17 mg) and 136(b) (42 mg) having the following physical data.

Compound 136(a)

1-(2,6-difluorophenyl)-5-[5-(2,4-difluorophenyl)-2-(1-hydroxy-1-methylethyl)-1,3-oxazol-4-yl]-2,4(1H, 3H)-pyrimidinedione TLC: Rf 0.49 (hexane:ethyl acetate=1:3);
NMR: δ 1.68 (s, 6H), 2.65 (s, 1H), 6.81-6.93 (m, 1H), 6.94-7.04 (m, 1H), 7.12 (t, J=8.1 Hz, 2H), 7.41-7.54 (m, 1H), 7.55-7.66 (m, 1H), 7.79 (s, 1H), 8.16 (s, 1H).

Compound 136(b)

1-(2,6-difluorophenyl)-5-[5-(2,4-difluorophenyl)-2-(1-hydroxy-1-methylethyl)-1,3-oxazol-4-yl]-2(1H)-pyrimidinone TLC: Rf 0.32 (hexane:ethyl acetate=1:3);
NMR: δ 1.70 (s, 6H), 2.61 (s, 1H), 6.94-7.17 (m, 4H), 7.41-7.53 (m, 1H), 7.53-7.63 (m, 1H), 8.00 (d, J=3.3 Hz, 1H), 8.76 (dd, J=3.3, 1.5 Hz, 1H).

Example 137

Methyl 4-[(2,6-difluorophenyl)amino]-4-oxobutanoate

To a solution of 2,6-difluoroaniline (3.2 mL) in N,N-dimethylformamide (20 mL) was added methyl succinyl chloride (3.7 mL) at room temperature and the mixture was stirred for an hour. To the reaction mixture was added water and the mixture was extracted with ethyl acetate. The obtained organic layer was dried and concentrated. The obtained residue was purified by column chromatography on silica gel (hexane:ethyl acetate=7:3→3:2) to give the title compound (1.7 g) having the following physical data.

TLC: Rf 0.26 (hexane:ethyl acetate=3:2);
NMR: δ 2.70-2.82 (m, 4H), 3.72 (s, 3H), 6.90-7.02 (m, 2H), 7.08 (br. s, 1H), 7.15-7.25 (m, 1H).

Example 138

Benzyl 4-[(2,6-difluorophenyl)amino]-4-oxobutanoate

To a solution of the compound prepared in Example 137 (5.4 g) in tetrahydrofuran (30 mL) were added 5N aqueous solution of sodium hydroxide (13.3 mL) and methanol (15 mL) and the mixture was stirred at room temperature for an hour. To the reaction mixture was added 2N hydrochloric acid, and the mixture was neutralized and extracted with ethyl acetate. The obtained organic layer was dried and concentrated. The obtained residue was added to N,N-dimethylformamide (25 mL). To the mixture were added benzyl bromide (2.72 mL) and potassium carbonate (3.16 g) and the mixture was stirred at room temperature for 2 hours. To the reaction mixture was added water and the mixture was extracted with ethyl acetate. The obtained organic layer was dried and concentrated. The obtained residue was washed with a mixed solution of ethyl acetate:hexane=7:3 to give the title compound (5.64 g) having the following physical data.

TLC: Rf 0.29 (hexane:ethyl acetate=7:3);
NMR: δ 2.70-2.88 (m, 4H), 5.15 (s, 2H), 6.89-6.99 (m, 2H), 7.08 (br. s, 1H), 7.14-7.24 (m, 1H), 7.29-7.37 (m, 5H).

Example 139

Benzyl 1-(2,6-difluorophenyl)-2-hydroxy-5-oxo-3-pyrrolidinecarboxylate

By the same procedure as a reaction of Example 122(a), using the compound prepared in Example 138 instead of the compound prepared in Example 121, the title compound having the following physical data was obtained.

TLC: Rf 0.25 (hexane:ethyl acetate=3:2);
NMR: δ 2.64-3.74 (m, 4H), 5.16-5.32 (m, 2H), 5.64 and 5.74 (dd, J=7.4, 6.1 Hz and J=6.8, 2.9 Hz, 1H), 6.94-7.06 (m, 2H), 7.26-7.42 (m, 6H).

Example 140

Benzyl 1-(2,6-difluorophenyl)-5-oxo-4,5-dihydro-1H-pyrrole-3-carboxylate

By the same procedure as a reaction of Example 122(b), using the compound prepared in Example 139 instead of the compound prepared in Example 122(a), the title compound having the following physical data was obtained.

TLC: Rf 0.62 (hexane:ethyl acetate=3:2);
NMR: δ 3.53 (d, J=2.0 Hz, 2H), 5.24 (s, 2H), 6.98-7.09 (m, 2H), 7.30-7.42 (m, 6H), 7.50-7.53 (m, 1H).

Example 141

1-(2,6-difluorophenyl)-5-oxo-3-pyrrolidine carboxylic acid

Under an atmosphere of hydrogen, to a mixed solution of the compound prepared in Example 140 (1.21 g) in ethanol (10 mL) and tetrahydrofuran (5 mL) was added 10% palladium/carbon (121 mg, 50% wt) and the mixture was stirred vigorously for 1.5 hours. The reaction mixture was filtered through Celite (trade name) and concentrated to give the title compound (869 mg) having the following physical data.
TLC: Rf 0.17 (dichloromethane:methanol=9:1);
NMR: δ 2.81-3.03 (m, 2H), 3.48-3.61 (m, 1H), 3.94-4.07 (m, 2H), 6.95-7.05 (m, 2H), 7.26-7.36 (m, 1H).

Example 142

1-(2,6-difluorophenyl)-4-[5-(2,4-difluorophenyl)-2-(1-hydroxy-1-methylethyl)-1,3-oxazol-4-yl]-2-pyrrolidinone By the same procedure as a series of reactions of Example 1→Example 2→Example 4→Example 8→Example 6, using the compound prepared in Example 141 instead of coumaric acid and using the commercial available carboxylic acids instead of 2,2-bis(hydroxymethyl)butyric acid, the compound of the present invention having the following physical data was obtained.
TLC: Rf 0.39 (ethyl acetate:hexane=3:2);
NMR: δ 1.68 (s, 3H), 1.68 (s, 3H), 2.73-2.84 (m, 2H), 2.93-3.04 (m, 1H), 3.79-3.93 (m, 2H), 4.01-4.09 (m, 1H), 6.91-7.07 (m, 4H), 7.20-7.32 (m, 1H), 7.42-7.52 (m, 1H).

Example 143

Methyl 1-methyl-6-oxo-1,6-dihydro-3-pyridinecarboxylate

By the same procedure as a reaction of Example 3, using methyl coumalate instead of the compound prepared in Example 2, the title compound having the following physical data was obtained.
TLC: Rf 0.39 (hexane:ethyl acetate=1:4);
NMR: δ 8.18 (d, J=2.7 Hz, 1H), 7.85 (dd, J=9.6, 2.7 Hz, 1H), 6.54 (d, J=9.6 Hz, 1H), 3.86 (s, 3H), 3.60 (s, 3H).

Example 144

Methyl 5-bromo-1-methyl-6-oxo-1,6-dihydro-3-pyridinecarboxylate

To a solution of the compound prepared in Example 143 (1.77 g) in acetic acid (20 mL) was added N-bromosuccinimide (3.2 g) and the mixture was stirred at 80° C. for 4 hours. The reaction mixture was poured into 1N aqueous solution of sodium hydroxide on ice bath and extracted with ethyl acetate. The obtained organic layer was dried and concentrated. The obtained residue was purified by column chromatography on silica gel (hexane:ethyl acetate=2:1→1:1) to give the title compound (2.18 g) having the following physical data.
TLC: Rf 0.54 (hexane:ethyl acetate=1:4);
NMR: δ 8.26 (d, J=2.4 Hz, 1H), 8.18 (d, J=2.4 Hz, 1H), 3.88 (s, 3H), 3.67 (s, 3H).

Example 145

Methyl 5-(2,6-difluorophenyl)-1-methyl-6-oxo-1,6-dihydro-3-pyridinecarboxylate

To a solution of the compound prepared in Example 144 (1.22 g) in 1,2-dimethoxyethane (25 mL) were added tris(dibenzylideneacetone)dipalladium (91 mg), 2,6-difluorophenylboronic acid (1.17 g) and 2-dicyclohexylphosphino-2',4',6'-triisopropy-1,1'-biphenyl (189 mg) and the mixture was stirred at 80° C. for 18.5 hours. The reaction mixture was filtered through Celite (trade name). To the filtrate was added water and the mixture was extracted with ethyl acetate. The obtained organic layer was dried and concentrated. The obtained residue was purified by column chromatography on silica gel (hexane:ethyl acetate=4:1→3:2) to give the title compound (688 mg) having the following physical data.
TLC: Rf 0.65 (hexane:ethyl acetate=1:3);
NMR: δ 8.29 (d, J=2.4 Hz, 1H), 7.98 (d, J=2.4 Hz, 1H), 7.32 (m, 1H), 7.01-6.91 (m, 2H), 3.88 (s, 3H), 3.68 (s, 3H).

Example 146

3-(2,6-difluorophenyl)-5-[5-(2,4-difluorophenyl)-2-(1-hydroxy-1-methylethyl)-1,3-oxazol-4-yl]-1-methyl-2(1H)-pyridinone By the same procedure as a series of reactions of Example A3→Example 1→Example 2→Example 3→Example 4→Example 8→Example 6, using the compound prepared in Example 145 and using the commercial available carboxylic acids instead of 2,2-bis(hydroxymethyl)butyric acid, the compound of the present invention having the following physical data was obtained.
TLC: Rf 0.29 (hexane:ethyl acetate=1:3);
NMR: δ 7.93 (d, J=2.4 Hz, 1H), 7.52 (m, 1H), 7.41 (m, 1H), 7.27 (m, 1H), 7.04-6.86 (m, 4H), 3.68 (s, 3H), 2.71 (s, 1H), 1.71 (s, 6H).

Example 147

5-[bromo(2,4-difluorophenyl)acetyl]-1-(2,6-difluorophenyl)-3,4-dihydro-2(1H)-pyridinone By the same procedure as a series of reactions of Example 137→Example 138→Example 139→Example 140→Example 141→Example 1→Example 2→Example 4, using ethyl glutaryl chloride instead of methyl succinyl chloride, the title compound having the following physical data was obtained.
TLC: Rf 0.62 (hexane:ethyl acetate=1:1);
NMR: δ 2.70-2.93 (m, 4H), 6.18 (s, 1H), 6.74-6.85 (m, 1H), 6.91-7.01 (m, 1H), 7.01-7.13 (m, 2H), 7.33-7.49 (m, 2H), 7.63-7.77 (m, 1H).

Example 148

1-(2,6-difluorophenyl)-5-[5-(2,4-difluorophenyl)-2-(1-hydroxy-1-methylethyl)-1,3-oxazol-4-yl]-3,4-dihydro-2(1H)-pyridinone By the same procedure as a series of reactions of Example 8→Example 6, using the compound prepared in Example 147 instead of the compound prepared in Example 4 and using the commercial available carboxylic acids instead of 2,2-bis(hydroxymethyl)butyric acid, the compound of the present invention having the following physical data was obtained.
TLC: Rf 0.33 (toluene:ethyl acetate=2:1);
NMR: δ 1.66 (s, 6H), 2.57 (t, J=7.7 Hz, 2H), 2.68 (s, 1H), 2.70-2.79 (m, 2H), 6.78 (s, 1H), 6.89-7.06 (m, 4H), 7.27-7.38 (m, 1H), 7.40-7.51 (m, 1H).

Example 149

5-[5-(2,4-difluorophenyl)-2-(1-hydroxy-1-methyl-ethyl)-1,3-oxazol-4-yl]-1-(2,6-dimethylphenyl)-3,4-dihydro-2(1H)-pyridinone By the same procedure as a series of reactions of Example 137→Example 138→Example 139→Example 140→Example 141→Example 1→Example 2→Example 4→Example 8→Example 6, using ethyl glutaryl chloride, using 2,6-dimethylaniline instead of 2,6-difluoroaniline and using the commercial available carboxylic acids instead of 2,2-bis(hydroxymethyl)butyric acid, the compound of the present invention having the following physical data was obtained.

TLC: Rf 0.26 (hexane:ethyl acetate=1:1);
NMR: δ 1.64 (s, 6H), 2.18 (s, 6H), 2.51-2.63 (m, 2H), 2.67-2.78 (m, 3H), 6.62 (s, 1H), 6.88-7.04 (m, 2H), 7.08-7.14 (m, 2H), 7.14-7.22 (m, 1H), 7.39-7.52 (m, 1H).

Example 150(1)~(2)

By the same procedure as a series of reactions of Example 5→Example 6→Example A3, using the compound prepared in Example 147 instead of the compound prepared in Example 4 and using sodium salts produced by the same procedure as a reaction of Example A1 using the compound prepared in Example A1 or the carboxylic acid prepared in Example A16, the compound of the present invention having the following physical data was obtained.

Example 150(1)

1-(2,6-difluorophenyl)-5-{5-(2,4-difluorophenyl)-2-[2-hydroxy-1-(hydroxymethyl)-1-methylethyl]-1,3-oxazol-4-yl}-3,4-dihydro-2(1H)-pyridinone TLC: Rf 0.35 (hexane:ethyl acetate=1:4);
NMR: δ 7.45 (m, 1H), 7.32 (m, 1H), 7.05-6.90 (m, 4H), 6.71 (s, 1H), 4.06-3.95 (m, 2H), 3.95-3.80 (m, 2H), 3.30 (br s, 2H), 2.76-2.71 (m, 2H), 2.59-2.54 (m, 2H), 1.23 (m, 3H).

Example 150(2)

1-(2,6-difluorophenyl)-5-[5-(2,4-difluorophenyl)-2-(1,2-dihydroxy-1-methylethyl)-1,3-oxazol-4-yl]-3,4-dihydro-2(1H)-pyridinone TLC: Rf 0.29 (hexane:ethyl acetate=1:2);
NMR: δ 1.55 (s, 3H), 2.56 (t, J=7.9 Hz, 2H), 2.69-2.78 (m, 2H), 2.82-2.93 (m, 1H), 3.34 (s, 1H), 3.62-3.73 (m, 1H), 3.99-4.07 (m, 1H), 6.73 (s, 1H), 6.88-7.04 (m, 4H), 7.26-7.38 (m, 1H), 7.41-7.51 (m, 1H).

Example 151

1-(2,6-difluorophenyl)-5-[5-(2,4-difluorophenyl)-2-(1,2-dihydroxy-2-methylpropyl)-1,3-oxazol-4-yl]-3,4-dihydro-2(1H)-pyridinone By the same procedure as a series of reactions of Example 5→Example 6→Example 13, using the compound prepared in Example 147 instead of the compound prepared in Example 4 and using the compound prepared in Example 135 instead of the compound prepared in Example A1, the compound of the present invention having the following physical data was obtained.

TLC: Rf 0.56 (hexane:ethyl acetate=1:4);
NMR: δ 1.24 (s, 3H), 1.37 (s, 3H), 2.49-2.63 (m, 2H), 2.69-2.79 (m, 2H), 2.81 (s, 1H), 3.06 (d, J=7.9 Hz, 1H), 4.53 (d, J=7.9 Hz, 1H), 6.71-6.81 (m, 1H), 6.89-7.08 (m, 4H), 7.24-7.40 (m, 1H), 7.40-7.55 (m, 1H).

Example 152

1-(2,6-difluorophenyl)-5-{5-(2,4-difluorophenyl)-2-[1,2-dihydroxy-1-(hydroxymethyl)ethyl]-1,3-oxazol-4-yl}-3,4-dihydro-2(1H)-pyridinone By the same procedure as a series of reactions of Example 5→Example 35→Example 6→Example A3, using the compound prepared in Example 147 instead of the compound prepared in Example 4 and using the compound prepared in Example A5 instead of the compound prepared in Example A1, the compound of the present invention having the following physical data was obtained.

TLC: Rf 0.33 (ethyl acetate);
NMR: δ 2.48 (t, J=6.6 Hz, 2H), 2.53-2.60 (m, 2H), 2.71-2.78 (m, 2H), 3.54 (s, 1H), 3.93 (dd, J=11.3, 6.6 Hz, 2H), 4.06 (dd, J=11.3, 6.6 Hz, 2H), 6.74-6.77 (m, 1H), 6.90-7.06 (m, 4H), 7.28-7.40 (m, 1H), 7.43-7.53 (m, 1H).

Example 153

Thioformamide

By the same procedure as a reaction of Example A18, using formamide instead of the compound prepared in Example A17, the title compound was obtained. The obtained compound was used for the next reaction without being purified.

Example 154

1-(2,6-difluorophenyl)-5-[5-(2,4-difluorophenyl)-1,3-thiazol-4-yl]-2(1H)-pyridinone By the same procedure as a series of reactions of Example 4→Example 56, using the compound prepared in Example 85 instead of the compound prepared in Example 3 and using the compound prepared in Example 153 instead of tetrahydro-2H-pyran-4-carbothioamide, the title compound having the following physical data was obtained.

TLC: Rf 0.33 (hexane:ethyl acetate=1:1);
NMR: δ 6.59 (dd, J=9.7, 0.7 Hz, 1H), 6.88-7.11 (m, 4H), 7.32-7.51 (m, 3H), 7.59 (dd, J=2.6, 0.7 Hz, 1H), 8.87 (s, 1H).

Example 155

1-(2,6-difluorophenyl)-5-[5-(2,4-difluorophenyl)-2-(1-hydroxy-1-methylethyl)-1,3-thiazol-4-yl]-2(1H)-pyridinone Under an atmosphere of argon, to a solution of the compound prepared in Example 154 (209 mg) in tetrahydrofuran (10 mL) was added 1.52 mol/L n-butyllithium/hexane solution (0.34 mL) at −78° C. and added successively acetone (57 (L), and the mixture was stirred for 30 minutes. The reaction mixture was risen to room temperature. To the reaction mixture was added 1N hydrochloric acid and the mixture was extracted with ethyl acetate. The obtained organic layer was dried and concentrated. The obtained residue was purified by preparative TLC (toluene:ethyl acetate=2:1) to give the compound of the present invention (58 mg) having the following physical data.

TLC: Rf 0.43 (hexane:ethyl acetate=1:1);
NMR: δ 1.72 (s, 6H), 2.82 (s, 1H), 6.54-6.64 (m, 1H), 6.88-7.00 (m, 2H), 7.01-7.12 (m, 2H), 7.30-7.53 (m, 4H).

Example 156

1-(2,6-difluorophenyl)-5-{5-(2,4-difluorophenyl)-2-[1,2-dihydroxy-1-(hydroxymethyl)ethyl]-1,3-thiazol-4-yl}-2(1H)-pyridinone By the same procedure as a series of reactions of Example 155→Example 13, using the compound prepared in Example 154 and using 2,2-dimethyl-1,3-dioxan-5-one instead of acetone, the compound of the present invention having the following physical data was obtained.
TLC: Rf 0.20 (ethyl acetate);
NMR: δ 2.61 (t, J=6.2 Hz, 2H), 3.88 (s, 1H), 4.00 (d, J=6.2 Hz, 4H), 6.58 (d, J=10.4 Hz, 1H), 6.87-7.00 (m, 2H), 7.00-7.12 (m, 2H), 7.28-7.48 (m, 4H).

Example 157(1)~(3)

By the same procedure as a series of reactions of Example 3→Example 51→Example 52→Example 53→Example 54→Example 55→Example 18, using the compound prepared in Example 2, using 2,6-dimethylaniline or 2,6-difluoroaniline instead of 4-chloro-2,6-dimethylaniline and using the commercial available carboxylic acids instead of tetrahydropyran-4-carboxylic acid, the compound of the present invention having the following physical data was obtained.

Example 157(1)

5-[4-(2,4-difluorophenyl)-2-(1,2-dihydroxy-1-methylethyl)-1,3-oxazol-5-yl]-1-(2,6-dimethylphenyl)-2(1H)-pyridinone TLC: Rf 0.35 (ethyl acetate);
NMR: δ 1.59 (s, 3H), 2.10 (s, 6H), 3.14 (t, J=5.4 Hz, 1H), 3.58-3.76 (m, 2H), 3.99-4.10 (m, 1H), 6.71 (d, J=9.5 Hz, 1H), 6.82-6.93 (m, 1H), 6.94-7.05 (m, 1H), 7.14-7.22 (m, 2H), 7.23-7.35 (m, 2H), 7.42-7.51 (m, 1H), 7.54-7.67 (m, 1H).

Example 157(2)

1-(2,6-difluorophenyl)-5-[4-(2,4-difluorophenyl)-2-(1,2-dihydroxy-1-methylethyl)-1,3-oxazol-5-yl]-2(1H)-pyridinone TLC: Rf 0.28 (hexane:ethyl acetate=1:3);
NMR: δ 1.61 (s, 3H), 2.83 (s, 1H), 3.25-3.57 (m, 1H), 3.70 (d, J=11.5 Hz, 1H), 4.10 (d, J=11.5 Hz, 1H), 6.67 (dd, J=9.7, 0.7 Hz, 1H), 6.86-7.15 (m, 4H), 7.36-7.50 (m, 3H), 7.53-7.65 (m, 1H).

Example 157(3)

1-(2,6-difluorophenyl)-5-[4-(2,4-difluorophenyl)-2-(1,2-dihydroxy-2-methylpropyl)-1,3-oxazol-5-yl]-2(1H)-pyridinone TLC: Rf 0.29 (hexane:ethyl acetate=1:3);
NMR: δ 1.29 (s, 3H), 1.39 (s, 3H), 2.74-3.35 (m, 1H), 2.82 (s, 1H), 4.57 (s, 1H), 6.67 (dd, J=9.4, 1.0 Hz, 1H), 6.85-7.15 (m, 4H), 7.36-7.52 (m, 3H), 7.53-7.67 (m, 1H).

Example 158

Methyl (2Z)-3-[(4-chloro-2,6-dimethylphenyl)amino]-2-butenoate

To a suspended solution of 4-chloro-2,6-dimethylaniline (24.0 g) in toluene (300 mL) were added methyl acetoacetate (17.9 g) and p-toluenesulfonic acid monohydrate (293 mg) and the mixture was heated to reflux and stirred for 4 hours. The reaction mixture was concentrated. To the obtained residue was added diisopropyl ether and the insoluble matter which was precipitated was removed. The filtrate was concentrated. The obtained residue was purified by preparative medium pressure liquid chromatography W-prep 2XY (column: main column 3L, inject column L; automatic condition setting: hexane:ethyl acetate=9:1, preparative isolation mode GR) to give the title compound (24.7 g) having the following physical data.
TLC: Rf 0.68 (hexane:ethyl acetate=4:1);
NMR: δ 9.62 (s, 1H), 7.08 (s, 2H), 4.72 (s, 1H), 3.69 (s, 3H), 2.19 (s, 6H), 1.59 (s, 3H).

Example 159

Methyl 1-(4-chloro-2,6-dimethylphenyl)-2-methyl-6-oxo-1,6-dihydro-3-pyridinecarboxylate To a solution of the compound prepared in Example 158 (23.5 g) in tetrahydrofuran (464 mL) was added sodium hydroxide (37.1 g) and the mixture was stirred at 50° C. for an hour. Furthermore, to the reaction mixture was added methyl propiolate (12.4 mL), and the mixture was heated to reflux and stirred for 2.5 hours. The reaction mixture was poured into 5N hydrochloric acid-ice and extracted with ethyl acetate. The obtained organic layer was dried and concentrated. The obtained residue was dissolved in N,N-dimethylformamide (200 mL). To the mixture were added iodomethane (8.7 mL) and potassium carbonate (38.4 g) on ice bath and the mixture was stirred at room temperature overnight. To the reaction mixture was added ethyl acetate (500 mL) and the insoluble matter which was precipitated was removed. The filtrate was washed with 1N hydrochloric acid and brine, dried and concentrated. The obtained residue was purified by preparative medium pressure liquid chromatography W-prep 2XY (column: main column 3L, inject column L; automatic condition setting: hexane:ethyl acetate=2:1, preparative isolation mode GR) to give the title compound (6.82 g) having the following physical data.
TLC: Rf 0.33 (hexane:ethyl acetate=2:1);
NMR: δ 8.02 (d, J=9.6 Hz, 1H), 7.25-7.20 (m, 2H), 6.56 (d, J=9.6 Hz, 1H), 3.87 (s, 3H), 2.31 (s, 3H), 2.00 (s, 6H).

Example 160

By the same procedure as a series of reactions of Example A3→Example 1→Example 2→Example 4→Example 8→Example 6, using the compound prepared in Example 159 instead of the compound prepared in Example A2 and using 3,3-dimethylacrylic acid instead of 2,2-bis(hydroxymethyl)butyric acid, the compounds of the present invention 160(a) and 160(b) having the following physical data were obtained.

Compound 160(a)

1-(4-chloro-2,6-dimethylphenyl)-5-[4-(2,4-difluorophenyl)-2-(2-methyl-1-propen-1-yl)-1,3-oxazol-5-yl]-6-methyl-2(1H)-pyridinone TLC: Rf 0.43 (hexane:ethyl acetate=2:1);
NMR: δ 1.6 (s, 3H), 2.0 (m, 9H), 2.3 (s, 3H), 6.2 (m, 1H), 6.7 (d, J=9.5 Hz, 1H), 6.8 (m, 1H), 7.0 (m, 1H), 7.2 (m, 2H), 7.5 (d, J=9.5 Hz, 1H), 7.7 (m, 1H).

Compound 160(b)

1-(4-chloro-2,6-dimethylphenyl)-5-[5-(2,4-difluorophenyl)-2-(2-methyl-1-propen-1-yl)-1,3-oxazol-4-yl]-6-methyl-2(1H)-pyridinone TLC: Rf 0.33 (hexane:ethyl acetate=1:1);
NMR: δ 7.54-7.43 (m, 2H), 7.19-7.16 (m, 2H), 6.99-6.82 (m, 2H), 6.62 (dd, J=9.3, 0.6 Hz, 1H), 6.22-6.17 (m, 1H), 2.28 (d, J=1.2 Hz, 3H), 2.05-2.00 (m, 9H), 1.66 (s, 3H).

Example 161

By the same procedure as a reaction of Example 18, using the compound prepared in Example 160 instead of the compound prepared in Example 7(26), the compounds of the present invention 161(a) and 161 (b) having the following physical data were obtained.

Compound 161(a)

1-(4-chloro-2,6-dimethylphenyl)-5-[4-(2,4-difluorophenyl)-2-(1,2-dihydroxy-2-methylpropyl)-1,3-oxazol-5-yl]-6-methyl-2(1H)-pyridinone TLC: Rf 0.50 (ethyl acetate);
NMR: δ 1.3 (s, 3H), 1.4 (s, 3H), 1.6 (s, 3H), 2.0 (s, 6H), 2.9 (s, 1H), 3.3 (m, 1H), 4.6 (m, 1H), 6.6 (d, J=9.5 Hz, 1H), 6.8 (m, 1H), 7.0 (m, 1H), 7.2 (m, 2H), 7.4 (d, J=9.5 Hz, 1H), 7.7 (m, 1H).

Compound 161(b)

1-(4-chloro-2,6-dimethylphenyl)-5-[5-(2,4-difluorophenyl)-2-(1,2-dihydroxy-2-methylpropyl)-1,3-oxazol-4-yl]-6-methyl-2(1H)-pyridinone TLC: Rf 0.48 (ethyl acetate:methanol=19:1);
NMR: δ 1.3 (s, 3H), 1.4 (s, 3H), 1.6 (s, 3H), 2.0 (s, 6H), 2.8 (s, 1H), 3.2 (d, J=7.9 Hz, 1H), 4.6 (d, J=7.9 Hz, 1H), 6.6 (d, J=9.5 Hz, 1H), 6.9 (m, 1H), 7.0 (m, 1H), 7.2 (m, 2H), 7.4 (d, J=9.5 Hz, 1H), 7.5 (m, 1H).

Example 162(1)~(19)

By the same procedure as a series of reactions of Example 85→Example 5→Example 6, using 4-chloro-2,6-dimethylaniline or the corresponding aniline compounds instead of 4-chloro-2,6-dimethylaniline and using the corresponding sodium salts (said sodium salts were produced by the same procedure as a reaction of Example A1, using the commercial available carboxylic acids or the carboxylic acid prepared in Example A16, 131(a) or (b)) instead of the compound prepared in Example A1, the compound of the present invention having the following physical data was obtained.

Example 162(1)

1-benzyl-5-[5-(2,4-difluorophenyl)-2-(1-hydroxy-1-methylethyl)-1,3-oxazol-4-yl]-2(1H)-pyridinone TLC: Rf 0.33 (ethyl acetate);
NMR: δ 1.7 (s, 6H), 2.7 (s, 1H), 5.1 (s, 2H), 6.6 (d, J=9.3 Hz, 1H), 6.9 (m, 2H), 7.4 (m, 7H), 7.6 (d, J=2.6 Hz, 1H).

Example 162(2)

1-(4-bromo-2,6-difluorophenyl)-5-[5-(2,4-difluorophenyl)-2-(1-hydroxy-1-methylethyl)-1,3-oxazol-4-yl]-2(1H)-pyridinone TLC: Rf 0.48 (ethyl acetate:hexane=2:1);
NMR: δ 1.7 (s, 6H), 2.7 (s, 1H), 6.6 (dd, J=9.7, 0.7 Hz, 1H), 7.0 (m, 2H), 7.3 (m, 2H), 7.5 (m, 2H), 7.6 (m, 1H).

Example 162(3)

1-(2,6-difluorophenyl)-5-[2-(1-hydroxy-1-methylethyl)-5-phenyl-1,3-oxazol-4-yl]-2(1H)-pyridinone TLC: Rf 0.41 (hexane:ethyl acetate=1:2);
NMR: δ 1.69 (s, 6H), 2.69 (s, 1H), 6.66 (d, J=9.53 Hz, 1H), 7.06 (m, 2H), 7.48 (m, 8H).

Example 162(4)

1-(2,6-difluorophenyl)-5-[5-(4-fluorophenyl)-2-(1-hydroxy-1-methylethyl)-1,3-oxazol-4-yl]-2(1H)-pyridinone TLC: Rf 0.30 (toluene:ethyl acetate=1:1);
NMR: δ 7.65-7.56 (m, 4H), 7.43 (m, 1H), 7.18-7.05 (m, 4H), 6.69 (dd, J=9.6, 0.6 Hz, 1H), 2.79 (s, 1H), 1.69 (s, 6H).

Example 162(5)

1-cyclohexyl-5-[5-(2,4-difluorophenyl)-2-(1-hydroxy-1-methylethyl)-1,3-oxazol-4-yl]-2(1H)-pyridinone TLC: Rf 0.15 (hexane:ethyl acetate=1:1);
NMR: δ 7.76 (d, J=2.4 Hz, 1H), 7.49 (m, 1H), 7.30 (m, 1H), 7.04-6.91 (m, 2H), 6.50 (d, J=9.0 Hz, 1H), 4.89 (m, 1H), 2.81 (s, 1H), 2.00-1.10 (m, 10H), 1.71 (s, 6H).

Example 162(6)

1-(2,6-difluorophenyl)-5-[5-(2,4-difluorophenyl)-2-(1,2-dihydroxy-1-methylethyl)-1,3-oxazol-4-yl]-2(1H)-pyridinone TLC: Rf 0.34 (hexane:ethyl acetate=1:3);
NMR: δ 1.60 (s, 3H), 2.82 (dd, J=8.1, 5.9 Hz, 1H), 3.40 (s, 1H), 3.71 (dd, J=11.5, 8.1 Hz, 1H), 4.06 (dd, J=11.5, 5.9 Hz, 1H), 6.64 (dd, J=9.7, 0.7 Hz, 1H), 6.90-7.15 (m, 4H), 7.38-7.49 (m, 2H), 7.49-7.59 (m, 1H), 7.62 (d, J=2.0 Hz, 1H).

Example 162(7)

1-(2,6-difluorophenyl)-5-[5-(2,4-difluorophenyl)-2-(2-methyl-1-propen-1-yl)-1,3-oxazol-4-yl]-2(1H)-pyridinone TLC: Rf 0.26 (hexane:ethyl acetate=2:1);
NMR: δ 2.00 (d, J=0.9 Hz, 3H), 2.25 (d, J=0.9 Hz, 3H), 6.09-6.17 (m, 1H), 6.64 (dd, J=9.7, 0.7 Hz, 1H), 6.89-7.15 (m, 4H), 7.35-7.58 (m, 3H), 7.62 (d, J=1.8 Hz, 1H).

Example 162(8)

1-(2,6-difluorophenyl)-5-[5-(2,4-difluorophenyl)-2-(2-hydroxy-2-methylpropyl)-1,3-oxazol-4-yl]-2(1H)-pyridinone TLC: Rf 0.39 (ethyl acetate:hexane=7:3);
NMR: δ 1.36 (s, 6H), 2.98 (s, 2H), 3.26 (s, 1H), 6.64 (d, J=9.7 Hz, 1H), 6.91-7.14 (m, 4H), 7.36-7.57 (m, 3H), 7.61-7.66 (m, 1H).

Example 162(9)

5-[5-(2,4-difluorophenyl)-2-(1-hydroxy-1-methylethyl)-1,3-oxazol-4-yl]-1-methyl-2(1H)-pyridinone TLC: Rf 0.41 (ethyl acetate:methanol=19:1);
NMR: δ 1.7 (s, 6H), 2.8 (s, 1H), 3.6 (s, 3H), 6.5 (d, J=9.3 Hz, 1H), 7.0 (m, 2H), 7.3 (m, 1H), 7.5 (m, 1H), 7.8 (d, J=2.4 Hz, 1H).

Example 162(10)

1-(4-chloro-2,6-dimethylphenyl)-5-{5-(2,4-difluorophenyl)-2-[(1S)-1,2-dihydroxy-1-methylethyl]-1,3-oxazol-4-yl}-2(1H)-pyridinone TLC: Rf 0.43 (ethyl acetate:methanol=19:1);
NMR: δ 1.60 (s, 3H), 2.09 (s, 6H), 2.77 (dd, J=7.9, 5.9 Hz, 1H), 3.38 (s, 1H), 3.72 (dd, J=11.4, 7.9 Hz, 1H), 4.06 (dd, J=11.4, 5.9 Hz, 1H), 6.67 (dd, J=9.5, 0.7 Hz, 1H), 6.90-7.07 (m, 2H), 7.18 (s, 2H), 7.40-7.43 (m, 1H), 7.47-7.61 (m, 2H).

Example 162(11)

1-(4-chloro-2,6-dimethylphenyl)-5-{5-(2,4-difluorophenyl)-2-[(1R)-1,2-dihydroxy-1-methylethyl]-1,3-oxazol-4-yl}-2(1H)-pyridinone TLC: Rf 0.43 (ethyl acetate:methanol=19:1);
NMR: δ 1.59 (s, 3H), 2.08 (s, 6H), 2.76 (dd, J=8.0, 5.8 Hz, 1H), 3.37 (s, 1H), 3.71 (dd, J=11.4, 8.0 Hz, 1H), 4.05 (dd, J=11.4, 5.9 Hz, 1H), 6.66 (d, J=9.5 Hz, 1H), 6.89-7.06 (m, 2H), 7.17 (s, 2H), 7.39-7.42 (m, 1H), 7.46-7.60 (m, 2H).

Example 162(12)

1-(2,6-difluorophenyl)-5-[5-(2,4-difluorophenyl)-2-isopropenyl-1,3-oxazol-4-yl]-2(1H)-pyridinone TLC: Rf 0.32 (hexane:ethyl acetate=3:2);
NMR: δ 2.19 (s, 3H), 5.38-5.48 (m, 1H), 5.97-6.03 (m, 1H), 6.63 (d, J=9.5 Hz, 1H), 6.87-7.14 (m, 4H), 7.33-7.59 (m, 3H), 7.62 (d, J=2.0 Hz, 1H).

Example 162(13)

1-(4-chloro-2,6-dimethylphenyl)-5-[5-(4-fluorophenyl)-2-(2-methyl-1-propen-1-yl)-1,3-oxazol-4-yl]-2(1H)-pyridinone TLC: Rf 0.47 (hexane:ethyl acetate=1:1);
NMR: δ 7.67 (dd, J=9.6, 2.7 Hz, 1H), 7.61-7.54 (m, 2H), 7.46 (dd, J=2.7, 0.9 Hz, 1H), 7.17 (s, 2H), 7.14-7.08 (m, 2H), 6.72 (dd, J=9.6, 0.9 Hz, 1H), 6.13 (m, 1H), 2.25 (s, 3H), 2.12 (s, 6H), 2.00 (s, 3H).

Example 162(14)

1-(4-chloro-2,6-dimethylphenyl)-5-[5-(2,4-difluorophenyl)-2-(2-methyl-1-propen-1-yl)-1,3-oxazol-4-yl]-2(1H)-pyridinone TLC: Rf 0.49 (ethyl acetate:hexane=3:2);
NMR: δ 2.00 (d, J=1.3 Hz, 3H), 2.09 (s, 6H), 2.24 (d, J=1.1 Hz, 3H), 6.11-6.15 (m, 1H), 6.67 (dd, J=9.6, 0.6 Hz, 1H), 6.89-7.05 (m, 2H), 7.15-7.18 (m, 2H), 7.41-7.44 (m, 1H), 7.48-7.60 (m, 2H).

Example 162(15)

1-cyclopentyl-5-[5-(2,4-difluorophenyl)-2-(1-hydroxy-1-methylethyl)-1,3-oxazol-4-yl]-2(1H)-pyridinone TLC: Rf 0.28 (hexane:ethyl acetate=1:2);
NMR: δ 1.48-1.86 (m, 12H), 2.08-2.29 (m, 2H), 2.84 (s, 1H), 5.21-5.39 (m, 1H), 6.50 (d, J=9.0 Hz, 1H), 6.89-7.07 (m, 2H), 7.30-7.41 (m, 1H), 7.43-7.57 (m, 1H), 7.71 (d, J=2.4 Hz, 1H).

Example 162(16)

1-cyclobutyl-5-[5-(2,4-difluorophenyl)-2-(1-hydroxy-1-methylethyl)-1,3-oxazol-4-yl]-2(1H)-pyridinone TLC: Rf 0.18 (hexane:ethyl acetate=1:2);
NMR: δ 1.71 (s, 6H), 1.75-1.96 (m, 2H), 2.07-2.29 (m, 2H), 2.41-2.58 (m, 2H), 2.82 (s, 1H), 5.05-5.24 (m, 1H), 6.45 (d, J=9.5 Hz, 1H), 6.89-7.06 (m, 2H), 7.27-7.35 (m, 1H), 7.43-7.56 (m, 1H), 7.87 (d, J=2.4 Hz, 1H).

Example 162(17)

1-(2,6-difluorophenyl)-5-[5-(4-fluorophenyl)-2-(2-methyl-1-propen-1-yl)-1,3-oxazol-4-yl]-2(1H)-pyridinone TLC: Rf 0.50 (toluene:ethyl acetate=2:1);
NMR: δ 7.66-7.59 (m, 3H), 7.42 (m, 1H), 7.20-7.00 (m, 5H), 6.70 (dd, J=9.0, 1.2 Hz, 1H), 6.13 (m, 1H), 2.26 (s, 3H), 2.00 (s, 3H).

Example 162(18)

5-[5-(2,4-difluorophenyl)-2-(2-methyl-1-propen-1-yl)-1,3-oxazol-4-yl]-1-(4-fluoro-2,6-dimethylphenyl)-2(1H)-pyridinone TLC: Rf 0.44 (hexane:ethyl acetate=1:1);
NMR: δ 7.57-7.50 (m, 2H), 7.45 (m, 1H), 7.04-6.86 (m, 4H), 6.68 (dd, J=9.6, 0.6 Hz, 1H), 6.13 (m, 1H), 2.24 (s, 3H), 2.10 (s, 6H), 2.00 (s, 3H).

Example 162(19)

1-(4-chloro-2,6-dimethylphenyl)-5-[5-(2,4-difluorophenyl)-2-(2-methyl-1-propen-1-yl)-1,3-oxazol-4-yl]-6-methyl-2(1H)-pyridinone TLC: Rf 0.33 (hexane:ethyl acetate=1:1);
NMR: δ 7.54-7.43 (m, 2H), 7.19-7.16 (m, 2H), 6.99-6.82 (m, 2H), 6.62 (dd, J=9.3, 0.6 Hz, 1H), 6.22-6.17 (m, 1H), 2.28 (d, J=1.2 Hz, 3H), 2.05-2.00 (m, 9H), 1.66 (s, 3H).

Example 163

Methyl (2Z)-3-[(2,6-difluorophenyl)amino]-2-butenoate

By the same procedure as a reaction of Example 158, using methyl acetoacetate and using 2,6-difluoroaniline instead of 4-chloro-2,6-dimethylaniline, the title compound having the following physical data was obtained.

TLC: Rf 0.40 (hexane:ethyl acetate=9:1);
NMR: δ 9.73 (br.s, 1H), 7.25-7.13 (m, 1H), 7.01-6.90 (m, 2H), 4.84 (s, 1H), 3.70 (s, 3H), 1.85 (s, 3H).

Example 164

Methyl 1-(2,6-difluorophenyl)-2-methyl-6-oxo-1,6-dihydro-3-pyridinecarboxylate

To a solution of the compound prepared in Example 163 (4.67 g) in tetrahydrofuran (100 mL) was added sodium hydroxide (8.24 g) and the mixture was stirred at 50° C. for 1.5 hours. Furthermore, to the reaction mixture was added methyl propiolate (2.75 mL) and the mixture was stirred at 50° C. for 10 minutes. The reaction mixture was poured into 5N hydrochloric acid-ice and extracted with ethyl acetate. The obtained organic layer was dried and concentrated. The obtained residue was coarsely purified by preparative medium pressure liquid chromatography W-prep 2XY (column: main column 3L, inject column L; automatic condition setting: hexane:ethyl acetate=2:1, preparative isolation mode GR). The obtained coarse crystal was washed with diisopropyl ether to give the title compound (507 mg) having the following physical data.

TLC: Rf 0.30 (hexane:ethyl acetate=2:1);
NMR: δ 8.01 (d, J=9.6 Hz, 1H), 7.58-7.42 (m, 1H), 7.20-7.05 (m, 2H), 6.56 (d, J=9.6 Hz, 1H), 3.87 (s, 3H), 2.48 (s, 3H).

Example 165

1-(2,6-difluorophenyl)-5-[5-(2,4-difluorophenyl)-2-(1-hydroxy-1-methylethyl)-1,3-oxazol-4-yl]-6-methyl-2(1H)-pyridinone By the same procedure as a reaction of Example 160, using the compound prepared in Example 164 instead of the compound prepared in Example 159, the compound of the present invention having the following physical data was obtained.

TLC: Rf 0.44 (hexane:ethyl acetate=1:2);
NMR: δ 1.7 (s, 6H), 1.8 (s, 3H), 2.7 (s, 1H), 6.6 (d, J=9.5 Hz, 1H), 6.8 (m, 1H), 7.0 (m, 1H), 7.1 (m, 2H), 7.4 (m, 2H), 7.7 (m, 1H).

Example 166(1)

1-(2,6-difluorophenyl)-5-[5-(2,4-difluorophenyl)-2-(1,2-dihydroxy-2-methylpropyl)-1,3-oxazol-4-yl]-6-methyl-2(1H)-pyridinone By the same procedure as a reaction of Example 18, using the compound prepared in Example 162(7) instead of the compound prepared in Example 7(26), the compound of the present invention having the following physical data was obtained.

TLC: Rf 0.34 (hexane:ethyl acetate=1:3);
NMR: δ 1.26 (s, 3H), 1.39 (s, 3H), 2.72 (s, 1H), 3.11 (d, J=7.7 Hz, 1H), 4.57 (d, J=7.7 Hz, 1H), 6.63 (d, J=9.7 Hz, 1H), 6.91-7.13 (m, 4H), 7.36-7.57 (m, 3H), 7.63 (d, J=2.6 Hz, 1H).

Example 166(2)

1-(4-chloro-2,6-dimethylphenyl)-5-[2-(1,2-dihydroxy-2-methylpropyl)-5-(4-fluorophenyl)-1,3-oxazol-4-yl]-2(1H)-pyridinone By the same procedure as a reaction of Example 18, using the compound prepared in Example 162(13) instead of the compound prepared in Example 7(26), the compound of the present invention having the following physical data was obtained.

TLC: Rf 0.31 (ethyl acetate);
NMR: δ 7.63-7.46 (m, 4H), 7.20-7.10 (m, 2H), 7.18 (s, 2H), 6.72 (dd, J=9.9, 0.6 Hz, 1H), 4.57 (d, J=7.8 Hz, 1H), 3.10 (d, J=7.8 Hz, 1H), 2.78 (s, 1H), 2.11 (s, 6H), 1.40 (s, 3H), 1.28 (s, 3H).

Example 166(3)

1-(2,6-difluorophenyl)-5-[2-(1,2-dihydroxy-2-methylpropyl)-5-(4-fluorophenyl)-1,3-oxazol-4-yl]-2(1H)-pyridinone By the same procedure as a reaction of Example 18, using the compound prepared in Example 162(17) instead of the compound prepared in Example 7(26), the compound of the present invention having the following physical data was obtained.

TLC: Rf 0.49 (ethyl acetate);
NMR: δ 7.66-7.55 (m, 4H), 7.44 (m, 1H), 7.20-7.05 (m, 4H), 6.70 (dd, J=9.6, 0.9 Hz, 1H), 4.57 (d, J=8.1 Hz, 1H), 3.07 (d, J=8.1 Hz, 1H), 2.81 (s, 1H), 1.40 (s, 3H), 1.28 (s, 3H).

Example 166(4)

5-[5-(2,4-difluorophenyl)-2-(1,2-dihydroxy-2-methylpropyl)-1,3-oxazol-4-yl]-1-(4-fluoro-2,6-dimethylphenyl)-2(1H)-pyridinone By the same procedure as a reaction of Example 18, using the compound prepared in Example 162(18) instead of the compound prepared in Example 7(26), the compound of the present invention having the following physical data was obtained.

TLC: Rf 0.09 (hexane:ethyl acetate=1:3);
NMR: δ 7.56-7.45 (m, 3H), 7.08-6.85 (m, 4H), 6.67 (dd, J=9.0, 1.2 Hz, 1H), 4.58 (d, J=7.8 Hz, 1H), 3.13 (d, J=7.8 Hz, 1H), 2.72 (s, 1H), 2.10 (s, 6H), 1.39 (s, 3H), 1.27 (s, 3H).

Example 166(5)

1-(4-chloro-2,6-dimethylphenyl)-5-[5-(2,4-difluorophenyl)-2-(1,2-dihydroxy-2-methylpropyl)-1,3-oxazol-4-yl]-6-methyl-2(1H)-pyridinone By the same procedure as a reaction of Example 18, using the compound prepared in Example 162(19) instead of the compound prepared in Example 7(26), the compound of the present invention having the following physical data was obtained.

TLC: Rf 0.48 (ethyl acetate:methanol=19:1);
NMR: δ 1.3 (s, 3H), 1.4 (s, 3H), 1.6 (s, 3H), 2.0 (s, 6H), 2.8 (s, 1H), 3.2 (d, J=7.9 Hz, 1H), 4.6 (d, J=7.9 Hz, 1H), 6.6 (d, J=9.5 Hz, 1H), 6.9 (m, 1H), 7.0 (m, 1H), 7.2 (m, 2H), 7.4 (d, J=9.5 Hz, 1H), 7.5 (m, 1H).

Example 167(1)

1-(2,6-difluorophenyl)-5-{5-(2,4-difluorophenyl)-2-[(1R)-1,2-dihydroxy-1-methylethyl]-1,3-oxazol-4-yl}-2(1H)-pyridinone By the same procedure as a reaction of Example 130(b), using the compound prepared in Example 162(12), the compound of the present invention having the following physical data was obtained.

TLC: Rf 0.29 (hexane:ethyl acetate=1:3);
NMR: δ 1.60 (s, 3H), 2.78 (dd, J=8.0, 5.7 Hz, 1H), 3.36 (s, 1H), 3.71 (dd, J=11.5, 8.0 Hz, 1H), 4.07 (dd, J=11.5, 5.7 Hz, 1H), 6.64 (dd, J=9.7, 0.7 Hz, 1H), 6.88-7.15 (m, 4H), 7.38-7.48 (m, 2H), 7.48-7.59 (m, 1H), 7.59-7.64 (m, 1H).

Example 167(2)

1-(2,6-difluorophenyl)-5-{5-(2,4-difluorophenyl)-2-[(1S)-1,2-dihydroxy-1-methylethyl]-1,3-oxazol-4-yl}-2(1H)-pyridinone By the same procedure as a reaction of Example 130(a), using the compound prepared in Example 162(12), the compound of the present invention having the following physical data was obtained.

TLC: Rf 0.29 (hexane:ethyl acetate=1:3);
NMR: δ 1.60 (s, 3H), 2.80 (dd, J=8.0, 5.4 Hz, 1H), 3.38 (s, 1H), 3.71 (dd, J=11.4, 8.0 Hz, 1H), 4.06 (dd, J=11.4, 5.4 Hz, 1H), 6.63 (dd, J=9.7, 0.7 Hz, 1H), 6.91-7.15 (m, 4H), 7.38-7.49 (m, 2H), 7.49-7.59 (m, 1H), 7.59-7.64 (m, 1H).

Example 168(1)~(2)

By the same procedure as a series of reactions of Example 4→Example 5→Example 6→Example 17→Example 35, using the compound prepared in Example 91 instead of the compound prepared in Example 3 and using carboxylic acid salt prepared in Example 177 or Example 178 instead of the compound prepared in Example A1, the compound of the present invention having the following physical data was obtained.

Example 168(1)

(1S)-1-[4-[1-(4-chloro-2,6-dimethylphenyl)-6-oxo-1,6-dihydro-3-pyridinyl]-5-(2,4-difluorophenyl)-1,3-oxazol-2-yl]-2-hydroxy-2-methylpropyl acetate TLC: Rf 0.45 (hexane:ethyl acetate=1:3);
NMR: δ 7.55-7.42 (m, 3H), 7.17 (s, 2H), 7.05-6.91 (m, 2H), 6.67 (dd, J=9.6, 0.6 Hz, 1H), 5.70 (s, 1H), 2.92 (s, 1H), 2.20 (s, 3H), 2.08 (s, 6H), 1.35 (s, 6H).

Example 168(2)

(1R)-1-[4-[1-(4-chloro-2,6-dimethylphenyl)-6-oxo-1,6-dihydro-3-pyridinyl]-5-(2,4-difluorophenyl)-1,3-oxazol-2-yl]-2-hydroxy-2-methylpropyl acetate TLC: Rf 0.45 (ethyl acetate:hexane=3:1);
NMR: δ 1.35 (s, 3H), 1.35 (s, 3H), 2.08 (s, 6H), 2.20 (s, 3H), 2.92 (s, 1H), 5.69 (s, 1H), 6.66 (dd, J=9.5, 0.7 Hz, 1H), 6.89-7.05 (m, 2H), 7.15-7.18 (m, 2H), 7.40-7.44 (m, 1H), 7.45-7.55 (m, 2H).

Example 168(3)

1-(4-chloro-2,6-dimethylphenyl)-5-{5-(2,4-difluorophenyl)-2-[(1S)-1,2-dihydroxy-2-methylpropyl]-1,3-oxazol-4-yl}-2(1H)-pyridinone By the same procedure as a reaction of Example A3, using the compound prepared in Example 168(1) instead of the compound prepared in Example A2, the compound of the present invention having the following physical data was obtained.

TLC: Rf 0.33 (ethyl acetate);
NMR: δ 7.55-7.43 (m, 3H), 7.17 (s, 2H), 7.05-6.90 (m, 2H), 6.66 (dd, J=9.3, 0.6 Hz, 1H), 4.57 (d, J=7.8 Hz, 1H), 3.08 (d, J=7.8 Hz, 1H), 2.68 (s, 1H), 2.08 (s, 6H), 1.39 (s, 3H), 1.27 (s, 3H).

Example 168(4)

1-(4-chloro-2,6-dimethylphenyl)-5-{5-(2,4-difluorophenyl)-2-[(1R)-1,2-dihydroxy-2-methylpropyl]-1,3-oxazol-4-yl}-2(1H)-pyridinone By the same procedure as a reaction of Example A3, using the compound prepared in Example 168(2) instead of the compound prepared in Example A2, the compound of the present invention having the following physical data was obtained.

TLC: Rf 0.29 (ethyl acetate);
NMR: δ 1.27 (s, 3H), 1.40 (s, 3H), 2.09 (s, 6H), 2.70 (s, 1H), 3.10 (d, J=7.7 Hz, 1H), 4.58 (d, J=7.7 Hz, 1H), 6.68 (dd, J=9.5, 0.7 Hz, 1H), 6.90-7.07 (m, 2H), 7.18 (s, 2H), 7.43-7.57 (m, 3H).

Example 169

1-[2,6-difluoro-4-(3-hydroxy-3-methyl-1-butyn-1-yl)phenyl]-5-[5-(2,4-difluorophenyl)-2-(1-hydroxy-1-methylethyl)-1,3-oxazol-4-yl]-2(1H)-pyridinone By the same procedure as a reaction of Example 32, using the compound prepared in Example 162(2) instead of the compound prepared in Example 10(2), the compound of the present invention having the following physical data was obtained.

TLC: Rf 0.28 (ethyl acetate:hexane=2:1);
NMR: δ 1.6 (s, 6H), 1.7 (s, 6H), 2.0 (s, 1H), 2.7 (s, 1H), 6.6 (d, J=9.5 Hz, 1H), 7.0 (m, 2H), 7.1 (m, 2H), 7.5 (m, 2H), 7.6 (m, 1H).

Example 170

Methyl 4-[5-[5-(2,4-difluorophenyl)-2-(1-hydroxy-1-methylethyl)-1,3-oxazol-4-yl]-2-oxo-1(1H)-pyridinyl]-3,5-difluorobenzoate By the same procedure as a reaction of Example 25, using the compound prepared in Example 162(2) instead of the compound prepared in Example 7(37), the compound of the present invention having the following physical data was obtained.

TLC: Rf 0.37 (ethyl acetate:hexane=2:1);

NMR: δ 1.7 (s, 6H), 2.7 (s, 1H), 4.0 (s, 3H), 6.6 (dd, J=9.8, 0.6 Hz, 1H), 7.0 (m, 2H), 7.5 (m, 2H), 7.6 (m, 1H), 7.8 (m, 2H).

Example 171

1-(4-acetyl-2,6-difluorophenyl)-5-[5-(2,4-difluorophenyl)-2-(1-hydroxy-1-methylethyl)-1,3-oxazol-4-yl]-2(1H)-pyridinone By the same procedure as a series of reactions of Example 33→Example 34, using the compound prepared in Example 162(2) instead of the compound prepared in Example 10(2), the compound of the present invention having the following physical data was obtained.
TLC: Rf 0.28 (ethyl acetate:hexane=2:1);
NMR: δ 1.7 (s, 6H), 2.6 (s, 3H), 2.7 (s, 1H), 6.6 (dd, J=9.7, 0.7 Hz, 1H), 7.0 (m, 2H), 7.5 (m, 2H), 7.7 (m, 3H).

Example 172

1-(2,6-difluorophenyl)-5-[5-(2,4-difluorophenyl)-2-(2-hydroxy-2-methylpropanoyl)-1,3-oxazol-4-yl]-2(1H)-pyridinone By the same procedure as a reaction of Example 54, using the compound prepared in Example 166(1) instead of the compound prepared in Example 53, the compound of the present invention having the following physical data was obtained.
TLC: Rf 0.63 (hexane:ethyl acetate=1:3);
NMR: δ 1.69 (s, 6H), 4.30 (s, 1H), 6.70 (dd, J=9.7, 0.7 Hz, 1H), 6.93-7.16 (m, 4H), 7.38-7.58 (m, 3H), 7.59-7.70 (m, 1H).

Example 173

Benzyl (2S)-2,3-dihydroxy-3-methylbutanoate

By the same procedure as a reaction of Example 130(a), using the compound prepared in Example 133(a), the title compound having the following physical data was obtained.
TLC: Rf 0.40 (ethyl acetate:hexane=3:2);
NMR: δ 1.17 (s, 3H), 1.26 (s, 3H), 2.51 (s, 1H), 3.12 (d, J=6.8 Hz, 1H), 4.01 (d, J=6.8 Hz, 1H), 5.23 (d, J=12.0 Hz, 1H), 5.29 (d, J=12.0 Hz, 1H), 7.34-7.41 (m, 5H).

Example 174

Benzyl (2R)-2,3-dihydroxy-3-methylbutanoate

By the same procedure as a reaction of Example 130(b), using the compound prepared in Example 133(a), the title compound having the following physical data was obtained.
TLC: Rf 0.40 (ethyl acetate:hexane=3:2);
NMR: δ 1.17 (s, 3H), 1.26 (s, 3H), 2.52 (s, 1H), 3.13 (d, J=6.8 Hz, 1H), 4.01 (d, J=6.8 Hz, 1H), 5.23 (d, J=12.0 Hz, 1H), 5.29 (d, J=12.0 Hz, 1H), 7.34-7.42 (m, 5H).

Example 175

Benzyl (4S)-2,2,5,5-tetramethyl-1,3-dioxolane-4-carboxylate

By the same procedure as a reaction of Example 134, using the compound prepared in Example 173 instead of the compound prepared in Example 133(b), the title compound having the following physical data was obtained.
TLC: Rf 0.47 (ethyl acetate:hexane=1:3);
NMR: δ 1.09 (s, 3H), 1.37 (d, J=0.5 Hz, 3H), 1.45 (s, 3H), 1.53 (d, J=0.5 Hz, 3H), 4.38 (s, 1H), 5.23 (s, 2H), 7.33-7.41 (m, 5H).

Example 176

Benzyl (4R)-2,2,2,5-tetramethyl-1,3-dioxolane-4-carboxylate

By the same procedure as a reaction of Example 134, using the compound prepared in Example 174 instead of the compound prepared in Example 133(b), the title compound having the following physical data was obtained.
TLC: Rf 0.47 (ethyl acetate:hexane=1:3);
NMR: δ 1.09 (s, 3H), 1.37 (d, J=0.5 Hz, 3H), 1.44 (s, 3H), 1.53 (d, J=0.5 Hz, 3H), 4.38 (s, 1H), 5.23 (s, 2H), 7.32-7.41 (m, 5H).

Example 177

Sodium (4R)-2,2,5,5-tetramethyl-1,3-dioxolane-4-carboxylate

By the same procedure as a reaction of Example 135, using the compound prepared in Example 175 instead of the compound prepared in Example 134, the title compound having the following physical data was obtained.
TLC: Rf 0.39 (dichloromethane:methanol:acetic acid=18:1:1);
NMR: δ 0.99 (s, 3H), 1.18 (s, 3H), 1.29 (s, 3H), 1.30 (s, 3H), 3.83 (s, 1H).

Example 178

Sodium (4R)-2,2,5,5-tetramethyl-1,3-dioxolane-4-carboxylate

By the same procedure as a reaction of Example 135, using the compound prepared in Example 176 instead of the compound prepared in Example 134, the title compound having the following physical data was obtained.
TLC: Rf 0.39 (dichloromethane:methanol:acetic acid=18:1:1);
NMR: δ 0.99 (s, 3H), 1.18 (s, 3H), 1.29 (s, 3H), 1.30 (s, 3H), 3.82 (s, 1H).

Example 179

(4S)-N-methoxy-N,2,2,4-tetramethyl-1,3-dioxolane-4-carboxamide

The compound prepared in Example 130(a) (12.4 g), acetone (150 mL), acetone dimethylacetal (18 mL) and p-toluenesulfonic acid monohydrate (290 mg) were stirred at room temperature for an hour. The reaction mixture was concentrated, poured into a cold aqueous solution of sodium hydrogen carbonate and extracted with a mixed solution of ethyl acetate-hexane (1:1). The obtained organic layer was washed with an aqueous saturated sodium hydrogen carbonate solution, water and brine, and dried over anhydrous magnesium sulfate. The solvent was concentrated in vacuum condition and dried to give the title compound (8.4 g) having the following physical data.
TLC: Rf 0.66 (hexane:ethyl acetate=1:2);

NMR: δ 1.37 (s, 3H), 1.46 (s, 3H), 1.51 (s, 3H), 3.26 (s, 3H), 3.73 (s, 3H), 3.78 (d, J=8.8 Hz, 1H), 4.59 (d, J=8.8 Hz, 1H).

Example 180

Lithium (4S)-2,2,4-trimethyl-1,3-dioxolane-4-carboxylate

The compound prepared in Example 179 (8.3 g) was dissolved in methanol (120 mL). To this solvent was added a solution of lithium hydroxide monohydrate (1.7g) in water (30 mL) and the mixture was stirred at room temperature for 48 hours. The reaction mixture was concentrated. To the obtained residue was added toluene, and the mixture was concentrated moreover and dried to give the title compound (7.4 g) having the following physical data.
NMR (DMSO-$D_6$): δ 1.24 (s, 3H), 1.25 (s, 3H), 1.27 (s, 3H), 3.52 (d, J=7.9Hz, 1H), 4.09 (d, J=7.9 Hz, 1H).

Example 181

Benzyl (4S)-2,2,4-trimethyl-1,3-dioxolane-4-carboxylate

To a solution of the compound prepared in Example 180 (5.9 g) in N,N-dimethylformamide (hereinafter abbreviated to DMF) (120 mL) were added benzyl bromide (4.3 mL) and potassium carbonate (9.9 g) and the reaction mixture was stirred at room temperature for 12 hours. The reaction mixture was filtered through Celite (trade name) and concentrated in vacuum condition to remove DMF. To the obtained residue was added water and the organic layer was extracted with ethyl acetate. The obtained organic layer was dried over magnesium sulfate and concentrated in vacuum condition. The obtained residue was purified by column chromatography on silica gel (hexane:ethyl acetate=6:1→4:1) to give the title compound (6.1 g) having the following physical data.
TLC: Rf 0.50 (hexane:ethyl acetate=4:1);
NMR: δ 1.41 (s, 3H), 1.42 (s, 3H), 1.52 (s, 3H), 3.78 (d, J=8.8 Hz, 1H), 4.38 (d, J=8.8 Hz, 1H), 5.16 (d, J=12.3 Hz, 1H), 5.22 (d, J=12.3 Hz, 1H), 7.28-7.42 (m, 5H).

Example 182

Benzyl (2S)-2,3-dihydroxy-2-methylpropanoate

To a solution of the compound prepared in Example 181 (6.0 g) in methanol (100 mL) was added p-toluenesulfonic acid monohydrate (230mg) and the reaction mixture was stirred at 55° C. for 12 hours. The reaction mixture was concentrated in vacuum condition. The obtained residue was purified by column chromatography on silica gel (hexane:ethyl acetate=1:1) to give the title compound (2.0 g) having the following physical data.
TLC: Rf 0.44 (hexane:ethyl acetate=2:3);
NMR: δ 1.36-1.37 (m, 3H), 2.07-2.22 (m, 1H), 3.50 (s, 1H), 3.59 (d, J=11.0 Hz, 1H), 3.74-3.92 (m, 1H), 5.18-5.29 (m, 2H), 7.28-7.44 (m, 5H).

Example 183

Benzyl (4S)-4-methyl-2-oxo-1,3-dioxolane-4-carboxylate

To a solution of the compound prepared in Example 182 (2.0 g) in dichloromethane (30 mL) were added pyridine (2.2g) and triphosgene (2.8 g) on ice bath and the reaction mixture was stirred for 10 minutes on ice bath. To the reaction mixture was added water and the mixture was extracted with ethyl acetate. The obtained organic layer was dried over magnesium sulfate and concentrated in vacuum condition. The obtained residue was purified by column chromatography on silica gel (hexane:ethyl acetate=5:2) to give the title compound (2.0 g) having the following physical data.
TLC: Rf 0.61 (hexane:ethyl acetate=1:1);
NMR: δ 1.69-1.77 (m, 3H), 4.20 (d, J=8.8 Hz, 1H), 4.63 (d, J=8.8 Hz, 1H), 5.27 (s, 2H), 7.29-7.47 (m, 5H).

Example 184

(4S)-4-methyl-2-oxo-1,3-dioxolane-4-carboxylic acid

Under an atmosphere of hydrogen, to a solution of the compound prepared in Example 183 (2.0 g) in ethanol (30 mL) was added palladium-carbon (10% wet, 650 mg) and the reaction mixture was stirred at room temperature for an hour. The reaction mixture was filtered through Celite (trade name) and the filtrate was concentrated to give the title compound (1.2 g) having the following physical data.
NMR: δ 1.80 (s, 3H), 4.27 (d, J=9.0 Hz, 1H), 4.73 (d, J=9.0 Hz, 1H), 6.89-7.22 (m, 1H).

Example 185

(4S)-4-methyl-2-oxo-1,3-dioxolane-4-carbonyl chloride

To a solution of the compound prepared in Example 184 (330 mg) in dichloromethane (11 mL) were added oxalyl chloride (290 μL) and DMF (0.1 mL) and the reaction mixture was stirred at room temperature for 10 minutes. The reaction mixture was concentrated in vacuum condition to give the title compound (2.0 g) having the following physical data as a coarse product. This compound was used for the next reaction without being purified.
NMR: δ 1.85 (s, 3H), 4.30 (d, J=9.5 Hz, 1H), 4.78 (d, J=9.5 Hz, 1H).

Example 186

(4R)-4-methyl-2-oxo-1,3-dioxolane-4-carbonyl chloride

By the same procedure as a series of reactions of Example 179→Example 180→Example 181→Example 182→Example 183→Example 184→Example 185, using the compound prepared in Example 130(b) instead of the compound prepared in Example 130(a), the title compound having the following physical data was obtained.
NMR: δ 1.85 (s, 3H), 4.30 (d, J=9.5 Hz, 1H), 4.78 (d, J=9.5 Hz, 1H).

Example 187

(4S)-5,5-dimethyl-2-oxo-1,3-dioxolane-4-carbonyl chloride

By the same procedure as a series of reactions of Example 183→Example 184→Example 185, using the compound prepared in Example 173 instead of the compound prepared in Example 182, the title compound having the following physical data was obtained.
NMR: δ 1.58 (s, 3H), 1.74 (s, 3H), 4.94 (s, 1H).

Example 188

(4R)-5,5-dimethyl-2-oxo-1,3-dioxolane-4-carbonyl chloride

By the same procedure as a series of reactions of Example 183→Example 184→Example 185, using the compound prepared in Example 174 instead of the compound prepared in Example 182, the title compound having the following physical data was obtained.

NMR: δ 1.58 (s, 3H), 1.74 (s, 3H), 4.94 (s, 1H).

Example 189

Ethyl 2-({[tert-butyl(diphenyl)silyl]oxy}methyl)acrylate

To a solution of 2-(hydroxymethyl)acrylic acid (520 mg) in DMF (5.0 mL) were added tert-butyldiphenylsilyl chloride (1.65 g) and imidazole (680 mg) and the reaction mixture was stirred at room temperature for 2 hours. The reaction mixture was poured into 1N hydrochloric acid and extracted with ethyl acetate. The organic layer was washed with an aqueous saturated sodium hydrogen carbonate solution and brine, dried over magnesium sulfate, and concentrated in vacuum condition. The obtained residue was purified by column chromatography on silica gel (hexane:ethyl acetate=20:1→9:1) to give the title compound (1.35 g) having the following physical data.

TLC: Rf 0.41 (hexane:ethyl acetate=19:1);

NMR: δ 1.07 (s, 9H), 1.25 (t, J=7.1 Hz, 3H), 4.16 (q, J=7.1 Hz, 2H), 4.41 (m, 2H), 6.08 (m, 1H), 6.31 (m, 1H), 7.34-7.45 (m, 6H), 7.63-7.68 (m, 4H).

Example 190

2-({[tert-butyl(diphenyl)silyl]oxy}methyl)acrylic acid

To a solution of the compound prepared in Example 189 (1.3 g) in ethanol (4.0 mL)/tetrahydrofuran (hereinafter abbreviated to THF) (1.0 mL) was added 5N aqueous solution of sodium hydroxide (0.72 mL) and the reaction mixture was stirred at room temperature for 4.5 hours. The reaction mixture was neutralized with 1N hydrochloric acid and extracted with ethyl acetate. The organic layer was washed with brine, dried over magnesium sulfate and concentrated in vacuum condition. The obtained residue was purified by column chromatography on silica gel (hexane:ethyl acetate=4:1) to give the title compound (788 mg) having the following physical data.

TLC: Rf 0.27 (hexane:ethyl acetate=4:1);

NMR: δ 1.08 (s, 9H), 4.41 (m, 2H), 6.16 (m, 1H), 6.42 (m, 1H), 7.34-7.46 (m, 6H), 7.63-7.68 (m, 4H).

Example 191

2-({[tert-butyl(diphenyl)silyl]oxy}methyl)acryloyl chloride

By the same procedure as a reaction of Example 185, using the compound prepared in Example 190 instead of the compound prepared in Example 184, the title compound was obtained.

Example 201

5-[bromo(2,4-difluorophenyl)acetyl]-1-(2,6-difluorophenyl)-2(1H)-pyridinone

By the same procedure as a reaction of Example 4, using the compound prepared in Example 85 instead of the compound prepared in Example 3, the title compound having the following physical data was obtained.

TLC: Rf 0.58 (ethyl acetate:methanol=2:3);

NMR: δ 6.29 (s, 1H), 6.71 (d, J=9.9 Hz, 1H), 6.79-6.90 (m, 1H), 6.94-7.04 (m, 1H), 7.09-7.19 (m, 2H), 7.44-7.57 (m, 1H), 7.64-7.75 (m, 1H), 7.97 (dd, J=9.9, 2.7 Hz, 1H), 8.17 (d, J=2.7 Hz, 1H).

Example 202

2-{1-(2,4-difluorophenyl)-2-[1-(2,6-difluorophenyl)-6-oxo-1,6-dihydro-3-pyridinyl]-2-oxoethyl}-1H-isoindole-1,3(2H)dione To a solution of the compound prepared in Example 201 (4.2 g) in DMF (50 mL) was added potassium phthalimide (1.8g) and the reaction mixture was stirred at room temperature for 3 hours. To the reaction mixture was added water and the mixture was extracted with ethyl acetate. The organic layer was dried over magnesium sulfate and concentrated in vacuum condition. The obtained residue was purified by column chromatography on silica gel (hexane:ethyl acetate=3:2) to give the title compound (3.0 g) having the following physical data.

TLC: Rf 0.42 (hexane:ethyl acetate=1:1);

NMR: δ 6.61 (d, J=9.1 Hz, 1H), 6.72 (s, 1H), 6.81-6.97 (m, 2H), 7.00-7.13 (m, 2H), 7.38-7.56 (m, 2H), 7.71-7.80 (m, 3H), 7.82-7.88 (m, 2H), 7.89-7.94 (m, 1H).

Example 203

5-[amino(2,4-difluorophenyl)acetyl]-1-(2,6-difluorophenyl)-2(1H)-pyridinone hydrochloride To a solution of the compound prepared in Example 202 (7.9 g) in dioxane (150 mL) was added 5N hydrochloric acid (150 mL) and the reaction mixture was stirred at 110° C. for 14 hours. After the reaction mixture was cooled to 0° C., it was adjusted to alkalescence with 5N aqueous solution of sodium hydroxide and extracted with ethyl acetate. The organic layer was washed with brine, dried over magnesium sulfate, filtered. To the filtrate was added 4N hydrogen chloride/ethyl acetate solution (7 mL) and the mixture was concentrated in vacuum condition. The obtained residue was washed with tert-butyl methyl ether and dried to give the title compound (4.9 g) having the following physical data.

TLC: Rf 0.46 (ethyl acetate:methanol=19:1);

NMR (DMSO-D6): δ 6.09-6.25 (m, 1H), 6.67 (d, J=9.7 Hz, 1H), 7.18-7.30 (m, 1H), 7.32-7.51 (m, 3H), 7.54-7.76 (m, 2H), 7.87-7.98 (m, 1H), 8.74 (s, 1H), 8.82-9.10 (m, 2H).

Example 204

(4S)-N-{1-(2,4-difluorophenyl)-2-[1-(2,6-difluorophenyl)-6-oxo-1,6-dihydro-3-pyridinyl]-2-oxoethyl}-5,5-dimethyl-2-oxo-1,3-dioxolane-4-carboxamide To a solution of the compound prepared in Example 187 (205 mg) in dichloromethane (3.0 mL) were added oxalyl chloride (0.12 mL) and DMF (0.013 mL), and the reaction mixture was stirred at room temperature for 30 minutes. The reaction mixture and triethylamine (0.41 mL) were added to a solution of the compound prepared in Example 203 (310 mg) in dichloromethane (5.0 mL) on ice bath. The reaction mixture was stirred at room temperature for an hour. The reaction mixture was poured into water and extracted with ethyl acetate. The organic layer was washed with brine, dried over magnesium sulfate and concentrated in vacuum condition. The obtained residue was purified by column chromatography on silica gel (hexane:ethyl acetate=3:2→1:1→2:3) to give the title compound (377 mg) having the following physical data.

TLC: Rf 0.35 (hexane:ethyl acetate=1:1);
NMR: δ 1.10 & 1.44 (s & s, 3H), 1.63 & 1.68 (s & s, 3H), 4.65 & 4.67 (s & s, 1H), 6.36 & 6.39 (d & d, J=6.7 Hz & J=6.8 Hz, 1H), 6.64 (m, 1H), 6.83-6.99 (m, 2H), 7.05-7.16 (m, 2H), 7.25 (m, 1H), 7.49 (m, 1H), 7.63-7.92 (m, 2H), 8.13 (m, 1H).

Example 205

1-(2,6-difluorophenyl)-5-{4-(2,4-difluorophenyl)-2-[(4S)-5,5-dimethyl-2-oxo-1,3-dioxolan-4-yl]-1,3-oxazol-5-yl}-2(1H)-pyridinone To a solution of the compound prepared in Example 204 (370 mg) in acetic anhydride (3.7 mL) was concentrated sulfuric acid (0.01 mL) and the reaction mixture was stirred at 110° C. for 9 hours. The reaction mixture was poured into an aqueous saturated sodium hydrogen carbonate solution and extracted with ethyl acetate. The organic layer was washed with brine, dried over magnesium sulfate and concentrated in vacuum condition. The obtained residue was purified by column chromatography on silica gel (hexane:ethyl acetate=7:3→3:2) to give the title compound (305 mg) having the following physical data.

TLC: Rf 0.32 (hexane:ethyl acetate=3:2);
NMR: δ 1.38 (s, 3H), 1.72 (s, 3H), 5.44 (s, 1H), 6.69 (dd, J=9.9, 0.7 Hz, 1H), 6.91-7.16 (m, 4H), 7.27-7.51 (m, 3H), 7.59 (m, 1H).

Example 206

1-(2,6-difluorophenyl)-5-{4-(2,4-difluorophenyl)-2-[(1S)-1,2-dihydroxy-2-methylpropyl]-1,3-oxazol-5-yl}-2(1H)-pyridinone To a solution of the compound prepared in Example 205 (305 mg) in methanol (2.0 mL)/THF (5.0 mL) was 1N aqueous solution of sodium hydroxide (1.83 mL) and the reaction mixture was stirred at room temperature for 10 minutes. The reaction mixture was neutralized with 1N hydrochloric acid and extracted with ethyl acetate. The organic layer was washed with brine, dried over magnesium sulfate and concentrated in vacuum condition. The obtained residue was purified by column chromatography on silica gel (hexane:ethyl acetate=4:1). The obtained residue was washed with diisopropyl ether and dried to give the title compound (231 mg) having the following physical data.

TLC: Rf 0.36 (ethyl acetate:hexane=4:1);
NMR: δ 1.29 (s, 3H), 1.40 (s, 3H), 2.90 (s, 1H), 3.06 (d, J=8.2 Hz, 1H), 4.57 (d, J=8.2 Hz, 1H), 6.68 (dd, J=9.5, 0.9 Hz, 1H), 6.88-7.05 (m, 2H), 7.05-7.14 (m, 2H), 7.39-7.51 (m, 3H), 7.55-7.65 (m, 1H).

Example 207

1-(2,6-difluorophenyl)-5-{4-(2,4-difluorophenyl)-2-[(1R)-1,2-dihydroxy-2-methylpropyl]-1,3-oxazol-5-yl}-2(1H)-pyridinone By the same procedure as a series of reactions of Example 204→Example 205→Example 206, using the compound prepared in Example 188 instead of the compound prepared in Example 187, the title compound having the following physical data was obtained.

TLC: Rf 0.36 (ethyl acetate:hexane=4:1);
NMR: δ 1.29 (s, 3H), 1.40 (s, 3H), 2.91 (s, 1H), 3.07 (d, J=8.2 Hz, 1H), 4.57 (d, J=8.2 Hz, 1H), 6.68 (dd, J=9.5, 0.9 Hz, 1H), 6.88-7.05 (m, 2H), 7.06-7.15 (m, 2H), 7.37-7.51 (m, 3H), 7.55-7.66 (m, 1H).

Example 208

(4S)-N-{1-(2,4-difluorophenyl)-2-[1-(2,6-difluorophenyl)-6-oxo-1,6-dihydro-3-pyridinyl]-2-oxoethyl}-4-methyl-2-oxo-1,3-dioxolane-4-carboxamide By the same procedure as a reaction of Example 204, using the compound prepared in Example 185 instead of the compound prepared in Example 187, the title compound having the following physical data was obtained.

TLC: Rf 0.35 (hexane:ethyl acetate=3:4);
NMR: δ 1.64 & 1.75 (s, 3H), 4.21 & 4.24 (d, J=9.0 Hz, 1H), 4.58 & 4.68 (d, J=9.0 Hz, 1H), 6.33 & 6.36 (d, J=6.6 & 7.0 Hz, 1H), 6.66 (d, J=9.7 Hz, 1H), 6.85-6.99 (m, 2H), 7.08-7.18 (m, 2H), 7.20-7.32 (m, 1H), 7.42-7.57 (m, 1H), 7.74 & 7.81 (d, J=6.6 & 6.9 Hz, 1H), 7.84-7.94 (m, 1H), 8.15 (d, J=2.6 Hz, 1H).

Example 209

1-(2,6-difluorophenyl)-5-{4-(2,4-difluorophenyl)-2-[(4S)-4-methyl-2-oxo-1,3-dioxolan-4-yl]-1,3-oxazol-5-yl}-2(1H)-pyridinone To a solution of the compound prepared in Example 208 (380 mg) in dichloromethane (14 mL) were added triphenylphosphine (990 mg), iodine (960 mg) and triethylamine (380 mg) and the reaction mixture was stirred at room temperature for an hour. To the reaction mixture was added water and the mixture was extracted with dichloromethane. The organic layer was dried over magnesium sulfate and concentrated in vacuum condition. The obtained residue was purified by column chromatography on silica gel (hexane:ethyl acetate=3:4) to give the title compound (330 mg) having the following physical data.

TLC: Rf 0.33 (hexane:ethyl acetate=3:4);
NMR: δ 2.02 (s, 3H), 4.42 (d, J=8.6 Hz, 1H), 5.14 (d, J=8.6 Hz, 1H), 6.69 (d, J=9.7 Hz, 1H), 6.89-6.99 (m, 1H), 6.99-7.07 (m, 1H), 7.07-7.17 (m, 2H), 7.36-7.53 (m, 3H), 7.54-7.66 (m, 1H).

Example 210

1-(2,6-difluorophenyl)-5-{4-(2,4-difluorophenyl)-2-[(1S)-1,2-dihydroxy-1-methylethyl]-1,3-oxazol-5-yl}-2(1H)-pyridinone By the same procedure as a reaction of Example 206, using the compound prepared in Example 209 instead of the compound prepared in Example 205, the title compound having the following physical data was obtained.
TLC: Rf 0.26 (ethyl acetate:hexane=4:1);
NMR: δ 1.61 (s, 3H), 2.90-3.03 (m, 1H), 3.38-3.48 (m, 1H), 3.70 (d, J=11.7 Hz, 1H), 4.10 (d, J=11.7 Hz, 1H), 6.66 (dd, J=9.5, 0.7 Hz, 1H), 6.87-7.04 (m, 2H), 7.05-7.14 (m, 2H), 7.37-7.50 (m, 3H), 7.54-7.63 (m, 1H).

Example 211

1-(2,6-difluorophenyl)-5-{4-(2,4-difluorophenyl)-2-[(1R)-1,2-dihydroxy-1-methylethyl]-1,3-oxazol-5-yl}-2(1H)-pyridinone By the same procedure as a series of reactions of Example 204→Example 209→Example 206, using the compound prepared in Example 186 instead of the compound prepared in Example 187, the title compound having the following physical data was obtained.
TLC: Rf 0.47 (ethyl acetate);
NMR: δ 1.61 (s, 3H), 2.92 (dd, J=8.7, 5.6 Hz, 1H), 3.38 (s, 1H), 3.70 (dd, J=11.5, 8.7 Hz, 1H), 4.11 (dd, J=11.5, 5.6 Hz, 1H), 6.67 (dd, J=9.7, 0.7 Hz, 1H), 6.89-6.97 (m, 1H), 6.97-7.05 (m, 1H), 7.06-7.15 (m, 2H), 7.36-7.52 (m, 3H), 7.53-7.65 (m, 1H).

Example 212

N-{1-(2,4-difluorophenyl)-2-[1-(2,6-difluorophenyl)-6-oxo-1,6-dihydro-3-pyridinyl]-2-oxoethyl}-3-hydroxy-2,2-dimethylpropanamide By the same procedure as a reaction of Example 53, using the compound prepared in Example 203 instead of the compound prepared in Example 52 and using 2,2-dimethyl-3-hydroxypropionic acid instead of tetrahydropyran-4-carboxylic acid, the title compound having the following physical data was obtained.
TLC: Rf 0.57 (hexane:ethyl acetate=3:7);
NMR: δ 1.17 (s, 3H), 1.21 (s, 3H), 2.73 (m, 1H), 3.49-3.62 (m, 2H), 6.37 (d, J=6.8 Hz, 1H), 6.66 (d, J=9.9 Hz, 1H), 6.82-6.93 (m, 2H), 7.06-7.18 (m, 2H), 7.26 (m, 1H), 7.42-7.63 (m, 2H), 7.92 (dd, J=9.9, 2.7 Hz, 1H), 8.20 (d, J=2.7 Hz, 1H).

Example 213

1-(2,6-difluorophenyl)-5-[4-(2,4-difluorophenyl)-2-(2-hydroxy-1,1-dimethylethyl)-1,3-oxazol-5-yl]-2(1H)-pyridinone By the same procedure as a series of reactions of Example 205→Example 206, using the compound prepared in Example 212 instead of the compound prepared in Example 204, the title compound having the following physical data was obtained.
TLC: Rf 0.23 (ethyl acetate:hexane=1:1);
NMR: δ 1.41 (s, 6H), 3.22 (t, J=7.0 Hz, 1H), 3.75 (d, J=7.0 Hz, 2H), 6.68 (dd, J=9.5, 0.7 Hz, 1H), 6.86-7.04 (m, 2H), 7.06-7.15 (m, 2H), 7.36-7.51 (m, 3H), 7.55-7.67 (m, 1H).

Example 214

1-(2,6-difluorophenyl)-5-{4-(2,4-difluorophenyl)-2-[2-hydroxy-1-(hydroxymethyl)-1-methylethyl]-1,3-oxazol-5-yl}-2(1H)-pyridinone By the same procedure as a series of reactions of Example 53→Example 205→Example 206, using the compound prepared in Example 203 instead of the compound prepared in Example 52 and using 2,2-(bis(hydroxymethyl)propionic acid instead of tetrahydropyran-4-carboxylic acid, the title compound having the following physical data was obtained.
TLC: Rf 0.44 (ethyl acetate);
NMR: δ 1.28 (s, 3H), 3.30 (t, J=6.5 Hz, 2H), 3.86-3.96 (m, 2H), 4.02-4.11 (m, 2H), 6.68 (dd, J=9.5, 0.9 Hz, 1H), 6.87-6.96 (m, 1H), 6.96-7.05 (m, 1H), 7.05-7.15 (m, 2H), 7.36-7.53 (m, 3H), 7.56-7.66 (m, 1H).

Example 215

1-{4-(2,4-difluorophenyl)-5-[1-(2,6-difluorophenyl)-6-oxo-1,6-dihydro-3-pyridinyl]-1,3-oxazol-2-yl}cyclopropyl acetate By the same procedure as a series of reactions of Example 53→Example 205, using the compound prepared in Example 203 instead of the compound prepared in Example 52 and using 1-hydroxy-1-cyclopropanecarboxylic acid instead of tetrahydropyran-4-carboxylic acid, the title compound having the following physical data was obtained.
TLC: Rf 0.49 (hexane:ethyl acetate=2:3);
NMR: δ 1.39-1.46 (m, 2H), 1.61-1.68 (m, 2H), 2.16 (s, 3H), 6.67 (dd, J=9.8, 0.8 Hz, 1H), 6.83-6.93 (m, 1H), 6.93-7.03 (m, 1H), 7.04-7.14 (m, 2H), 7.32 (d, J=2.6 Hz, 1H), 7.35-7.50 (m, 2H), 7.56-7.68 (m, 1H).

Example 216

1-(2,6-difluorophenyl)-5-[4-(2,4-difluorophenyl)-2-propionyl-1,3-oxazol-5-yl]-2(1H)-pyridinone By the same procedure as a reaction of Example 206, using the compound prepared in Example 215 instead of the compound prepared in Example 205, the title compound having the following physical data was obtained.
TLC: Rf 0.54 (hexane:ethyl acetate=2:3);
NMR: δ 1.25 (t, J=7.3 Hz, 3H), 3.12 (q, J=7.3 Hz, 2H), 6.66 (d, J=9.7 Hz, 1H), 6.91-7.00 (m, 1H), 7.00-7.14 (m, 3H), 7.39-7.51 (m, 2H), 7.56-7.66 (m, 1H), 7.67 (d, J=2.4 Hz, 1H).

Example 217

1-(2,6-difluorophenyl)-5-[4-(2,4-difluorophenyl)-2-(1-ethyl-1-hydroxypropyl)-1,3-oxazol-5-yl]-2(1H)-pyridinone By the same procedure as a reaction of Example 36, using the compound prepared in Example 216 instead of the compound prepared in Example 35 and using ethyl magnesium bromide instead of methyl magnesium bromide, the title compound having the following physical data was obtained.
TLC: Rf 0.63 (hexane:ethyl acetate=1:2);
NMR: δ 0.91 (t, J=7.4 Hz, 6H), 1.81-2.08 (m, 4H), 2.91 (s, 1H), 6.68 (dd, J=9.6, 0.8 Hz, 1H), 6.83-7.16 (m, 4H), 7.35-7.52 (m, 3H), 7.58-7.70 (m, 1H).

Example 218

1-(2,6-difluorophenyl)-5-[4-(2,4-difluorophenyl)-2-(1-hydroxycyclopropyl)-1,3-oxazol-5-yl]-2(1H)-pyridinone The compound prepared in Example 215 was dissolved in a mixed solution of methanol (6 mL) and 5N hydrochloric acid (2 mL) and refluxed at 90° C. for an hour. The reaction mixture was concentrated in vacuum condition. The obtained residue was washed with diisopropyl ether to give the title compound (110 mg) having the following physical data.

TLC: Rf 0.29 (hexane:ethyl acetate=2:3);
NMR: δ 1.32-1.40 (m, 4H), 3.39-3.51 (m, 1H), 6.66 (d, J=10.6 Hz, 1H), 6.86-7.15 (m, 4H), 7.33-7.51 (m, 3H), 7.55-7.67 (m, 1H).

Example 219

1-(2,6-difluorophenyl)-5-[4-(2,4-difluorophenyl)-2-(1-hydroxycyclobutyl)-1,3-oxazol-5-yl]-2(1H)-pyridinone By the same procedure as a series of reactions of Example 53→Example 205→Example 218, using the compound prepared in Example 203 instead of the compound prepared in Example 52 and using 1-hydroxy-1-cyclobutanecarboxylic acid instead of tetrahydropyran-4-carboxylic acid, the title compound having the following physical data was obtained.

TLC: Rf 0.39 (ethyl acetate:hexane=2:1);
NMR: δ 1.88-2.08 (m, 2H), 2.39-2.53 (m, 2H), 2.70-2.82 (m, 2H), 2.96 (s, 1H), 6.68 (d, J=10.4 Hz, 1H), 6.88-7.14 (m, 4H), 7.39-7.49 (m, 3H), 7.59-7.68 (m, 1H).

Example 220

1-(2,6-difluorophenyl)-5-[4-(2,4-difluorophenyl)-2-(2-hydroxy-2-methylpropyl)-1,3-oxazol-5-yl]-2(1H)-pyridinone By the same procedure as a series of reactions of Example 53→Example 209, using the compound prepared in Example 203 instead of the compound prepared in Example 52 and using 3-hydroxy-3-methylbutane acid instead of tetrahydropyran-4-carboxylic acid, the title compound having the following physical data was obtained.

TLC: Rf 0.39 (ethyl acetate:hexane=7:3);
NMR: δ 1.37 (s, 6H), 2.98 (s, 2H), 3.34 (s, 1H), 6.66 (d, J=10.4 Hz, 1H), 6.86-7.12 (m, 4H), 7.36-7.50 (m, 3H), 7.54-7.65 (m, 1H).

Example 221

2-{4-(2,4-difluorophenyl)-5-[1-(2,6-difluorophenyl)-6-oxo-1,6-dihydro-3-pyridinyl]-1,3-oxazol-2-yl}-2-propen-1-yl acetate By the same procedure as a series of reactions of Example 204→Example 205, using the compound prepared in Example 191 instead of the compound prepared in Example 187, the title compound having the following physical data was obtained.

TLC: Rf 0.34 (hexane:ethyl acetate=3:2);
NMR: δ 2.13 (s, 3H), 5.07 (s, 2H), 5.73 (s, 1H), 6.23 (s, 1H), 6.68 (d, J=10.6 Hz, 1H), 6.87-7.15 (m, 4H), 7.39-7.52 (m, 3H), 7.57-7.68 (m, 1H).

Example 222

2-{4-(2,4-difluorophenyl)-5-[1-(2,6-difluorophenyl)-6-oxo-1,6-dihydro-3-pyridinyl]-1,3-oxazol-2-yl}-2,3-dihydroxypropyl acetate By the same procedure as a reaction of Example 23, using the compound prepared in Example 221 instead of the compound prepared in Example 7(33), the title compound having the following physical data was obtained.

TLC: Rf 0.31 (hexane:ethyl acetate=1:4);
NMR: δ 2.09 (s, 3H), 2.78 (t, J=7.1 Hz, 1H), 3.60 (s, 1H), 3.92 (dd, J=11.7, 7.1 Hz, 1H), 4.09 (dd, J=11.7, 7.1 Hz, 1H), 4.48 (d, J=11.7 Hz, 1H), 4.56 (d, J=11.7 Hz, 1H), 6.66 (dd, J=9.6, 0.8 Hz, 1H), 6.87-7.13 (m, 4H), 7.36-7.49 (m, 3H), 7.53-7.63 (m, 1H).

Example 223

1-(2,6-difluorophenyl)-5-{4-(2,4-difluorophenyl)-2-[1,2-dihydroxy-1-(hydroxymethyl)ethyl]-1,3-oxazol-5-yl}-2(1H)-pyridinone By the same procedure as a reaction of Example 206, using the compound prepared in Example 222 instead of the compound prepared in Example 205, the title compound having the following physical data was obtained.

TLC: Rf 0.29 (dichloromethane:methanol=9:1);
NMR: δ 2.55 (dd, J=7.5, 6.2 Hz, 2H), 3.61 (s, 1H), 3.96 (dd, J=11.5, 7.5 Hz, 2H), 4.10 (dd, J=11.5, 6.2 Hz, 2H), 6.67 (dd, J=9.7, 0.7 Hz, 1H), 6.88-7.06 (m, 2H), 7.06-7.15 (m, 2H), 7.38-7.51 (m, 3H), 7.55-7.65 (m, 1H).

Example 224(1)~(4)

By the same procedure as a series of reactions of Example 202→Example 203→Example 204→Example 205→Example 206, using the compound prepared in Example 4 instead of the compound prepared in Example 201 and using the corresponding carboxylic acid chloride instead of the compound prepared in Example 187, the following compounds were obtained.

Example 224(1)

1-(4-chloro-2,6-dimethylphenyl)-5-{4-(2,4-difluorophenyl)-2-[(1S)-1,2-dihydroxy-1-methylethyl]-1,3-oxazol-5-yl}-2(1H)-pyridinone TLC: Rf 0.22 (ethyl acetate:hexane=4:1);
NMR: δ 1.61 (s, 3H), 2.08 (s, 6H), 2.88-3.02 (m, 1H), 3.34-3.47 (m, 1H), 3.64-3.77 (m, J=12.0 Hz, 1H), 4.10 (d, J=12.0 Hz, 1H), 6.71 (d, J=9.7 Hz, 1H), 6.84-6.93 (m, 1H), 6.97-7.05 (m, 1H), 7.19 (s, 2H), 7.25-7.27 (m, 1H), 7.45-7.51 (m, 1H), 7.57-7.66 (m, 1H).

Example 224(2)

1-(4-chloro-2,6-dimethylphenyl)-5-{4-(2,4-difluorophenyl)-2-[(1R)-1,2-dihydroxy-1-methylethyl]-1,3-oxazol-5-yl}-2(1H)-pyridinone TLC: Rf 0.22 (ethyl acetate:hexane=4:1);
NMR: δ 1.61 (s, 3H), 2.08 (s, 6H), 2.86-3.02 (m, 1H), 3.34-3.46 (m, 1H), 3.71 (d, J=11.5 Hz, 1H), 4.10 (d, J=11.5 Hz, 1H), 6.71 (dd, J=9.7, 0.5 Hz, 1H), 6.83-6.94 (m, 1H), 6.97-7.06 (m, 1H), 7.19 (s, 2H), 7.24-7.29 (m, 1H), 7.45-7.52 (m, 1H), 7.56-7.66 (m, 1H).

Example 224(3)

1-(4-chloro-2,6-dimethylphenyl)-5-{4-(2,4-difluorophenyl)-2-[(1S)-1,2-dihydroxy-2-methylpropyl]-1,3-oxazol-5-yl}-2(1H)-pyridinone TLC: Rf 0.49 (ethyl acetate);
NMR: δ 1.30 (s, 3H), 1.40 (s, 3H), 2.08 (s, 6H), 2.93 (s, 1H), 3.10 (d, J=8.2 Hz, 1H), 4.56 (d, J=8.2 Hz, 1H), 6.72 (d, J=9.5 Hz, 1H), 6.83-6.94 (m, 1H), 6.96-7.06 (m, 1H), 7.18 (s, 2H), 7.23-7.29 (m, 1H), 7.44-7.52 (m, 1H), 7.56-7.68 (m, 1H).

Example 224(4)

1-(4-chloro-2,6-dimethylphenyl)-5-{4-(2,4-difluorophenyl)-2-[(1R)-1,2-dihydroxy-2-methylpropyl]-1,3-oxazol-5-yl}-2(1H)-pyridinone TLC: Rf 0.49 (ethyl acetate);
NMR: δ 1.30 (s, 3H), 1.40 (s, 3H), 2.08 (s, 6H), 2.94 (s, 1H), 3.13 (d, J=8.2 Hz, 1H), 4.56 (d, J=8.2 Hz, 1H), 6.72 (d, J=9.7 Hz, 1H), 6.83-6.94 (m, 1H), 6.96-7.06 (m, 1H), 7.18 (s, 2H), 7.23-7.29 (m, 1H), 7.44-7.52 (m, 1H), 7.56-7.68 (m, 1H).

Example 225(1)~(2)

By the same procedure as a series of reactions of Example 5→Example 6, using the compound prepared in Example 201 instead of the compound prepared in Example 4 and using the corresponding sodium carboxylates instead of the compound prepared in Example A1, the following compounds were obtained.

Example 225(1)

1-(2,6-difluorophenyl)-5-[5-(2,4-difluorophenyl)-2-(2-hydroxy-1,1-dimethylethyl)-1,3-oxazol-4-yl]-2(1H)-pyridinone TLC: Rf 0.29 (ethyl acetate:hexane=3:2);
NMR: δ 1.40 (s, 6H), 3.22 (t, J=6.8 Hz, 1H), 3.75 (d, J=6.8 Hz, 2H), 6.63 (dd, J=9.7, 0.7 Hz, 1H), 6.91-7.14 (m, 4H), 7.38-7.55 (m, 3H), 7.58-7.62 (m, 1H).

Example 225(2)

1-(2,6-difluorophenyl)-5-[5-(2,4-difluorophenyl)-2-(hydroxymethyl)-1,3-oxazol-4-yl]-2(1H)-pyridinone TLC: Rf 0.26 (ethyl acetate:hexane=3:2);
NMR: δ 2.30 (t, J=4.9 Hz, 1H), 4.80 (d, J=4.9 Hz, 2H), 6.64 (dd, J=9.8, 0.6 Hz, 1H), 6.92-7.14 (m, 4H), 7.37-7.59 (m, 3H), 7.66-7.70 (m, 1H).

Example 226(1)~(4)

By the same procedure as a series of reactions of Example 8→Example 6, using the compound prepared in Example 201 instead of the compound prepared in Example 4 and using the corresponding carboxylic acids or sodium carboxylates instead of 2,2-bis(hydroxymethyl)butyric acid, the following compounds were obtained.

Example 226(1)

1-(2,6-difluorophenyl)-5-[5-(2,4-difluorophenyl)-2-(1-hydroxycyclopropyl)-1,3-oxazol-4-yl]-2(1H)-pyridinone TLC: Rf 0.32 (ethyl acetate:hexane=3:2);
NMR: δ 1.34-1.40 (m, 4H), 3.13-3.41 (m, 1H), 6.63 (dd, J=9.7, 0.7 Hz, 1H), 6.89-7.13 (m, 4H), 7.37-7.54 (m, 3H), 7.66-7.70 (m, 1H).

Example 226(2)

1-(2,6-difluorophenyl)-5-[5-(2,4-difluorophenyl)-2-(1-hydroxycyclobutyl)-1,3-oxazol-4-yl]-2(1H)-pyridinone TLC: Rf 0.37 (ethyl acetate:hexane=2:1);
NMR: δ 1.88-2.09 (m, 2H), 2.38-2.54 (m, 2H), 2.65-2.80 (m, 2H), 3.05 (s, 1H), 6.63 (dd, J=9.6, 0.6 Hz, 1H), 6.91-7.12 (m, 4H), 7.36-7.59 (m, 3H), 7.64-7.68 (m, 1H).

Example 226(3)

1-(2,6-difluorophenyl)-5-{5-(2,4-difluorophenyl)-2-[(4S)-2,2,5,5-tetramethyl-1,3-dioxolan-4-yl]-1,3-oxazol-4-yl}-2(1H)-pyridinone TLC: Rf 0.53 (hexane:ethyl acetate=1:2);
NMR: δ 1.16 (s, 3H), 1.46 (s, 3H), 1.52 (s, 3H), 1.61 (s, 3H), 4.96 (s, 1H), 6.63 (dd, J=9.7, 0.7 Hz, 1H), 6.95-7.13 (m, 4H), 7.44-7.55 (m, 3H), 7.69-7.73 (m, 1H).

Example 226(4)

1-(2,6-difluorophenyl)-5-{5-(2,4-difluorophenyl)-2-[(4R)-2,2,5,5-tetramethyl-1,3-dioxolan-4-yl]-1,3-oxazol-4-yl}-2(1H)-pyridinone TLC: Rf 0.53 (hexane:ethyl acetate=1:2);
NMR: δ 1.16 (s, 3H), 1.46 (s, 3H), 1.52 (s, 3H), 1.61 (s, 3H), 4.96 (s, 1H), 6.63 (dd, J=9.7, 0.7 Hz, 1H), 6.94-7.14 (m, 4H), 7.40-7.56 (m, 3H), 7.69-7.72 (m, 1H).

Example 227

1-(2,6-difluorophenyl)-5-{5-(2,4-difluorophenyl)-2-[(1S)-1,2-dihydroxy-2-methylpropyl]-1,3-oxazol-4-yl}-2(1H)-pyridinone By the same procedure as a reaction of Example 17, using the compound prepared in Example 226(3) instead of the compound prepared in Example 7(24), the title compound having the following physical data was obtained.
TLC: Rf 0.39 (hexane:ethyl acetate=1:4);
NMR: δ 1.26 (s, 3H), 1.39 (s, 3H), 2.77 (s, 1H), 3.20 (d, J=7.7 Hz, 1H), 4.58 (d, J=7.7 Hz, 1H), 6.64 (d, J=9.7 Hz, 1H), 6.91-7.17 (m, 4H), 7.36-7.59 (m, 3H), 7.61-7.69 (m, 1H).

Example 227(1)

1-(2,6-difluorophenyl)-5-{5-(2,4-difluorophenyl)-2-[(1R)-1,2-dihydroxy-2-methylpropyl]-1,3-oxazol-4-yl}-2(1H)-pyridinone By the same procedure as a reaction of Example 17, using the compound prepared in Example 226(4) instead of the compound prepared in Example 7(24), the title compound having the following physical data was obtained.
TLC: Rf 0.42 (ethyl acetate);
NMR: δ 1.26 (s, 3H), 1.39 (s, 3H), 2.74 (s, 1H), 3.12 (d, J=7.9 Hz, 1H), 4.58 (d, J=7.9 Hz, 1H), 6.64 (dd, J=9.7, 0.5 Hz, 1H), 6.93-7.14 (m, 4H), 7.38-7.57 (m, 3H), 7.62-7.67 (m, 1H).

Example 228

Ethyl 5-(2,4-difluorophenyl)-4-[1-(2,6-difluorophenyl)-6-oxo-1,6-dihydro-3-pyridinyl]-1,3-thiazole-2-carboxylate By the same procedure as a series of reactions of Example 4→Example 56, using the compound prepared in Example 85 instead of the compound prepared in Example 3 and using ethyl thiooxamate instead of the compound prepared in Example A18, the title compound having the following physical data was obtained.

TLC: Rf 0.31 (hexane:ethyl acetate=3:2);
NMR: δ 1.44 (t, J=7.1 Hz, 3H), 4.49 (q, J=7.1 Hz, 2H), 6.58 (d, J=9.7 Hz, 1H), 6.92-7.09 (m, 4H), 7.34-7.47 (m, 3H), 7.61-7.64 (m, 1H).

Example 229

1-(2,6-difluorophenyl)-5-[5-(2,4-difluorophenyl)-2-(hydroxymethyl)-1,3-thiazol-4-yl]-2(1H)-pyridinone To a solution of the compound prepared in Example 228 (1.17 g) in THF (10 mL) was added lithium borohydride (53 mg) at 0° C. and the reaction mixture was stirred at 0° C. for 2 hours. Furthermore the reaction mixture was stirred at room temperature for 2 hours. To the reaction mixture was added 1N hydrochloric acid and the mixture was extracted with ethyl acetate. The organic layer was dried over magnesium sulfate and concentrated in vacuum condition. The obtained residue was purified by column chromatography on silica gel (hexane:ethyl acetate=2:3) to give the title compound (819 mg) having the following physical data.

TLC: Rf 0.22 (hexane:ethyl acetate=3:2);
NMR: δ 2.53 (t, J=6.2 Hz, 1H), 4.97 (d, J=6.2 Hz, 2H), 6.58 (d, J=9.7 Hz, 1H), 6.90-7.10 (m, 4H), 7.32-7.47 (m, 3H), 7.53-7.56 (m, 1H).

Example 230

5-(2,4-difluorophenyl)-4-[1-(2,6-difluorophenyl)-6-oxo-1,6-dihydro-3-pyridinyl]-1,3-thiazole-2-carboxaldehyde By the same procedure as a reaction of Example 19, using the compound prepared in Example 229 instead of the compound prepared in Example 7(27), the title compound having the following physical data was obtained.

TLC: Rf 0.60 (hexane:ethyl acetate=3:2);
NMR: δ 6.63 (dd, J=9.7, 0.7 Hz, 1H), 6.93-7.12 (m, 4H), 7.35-7.50 (m, 3H), 7.55-7.58 (m, 1H), 9.96 (s, 1H).

Example 231

1-(2,6-difluorophenyl)-5-[5-(2,4-difluorophenyl)-2-(2-methyl-1-propen-1-yl)-1,3-thiazol-4-yl]-2(1H)-pyridinone A suspended solution of triphenylphosphonium salt (341 mg) of isopropyl iodide in anhydrous THF (2.0 mL) was stirred vigorously. To the reaction mixture was added n-butyllithium (0.5 mL, 1.57 M/hexane) at 0° C. and the the mixture was stirred for 5 minutes. A solution of the compound prepared in Example 230 (340 mg) in dichloromethane (5.0 mL) was added to the reaction mixture at 0° C. and stirred at room temperature for an hour. To the reaction mixture was added water and the mixture was extracted with ethyl acetate. The organic layer was washed with brine, dried over magnesium sulfate and concentrated in vacuum condition. The obtained residue was purified by column chromatography on silica gel (hexane:ethyl acetate=3:2) to give the title compound (226 mg) having the following physical data.

TLC: Rf 0.36 (hexane:ethyl acetate=3:2);
NMR: δ 2.10 (s, 3H), 2.17 (s, 3H), 6.49-6.53 (m, 1H), 6.59 (dd, J=9.2, 1.2 Hz, 1H), 6.89-7.09 (m, 4H), 7.32-7.53 (m, 4H).

Example 232

1-(2,6-difluorophenyl)-5-[5-(2,4-difluorophenyl)-2-(1,2-dihydroxy-2-methylpropyl)-1,3-thiazol-4-yl]-2(1H)-pyridinone By the same procedure as a reaction of Example 18, using the compound prepared in Example 231 instead of the compound prepared in Example 7(26), the title compound having the following physical data was obtained.

TLC: Rf 0.35 (ethyl acetate:hexane=7:3);
NMR: δ 1.31 (s, 3H), 1.33 (s, 3H), 3.08 (s, 1H), 3.33 (d, J=5.9 Hz, 1H), 4.73 (d, J=5.9 Hz, 1H), 6.59 (dd, J=9.5, 0.9 Hz, 1H), 6.88-7.00 (m, 2H), 7.00-7.10 (m, 2H), 7.29-7.49 (m, 4H).

Biological Examples

The whole operation was performed using the conventional method based on a fundamental biological technique. Also, as shown below, the measurement method used in the present invention is a method of which the measurement precision and/or the measurement sensitivity were enhanced and/or improved in order to evaluate the compounds of the present invention. Details of such experimental methods were shown below.

It was proven by the following Examples that the compounds of the present invention have inhibitory activity on p38a MAP kinase.

Biological Example 1

Study on p38α MAP Kinase Inhibitory Activity

Using activating transcription factor-2 (hereinafter abbreviated to ATF2) which is a substrate for p38α MAP kinase, the inhibitory action of the compounds of the present invention was investigated on the phosphorylation by a recombinant human p38α MAP kinase.

Experimental Method

A kinase buffer (25 mM Tris-HCl (pH 7.5), 5 mM β-glycerophosphate, 2 mM dithiothreitol, 0.1 mM Na3VO$_4$, 10 mM MgCl$_2$) containing a recombinant human p38α MAP kinase (Upstate Biotechnology #14-251) was added to a 384-well plate (5 µL) (6.25 ng protein/well) for fluorescence measurement. After addition of a kinase buffer (5 µL) containing the compound of the present invention, the resulting mixture was incubated at room temperature for 20 minutes. A substrate mixture (5 µL) of biotinylated ATF2 of 5 µg/mL (Upstate Biotechnology #14-432), adenosine triphosphate (90 µmol/L) (Sigma #FL-AAS) and anti-phosphorylated ATF2 antibody (20-fold dilution) (Cell Signaling Technology #9221L) prepared separately was added thereto, and enzyme reaction was carried out at 30° C. for 30 minutes. After the reaction, Hepes buffer (5 µL) containing 0.25% BSA and 100 mM EDTA was added to stop the enzyme reaction. The amount of a complex of the phosphorylated ATF2 and anti-phosphorylated ATF2 antibody produced by the reaction was measured using an Alpha Screen™ Rabbit Detection kit (Packard #6760607).

The p38α MAP kinase inhibitory activity, which is the effect of the compound of the present invention, was calculated as an inhibition rate (%) according to the following equation:

Inhibition rate (%)={(AC-AX)/(AC-AB)}×100 wherein AB is a measured value without addition of the enzyme;

AC is a measured value with addition of the enzyme in the absence of a test compound; and AX is a measured value with addition of the enzyme in the presence of a test compound.

Inhibition rate of compounds with each concentration was calculated, and a value indicating 50% inhibition ($IC_{50}$) was determined from the inhibition curve.

As a result, as indicated in table 1, it was confirmed that the compound of the present invention has very strong p38 MAP kinase inhibitory activity.

| Compound | $IC_{50}$ (nM) |
|---|---|
| Compound 6a of Example 6 | 12.0 |
| Compound of Example 7 (21) | 3.5 |
| Compound of Example 7 (39) | 2.8 |
| Compound 89 (b) of Example 89 | 1.7 |
| Compound of Example 167 (1) | 4.4 |
| Compound of Example 167 (2) | 3.8 |
| Compound of Example 206 | 3.3 |
| Compound of Example 207 | 3.7 |
| Compound of Example 210 | 5.8 |
| Compound of Example 211 | 5.6 |
| Compound of Example 220 | 8.0 |
| Compound of Example 223 | 3.3 |
| Compound of Example 227 | 3.9 |
| Compound of Example 227 (1) | 4.8 |

Also, it was proven by the following Examples that the compounds of the present invention have inhibitory activity on TNF-a production.

Biological Example 2

Inhibitory Activity against TNF-α Production using Human Cell Lines

Using THP-1 which is a human monocytic cell line, the inhibitory effect of the compound of the present invention against TNF-α production stimulated by lipopolysaccharide (LPS) was studied.

Experimental Method

Each 50 μL of lipopolysaccharide (LPS; 055:B5, Difco) prepared to a concentration of 40 ng/mL using RPMI-1640 medium containing 10% fetal calf serum (hereinafter abbreviated to RPMI-1640) and RPMI-1640 containing the compound of the present invention was added to a 96-well plate for cell culture. 100 μL of the cell suspension of THP-1 (Dainippon Pharmaceutical Co., Ltd, #06-202) prepared to a cell density of $2 \times 10^6$ cells/mL using RPMI-1640 was added and cultured for 90 minutes at 37° C. in an incubator (5% $CO_2$, 95% air). After completion of the reaction, the culture medium supernatant was recovered and the amount of produced TNF-α was measured using an ELISA kit (Invitrogen, #850090192).

The inhibitory activity against TNF-α production, which is the effect of the compound of the present invention, was calculated as an inhibition rate (%) by the following equation:

Inhibition rate (%)={(AC-AX)/(AC-AB)}×100 wherein AB is a measured value without LPS induction;

AC is a measured value with LPS induction in the absence of a test compound; and AX is a measured value with LPS induction in the presence of a test compound.

Inhibition rate of compounds with each concentration was calculated, and a value indicating 50% inhibition ($IC_{50}$) was determined from the inhibition curve. As a result, as indicated in table 2, the compound of the present invention showed the very strong inhibitory activity against TNF-α production.

| Compound | $IC_{50}$ (nM) |
|---|---|
| Compound 6a of Example 6 | 2.6 |
| Compound of Example 7 (21) | 1.7 |
| Compound of Example 7 (39) | 1.8 |
| Compound 89 (b) of Example 89 | 0.7 |
| Compound of Example 167 (1) | 0.8 |
| Compound of Example 167 (2) | 1.1 |
| Compound of Example 206 | 0.9 |
| Compound of Example 207 | 0.6 |
| Compound of Example 210 | 0.7 |
| Compound of Example 211 | 0.6 |
| Compound of Example 220 | 1.4 |
| Compound of Example 223 | 2.1 |
| Compound of Example 227 | 1.7 |
| Compound of Example 227 (1) | 0.7 |

Biological Example 3

Rat Cytokine-Production Model

The in vivo effect of the compound of the present invention was studied on TNF-α production induced by lipopolysaccharide (LPS) in rats.

Experimental Method

A vehicle containing the compound of the present invention was orally administered to male SD rat (Charles River Japan, Inc.), and after 8 hours, lipopolysaccharide (LPS, 055:B5, Difco) was intravenously administered at the dose of 10 μg/kg (5 animals/group). Only a vehicle was orally administered to a control group (5 animals). Ninety minutes after the LPS treatment, heparinized blood collection was performed via the abdominal vena cava under anesthesia with ether, and blood plasma was obtained by centrifugation (12,000 rpm, 3 minutes, 4° C.). The obtained blood plasma sample was stored at −80° C. until it was used. TNF-α in the blood plasma was measured using an ELISA kit from R&D System (#RTA00).

The inhibitory activity of the compound of the present invention against TNF-α production was calculated as an inhibition rate (%) according to the following equation:

Inhibition rate (%)={(AC-AX)/AC}×100 wherein AC is a measured value in case where no test compound was administered under LPS induction, and AX is a measured value in case where a test compound was administered under LPS induction.

As a result, as indicated in table 3, the compound of the present invention showed the very strong inhibitory activity against TNF-α production.

| Compound | Inhibition rate (%) (Dose of compound: 0.3 mg/kg) |
| --- | --- |
| Compound of Example 7 (21) | 85 |
| Compound of Example 7 (39) | 64 |
| Compound 89 (b) of Example 89 | 82 |
| Compound of Example 167 (1) | 73 |
| Compound of Example 167 (2) | 64 |
| Compound of Example 206 | 79 |
| Compound of Example 207 | 94 |
| Compound of Example 210 | 49 |
| Compound of Example 211 | 85 |
| Compound of Example 220 | 88 |
| Compound of Example 223 | 72 |
| Compound of Example 227 | 65 |
| Compound of Example 227 (1) | 88 |

It was proved for example by the following tests that the compounds of the present invention do not show the phospholipidosis inducing activity in an in vitro experiment described below.

Biological Example 4

Study by a Phospholipidosis Detection System using a Fluorescence Labeling Phospholipid Analog Experiment Method (i) Measurement of Phospholipid Accumulation Cell suspension ($7\times10^4$ cells/ml) of Chinese hamster lung cells (CHL/IU) prepared using MEM (minimum essential medium) was added to a 96 well plate (96 well clear bottom plate) by 100 µL/necessary number of wells (2 wells for 1 dosage) and cultured for about 24 hours. After the culturing and subsequent removal of the supernatants on the 96 well plate, the compounds having respective concentrations prepared by dissolving or suspending in MEM medium containing 25 µmol/L of nitrobenzoxazole dipalmitoyl phosphatidyl ethanolamine (NBD-PE) (hereinafter abbreviated to NBD-PE medium) were added thereto by 100 µL/ well and treated for about 24 hours. Treating concentration of each compound was set to be 6.25, 12.5, 25, 50 or 100 µmol/L. Amiodarone hydrochloride was used as a positive control substance, and its treating concentration was set to be 1.25, 2.5, 5, 10 or 20 µmol/L. In this connection, 5 wells of an untreated control (MEM medium alone) or an NBD-PE control (prepared by adding 1/100 volume of DMSO to the NBD-PE medium) were arranged for each compound and cultured in the same manner. After completion of the culturing and subsequent two times of washing with 100 µL/well of phosphate buffered saline (hereinafter abbreviated to PBS) (−), 100 µL of the MEM medium was added to all of the treated wells including two empty wells for the WST-1 background control and cultured for about 0.5 hour. Fluorescence intensity of each well was measured using a microplate reader (manufactured by Molecular Devices, SPECTRA max M2; excitation wavelength 485 nm/fluorescence wavelength 535 nm).

(ii) Analysis

Using average value of 2 wells for each dosage, the phospholipid increasing ratio (%) based on NBD-PE control was calculated using the following formula.

Phospholipid accumulation increasing ratio (%)=100×
(fluorescence intensity of substance to be tested−
fluorescence intensity of untreated control)/(fluorescence intensity of NBD-PE control−
fluorescence intensity of untreated control)

(iii) Cytotoxicity Test

The Pre value was calculated by measuring the 96 well plate which was measured in the measurement of phospholipid accumulation, using the microplate reader (manufactured by Molecular Devices, SPECTRA max M2) at a dominant wavelength of 450 nm and a correction wavelength of 690 nm. Premix WST-1 was added to the pre-measured 96 well plate by 5 µL/well. After 2 to 4 hours of culture, the Aft value was calculated by measuring in the same manner as in the Pre measurement. The background control value was subtracted from each of the measured values. Using the value obtained by subtracting the Pre value from the Aft value, the cell growth ratio (%) was calculated using the following formula.

Cell growth ratio (%)=100×(OD of substance to be tested)/(OD of NBD-PE control)

(iv) Judgment

The tested dosage which showed a value of 25% or more of the maximum phospholipid accumulation increasing ratio of amiodarone as the positive control was judged positive. In this connection, the dosage which showed a cell growth ratio of 50% or less in the cytotoxicity test was not used in the judgment of the presence or absence of the phospholipidosis inducing activity.

As a result, as indicated in Table 4, it was found that the compounds of the present invention do not show the phospholipidosis inducing activity in the in vitro test system.

| Compound | Pospholipid accumulation increasing ratio (% of 30 uM amiodarone) (Dose of compound: 100 uM) | Judgment |
| --- | --- | --- |
| Compound of Example 7 (21) | 8 | Negative |
| Compound of Example 7 (39) | 11 | Negative |
| Compound of Example 167 (1) | 3 | Negative |
| Compound of Example 167 (2) | 18 | Negative |
| Compound of Example 206 | 10 | Negative |
| Compound of Example 207 | 11 | Negative |
| Compound of Example 210 | 8 | Negative |
| Compound of Example 211 | 8 | Negative |
| Compound of Example 220 | 11 | Negative |
| Compound of Example 223 | 12 | Negative |
| Compound of Example 227 | 12 | Negative |
| Compound of Example 227 (1) | 13 | Negative |

Biological Example 5

Evaluation of Artificial Lipid Membrane Binding using a Biacore S51 (Registered Trademark) System Experiment Method (i) Preparation of Liposome Using an aspirator, 10 mM of 1,2-dioleoyl-sn-glycero-3-phosphate monosodium salt (hereinafter abbreviated to DOPA) chloroform solution was evaporated to be dryness, and 0.6 mL of PBS/5% dimethyl sulfoxide (hereinafter abbreviated to DMSO) was added thereto. After carrying out thorough suspension by vortex, freezing and thawing were repeated for 5 times. Liposomes were prepared using a liposome preparation device (manufactured by Avestin Inc.) and two syringes and diluted to be 0.5 mM with PBS/5% DMSO just before the immobilization.

(ii) Preparation of Measuring Compounds

Each compound having a final concentration in PBS/5% DMSO of 50 µM was prepared by adding 38 µL of 1× PBS to 2 µL of 10 mM DMSO solution and further adding 360 µL of 1× PBS/5% DMSO and measured.

(iii) Analysis

All of the following analyses were carried out using the Biacore S51 (registered trademark) system, and the measuring conditions were set up by Biacore S51 Control Software.

The measuring temperature was set to be 37° C., and PBS/ 5% DMSO (pH 7.4 or pH 6.0) was used as the buffer. Series S Sensor Chip L1 was used as the sensor chip. DOPA was immobilized on one of the measuring spots on the sensor surface, and the central spot was used as the reference.

Immobilization of the liposomes was carried out for about 3 minutes at a flow rate of 10 µL/minute, and then each compound was added thereto at a flow rate of 30 µL/minute to measure the interaction. The measuring conditions are as shown in the following.

Assay buffer: PBS/5% DMSO (pH 7.4 or pH 6.0)
Measuring temperature: 37° C.
Sensor chip: Series S Sensor Chip L1
Flow rate: 10 µL/minute at the time of liposome immobilization, 30 µL/minute at the time of interaction measurement
Regeneration: 20 mM CHAPS (3-[(3-cholamidopropyl) dimethylammonio]-1-propanesulfonate), an isopropanol/50 mM aqueous solution of sodium hydroxide=40/60 (volume ratio) mixed solution (60 seconds)

(iv) Data Treatment

The data treatment was carried out in accordance with the method of Abdiche et al. (*Analytical Biochemistry*, 328, 233-243 (2004)) using Biacore S51 Evaluation Software.

After correcting infinitesimal error of the concentration of DMSO contained in the sample solution, the value of binding response (RU) obtained by subtracting the value of reference was divided by the sample molecular weight. Additionally, since the thus obtained value is proportional to the capturing amount of liposome, it was divided by the capturing amount at the time of the cycling and multiplied by $10^6$ to be used as the correction value (correction value=1000000×RU (compound to be tested)/molecular weight (compound to be tested) RU (liposome)).

By adding propranolol, amiodarone, desipramine, imipramine and procaine as controls, it was confirmed that variation of the binding response is within about 10 to 15%.

(v) Judgment

Compounds having a binding response value after correction of 100 or more were judged positive.

As a result, as indicated in Table 5, it was found that the compounds of the present invention do not show the phospholipidosis inducing activity in the in vitro Experiment system.

| Compound | Binding Level (RU) | Judgment |
| --- | --- | --- |
| Compound of Example 7 (21) | 18.3 | Negative |
| Compound of Example 7 (39) | 11.1 | Negative |
| Compound 89 (b) of Example 89 | 15.5 | Negative |
| Compound of Example 167 (1) | 19.6 | Negative |
| Compound of Example 167 (2) | 22.2 | Negative |
| Compound of Example 206 | 14.7 | Negative |
| Compound of Example 207 | 12.8 | Negative |
| Compound of Example 211 | 11.1 | Negative |
| Compound of Example 220 | 15.5 | Negative |
| Compound of Example 223 | 8.7 | Negative |
| Compound of Example 227 | 22.5 | Negative |
| Compound of Example 227 (1) | 21.0 | Negative |

Formulation Examples

Formulation Example 1

1-(4-chloro-2,6-dimethylphenyl)-5-{5-(2,4-difluorophenyl)-2-[2-hydroxy-1-(hydroxymethyl)-1-methylethyl]-1,3-oxazol-4-yl}-2(1H)-pyridinone (5.0 kg), carboxymethylcellulose calcium (disintegrator) (0.2 kg), magnesium stearate (lubricant) (0.1 kg) and microcrystalline cellulose (4.7 kg) were admixed in a conventional manner, and tabletted to obtain 100,000 tablets containing an active ingredient of 50 mg/tablet.

Formulation Example 2

1-(4-chloro-2,6-dimethylphenyl)-5-{5-(2,4-difluorophenyl)-2-[2-hydroxy-1-(hydroxymethyl)-1-methylethyl]-1,3-oxazol-4-yl}-2(1H)-pyridinone (2.0 kg), mannitol (20 kg), and distilled water (500 L) were admixed in a conventional manner, filtered with a dust filter, filled in ampoules (5 mL each), and heat-sterilized in an autoclave to obtain 100,000 ampoules containing an active ingredient of 20 mg/ampoule.

INDUSTRIAL APPLICABILITY

Since the compounds represented by formula (I), or their salts, N-oxides or solvates, or prodrugs thereof have a low toxicity, they can be used as raw materials for drug medicines. Also, they are useful as an agent for the prevention and/or treatment of cytokine-mediated diseases such as rheumatoid arthritis and so forth, because they have p38 MAP kinase inhibitory activity.

The invention claimed is:

1. A compound represented by formula (Ia), (Ib), (Ic), or (Id):

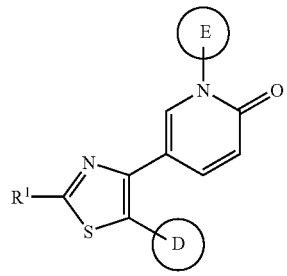

(Ia)

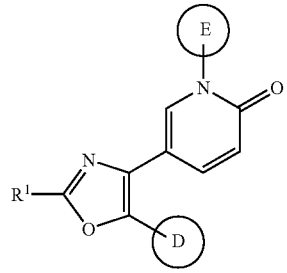

(Ib)

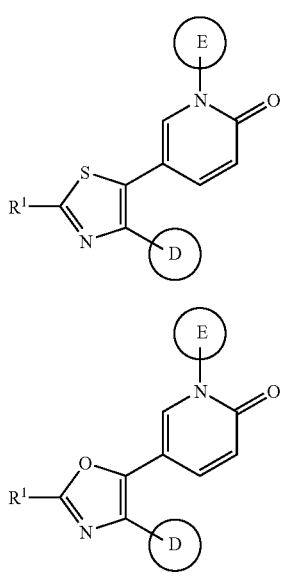

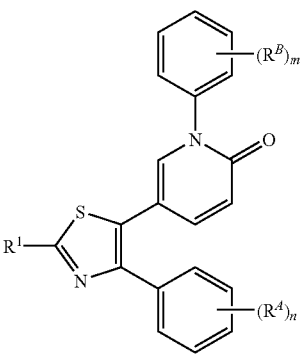

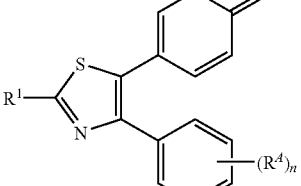

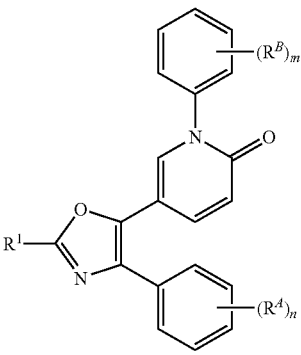

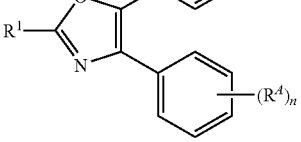

in which ring D and ring E are each independently a C5-10 monocyclic or bicyclic carbon ring which may be substituted; and R$^1$ is a hydroxyl group which may be protected, a hydrocarbon group substituted by the hydroxyl group which may be protected, a cyclic group substituted by the hydroxyl group which may be protected, a cyclic ether group which may be substituted, or a cyclic thioether group which may be substituted.

2. The compound according to claim 1, represented by formula (I-A), (I-B), (I-C), or (I-D):

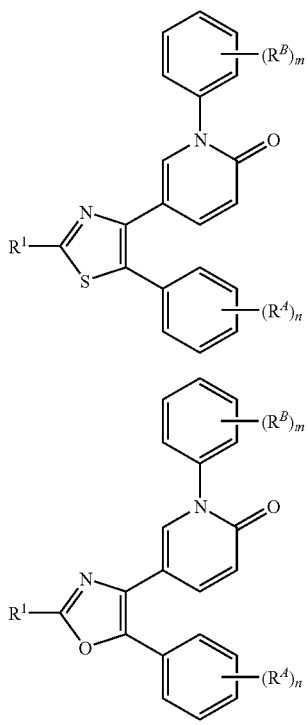

in which R$^A$ is a C1-4 alkyl group which may be substituted, a C1-4 alkoxy group which may be substituted or halogen atom;

R$^B$ is a C1-8 alkyl group which may be substituted, a C2-8 alkynyl group which may be substituted or halogen atom;

n represents 0 or an integer of 1 to 5;

m represents 0 or an integer of 1 to 5;

wherein when n is 2 or more, R$^A$ may be the same or different, and when m is 2 or more, R$^B$ may be the same or different; and R$^1$ has the same meanings as described in claim 1.

3. The compound according to claim 1, wherein the hydrocarbon group substituted by the hydroxyl group which may be protected is C1-8 alkyl group substituted by 1-3 hydroxyl group(s), and the cyclic group substituted by the hydroxyl group which may be protected is C3-6 monocyclic carbon ring substituted by 1-2 hydroxyl group(s).

4. The compound according to claim 1 selected from a group that consists of 1-(2,6-difluorophenyl)-5-[5-(2,4-difluorophenyl)-2-(1-hydroxy-1-methylethyl)-1,3-oxazol-4-yl]-2(1H)-pyridinone, 1-(2,6-difluorophenyl)-5-{5-(2,4-difluorophenyl)-2-[1,2-dihydroxy-1-(hydroxymethyl)ethyl]-1,3-oxazol-4-yl}-2(1H)-pyridinone, 1-(2,6-difluorophenyl)-5-[4-(2,4-difluorophenyl)-2-(1-hydroxy-1-methylethyl)-1,3-oxazol-5-yl]-2(1H)-pyridinone, 1-(2,6-difluorophenyl)-5-{5-(2,4-difluorophenyl)-2-[(1R)-1,2-dihydroxy-1-methylethyl]-1,3-oxazol-4-yl}-2(1H)-pyridinone, 1-(2,6-difluorophenyl)-5-{5-(2,4-difluorophenyl)-2-[(1S)-1,2-dihydroxy-1-methylethyl]-1,3-oxazol-4-yl}-2(1H)-pyridinone, 1-(2,6-difluorophenyl)-5-{4-(2,4-difluorophenyl)-2-[(1S)-1,2-dihydroxy-2-methylpropyl]-1,3-oxazol-5-yl}-2(1H)-pyridinone, 1-(2,6-difluorophenyl)-5-{4-(2,4-difluorophenyl)-2-[(1R)-1,2-dihydroxy-2-methylpropyl]-1,3-oxazol-5-yl}-2(1H)-pyridinone, 1-(2,6-difluorophenyl)-5-{4-(2,4-difluorophenyl)-2-[(1S)-1,2-dihydroxy-1-methylethyl]-1,3-oxazol-5-yl}-2(1H)-pyridinone, 1-(2,6-difluorophenyl)-5-{4-(2,4-difluorophenyl)-2-[(1R)-1,2-dihydroxy-1-methylethyl]-1,3-oxazol-5-yl}-2(1H)-pyridinone, 1-(2,6-difluorophenyl)-5-[4-(2,4-difluorophenyl)-2-(2-hydroxy-2-methylpropyl)-1,3-oxazol-5-yl]-2(1H)-pyridinone, 1-(2,6-difluorophenyl)-5-{4-(2,4-difluorophenyl)-2-[1,2-dihydroxy-1-(hydroxymethyl)ethyl]-1,3-oxazol-5-yl}-2(1H)-pyridinone, 1-(2,6-difluorophenyl)-5-{5-(2,4-difluorophenyl)-2-[(1S)-1,2-dihydroxy-2-methylpropyl]-1,3-oxazol-4-yl}-2(1H)-pyridinone, or 1-(2,6-difluorophenyl)-5-{5-(2,4-difluorophenyl)-2-[(1R)-1,2-dihydroxy-2-methylpropyl]-1,3-oxazol-4-yl}-2(1H)-pyridinone.

5. A pharmaceutical composition comprising a compound represented by formula (I) described in claim 1, a salt thereof.

6. The composition according to claim 5, which is a p38 MAP kinase inhibitor and/or a TNF-α production inhibitor.

7. A medicine comprising a compound represented by formula (I) described in claim 1, or a salt thereof, and one or two or more compound(s) selected from the group consisting of a non-steroidal anti-inflammatory agent, a disease modifying anti-rheumatic drug, an anticytokine protein preparation, a cytokine inhibitor, an immunomodulator, a steroidal agent, an adhesion molecule inhibitor, an elastase inhhibitor, a cannabinoid-2 receptor stimulant, a prostaglandin, a prostaglandin synthase inhibitor, a phosphodiesterase inhibitor and a metalloproteinase inhibitor in combination.

* * * * *